US012583856B2

(12) United States Patent
Bifulco et al.

(10) Patent No.: US 12,583,856 B2
(45) Date of Patent: Mar. 24, 2026

(54) INHIBITORS OF PROTEIN KINASE A

(71) Applicant: Blueprint Medicines Corporation, Cambridge, MA (US)

(72) Inventors: Neil Bifulco, Cambridge, MA (US); Joseph L. Kim, Cambridge, MA (US); Stefanie Sandra Schalm, Cambridge, MA (US); Kevin J. Wilson, Cambridge, MA (US); Michael Ross Palmer, Cambridge, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 420 days.

(21) Appl. No.: 18/275,119

(22) PCT Filed: Feb. 1, 2022

(86) PCT No.: PCT/US2022/014674

§ 371 (c)(1),
(2) Date: Jul. 31, 2023

(87) PCT Pub. No.: WO2022/165402

PCT Pub. Date: Aug. 4, 2022

(65) Prior Publication Data

US 2024/0132490 A1 Apr. 25, 2024

Related U.S. Application Data

(60) Provisional application No. 63/144,029, filed on Feb. 1, 2021.

(51) Int. Cl.
*C07D 471/04* (2006.01)
*A61P 35/00* (2006.01)

(52) U.S. Cl.
CPC ............ *C07D 471/04* (2013.01); *A61P 35/00* (2018.01)

(58) Field of Classification Search
None
See application file for complete search history.

(56) References Cited

FOREIGN PATENT DOCUMENTS

| | | | | |
|---|---|---|---|---|
| WO | WO-2007084667 A2 * | 7/2007 | ................ | A61P 9/10 |
| WO | 2013/033620 A1 | 3/2013 | | |

OTHER PUBLICATIONS

International Search Report and Written Opinion for Application No. PCT/US2022/014674, dated Apr. 29, 2022, 7 pages.

* cited by examiner

*Primary Examiner* — Jeffrey S Lundgren
*Assistant Examiner* — Anthony Joseph Seitz
(74) *Attorney, Agent, or Firm* — McCarter & English, LLP; Steven G. Davis; Wei Song

(57) ABSTRACT

Described herein are compounds of Formula (I) and pharmaceutically acceptable salts thereof and solvates of any of the foregoing capable of inhibiting protein kinase A and/or its mutants, pharmaceutical compositions comprising at least one of the compounds, pharmaceutically acceptable salts thereof, and solvates of any of the foregoing, processes for making the compounds, pharmaceutically acceptable salts thereof, and solvates of any of the foregoing, and methods of using the same.

(Continued)

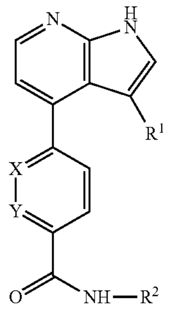
(I)
20 Claims, 2 Drawing Sheets

INHIBITORS OF PROTEIN KINASE A

CROSS-REFERENCE TO RELATED APPLICATIONS

This application is a 35 U.S.C. § 371 national stage filing of International Application No. PCT/US2022/014674, filed on Feb. 1, 2022, which in turn claims priority from U.S. Provisional Application No. 63/144,029, filed Feb. 1, 2021. The entire contents of each of the foregoing applications are incorporated herein by reference.

BACKGROUND

Disclosed herein are novel compounds, pharmaceutically acceptable salts thereof, and solvates of any of the foregoing, pharmaceutical compositions comprising at least one of the same, processes for making the same, and methods of using the same. The disclosed compounds are substituted pyrrolo[2,3-b]pyridin-4-yl benzamide compounds and, as discussed below, may be capable of inhibiting Protein Kinase A (PKA), e.g., capable of inhibiting PRKACA (Protein Kinase CAMP-Activated Catalytic Subunit Alpha) and/or PRKACB (Protein Kinase CAMP-Activated Catalytic Subunit Beta). The disclosed compounds may be useful in the treatment and prevention of diseases treatable with a Protein Kinase A (PKA) inhibitor, including diseases and disorders associated with aberrant PKA signaling.

PKA, also known as cAMP-dependent protein kinase, is a serine-threonine kinase comprising subunits, two of which are catalytically active (PRKACA and PRKACB), and four of which regulate enzyme activity (PRKAR subunits). The PRKACA gene encodes the catalytic Ca subunit of the 3',5'-cyclic adenosine monophosphate (cAMP)-dependent protein kinase A (PKA) and belongs to the AGC family of Serine/Threonine kinases (Manning, G. et al., *Science* 298: 1912-34 (2002)). The PRKACB catalytic subunit is structurally similar to the PRKACA catalytic subunit. For example, in humans, PRKACB, C-β-1, is a 350-residue protein with 93% sequence identity to PRKACA, C-α-1 (Soberg, K. et al., *PLoS One* 12: e0181091 (2017)).

PKAs are ubiquitous intracellular cAMP effectors that regulate multiple processes. Illustratively, PKA signaling regulates many physiological processes, including regulation of glycogen, sugar, and lipid metabolism. When the subunits of PKA are bound together, the heterotetrameric enzyme is inactive. However, a signal that causes an increase in intracellular cAMP concentration activates PKA activity. When cAMP levels within the cell rise in response to membrane signaling, cAMP binds cooperatively to paired binding pockets on each of the regulatory subunits, causing release of free, catalytically active PKA monomers. The catalytic subunits are released and in turn phosphorylate a variety of target proteins, ultimately modifying their biological activity. Normal PKA signaling activity in cells may be imbalanced due to a genetic alteration, such as a mutation or fusion in PKA, e.g., a mutation or fusion in one of the PKA subunits). For example, dysregulated PKA signaling may be characterized by a direct genetic alteration in a PKA catalytic subunit, e.g., PRKACA.

Aberrant PKA signaling is associated with human disease. For example, activated PKA signaling can drive tumorigenesis. More particularly, abberant PKA signaling activation through the catalytic PKA subunits, e.g., PRKACA and PRKACB in the ACTH-cAMP-PKA pathway (Soon, P. et al, *Oncologist* 13:548-561 (2008)), has been associated with various other diseases. Non-limiting examples of diseases associated with constitutive activation of PKA signaling include, but are not limited to, multiple neoplasia syndrome (e.g., Carney complex), Cushing's disease, pituitary tumors, kidney cancer, ovarian and testicular human stromal Leydig cell tumors, thyroid adenomas, villous colon cancers, intraductal papillary mucinous neoplasms, intrahepatic cholangiocarcinomas, McCune-Albright syndrome, and polycystic kidney disease.

Current treatment options are inadequate for many patients suffering from diseases associated with constitutive activation of PKA signaling. Accordingly, a need exists for novel PRKACA or PRKACB kinase inhibitors.

SUMMARY

Disclosed herein are novel substituted pyrrolo[2,3-b]pyridin-4-yl benzamide compounds, pharmaceutically acceptable salts thereof, and solvates of any of the foregoing. These may be selective inhibitors of the PKA catalytic subunits PRKACA and/or PRKACB. The selective PRKACA and/or PRKACB inhibitors are useful for treating diseases and disorders associated with aberrant PKA signaling. For example, the substituted pyrrolo[2,3-b]pyridin-4-yl benzamide compounds of this disclosure are useful for treating diseases such as cancer, e.g., lung cancer.

In some embodiments, the present disclosure features a compound of Formula (I), a pharmaceutically acceptable salt thereof, or a solvate of any of the foregoing:

(I)

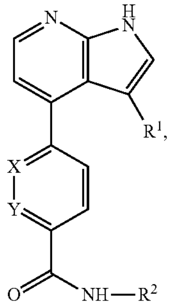

wherein each of X, Y, $R^1$, and $R^2$ is defined as described herein.

In some embodiments, the present disclosure provides pharmaceutical compositions comprising at least one compound chosen from compounds of Formula (I), pharmaceutically acceptable salts thereof, and solvates of any of the foregoing, and at least one pharmaceutically acceptable excipient.

In some embodiments, the present disclosure provides a method of inhibiting constitutive activation of protein kinase A signaling in a cell, the method comprising contacting a cell with an effective amount of a compound of Formula (I), a pharmaceutically acceptable salt thereof, or a solvate of any of the foregoing, or a pharmaceutical composition comprising at least one compound chosen from compounds of Formula (I), pharmaceutically acceptable salts thereof, and solvates of any of the foregoing.

In some embodiments, the present disclosure provides a method of modulating FLC gene expression, the method comprising contacting a cell with an effective amount of a compound of Formula (I), a pharmaceutically acceptable salt thereof, or a solvate of any of the foregoing, or a pharmaceutical composition comprising at least one compound chosen from compounds of Formula (I), pharmaceutically acceptable salts thereof, and solvates of any of the foregoing.

In some embodiments, the present disclosure provides a compound for inhibiting proliferation in vitro using a compound of Formula (I), a pharmaceutically acceptable salt thereof, or a solvate of any of the foregoing, or a pharmaceutical composition comprising at least one compound chosen from compounds of Formula (I), pharmaceutically acceptable salts thereof, and solvates of any of the foregoing.

In some embodiments, the present disclosure provides a method of treating a subject afflicted with a disease mediated by PRKACA or PRKACB. In some embodiments, the method comprises administering to the subject a therapeutically effective amount of a compound of Formula (I), a pharmaceutically acceptable salt thereof, or a solvate of any of the foregoing, or a pharmaceutical composition comprising at least one compound chosen from compounds of Formula (I), pharmaceutically acceptable salts thereof, or solvates of any of the foregoing.

In some embodiments, the disease mediated by PRKACA or PRKACB is characterized by constitutive activation of protein kinase A signaling. In some embodiments, the disease mediated by PRKACA or PRKACB is characterized by a PRKACA or PRKACB fusion. In some embodiments, the disease mediated by PRKACA or PRKACB is characterized by a PRKACA fusion. In some embodiments, the disease mediated by PRKACA or PRKACB is characterized by a PRKACB fusion. In some embodiments, the disease mediated by PRKACA or PRKACB is characterized by a DNAJB1-PRKAC fusion. In some embodiments, the disease mediated by PRKACA or PRKACB is characterized by an activating mutation in PRKACA or PRKACB. In some embodiments, the disease mediated by PRKACA or PRKACB is characterized by an activating mutation in PRKACA. In some embodiments, the disease mediated by PRKACA or PRKACB is characterized by an activating mutation in PRKACB. In some embodiments, the disease mediated by PRKACA or PRKACB is characterized by an L205R mutation in PRKACA. In some embodiments, the disease mediated by PRKACA or PRKACB is characterized by a GNAS gene mutation. In some embodiments, the disease mediated by PRKACA or PRKACB is characterized by one or more mutations in PKD1 (polycystin-1 protein, PC-1) and/or PKD2 (polycystin-2 protein, PC-2).

In some embodiments, the disease mediated by PRKACA or PRKACB is a fibrolamellar carcinoma. In some embodiments, the disease mediated by PRKACA or PRKACB is a multiple neoplasia syndrome. In some embodiments, the disease mediated by PRKACA or PRKACB is Carney complex (CNC). In some embodiments, the disease mediated by PRKACA or PRKACB is a polycystic kidney disease (PKD). In some embodiments, the disease mediated by PRKACA or PRKACB is a pituitary cancer. In some embodiments, the disease mediated by PRKACA or PRKACB is a kidney cancer. In some embodiments, the disease mediated by PRKACA or PRKACB is an ovarian cancer. In some embodiments, the disease mediated by PRKACA or PRKACB is a testicular cancer (e.g., testicular human stromal Leydig cell tumor). In some embodiments, the disease mediated by PRKACA or PRKACB is a thyroid ademona. In some embodiments, the disease mediated by PRKACA or PRKACB is a villous colon cancer. In some embodiments, the disease mediated by PRKACA or PRKACB is an intraductal papillary mucinous neoplasm (IPMN). In some embodiments, the disease mediated by PRKACA or PRKACB is an intrahepatic cholangiocarcinoma. In some embodiments, the disease mediated by PRKACA or PRKACB is an inflammatory liver cancer (e.g., characterized by STAT3 activation). In some embodiments, the disease mediated by PRKACA or PRKACB is adrenocortical adenoma. In some embodiments, the disease mediated by PRKACA or PRKACB is McCune-Albright syndrome.

In some embodiments, the McCune-Albright syndrome is associated with fibrous dysplasia of bone (FD), café-au-lait macules, precocious puberty, hyperthyroidism, Cushing syndrome, and/or pituitary gigantism/acromegaly.

In some embodiments, the present disclosure provides a method of treating cancer or inhibiting tumorigenesis associated with a cancer in a patient in need of such treatment. In some embodiments, the method comprises administering to the patient a therapeutically effective amount of a compound of Formula (I), a pharmaceutically acceptable salt thereof, or a solvate of any of the foregoing, or a pharmaceutical composition comprising at least one compound chosen from compounds of Formula (I), pharmaceutically acceptable salts thereof, and solvates of any of the foregoing.

In some embodiments, the present disclosure provides a compound of Formula (I), a pharmaceutically acceptable salt thereof, or a solvate of any of the foregoing, or a pharmaceutical composition comprising at least one compound chosen from compounds of Formula (I), pharmaceutically acceptable salts thereof, and solvates of any of the foregoing for use in therapy.

In some embodiments, the present disclosure provides a compound of Formula (I), a pharmaceutically acceptable salt thereof, or a solvate of any of the foregoing, or a pharmaceutical composition comprising at least one compound chosen from compounds of Formula (I), pharmaceutically acceptable salts thereof, and solvates of any of the foregoing for use in the treatment of a disease mediated by PRKACA or PRKACB.

In some embodiments, the present disclosure provides a use of a compound of Formula (I), a pharmaceutically acceptable salt thereof, or a solvate of any of the foregoing in the manufacture of a medicament for the treatment of cancer or the inhibition of tumorigenesis.

In some embodiments, the present disclosure provides a use of a compound of Formula (I), a pharmaceutically acceptable salt thereof, or a solvate of any of the foregoing, or a pharmaceutical composition comprising at least one compound chosen from compounds of Formula (I), pharmaceutically acceptable salts thereof, and solvates of any of the foregoing for use in the treatment of a disease mediated by PRKACA or PRKACB.

In some embodiments, the present disclosure provides a method of inhibiting PKA activity. In some embodiments, the method comprises administering to a subject a therapeutically effective amount of a compound of Formula (I), a pharmaceutically acceptable salt thereof, or a solvate of any of the foregoing, or a pharmaceutical composition comprising at least one compound chosen from compounds of Formula (I), pharmaceutically acceptable salts thereof, and solvates of any of the foregoing. In some embodiments, the PKA activity is aberrant. In some embodiments, the PKA activity is aberrant due to at least one PKA-alteration.

In some embodiments, the at least one PKA-alteration is a gene fusion. In some embodiments, the at least one PKA-alteration is a DNAJB1-PRKACA kinase fusion. In some embodiments, the at least one PKA-alteration is a genetic mutation. In some embodiments, the at least one PKA-alteration is a heterozygous germline inactivating mutation of the PKA regulatory subunit RIα and/or R2β genes (PRKAR1A and/or PRKAR2B). In some embodiments, the at least one PKA-alteration is an activating hotspot L205R mutations in PRKACA. In some embodiments, the PKA-alteration is a GNAS mutation. In some embodiments, the at least one PKA-alteration is a somatic heterozygous gain of-function mutation of the GNAS gene. In some embodiments, the at least one PKA-alteration is a mosaic GNAS activating mutation. In some embodiments, the at least one PKA-alteration is a mutation in PKD1 (polycystin-1 protein, PC-1). In some embodiments, the at least one PKA-alteration is a mutation in PKD2 (polycystin-2, PC-2 protein). In some embodiments, the at least one PKA-alteration includes a mutation in PKD1 and a mutation in PKD2.

In some embodiments, the present disclosure provides a compound of Formula (I), a pharmaceutically acceptable salt thereof, or a solvate of any of the foregoing, or a pharmaceutical composition comprising at least one compound chosen from compounds of Formula (I), pharmaceutically acceptable salts thereof, and solvates of any of the foregoing for use in inhibiting PKA activity.

In some embodiments, a compound of Formula (I), a pharmaceutically acceptable salt thereof, or a solvate of any of the foregoing is useful for inhibiting keratin 7 expression. Keratin 7 expression is a marker for some diseases characterized by aberrant PKA activity, e.g., hepatocellular carcinoma and fibrolamellar carcinoma (Van Eyken, P. et al., *Histopathology* 17(2):101-07 (1990)).

In some embodiments, the present disclosure provides a compound of Formula (I), a pharmaceutically acceptable salt thereof, or a solvate of any of the foregoing, or a pharmaceutical composition comprising at least one compound chosen from compounds of Formula (I), pharmaceutically acceptable salts thereof, and solvates of any of the foregoing for use in inhibiting keratin 7 expression.

In some embodiments, a compound of Formula (I), a pharmaceutically acceptable salt thereof, or a solvate of any of the foregoing does not substantially inhibit ROCK2 activity. Some ROCK2 inhibitors decrease blood pressure, an adverse effect that leads to poor clinical outcomes in some patients (*Journal of Clinical Oncology* 33, no. 15_suppl (May 2015) 2566-2566).

In some embodiments, the present disclosure provides a use of a compound of Formula (I), a pharmaceutically acceptable salt thereof, or a solvate of any of the foregoing in the manufacture of a medicament for the inhibition of PKA activity.

In some embodiments, the present disclosure provides a method for treating cancer in a patient in need thereof, the method comprising (a) obtaining a biological sample from the patient; (b) detecting the presence of at least one PKA-alteration in the biological sample; and (c) administering a compound of Formula (I), a pharmaceutically acceptable salt thereof, or a solvate of any of the foregoing, or a pharmaceutical composition comprising at least one compound chosen from compounds of Formula (I), pharmaceutically acceptable salts thereof, and solvates of any of the foregoing if the PKA-alteration is detected.

In some embodiments, the methods described herein further comprise various evaluations prior to, during, and/or following treatment with a compound, a salt, or a solvate of the present disclosure. In some embodiments, prior to, during, and/or following treatment with a compound, a salt, or a solvate of the present disclosure, the method further comprises evaluating, e.g., evaluating disease progression in the subject. This may be achieved by spectroscopic analysis, e.g., magnetic resonance-based analysis, e.g., MRI, positron emission tomography (PET), micro computed tomography (μCT), or by histology.

In some embodiments, the methods described herein further comprise evaluating a pre-treatment or baseline level of the disease progression in a subject, e.g., using spectroscopic analysis, e.g., magnetic resonance-based analysis, e.g., MRI, positron emission tomography (PET), micro computed tomography (μCT), or by histology. In some embodiments, the methods further comprise administering to the subject a compound of the disclosure; evaluating the post-treatment level of disease progression, regression, or stasis, e.g., using spectroscopic analysis, e.g., magnetic resonance-based analysis, e.g., MRI, positron emission tomography (PET), micro computed tomography (μCT), or by histology; comparing the post-treatment level of disease progression, regression, or stasis in the subject with the pre-treatment or baseline level of disease progression; and determining whether to continue treatment, e.g., using spectroscopic analysis, e.g., magnetic resonance-based analysis, e.g., MRI, positron emission tomography (PET), micro computed tomography (μCT), or by histology.

The disclosure also provides methods of using compounds that inhibit genetically altered PKA catalytic subunits e.g., PRKACA or fusions thereof, to a subject. In addition, the disclosure provides methods of using compounds for the treatment of a disease or disorder associated with constitutive activation of PKA signaling. For example, fibrolamellar carcinomas (FLC) are a unique type of primary liver cancer that most commonly occurs in children and young adults. FLC is associated with constitutive activation of PKA signaling. Because fibrolamellar variant of hepatocellular carcinoma (FL-HCC) tumors are largely resistant to chemotherapy, effective new treatment options are urgently needed.

Other features and advantages of the disclosure will be apparent from the detailed description and the claims.

BRIEF DESCRIPTIONS OF DRAWINGS

FIG. 1 shows Western blot analysis of PRKACA knockdown in NOD-SCID mouse FLC patient-derived xenograft (PDX) tumor samples 10, 20, and 28 days after doxycycline (dox) induction of dox-inducible non-targeting (NT) control or PRKACA shRNAs. A "+" symbol in the doxycycline (dox) row indicates that the mouse from which the sample was obtained was treated with doxycycline to induce shRNA expression. Actin was used as a loading control.

DETAILED DESCRIPTION

Figure 1:
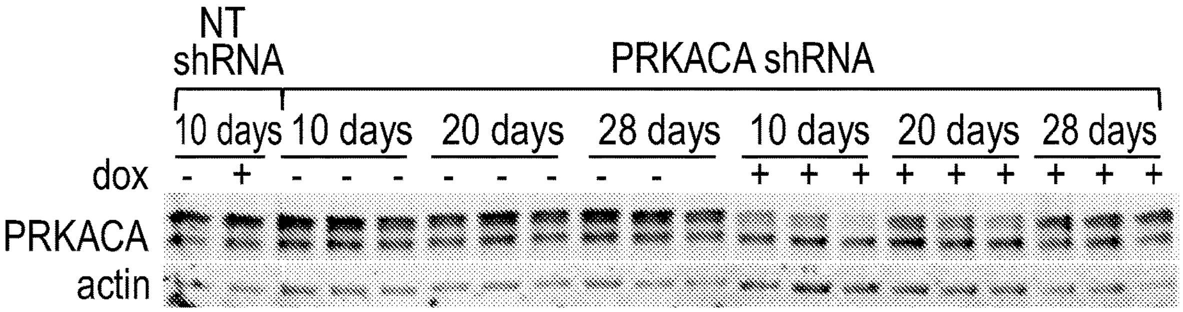

The present disclosure provides inhibitors (e.g., compounds of Formula (I), a pharmaceutically acceptable salt thereof, or a solvate of any of the foregoing) of protein kinase A (PKA) and mutants thereof, as discussed herein.

The present disclosure further provides methods for using the compounds of the disclosure, pharmaceutically acceptable salts thereof, or solvates of any of the foregoing, or pharmaceutical compositions comprising at least one compound chosen from compounds of Formula (I), pharmaceutically acceptable salts thereof, and solvates of any of the foregoing to treat a subject or patient afflicted with a disease mediated by PKA, e.g., fibrolamellar carcinoma, multiple neoplasia syndrome (e.g., Carney complex), pituitary cancer, kidney cancer, ovarian cancer, testicular cancer (e.g., testicular human stromal Leydig cell tumor), thyroid ademona, Villous colon cancer, intraductal papillary mucinous neoplasms (IPMN), intrahepatic cholangiocarcinomas, inflammatory liver cancer (e.g., inflammatory liver cancer characterized by STAT3 activation), adrenocortical adenoma, and/or McCune-Albright syndrome.

In some embodiments, the present disclosure provides a compound of Formula (I), a pharmaceutically acceptable salt thereof, or a solvate of any of the foregoing:

(I)

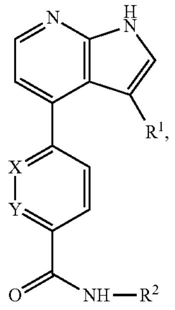

wherein each of X, Y, $R^1$, and $R^2$ is defined as described herein.

The details of construction and the arrangement of components set forth in the following description are not meant to be limiting. Other embodiments and different ways to practice the disclosure are expressly included. Also, the phraseology and terminology used herein are for the purpose of description and should not be regarded as limiting. The use of "including," "includes," "include," "comprising," "having," "containing," "involving," and variations thereof is meant to encompass the items listed thereafter and equivalents thereof as well as additional items.

"Alkyl," as used herein, refers to a monovalent radical of a saturated straight or branched hydrocarbon, such as a straight or branched group of 1-12, 1-10, 1-6, or 1-4 carbon atoms, referred to herein as $C_1$-$C_{12}$ alkyl, $C_1$-$C_{10}$ alkyl, $C_1$-$C_6$ alkyl, and $C_1$-$C_4$ alkyl, respectively. Non-limiting representative alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

"Chromane," as used herein, refers to a radical of the compound

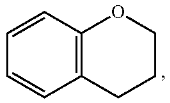

which may be bonded to the core structure through any atom where the valence of that atom is not exceeded. As described herein, a chromane may be optionally substituted.

As used herein, "halogen," "halide," and "halo" refer to a radical of any halogen, e.g., —F, —Cl, —Br, or —I.

"Haloalkyl," as used herein, refers to a monovalent, straight or branched alkyl chain, where at least one carbon atom is substituted with at least one hydroxyl group.

"Hydroxy" or "hydroxyl," as used herein, refers to —OH.

"Hydroxyalkyl," as used herein, refers to a monovalent, straight or branched alkyl chain, where at least one carbon atom is substituted with at least one hydroxyl group.

"Indane," as used herein, refers to a radical of the compound

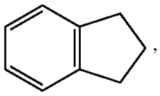

which may be bonded to the core struction through any atom where the valence of that atom is not exceeded. As described herein, an indane may be optionally substituted.

"Inhibitor," as used herein, refers to a compound that inhibits an enzyme such that a reduction in activity of the enzyme can be observed, e.g., in a biochemical assay or such that reduction of phosphorylation of a downstream target can be observed, e.g., in a cellular assay. In some embodiments, an inhibitor has an $IC_{50}$ of less than 1 μM, less than 500 nM, less than 250 nM, less than 100 nM, less than 50 nM, or less than 10 nM. A PKA inhibitor refers to a compound that inhibits PKA (wild-type and or mutant forms).

"Selective inhibitor," as used herein in reference to a specific kinase or catalytic subunit, refers to a compound or a pharmaceutically acceptable salt or solvate thereof that selectively inhibits the specific kinase or catalytic subunit over another kinase or catalytic subunit and exhibits at least a 2-fold selectivity for the specific kinase of catalytic subunit over another kinase or catalytic subunit. For example, a selective inhibitor exhibits at least a 10-fold selectivity; at least a 15-fold selectivity; at least a 20-fold selectivity; at least a 30-fold selectivity; at least a 40-fold selectivity; at least a 50-fold selectivity; at least a 60-fold selectivity; at least a 70-fold selectivity; at least a 80-fold selectivity; at least a 90-fold selectivity; at least 100-fold, at least 125-fold, at least 150-fold, at least 175-fold, or at least 200-fold selectivity for the specific kinase or catalytic subunit over another kinase or catalytic subunit. In some embodiments, selectivity for the specific kinase or catalytic subunit over another kinase or catalytic subunit is measured in a cellular assay. In other embodiments, selectivity for the specific kinase or catalytic subunit over another kinase or catalytic subunit is measured in a biochemical assay.

"Monocyclic heterocycle" and "bicyclic heterocycle" refer to a monocyclic or bicyclic, respectively, ring system wherein at least one ring comprises at least one heteroatom (e.g., N, O, P, or S). In certain instances, a ring may comprise one, two, three, or four ring heteroatoms.

Non-limiting representative monocyclic and bicyclic heterocyclic ring systems include ring systems in which (i) every ring is non-aromatic and at least one ring comprises a heteroatom, e.g., tetrahydrofuranyl, tetrahydropyranyl, tetrahydrothienyl, pyrrolidinyl, pyranyl, thianyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl or 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c] pyridine or 1,2,3,4-tetrahydro-2,6-naphthyridine.

"Protein Kinase A" or "PKA," as used herein, refers to any form of the protein kinase A protein, including wild-type and all variant forms (including, without limitation, mutant forms and splice variants).

"Substituted," whether preceded by the term "optionally" or not, refers herein to moieties having substituents replacing a hydrogen on one or more carbons of the backbone. One of ordinary skill in the art will understand that "substitution" or "substituted with" includes the implicit proviso that such substitution is in accordance with the permitted valence of the substituted atom and of the substituent, and that the substitution results in a stable compound, e.g., which does not spontaneously undergo transformation such as by rearrangement, cyclization, elimination, etc. As used herein, unless otherwise limited, the term "substituted" is contemplated to include all permissible substituents of organic compounds. In a broad aspect, the permissible substituents include acyclic and cyclic, branched and unbranched, carbocyclic and heterocyclic, and aromatic and non-aromatic substituents of organic compounds. There can be one or more permissible substituents in a substitution and the substituents can be the same or different.

In some embodiments, each substitutent is independently chosen from halogens, hydroxyl, $C_1$-$C_4$ alkyls, $C_1$-$C_4$ haloalkyls, 4-8-membered monocyclic heterocycles, 4-8-membered bicyclic heterocycles, $NR^3R^4$, and $OC_1$-$C_4$ alkyls, wherein: each 4-8-membered monocyclic heterocycle, 4-8-membered bicyclic heterocycle, 4-8-membered monocyclic heterocycle, 4-8-membered bicyclic heterocycle, $C_1$-$C_4$ alkyl, and $OC_1$-$C_4$ alkyl is optionally substituted with one to three groups independently chosen from $C_1$-$C_4$ alkyls, $C_1$-$C_4$ hydroxyalkyls, $C_1$-$C_4$ haloalkyls, $OC_1$-$C_4$ alkyls, $OC_1$-$C_4$ hydroxyalkyls, halogens, hydroxyl, and $C(O)NR^5R^6$; each $R^3$ and $R^4$ is independently chosen from hydrogen and $C_1$-$C_4$ alkyls; and each $R^5$ and $R^6$ is independently chosen from hydrogen and $C_1$-$C_4$ alkyls.

As used herein, the definition of each expression, e.g., alkyl, m, n, etc., when it occurs more than once in any structure, is intended to be independent of its definition elsewhere in the same structure.

As used herein, the terms "patient," "subject," "individual," and "host" refer to either a human or a non-human animal. In some embodiments, the "patient," "subject," "individual," or "host" may be suffering from or suspected of suffering from a disease or disorder, e.g., a cancer mediated by PKA.

As used herein, "treat" and "treating" such a disease or disorder refers to ameliorating at least one symptom of the disease or disorder. These terms, when used in connection with a disease such as a cancer, refer to one or more of: impeding growth of the cancer; causing the cancer to shrink in terms of weight and/or volume; extending the expected survival time of the patient; inhibiting tumor growth; reducing tumor mass; reducing size or number of metastatic lesions; inhibiting the development of new metastatic lesions; prolonging survival; prolonging progression-free survival; prolonging time to progression; and/or enhancing quality of life.

The phrase "therapeutically effective amount," as used herein, means that amount of a compound or combination of the disclosure that is effective to treat a disease or disorder at a reasonable benefit/risk ratio. The therapeutically effective amount of the compound or combination will vary depending upon the subject and disease or disorder being treated, the weight and age of the subject, the severity of the disease or disorder, the manner of administration, and the like, which can readily be determined by one of ordinary skill in the art.

The compounds described herein may contain unnatural proportions of atomic isotopes at one or more of the atoms that constitute such compounds. For example, the compounds may be radiolabeled with radioactive isotopes, such as, for example, tritium (3H) or carbon-14 ($^{14}C$). All isotopic variations of the compounds disclosed herein, whether radioactive or not, are intended to be encompassed within the scope of the present disclosure. For example, deuterated compounds or compounds containing $^{13}C$ are intended to be encompassed within the scope of the disclosure.

Certain compounds can exist in different tautomeric forms, and all possible tautomeric forms of all of the compounds described herein are intended to be encompassed within the scope of the disclosure.

The "enantiomeric excess," "% enantiomeric excess," or "ee" of a composition can be calculated using the equation shown below. In the example shown below, a composition contains 90% of one enantiomer, e.g., the S-enantiomer, and 10% of the other enantiomer, e.g., the R-enantiomer.

$$ee = \frac{90 - 10}{100} = 80\%$$

Thus, a composition containing 90% of one enantiomer and 10% of the other enantiomer is said to have an enantiomeric excess of 80%. Some of the compositions described herein contain an enantiomeric excess of at least 50%, at least 75%, at least 80%, at least 85%, at least 90%, at least 95%, or at least 99% of one enantiomer. Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure.

The compounds described herein can be in the form of the free base or a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts. See, e.g., Berge et al., "Pharmaceutical Salts," *J. Pharm. Sci.* 66:1-19 (1977).

Certain compounds disclosed herein can exist in unsolvated form as well as solvates, including hydrates. In general, the solvates are encompassed within the scope of the present disclosure.

In some embodiments, the present disclosure features a compound of Formula (I):

(I)

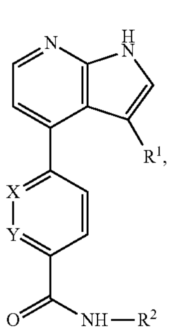

a pharmaceutically acceptable salt thereof, or a solvate of any of the foregoing, wherein:

X is chosen from CH and N;

Y is chosen from CH and N, provided that X and Y are not both N;

$R^1$ is chosen from H, halogens, and $C_1$-$C_4$ alkyls; and $R^2$ is chosen from optionally substituted indane and optionally substituted chromane.

In some embodiments, each optional substituent is independently chosen from halogens, hydroxyl, $C_1$-$C_4$ alkyls, $C_1$-$C_4$ haloalkyls, 4-8-membered monocyclic heterocycles, 4-8-membered bicyclic heterocycles, 4-8-membered bicyclic heterocycles $NR^3R^4$, and $OC_1$-$C_4$ alkyl, wherein:

each 4-8-membered monocyclic heterocycle, 4-8-membered bicyclic heterocycle, $C_1$-$C_4$ alkyl, and $OC_1$-$C_4$ alkyl is optionally substituted with one to three groups independently chosen from $C_1$-$C_4$ alkyls, $C_1$-$C_4$ hydroxyalkyls, $C_1$-$C_4$ haloalkyls, $OC_1$-$C_4$ alkyls, $OC_1$-$C_4$ hydroxyalkyls, halogens, hydroxyl, and $C(O)NR^5R^6$;

each $R^3$ and $R^4$ is independently chosen from hydrogen and $C_1$-$C_4$ alkyls; and each $R^5$ and $R^6$ is independently chosen from hydrogen and $C_1$-$C_4$ alkyls.

In some embodiments, the present disclosure features a compound of Formula (Ia):

(Ia)

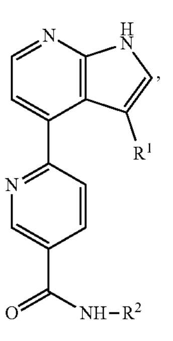

a pharmaceutically acceptable salt thereof, or a solvate of any of the foregoing, wherein:

$R^1$ is chosen from H, halogens, and $C_1$-$C_4$ alkyls; and $R^2$ is chosen from optionally substituted indane and optionally substituted chromane.

In some embodiments, each optional substituent is independently chosen from halogens, hydroxyl, $C_1$-$C_4$ alkyls, $C_1$-$C_4$ haloalkyls, 4-8-membered monocyclic heterocycles, 4-8-membered bicyclic heterocycles, $NR^3R^4$, and $OC_1$-$C_4$ alkyls, wherein:

each 4-8-membered monocyclic heterocycle, 4-8-membered bicyclic heterocycle, $C_1$-$C_4$ alkyl, and $OC_1$-$C_4$ alkyl is optionally substituted with one to three groups independently chosen from $C_1$-$C_4$ alkyls, $C_1$-$C_4$ hydroxyalkyls, $C_1$-$C_4$ haloalkyls, $OC_1$-$C_4$ alkyls, $OC_1$-$C_4$ hydroxyalkyls, halogens, hydroxyl, and $C(O)NR^5R^6$;

each $R^3$ and $R^4$ is independently chosen from hydrogen and $C_1$-$C_4$ alkyls; and each $R^5$ and $R^6$ is independently chosen from hydrogen and $C_1$-$C_4$ alkyls.

In some embodiments, the present disclosure features a compound of Formula (Ib):

(Ib)

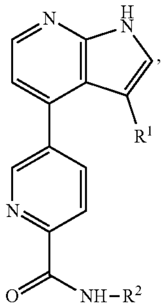

a pharmaceutically acceptable salt thereof, or a solvate of any of the foregoing, wherein:

$R^1$ is chosen from H, halogens, and $C_1$-$C_4$ alkyls; and $R^2$ is chosen from optionally substituted indane and optionally substituted chromane.

In some embodiments, each optional substituent is independently chosen from halogens, hydroxyl, $C_1$-$C_4$ alkyls, $C_1$-$C_4$ haloalkyls, 4-8-membered monocyclic heterocycles, 4-8-membered bicyclic heterocycles, $NR^3R^4$, and $OC_1$-$C_4$ alkyls, wherein:

each 4-8-membered monocyclic heterocycle, 4-8-membered bicyclic heterocycle, $C_1$-$C_4$ alkyl, and $OC_1$-$C_4$ alkyl is optionally substituted with one to three groups independently chosen from $C_1$-$C_4$ alkyls, $C_1$-$C_4$ hydroxyalkyls, $C_1$-$C_4$ haloalkyls, $OC_1$-$C_4$ alkyls, $OC_1$-$C_4$ hydroxyalkyls, halogens, hydroxyl, and $C(O)NR^5R^6$;

each $R^3$ and $R^4$ is independently chosen from hydrogen and $C_1$-$C_4$ alkyls; and each $R^5$ and $R^6$ is independently chosen from hydrogen and $C_1$-$C_4$ alkyls.

In some embodiments, the present disclosure features a compound of Formula (Ic):

(Ic)

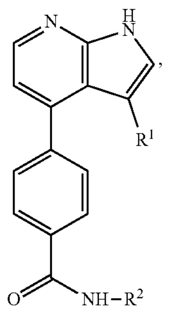

a pharmaceutically acceptable salt thereof, or a solvate of any of the foregoing, wherein:

$R^1$ is chosen from H, halogens, and $C_1$-$C_4$ alkyls; and $R^2$ is chosen from optionally substituted indane and optionally substituted chromane.

In some embodiments, each optional substituent is independently chosen from halogens, hydroxyl, $C_1$-$C_4$ alkyls, $C_1$-$C_4$ haloalkyls, 4-8-membered monocyclic heterocycles, 4-8-membered bicyclic heterocycles, $NR^3R^4$, and $OC_1$-$C_4$ alkyls, wherein:

each 4-8-membered monocyclic heterocycle, 4-8-membered bicyclic heterocycle, $C_1$-$C_4$ alkyl, and $OC_1$-$C_4$ alkyl is optionally substituted with one to three groups independently chosen from $C_1$-$C_4$ alkyls, $C_1$-$C_4$ hydroxyalkyls, $C_1$-$C_4$ haloalkyls, $OC_1$-$C_4$ alkyls, $OC_1$-$C_4$ hydroxyalkyls, halogens, hydroxyl, and $C(O)NR^5R^6$;

each $R^3$ and $R^4$ is independently chosen from hydrogen and $C_1$-$C_4$ alkyls; and each $R^5$ and $R^6$ is independently chosen from hydrogen and $C_1$-$C_4$ alkyls.

In some embodiments of Formulae (I), (Ia), (Ib), and (Ic), $R^1$ is hydrogen. In some embodiments of Formulae (I), (Ia), (Ib), and (Ic), $R^1$ is chosen from halogens. In some embodiments of Formulae (I), (Ia), (Ib), and (Ic), $R^1$ is chosen from $C_1$-$C_4$ alkyls.

In some embodiments of Formulae (I), (Ia), (Ib), and (Ic), $R^1$ is fluorine. In some embodiments of Formulae (I), (Ia), (Ib), and (Ic), $R^1$ is chlorine. In some embodiments of Formulae (I), (Ia), (Ib), and (Ic), $R^1$ is bromine. In some embodiments of Formulae (I), (Ia), (Ib), and (Ic), $R^1$ is iodine.

In some embodiments of Formulae (I), (Ia), (Ib), and (Ic), $R^1$ is methyl. In some embodiments of Formulae (I), (Ia), (Ib), and (Ic), $R^1$ is ethyl. In some embodiments of Formulae (I), (Ia), (Ib), and (Ic), $R^1$ is propyl. In some embodiments of Formulae (I), (Ia), (Ib), and (Ic), $R^1$ is butyl.

In some embodiments of Formulae (I), (Ia), (Ib), and (Ic), $R^1$ is chosen from hydrogen, fluorine, and methyl.

In some embodiments of Formula (I), X is CH or N. In some embodiments of Formula (I), X is CH. In some embodiments of Formula (I), X is N.

In some embodiments of Formula (I), Y is CH or N, provided that X and Y are not both N. In some embodiments of Formula (I), Y is CH. In some embodiments of Formula (I), Y is N. In some embodiments of Formula (I), X is CH and Y is CH. In some embodiments of Formula (I), X is CH and Y is N. In some embodiments of Formula (I), X is N and Y is CH.

In some embodiments of Formulae (I), (Ia), (Ib), and (Ic), $R^2$ is indane. In some embodiments of Formulae (I), (Ia), (Ib), and (Ic), $R^2$ is substituted indane. In some embodiments of Formulae (I), (Ia), (Ib), and (Ic), $R^2$ is chromane. In some embodiments of Formulae (I), (Ia), (Ib), and (Ic), $R^2$ is substituted chromane.

In some embodiments of Formulae (I), (Ia), (Ib), and (Ic), $R^2$ is chosen from indane substituted with one group chosen from halogens, hydroxyl, and $C_1$-$C_4$ alkyls and chromane substituted with one group chosen from halogens, hydroxyl, and $C_1$-$C_4$ alkyls. In some embodiments of Formulae (I), (Ia), (Ib), and (Ic), $R^2$ is chosen from indane substituted with one or two independently chosen halogens and chromane substituted with one or two independently chosen halogens. In some embodiments of Formulae (I), (Ia), (Ib), and (Ic), $R^2$ is chosen from indane substituted with one group chosen from halogens and hydroxyl and chromane substituted with one group chosen from halogens and hydroxyl. In some embodiments of Formulae (I), (Ia), (Ib), and (Ic), $R^2$ is chosen from indane substituted with one or two independently chosen halogens and one hydroxyl and chromane substituted with one or two independently chosen halogens and one hydroxyl. In some embodiments of Formulae (I), (Ia), (Ib), and (Ic), $R^2$ is chosen from indane substituted with one or two independently chosen halogens, one hydroxyl, and one group chosen from $C_1$-$C_4$ alkyls and $C_1$-$C_4$ haloalkyls and chromane substituted with one or two independently chosen halogens, one hydroxyl, and one group chosen from $C_1$-$C_4$ alkyls and $C_1$-$C_4$ haloalkyls.

In some embodiments of Formulae (I), (Ia), (Ib), and (Ic), $R^2$ is chosen from indane substituted with one or two independently chosen halogens and one group chosen from 4-8-membered monocyclic heterocycles and 4-8-membered bicyclic heterocycles, wherein each 4-8 membered monocyclic heterocycle and 4-8 membered bicyclic heterocyle is optionally substituted with one to three groups independently chosen from $C_1$-$C_4$ alkyls, $C_1$-$C_4$ haloalkyls, $C_1$-$C_4$ hydroxyalkyls, $OC_1$-$C_4$ alkyls, $OC_1$-$C_4$ hydroxyalkyls, halogens, hydroxyl, and $C(O)NR^5R^6$ and chromane substituted with one or two independently chosen halogens and one group chosen from one group chosen from 4-8-membered monocyclic heterocycles and 4-8-membered bicyclic heterocycles, wherein each 4-8 membered monocyclic heterocycle and 4-8 membered bicyclic heterocyle is optionally substituted with one to three groups independently chosen from $C_1$-$C_4$ alkyls, $C_1$-$C_4$ haloalkyls, $C_1$-$C_4$ hydroxyalkyls, $OC_1$-$C_4$ alkyls, $OC_1$-$C_4$ hydroxyalkyls, halogens, hydroxyl, and $C(O)NR^5R^6$, wherein: each $R^3$ and $R^4$ is independently chosen from hydrogen and $C_1$-$C_4$ alkyls; and each $R^5$ and $R^6$ is independently chosen from hydrogen and $C_1$-$C_4$ alkyls. In some embodiments of Formulae (I), (Ia), (Ib), and (Ic), the 4-8-membered monocyclic heterocycle is an azetidine optionally substituted with one or two groups independently chosen from $C_1$-$C_4$ alkyls, $OC_1$-$C_4$ alkyls, halogens, hydroxyl, $C(O)NH_2$, and $C(O)N(CH_3)_2$ or a pyrrolidine optionally substituted with one or two groups independently chosen from $C_1$-$C_4$ alkyls, $OC_1$-$C_4$ alkyls, halogens, hydroxyl, $C(O)NH_2$, and $C(O)N(CH_3)_2$. In some embodiments of Formulae (I), (Ia), (Ib), and (Ic), each halogen is independently fluorine or chlorine.

In some embodiments of Formulae (I), (Ia), (Ib), and (Ic), $R^2$ is chosen from:

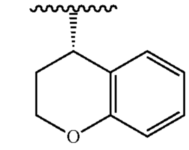,
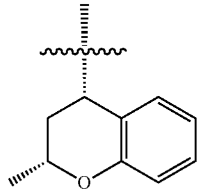,
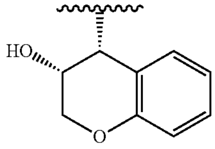,
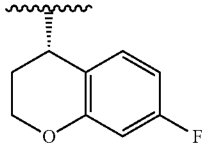,
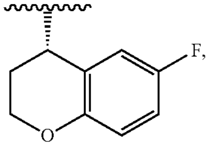
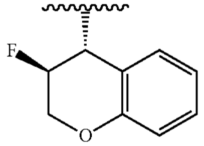,
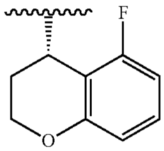,
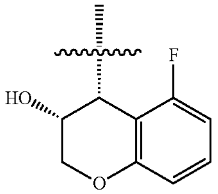,
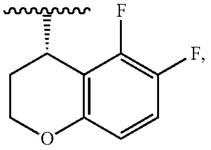
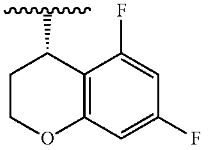,
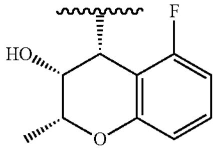,
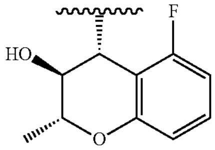,
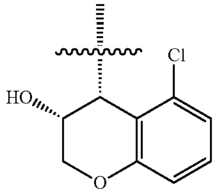,
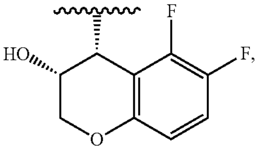
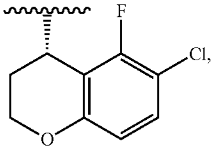
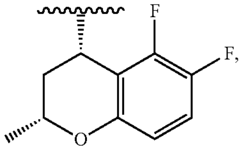
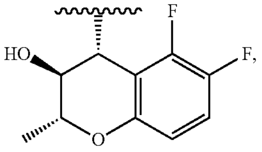
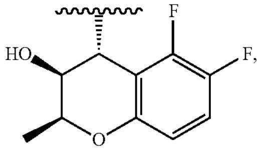
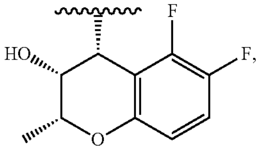
-continued
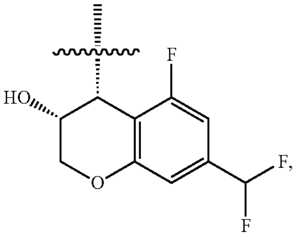 and
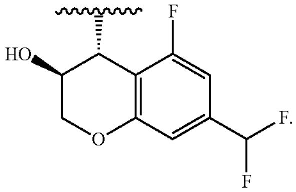
In some embodiments of Formulae (I), (Ia), (Ib), and (Ic), $R^2$ is
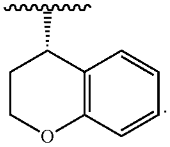 [SMILES: *[C@H]1CCOc2ccccc21]
In some embodiments of Formulae (I), (Ia), (Ib), and (Ic), $R^2$ is
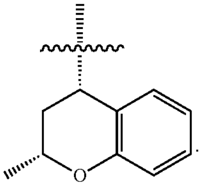
In some embodiments of Formulae (I), (Ia), (Ib), and (Ic), $R^2$ is
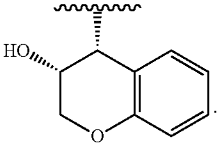 [SMILES: *[C@@H]1c2ccccc2OC[C@@H]1O]
In some embodiments of Formulae (I), (Ia), (Ib), and (Ic), $R^2$ is
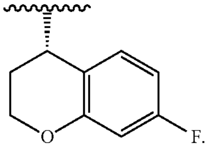 [SMILES: *[C@H]1CCOc2cc(F)ccc21]

In some embodiments of Formulae (I), (Ia), (Ib), and (Ic), $R^2$ is

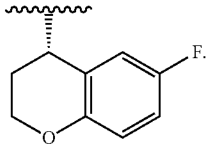 [SMILES: *[C@H]1CCOc2ccc(F)cc21]

In some embodiments of Formulae (I), (Ia), (Ib), and (Ic), $R^2$ is

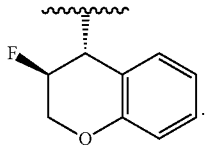

In some embodiments of Formulae (I), (Ia), (Ib), and (Ic), $R^2$ is

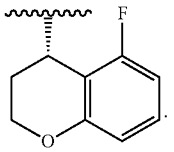 [SMILES: *[C@H]1CCOc2cccc(F)c21]

In some embodiments of Formulae (I), (Ia), (Ib), and (Ic), $R^2$ is

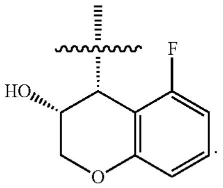

In some embodiments of Formulae (I), (Ia), (Ib), and (Ic), $R^2$ is

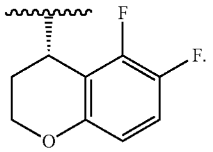 [SMILES: *[C@H]1CCOc2ccc(F)c(F)c21]

In some embodiments of Formulae (I), (Ia), (Ib), and (Ic), $R^2$ is

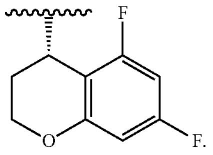 [SMILES: *[C@H]1CCOc2cc(F)cc(F)c21]

In some embodiments of Formulae (I), (Ia), (Ib), and (Ic), $R^2$ is

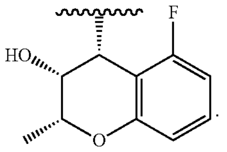

In some embodiments of Formulae (I), (Ia), (Ib), and (Ic), $R^2$ is

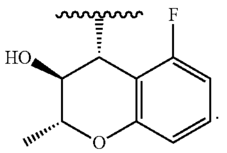 [SMILES: *[C@@H]1c2c(F)cccc2O[C@H](C)[C@H]1O]

In some embodiments of Formulae (I), (Ia), (Ib), and (Ic), $R^2$ is

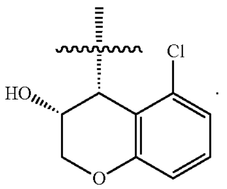

In some embodiments of Formulae (I), (Ia), (Ib), and (Ic), $R^2$ is

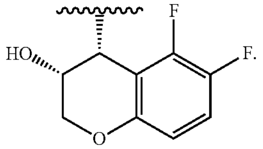 [SMILES: *[C@@H]1c2c(ccc(F)c2F)OC[C@@H]1O]

In some embodiments of Formulae (I), (Ia), (Ib), and (Ic), $R^2$ is

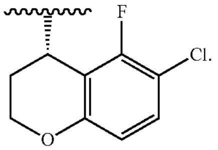 [SMILES: *[C@H]1CCOc2ccc(Cl)c(F)c21]

In some embodiments of Formulae (I), (Ia), (Ib), and (Ic), $R^2$ is

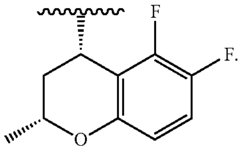 [SMILES: *[C@H]1C[C@@H](C)Oc2ccc(F)c(F)c21]

In some embodiments of Formulae (I), (Ia), (Ib), and (Ic), $R^2$ is
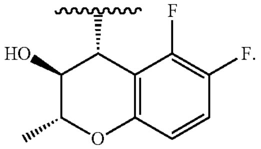 [SMILES: *[C@@H]1c2c(ccc(F)c2F)O[C@H](C)[C@H]1O]
In some embodiments of Formulae (I), (Ia), (Ib), and (Ic), $R^2$ is
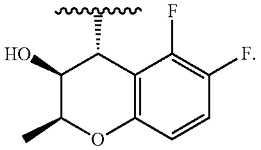 [SMILES: *[C@@H]1c2c(ccc(F)c2F)O[C@@H](C)[C@H]1O]
In some embodiments of Formulae (I), (Ia), (Ib), and (Ic), $R^2$ is
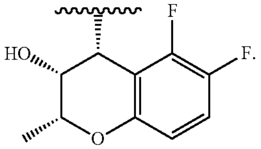 [SMILES: *[C@@H]1c2c(ccc(F)c2F)O[C@H](C)[C@@H]1O]
In some embodiments of Formulae (I), (Ia), (Ib), and (Ic), $R^2$ is
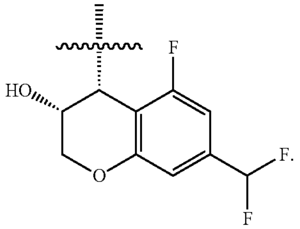
In some embodiments of Formulae (I), (Ia), (Ib), and (Ic), $R^2$ is
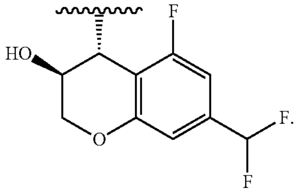 [SMILES: *[C@@H]1c2c(F)cc(C(F)F)cc2OC[C@H]1O]
In some embodiments of Formulae (I), (Ia), (Ib), and (Ic), $R^2$ is chosen from:
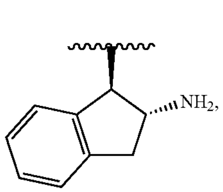
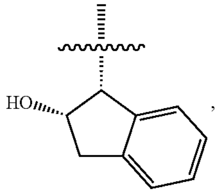
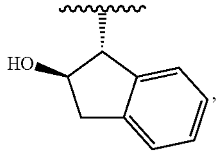
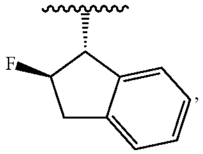
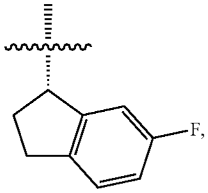
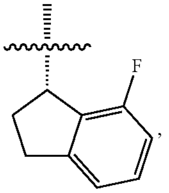
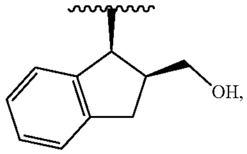
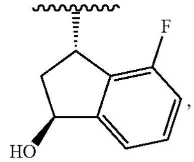
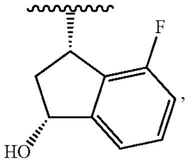
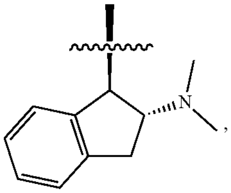
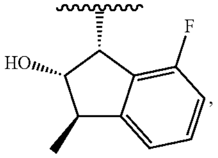
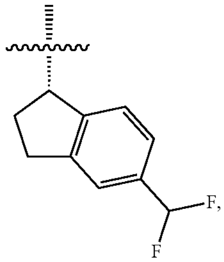
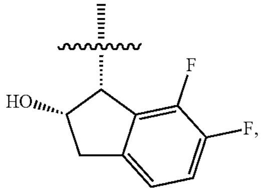
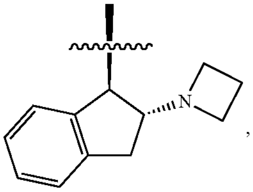
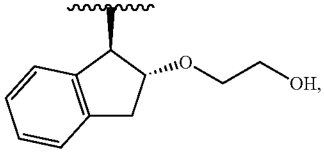
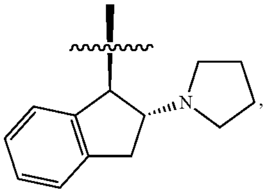
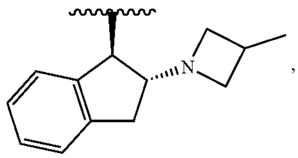

-continued
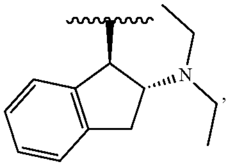
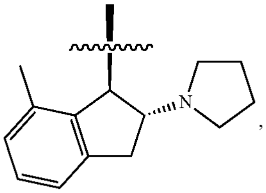
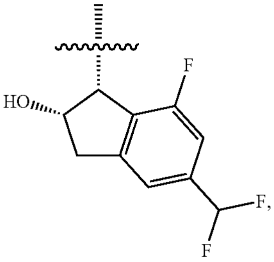
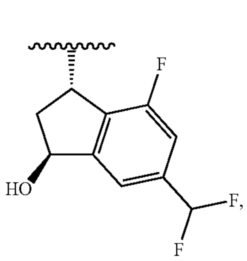
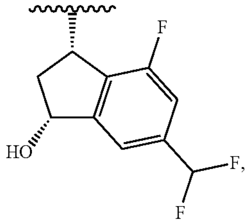
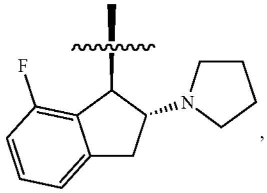
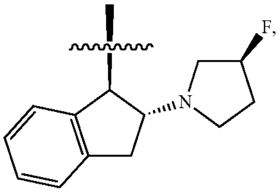
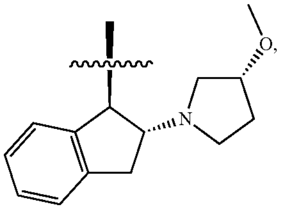
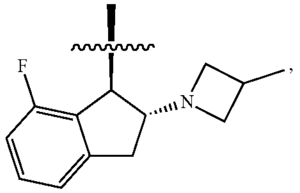
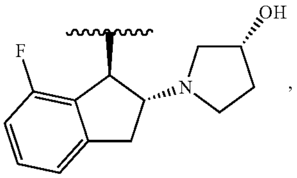
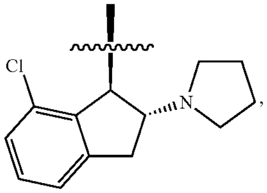
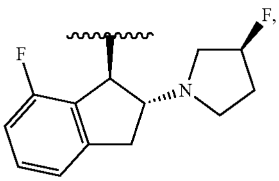
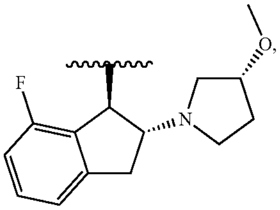
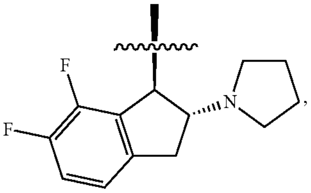
-continued
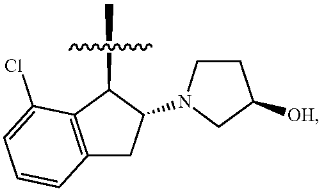
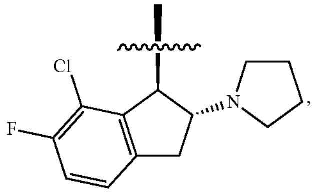
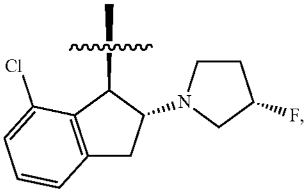
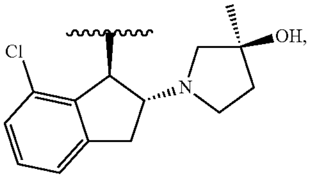
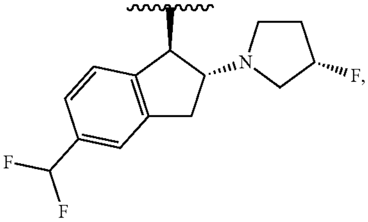
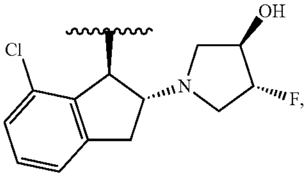
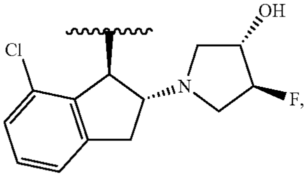
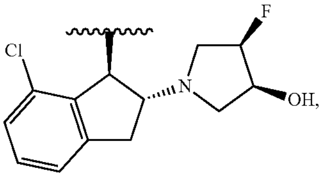
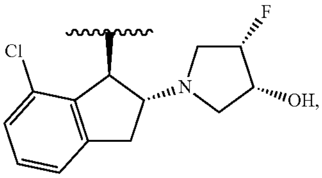

-continued

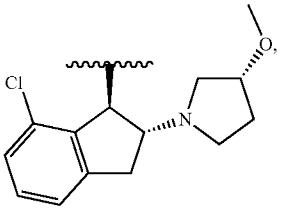

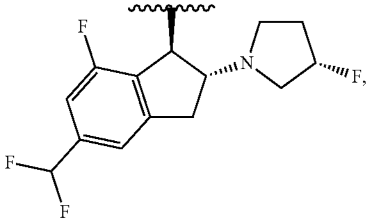

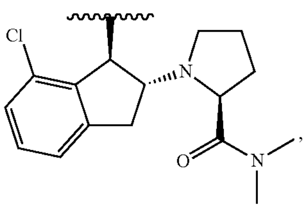

and

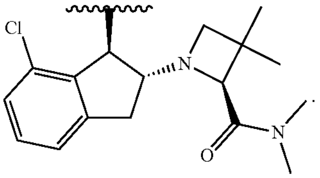

In some embodiments of Formulae (I), (Ia), (Ib), and (Ic), $R^2$ is

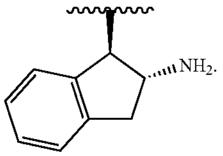 [SMILES: *[C@@H]1c2ccccc2C[C@H]1N]

In some embodiments of Formulae (I), (Ia), (Ib), and (Ic), $R^2$ is

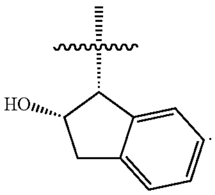

In some embodiments of Formulae (I), (Ia), (Ib), and (Ic), $R^2$ is

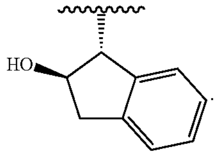 [SMILES: *[C@@H]1c2ccccc2C[C@H]1O]

In some embodiments of Formulae (I), (Ia), (Ib), and (Ic), $R^2$ is

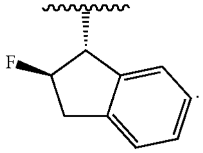 [SMILES: *[C@@H]1c2ccccc2C[C@H]1F]

In some embodiments of Formulae (I), (Ia), (Ib), and (Ic), $R^2$ is

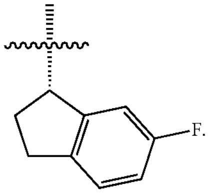

In some embodiments of Formulae (I), (Ia), (Ib), and (Ic), $R^2$ is

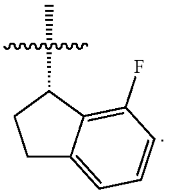

In some embodiments of Formulae (I), (Ia), (Ib), and (Ic), $R^2$ is

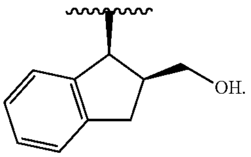 [SMILES: *[C@@H]1c2ccccc2C[C@@H]1CO]

In some embodiments of Formulae (I), (Ia), (Ib), and (Ic), $R^2$ is

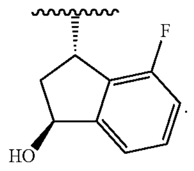 [SMILES: *[C@H]1C[C@H](O)c2cccc(F)c21]

In some embodiments of Formulae (I), (Ia), (Ib), and (Ic), $R^2$ is

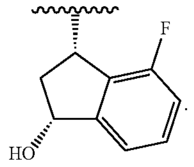 [SMILES: *[C@H]1C[C@@H](O)c2cccc(F)c21]

In some embodiments of Formulae (I), (Ia), (Ib), and (Ic), $R^2$ is

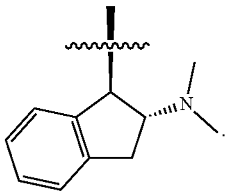

In some embodiments of Formulae (I), (Ia), (Ib), and (Ic), $R^2$ is

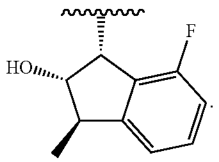 [SMILES: *[C@@H]1c2c(F)cccc2[C@@H](C)[C@@H]1O]

In some embodiments of Formulae (I), (Ia), (Ib), and (Ic), $R^2$ is

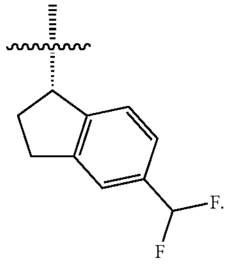

In some embodiments of Formulae (I), (Ia), (Ib), and (Ic), $R^2$ is

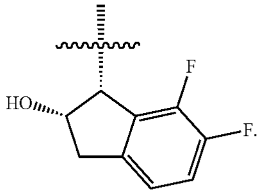

In some embodiments of Formulae (I), (Ia), (Ib), and (Ic), $R^2$ is

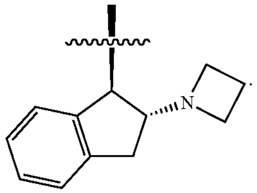

In some embodiments of Formulae (I), (Ia), (Ib), and (Ic), $R^2$ is

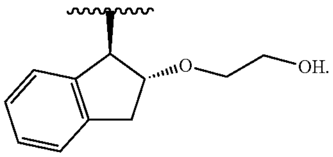 [SMILES: *[C@@H]1c2ccccc2C[C@H]1OCCO]

In some embodiments of Formulae (I), (Ia), (Ib), and (Ic), $R^2$ is

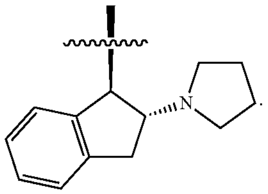

In some embodiments of Formulae (I), (Ia), (Ib), and (Ic), $R^2$ is

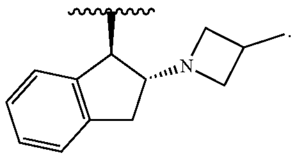 [SMILES: *[C@@H]1c2ccccc2C[C@H]1N1CC(C)C1]

In some embodiments of Formulae (I), (Ia), (Ib), and (Ic), $R^2$ is

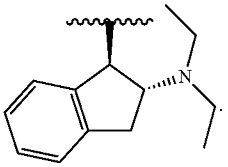 [SMILES: *[C@@H]1c2ccccc2C[C@H]1N(CC)CC]

In some embodiments of Formulae (I), (Ia), (Ib), and (Ic), $R^2$ is

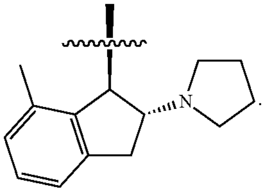

In some embodiments of Formulae (I), (Ia), (Ib), and (Ic), $R^2$ is

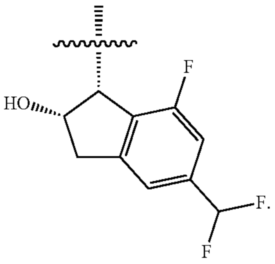

In some embodiments of Formulae (I), (Ia), (Ib), and (Ic), $R^2$ is

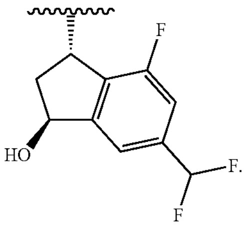 [SMILES: *[C@H]1C[C@H](O)c2cc(C(F)F)cc(F)c21]

In some embodiments of Formulae (I), (Ia), (Ib), and (Ic), $R^2$ is

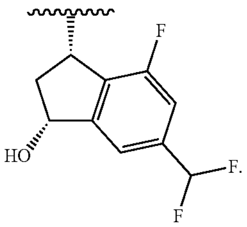 [SMILES: *[C@H]1C[C@@H](O)c2cc(C(F)F)cc(F)c21]

In some embodiments of Formulae (I), (Ia), (Ib), and (Ic), $R^2$ is

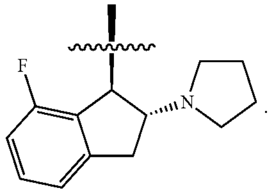

In some embodiments of Formulae (I), (Ia), (Ib), and (Ic), $R^2$ is

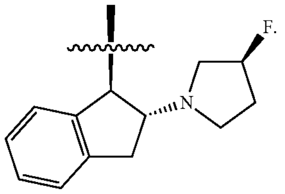

In some embodiments of Formulae (I), (Ia), (Ib), and (Ic), $R^2$ is

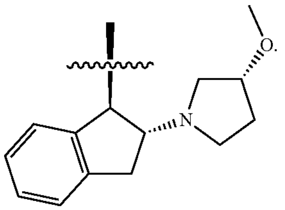

In some embodiments of Formulae (I), (Ia), (Ib), and (Ic), $R^2$ is

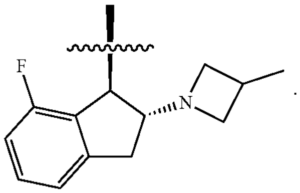

In some embodiments of Formulae (I), (Ia), (Ib), and (Ic), $R^2$ is

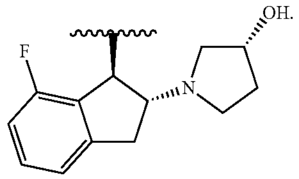 [SMILES: *[C@@H]1c2c(F)cccc2C[C@H]1N1CC[C@@H](O)C1]

In some embodiments of Formulae (I), (Ia), (Ib), and (Ic), $R^2$ is

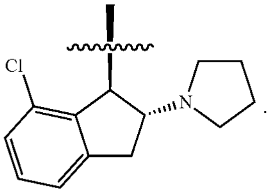

In some embodiments of Formulae (I), (Ia), (Ib), and (Ic), $R^2$ is

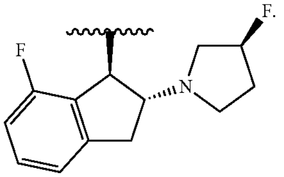 [SMILES: *[C@@H]1c2c(F)cccc2C[C@H]1N1CC[C@H](F)C1]

In some embodiments of Formulae (I), (Ia), (Ib), and (Ic), $R^2$ is

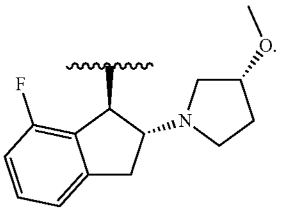 [SMILES: *[C@@H]1c2c(F)cccc2C[C@H]1N1CC[C@@H](OC)C1]

In some embodiments of Formulae (I), (Ia), (Ib), and (Ic), $R^2$ is

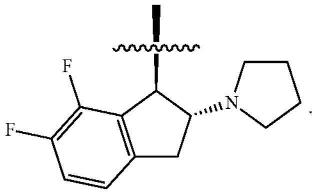

In some embodiments of Formulae (I), (Ia), (Ib), and (Ic), $R^2$ is

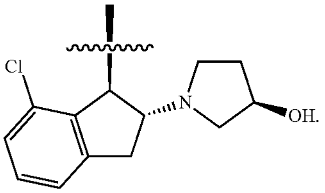

In some embodiments of Formulae (I), (Ia), (Ib), and (Ic), $R^2$ is

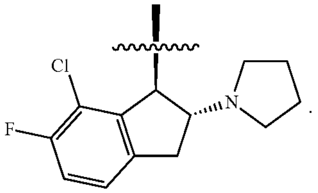

In some embodiments of Formulae (I), (Ia), (Ib), and (Ic), $R^2$ is

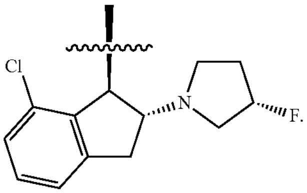

In some embodiments of Formulae (I), (Ia), (Ib), and (Ic), $R^2$ is

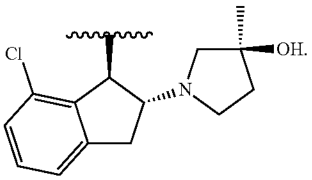 [SMILES: *[C@@H]1c2c(Cl)cccc2C[C@H]1N1CC[C@](C)(O)C1]

In some embodiments of Formulae (I), (a), (b), and (Ic), $R^2$ is

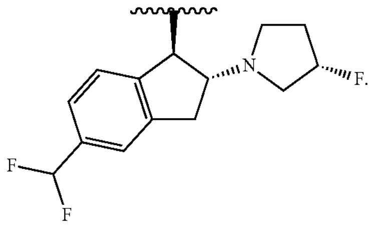 [SMILES: *[C@@H]1c2ccc(C(F)F)cc2C[C@H]1N1CC[C@H](F)C1]

In some embodiments of Formulae (I), (Ia), (Ib), and (Ic), $R^2$ is

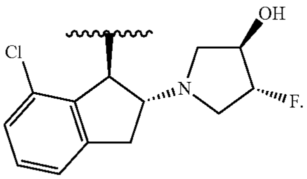 [SMILES: *[C@@H]1c2c(Cl)cccc2C[C@H]1N1C[C@@H](O)[C@H](F)C1]

In some embodiments of Formulae (I), (Ia), (Ib), and (Ic), $R^2$ is

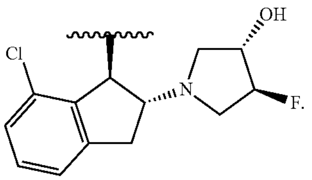 [SMILES: *[C@@H]1c2c(Cl)cccc2C[C@H]1N1C[C@H](O)[C@@H](F)C1]

In some embodiments of Formulae (I), (Ia), (Ib), and (Ic), $R^2$ is

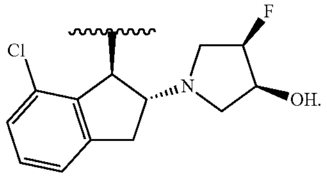 [SMILES: *[C@@H]1c2c(Cl)cccc2C[C@H]1N1C[C@@H](F)[C@@H](O)C1]

In some embodiments of Formulae (I), (Ia), (Ib), and (Ic), $R^2$ is

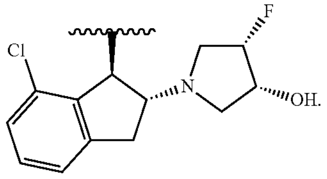 [SMILES: *[C@@H]1c2c(Cl)cccc2C[C@H]1N1C[C@@H](O)[C@@H](F)C1]

In some embodiments of Formulae (I), (Ia), (Ib), and (Ic), $R^2$ is

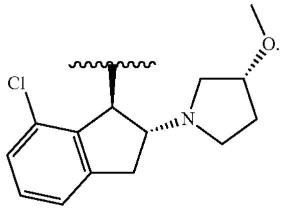 [SMILES: *[C@@H]1c2c(Cl)cccc2C[C@H]1N1CC[C@@H](OC)C1]

In some embodiments of Formulae (I), (Ia), (Ib), and (Ic), $R^2$ is

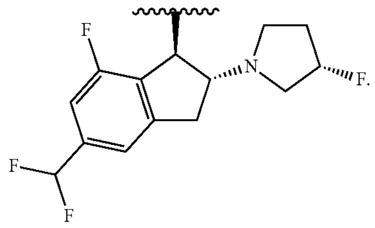 [SMILES: *[C@@H]1c2c(F)cc(C(F)F)cc2C[C@H]1N1CC[C@H](F)C1]

In some embodiments of Formulae (I), (Ia), (Ib), and (Ic), $R^2$ is

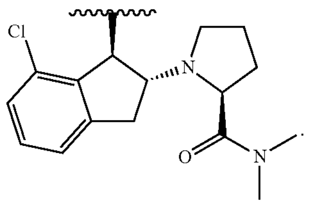 [SMILES: *[C@@H]1c2c(Cl)cccc2C[C@H]1N1CCC[C@H]1C(=O)N(C)C]

In some embodiments of Formulae (I), (Ia), (Ib), and (Ic), $R^2$ is

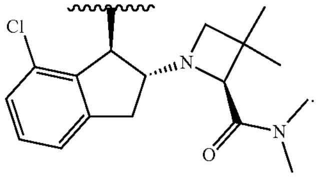 [SMILES: *[C@@H]1c2c(Cl)cccc2C[C@H]1N1CC(C)(C)[C@H]1C(=O)N(C)C]

In some embodiments, the compound is a compound of Formula (I) chosen from compounds in Table 1.

In another aspect, the present disclosure features a pharmaceutical composition comprising at least one compound chosen from compounds of Formula (I) (e.g., compounds in Table 1), pharmaceutically acceptable salts thereof, and solvates of any of the foregoing, and at least one pharmaceutically acceptable excipient.

Table 1 below shows the structures of example compounds described herein.

TABLE 1

| # | Synthetic protocol | Structure | LCMS (M + 1) | NMR |
|---|---|---|---|---|
| 100 | 18 | 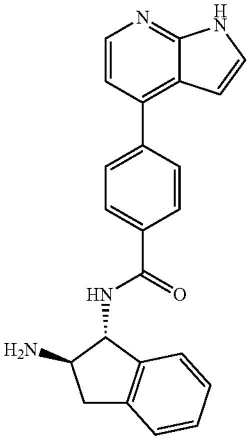 [SMILES: N[C@@H]1Cc2ccccc2[C@H]1NC(=O)c1ccc(-c2ccnc3[nH]ccc23)cc1] | 369 | $^1$H-NMR (400 MHz, $CD_3OD$) δ ppm 8.47 (d, 1H, J = 5.6 Hz), 8.18 (d, 2H, J = 8.4 Hz), 8.00 (d, 2H, J = 8.4 Hz), 7.76 (d, 1H, J = 3.6 Hz), 7.68 (d, 1H, J = 6.4 Hz), 7.37-7.34 (m, 4H), 6.97 (d, 1H, J = 3.2 Hz), 5.78 (d, 1H, J = 7.2 Hz), 4.01 (dd, 1H, J = 16.0, 8.0 Hz), 3.52 (dd, 1H, J = 16.0, 8.0 Hz), 3.07 (dd, 1H, J = 16.0, 8.4 Hz). |
| 101 | 1 | 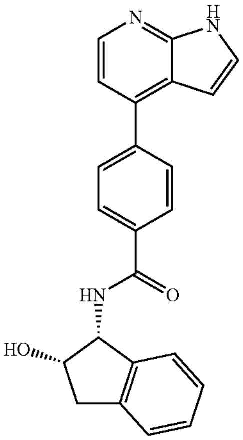 [SMILES: O=C(N[C@@H]1c2ccccc2C[C@@H]1O)c1ccc(-c2ccnc3[nH]ccc23)cc1] | 370 | $^1$H-NMR (400 MHz, $CD_3OD$) δ ppm 8.40 (d, 1H, J = 5.6 Hz), 8.15 (d, 2H, J = 8.4 Hz), 7.97 (d, 2H, J = 8.0 Hz), 7.66 (d, 1H, J = 4.0 Hz), 7.54 (d, 1H, J = 6.0 Hz), 7.35-7.24 (m, 4H), 6.90 (d, 1H, J = 3.2 Hz), 5.61 (d, 1H, J = 4.8 Hz), 4.72-4.70 (m, 1H), 3.22 (d, 1H, J = 5.2 Hz), 3.02 (d, 1H, J = 16.0 Hz). |
| 102 | 1 | 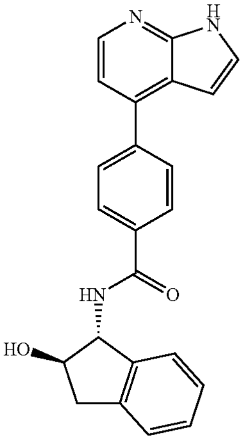 [SMILES: O=C(N[C@@H]1c2ccccc2C[C@H]1O)c1ccc(-c2ccnc3[nH]ccc23)cc1] | 370 | $^1$H-NMR (400 MHz, DMSO-$d_6$) δ ppm 8.87 (d, 1H, J = 8.4 Hz), 8.35 (d, 1H, J = 5.2 Hz), 8.12 (d, 2H, J = 7.6 Hz), 7.89 (d, 2H, J = 8.0 Hz), 7.62 (br. s, 1H), 7.31 (d, 1H, J = 4.8 Hz), 7.22-7.12 (m, 4H), 6.68 (s, 1H), 5.34 (t, 1H, J = 7.6 Hz), 4.47 (br. s, 1H), 3.19 (dd, 1H, J = 15.6, 7.2 Hz), 2.76 (dd, 1H, J = 15.2, 8.0 Hz). |
| 103 | 1 | 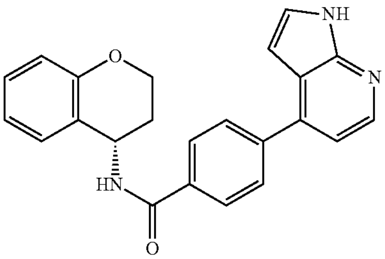 [SMILES: O=C(N[C@H]1CCOc2ccccc21)c1ccc(-c2ccnc3[nH]ccc23)cc1] | 370 | $^1$H-NMR (400 MHz, DMSO-$d_6$) δ ppm 11.81 (br. s, 1H), 8.94 (d, 1H, J = 8.4 Hz), 8.27 (d, 1H, J = 4.8 Hz), 8.06 (d, 2H, J = 8.0 Hz), 7.83 (d, 2H, J = 8.0 Hz), 7.54 (s, 1H), 7.21-7.13 (m, 3H), 6.86 (d, 1H, J = 7.2 Hz), 6.78 (d, 1H, J = 8.4 Hz), 6.59 (s, 1H), 5.30 (d, 2H, J = 6.4 Hz), 4.32-4.20 (m, 2H), 2.09-2.07 (m, 2H). |

TABLE 1-continued
| # | Synthetic protocol | Structure | LCMS (M + 1) | NMR |
|---|---|---|---|---|
| 104 | 1, 19 | 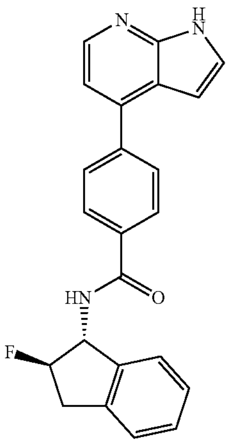 [SMILES: O=C(N[C@@H]1c2ccccc2C[C@H]1F)c1ccc(-c2ccnc3[nH]ccc23)cc1] | 372 | $^1$H-NMR (400 MHz, $CD_3OD$) δ ppm 8.39 (d, 1H, J = 5.6 Hz), 8.09 (d, 2H, J = 8.0 Hz), 7.94 (d, 2H, J = 8.0 Hz), 7.64 (d, 1H, J = 3.2 Hz), 7.51 (d, 1H, J = 5.2 Hz), 7.35-7.31 (m, 4H), 6.87 (d, 1H, J = 3.2 Hz), 5.69 (d, 1H, J = 19.6 Hz), 5.38 (dd, 1H, J = 52.4, 5.2 Hz), 3.58-3.46 (m, 1H), 3.21-3.14 (m, 1H). |
| 105 | 2 | 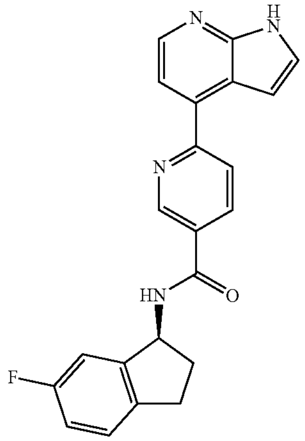 [SMILES: O=C(N[C@H]1CCc2ccc(F)cc21)c1ccc(-c2ccnc3[nH]ccc23)nc1] | 373 | $^1$H-NMR (400 MHz, $CD_3OD$) δ ppm 9.21 (s, 1H), 8.41 (d, 1H, J = 8.0 Hz), 8.34 (s, 1H), 8.13 (d, 1H, J = 8.0 Hz), 7.61 (s, 1H), 7.53 (s, 1H), 7.26 (s, 1H), 7.07 (d, 1H, J = 8.4 Hz), 6.98 (s, 2H), 5.68 (s, 1H), 3.05-3.04 (m, 1H), 2.93-2.91 (m, 1H), 2.67 (br. s, 1H), 2.13 (m, 1H). |
| 106 | 2 | 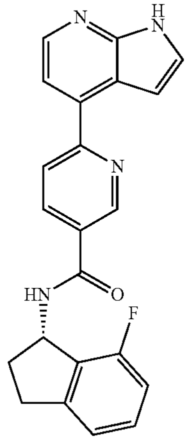 [SMILES: O=C(N[C@H]1CCc2cccc(F)c21)c1ccc(-c2ccnc3[nH]ccc23)nc1] | 373 | $^1$H-NMR (400 MHz, $CD_3OD$) δ ppm 9.21 (s, 1H), 8.42-8.40 (m, 2H), 8.20 (d, 1H, J = 7.6 Hz), 7.82 (s, 1H), 7.70 (s, 1H), 7.29 (s, 1H), 7.17 (s, 1H), 7.13-7.11 (m, 1H), 6.95-6.91 (m, 1H), 5.87 (s, 1H), 3.19-3.17 (m, 1H), 3.00-2.96 (m, 1H), 2.67-2.65 (m, 1H), 2.14-2.13 (m, 1H). |

TABLE 1-continued

| # | Synthetic protocol | Structure | LCMS (M + 1) | NMR |
|---|---|---|---|---|
| 107 | 2 | 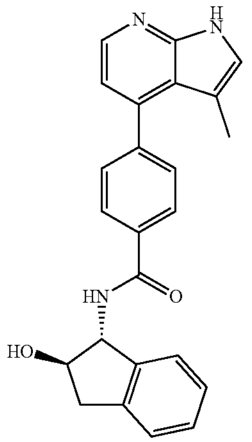 [SMILES: Cc1c[nH]c2nccc(-c3ccc(C(=O)N[C@@H]4c5ccccc5C[C@H]4O)cc3)c12] | 384 | $^1$H-NMR (400 MHz, $CD_3OD$) δ ppm 8.34 (d, 1H, J = 5.6 Hz), 8.09 (d, 2H, J = 8.0 Hz), 7.66 (d, 2H, J = 8.0 Hz), 7.42 (s, 1H), 7.33 (d, 1H, J = 5.6 Hz), 7.24 (br. s, 4H), 5.50 (d, 1H, J = 6.4 Hz), 4.57-4.52 (m, 1H), 3.34 (s, 1H), 2.92-2.87 (m, 1H), 1.97 (s, 3H). |
| 108 | 1 | 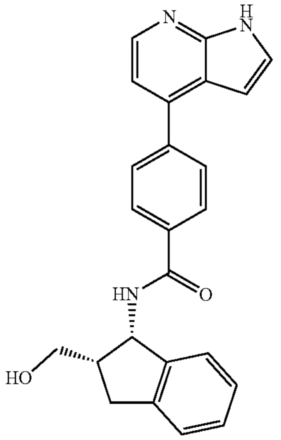 [SMILES: O=C(N[C@@H]1c2ccccc2C[C@@H]1CO)c1ccc(-c2ccnc3[nH]ccc23)cc1] | 384 | $^1$H-NMR (400 MHz, $CD_3OD$) δ ppm 8.25 (d, 1H, J = 4.4 Hz), 7.99 (d, 2H, J = 8.0 Hz), 7.85 (d, 2H, J = 8.0 Hz), 7.45 (d, 1H, J = 3.2 Hz), 7.37 (d, 1H, J = 6.4 Hz), 7.26-7.23 (m, 4H), 6.66 (s, 1H), 5.71 (d, 1H, J = 7.2 Hz), 3.80-3.76 (m, 1H), 3.65-3.61 (m, 1H), 3.04-2.89 (m, 3H). |
| 109 | 1 | 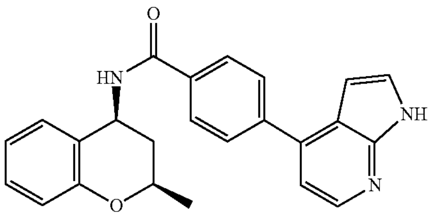 [SMILES: C[C@@H]1C[C@H](NC(=O)c2ccc(-c3ccnc4[nH]ccc34)cc2)c2ccccc2O1] | 384 | $^1$H NMR (400 MHz, DMSO-d6) δ 11.82 (s, 1H), 8.88 (d, J = 8.8 Hz, 1H), 8.30 (d, J = 4.9 Hz, 1H), 8.08 (d, J = 8.4 Hz, 2H), 7.86 (d, J = 8.4 Hz, 2H), 7.56 (dd, J = 3.5, 2.6 Hz, 1H), 7.23 (d, J = 5.0 Hz, 1H), 7.19-7.07 (m, 2H), 6.86 (td, J = 7.5, 1.2 Hz, 1H), 6.76 (dd, J = 8.1, 1.2 Hz, 1H), 6.62 (dd, J = 3.5, 1.8 Hz, 1H), 5.52-5.42 (m, 1H), 4.43-4.30 (m, 1H), 2.22-2.11 (m, 1H), 1.94-1.82 (m, 1H), 1.36 (dd, J = 6.3, 3.5 Hz, 3H). |
| 110 | 1, 3 | 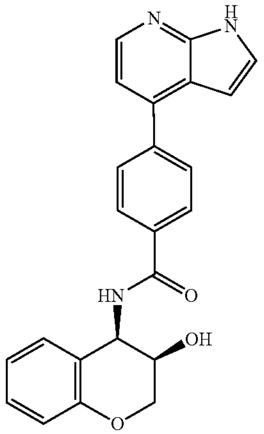 [SMILES: O=C(N[C@@H]1c2ccccc2OC[C@@H]1O)c1ccc(-c2ccnc3[nH]ccc23)cc1] | 386 | $^1$H-NMR (400 MHz, CD3OD) δ ppm 8.43 (d, 1H, J = 4.4 Hz), 8.16 (d, 2H, J = 7.6 Hz), 7.98 (d, 2H, J = 7.6 Hz), 7.71 (s, 1H), 7.60 (d, 1H, J = 4.8 Hz), 7.28 (d, 1H, J = 6.8 Hz), 7.18 (t, 1H, J = 7.6 Hz), 6.95 (br. s, 2H), 6.84 (d, 1H, J = 8.0 Hz), 5.59 (s, 1H), 4.28 (br. s, 3H). |

TABLE 1-continued

| # | Synthetic protocol | Structure | LCMS (M + 1) | NMR |
|---|---|---|---|---|
| 111 | 1 | 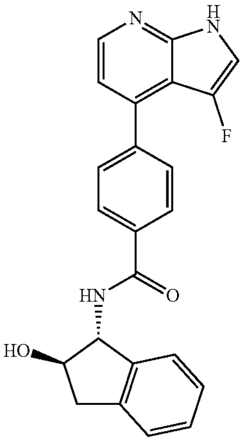 | 388 | $^1$H NMR (400 MHz, DMSO-d6) δ 11.78-11.62 (m, 1H), 8.84 (d, J = 8.5 Hz, 1H), 8.33 (d, J = 4.9 Hz, 1H), 8.06 (d, J = 8.4 Hz, 2H), 7.74 (dd, J = 8.4, 2.8 Hz, 2H), 7.54 (t, J = 2.4 Hz, 1H), 7.27-7.07 (m, 5H), 5.40-5.24 (m, 2H), 4.45 (qd, J = 7.4, 5.7 Hz, 1H), 3.18 (dd, J = 15.5, 7.2 Hz, 1H), 2.75 (dd, J = 15.5, 7.7 Hz, 1H). |
| 112 | 21 | 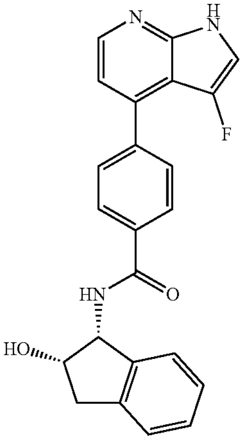 [SMILES: O=C(N[C@@H]1c2ccccc2C[C@@H]1O)c1ccc(-c2ccnc3[nH]cc(F)c23)cc1] | 388 | $^1$H NMR (400 MHz, DMSO-d6) δ 11.68 (s, 1H), 8.43-8.26 (m, 2H), 8.16-8.01 (m, 2H), 7.73 (dd, J = 8.4, 2.8 Hz, 2H), 7.54 (t, J = 2.4 Hz, 1H), 7.32-7.11 (m, 5H), 5.47 (dd, J = 8.6, 5.2 Hz, 1H), 5.10 (d, J = 4.6 Hz, 1H), 4.53 (qd, J = 5.1, 2.1 Hz, 1H), 3.11 (dd, J = 16.1, 5.2 Hz, 1H), 2.89 (dd, J = 16.3, 2.0 Hz, 1H). |
| 113 | 1 | 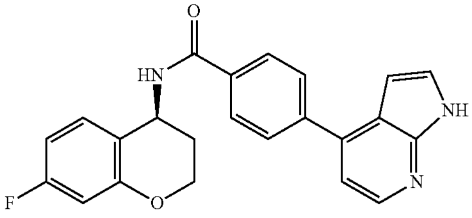 [SMILES: O=C(N[C@H]1CCOc2cc(F)ccc21)c1ccc(-c2ccnc3[nH]ccc23)cc1] | 388 | $^1$H NMR (400 MHz, DMSO-d6) δ 9.06 (t, J = 6.0 Hz, 1H), 8.76 (d, J = 7.0 Hz, 1H), 8.48 (s, 1H), 8.05 (d, J = 9.0 Hz, 1H), 7.99 (d, J = 8.4 Hz, 2H), 7.81 (d, J = 8.4 Hz, 2H), 7.42-7.35 (m, 1H), 7.33 (d, J = 4.4 Hz, 4H), 7.24 (dq, J = 8.6, 4.1 Hz, 1H), 6.99 (t, J = 6.8 Hz, 1H), 4.50 (d, J = 6.0 Hz, 2H). |
| 114 | 1 | 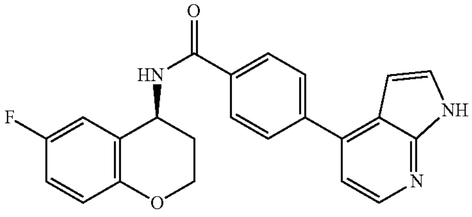 [SMILES: O=C(N[C@H]1CCOc2ccc(F)cc21)c1ccc(-c2ccnc3[nH]ccc23)cc1] | 388 | $^1$H NMR (400 MHz, DMSO-d6) δ 11.84 (s, 1H), 9.00 (d, J = 8.2 Hz, 1H), 8.30 (d, J = 5.0 Hz, 1H), 8.09 (d, J = 8.3 Hz, 2H), 7.86 (d, J = 8.2 Hz, 2H), 7.57 (t, J = 3.0 Hz, 1H), 7.23 (d, J = 5.0 Hz, 1H), 7.01 (ddd, J = 16.2, 8.2, 3.0 Hz, 2H), 6.83 (dd, J = 8.8, 4.9 Hz, 1H), 6.62 (dd, J = 3.6, 1.8 Hz, 1H), 5.31 (q, J = 6.9 Hz, 1H), 4.37-4.18 (m, 2H), 2.19-2.01 (m, 2H). |
| 115 | 1 | 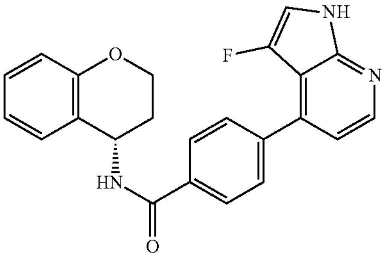 [SMILES: O=C(N[C@H]1CCOc2ccccc21)c1ccc(-c2ccnc3[nH]cc(F)c23)cc1] | 388 | Not available |

TABLE 1-continued
| # | Synthetic protocol | Structure | LCMS (M + 1) | NMR |
|---|---|---|---|---|
| 116 | 1, 3, 19 | 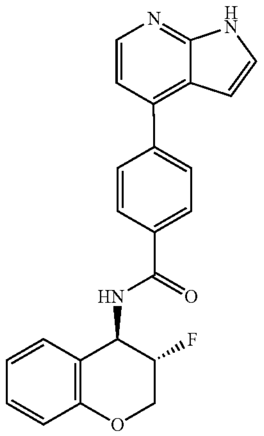 [SMILES: O=C(N[C@@H]1c2ccccc2OC[C@H]1F)c1ccc(-c2ccnc3[nH]ccc23)cc1] | 388 | $^1$H-NMR (400 MHz, $CD_3OD$) δ ppm 8.40 (d, 1H, J = 5.2 Hz), 8.07 (d, 2H, J = 8.4 Hz), 7.93 (d, 2H, J = 8.0 Hz), 7.68 (s, 1H), 7.55 (d, 1H, J = 5.6 Hz), 7.31-7.22 (m, 2H), 7.01-6.99 (m, 1H), 6.91-6.89 (m, 2H), 5.36 (d, 1H, J = 10.4 Hz), 5.01 (d, 1H, J = 46.0 Hz), 4.42-4.26 (m, 2H). |
| 117 | 22 | 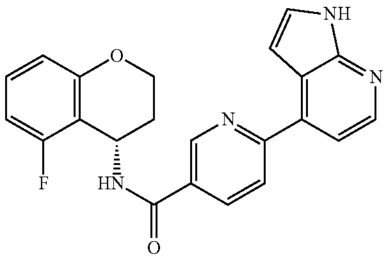 [SMILES: O=C(N[C@H]1CCOc2cccc(F)c21)c1ccc(-c2ccnc3[nH]ccc23)nc1] | 389 | $^1$H NMR (400 MHz, DMSO-d6) δ 11.83 (s, 1H), 9.26-9.17 (m, 2H), 8.43-8.30 (m, 2H), 8.15 (dd, J = 8.3, 0.8 Hz, 1H), 7.65-7.55 (m, 2H), 7.24 (td, J = 8.3, 6.7 Hz, 1H), 6.98 (dd, J = 3.5, 1.9 Hz, 1H), 6.73 (t, J = 8.8 Hz, 2H), 5.36 (d, J = 6.1 Hz, 1H), 4.32 (d, J = 11.1 Hz, 1H), 1.27 (d, J = 12.1 Hz, 3H). |
| 118 | 2, 15 | 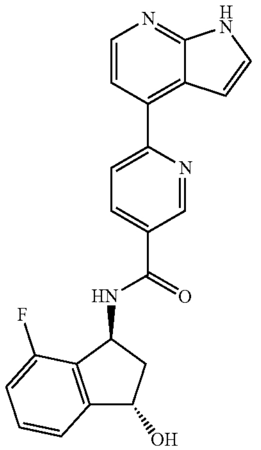 [SMILES: O=C(N[C@H]1C[C@H](O)c2cccc(F)c21)c1ccc(-c2ccnc3[nH]ccc23)nc1] | 389 | $^1$H-NMR (400 MHz, $CD_3OD$) δ ppm 9.20 (d, 1H, J = 1.2 Hz), 8.45 (d, 1H, J = 6.0 Hz), 8.40 (dd, 1H, J = 8.0, 2.0 Hz), 8.23 (d, 1H, J = 8.4 Hz), 7.92 (d, 1H, J = 6.0 Hz), 7.71 (d, 1H, J = 2.8 Hz), 7.29-7.28 (m, 1H), 7.26-7.25 (m, 2H), 7.05 (t, 1H, J = 8.8 Hz), 5.90-5.98 (m, 1H), 5.43-5.42 (m, 1H), 2.49-2.46 (m, 2H). |

TABLE 1-continued

| # | Synthetic protocol | Structure | LCMS (M + 1) | NMR |
|---|---|---|---|---|
| 119 | 2, 15 | 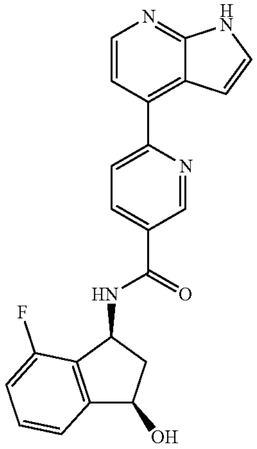 [SMILES: O=C(N[C@H]1C[C@@H](O)c2cccc(F)c21)c1ccc(-c2ccnc3[nH]ccc23)nc1] | 389 | $^1$H-NMR (400 MHz, $CD_3OD$) δ ppm 9.23 (d, 1H, J = 2.4 Hz), 8.44-8.41 (m, 2H), 8.22 (d, 1H, J = 8.0 Hz), 7.84 (d, 1H, J = 5.2 Hz), 7.67 (d, 1H, J = 3.6 Hz), 7.41-7.40 (m, 1H), 7.31 (d, 1H, J = 7.2 Hz), 7.19 (d, 1H, J = 3.6 Hz), 7.06 (t, 1H, J = 9.2 Hz), 5.73-5.72 (m, 1H), 5.17 (t, 1H, J = 6.8 Hz), 3.07-3.04 (m, 1H), 2.02-1.98 (m, 1H). |
| 120 | 1, 17 | 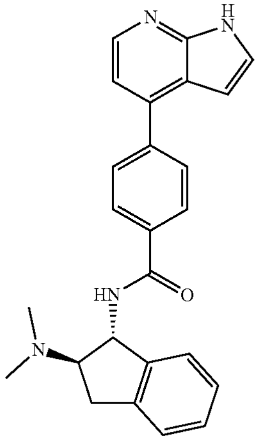 [SMILES: CN(C)[C@@H]1Cc2ccccc2[C@H]1NC(=O)c1ccc(-c2ccnc3[nH]ccc23)cc1] | 397 | $^1$H-NMR (400 MHz, $CD_3OD$) δ ppm 8.37 (br. s, 1H), 8.13 (d, 2H, J = 7.6 Hz), 7.91 (d, 2H, J = 7.6 Hz), 7.62 (br. s, 1H), 7.45 (br. s, 1H), 7.40-7.31 (m, 4H), 6.82 (br. s, 1H), 6.06 (br. s, 1H), 4.16 (d, 1H, J = 8.0 Hz), 3.61 (dd, 1H, J = 8.8, 15.6 Hz), 3.28-3.23 (m, 1H), 3.10 (br. s, 6H). |
| 121 | 2 | 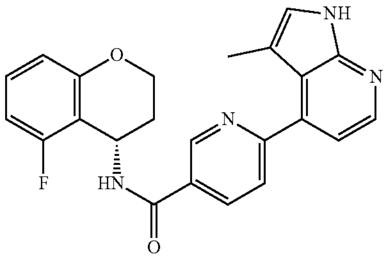 [SMILES: Cc1c[nH]c2nccc(-c3ccc(C(=O)N[C@H]4CCOc5cccc(F)c54)cn3)c12] | 403 | $^1$H-NMR (400 MHz, $CD_3OD$) δ ppm 9.13 (d, 2H, J = 1.6 Hz), 8.40 (dd, 1H, J = 8.0, 2.4 Hz), 8.36 (d, 1H, J = 6.4 Hz), 7.82 (d, 1H, J = 8.4 Hz), 7.40-7.37 (m, 2H), 7.24-7.20 (m, 1H), 6.70-6.65 (m, 2H), 5.45 (s, 1H), 4.37-4.35 (m, 1H), 4.25-4.20 (m, 1H), 2.21-2.17 (m, 2H), 1.96 (s, 3H). |
| 122 | 1, 4, 11 | 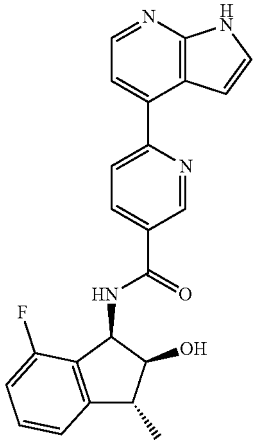 [SMILES: C[C@@H]1c2cccc(F)c2[C@@H](NC(=O)c2ccc(-c3ccnc4[nH]ccc34)nc2)[C@H]1O] | 403 | $^1$H-NMR (400 MHz, $CD_3OD$) δ ppm 9.19 (d, 1H, J = 1.6 Hz), 8.39 (dd, 1H, J = 8.0, 2.4 Hz), 8.32 (d, 1H, J = 4.8 Hz), 8.09 (d, 1H, J = 8.0 Hz), 7.58 (d, 1H, J = 4.8 Hz), 7.52 (d, 1H, J = 3.6 Hz), 7.36-7.34 (m, 1H), 7.10 (d, 1H, J = 7.6 Hz), 6.97-6.95 (m, 2H), 5.84 (d, 1H, J = 6.0 Hz), 4.16 (t, 1H, J = 6.0 Hz), 3.35-3.33 (m, 1H), 1.39 (d, 3H, J = 7.2 Hz). |

TABLE 1-continued
| # | Synthetic protocol | Structure | LCMS (M + 1) | NMR |
|---|---|---|---|---|
| 123 | 1, 3 | 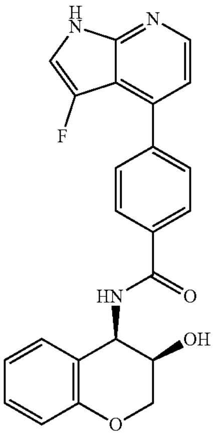 [SMILES: O=C(N[C@@H]1c2ccccc2OC[C@@H]1O)c1ccc(-c2ccnc3[nH]cc(F)c23)cc1] | 404 | $^1$H NMR (400 MHz, DMSO-d6) δ 11.68 (s, 1H), 8.47 (d, J = 8.9 Hz, 1H), 8.33 (d, J = 4.9 Hz, 1H), 8.09 (d, J = 8.4 Hz, 2H), 7.73 (dd, J = 8.4, 2.8 Hz, 2H), 7.55 (t, J = 2.5 Hz, 1H), 7.21-7.10 (m, 3H), 6.87 (td, J = 7.5, 1.2 Hz, 1H), 6.77 (dd, J = 8.2, 1.2 Hz, 1H), 5.47 (dd, J = 8.9, 4.1 Hz, 1H), 5.36 (d, J = 4.4 Hz, 1H), 4.22-4.17 (m, 2H), 4.11-4.04 (m, 1H). |
| 124 | 1, 3 | 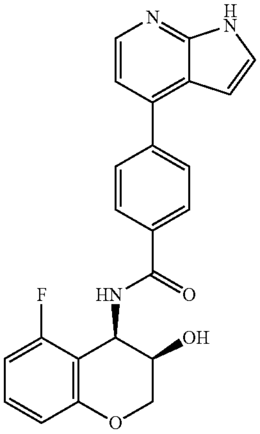 [SMILES: O=C(N[C@@H]1c2c(F)cccc2OC[C@@H]1O)c1ccc(-c2ccnc3[nH]ccc23)cc1] | 404 | $^1$H NMR (400 MHz, DMSO-d6) δ 11.83 (s, 1H), 8.59 (d, J = 8.8 Hz, 1H), 8.29 (d, J = 4.9 Hz, 1H), 8.07 (d, J = 8.4 Hz, 2H), 7.83 (d, J = 8.3 Hz, 2H), 7.56 (t, J = 3.0 Hz, 1H), 7.28-7.16 (m, 2H), 6.77-6.66 (m, 2H), 6.61 (dd, J = 3.6, 1.9 Hz, 1H), 5.65-5.58 (m, 1H), 5.31 (d, J = 4.7 Hz, 1H), 4.18-4.01 (m, 3H). |
| 125 | 1, 12 | 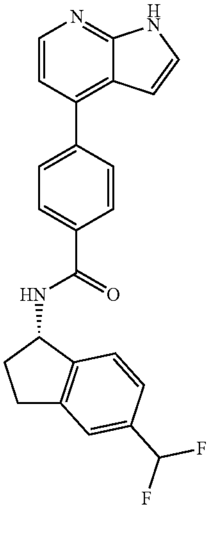 [SMILES: O=C(N[C@H]1CCc2cc(C(F)F)ccc21)c1ccc(-c2ccnc3[nH]ccc23)cc1] | 404 | $^1$H-NMR (400 MHz, $CD_3OD$) δ ppm 2.27 (d, 1H, J = 5.2 Hz), 8.04 (d, 2H, J = 8.4 Hz), 8.87 (d, 2H, J = 8.4 Hz), 7.48-7.41 (m, 4H), 7.25 (d, 1H, J = 4.8 Hz), 6.74 (t, 1H, J = 56.0 Hz), 6.68 (d, 1H, J = 3.6 Hz), 5.73-5.71 (m, 1H), 3.13-3.10 (m, 1H), 3.01-2.99 (m, 1H), 2.69-2.65 (m, 1H), 2.14-2.08 (m, 1H). |

TABLE 1-continued

| # | Synthetic protocol | Structure | LCMS (M + 1) | NMR |
|---|---|---|---|---|
| 126 | 1, 3 | 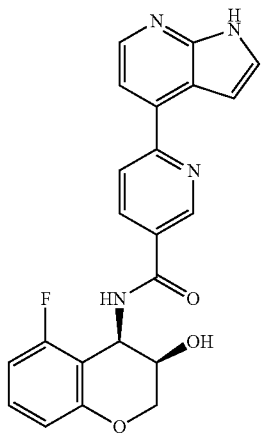 [SMILES: O=C(N[C@@H]1c2c(F)cccc2OC[C@@H]1O)c1ccc(-c2ccnc3[nH]ccc23)nc1] | 405 | $^1$H NMR (400 MHz, DMSO-d6) δ 11.83 (s, 1H), 9.21 (dd, J = 2.4, 0.8 Hz, 1H), 8.77 (d, J = 8.9 Hz, 1H), 8.39 (dd, J = 8.3, 2.3 Hz, 1H), 8.33 (d, J = 5.0 Hz, 1H), 8.15 (dd, J = 8.3, 0.8 Hz, 1H), 7.62 (d, J = 5.0 Hz, 1H), 7.61-7.56 (m, 1H), 7.22 (td, J = 8.3, 6.6 Hz, 1H), 6.98 (dd, J = 3.5, 1.9 Hz, 1H), 6.78-6.64 (m, 2H), 5.61 (dd, J = 8.8, 4.1 Hz, 1H), 5.34 (d, J = 5.0 Hz, 1H), 4.19-4.03 (m, 3H). |
| 127 | 1, 3 | 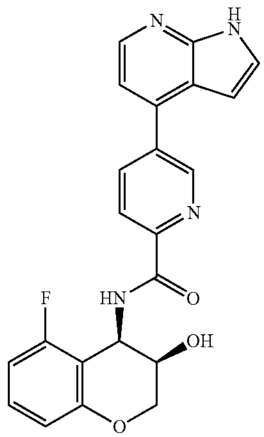 [SMILES: O=C(N[C@@H]1c2c(F)cccc2OC[C@@H]1O)c1ccc(-c2ccnc3[nH]ccc23)cn1] | 405 | $^1$H NMR (400 MHz, DMSO-d6) δ 11.94 (s, 1H), 8.98 (d, J = 2.1 Hz, 1H), 8.71 (d, J = 9.7 Hz, 1H), 8.40 (dd, J = 8.1, 2.3 Hz, 1H), 8.34 (d, J = 4.9 Hz, 1H), 8.25 (d, J = 8.1 Hz, 1H), 7.62 (t, J = 3.0 Hz, 1H), 7.32 (d, J = 4.9 Hz, 1H), 7.25-7.16 (m, 1H), 6.74-6.62 (m, 3H), 5.59 (dd, J = 9.9, 4.7 Hz, 1H), 5.53 (d, J = 5.1 Hz, 1H), 4.21-4.01 (m, 3H). |
| 128 | 1 | 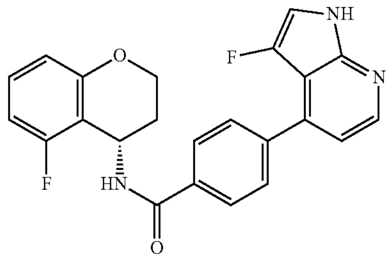 [SMILES: O=C(N[C@H]1CCOc2cccc(F)c21)c1ccc(-c2ccnc3[nH]cc(F)c23)cc1] | 406 | $^1$H NMR (400 MHz, DMSO-d6) δ 9.05 (d, J = 7.4 Hz, 1H), 8.32 (d, J = 4.9 Hz, 1H), 8.03-7.98 (m, 2H), 7.70 (dd, J = 8.3, 2.8 Hz, 2H), 7.53 (d, J = 2.0 Hz, 1H), 7.23 (td, J = 8.2, 6.6 Hz, 1H), 7.16 (d, J = 4.9 Hz, 1H), 6.71 (t, J = 8.7 Hz, 2H), 5.35 (d, J = 7.1 Hz, 1H), 4.28 (ddd, J = 14.1, 11.1, 5.1 Hz, 2H), 2.09-1.96 (m, 2H), 1.71 (q, J = 3.3 Hz, 1H). |
| 129 | 1, 6, 20 | 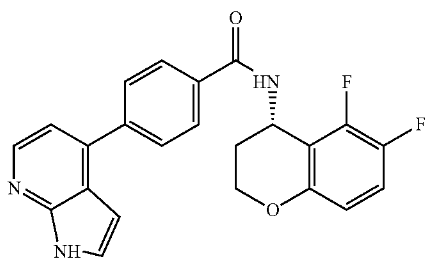 [SMILES: O=C(N[C@H]1CCOc2ccc(F)c(F)c21)c1ccc(-c2ccnc3[nH]ccc23)cc1] | 406 | $^1$H-NMR (400 MHz, $CD_3OD$) δ ppm 8.41 (d, 1H, J = 4.0 Hz), 8.05 (d, 2H, J = 7.2 Hz), 7.93 (d, 2H, J = 7.6 Hz), 7.68 (s, 1H), 7.56 (d, 1H, J = 4.4 Hz), 7.17-7.10 (m, 1H), 6.90 (s, 1H), 6.68 (d, 1H, J = 8.0 Hz), 5.49 (s, 1H), 4.36-4.33 (m, 1H), 4.22 (br. s, 1H), 2.19 (br. s, 2H). |

TABLE 1-continued
| # | Synthetic protocol | Structure | LCMS (M + 1) | NMR |
|---|---|---|---|---|
| 130 | 20, 22 | 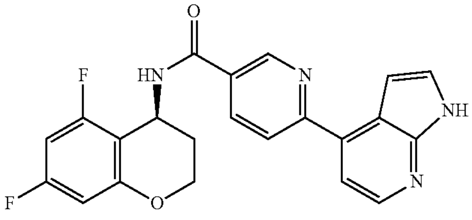 | 406 | Not available |
| 131 | 1 | 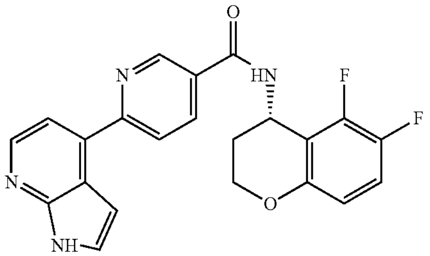 [SMILES: O=C(N[C@H]1CCOc2ccc(F)c(F)c21)c1ccc(-c2ccnc3[nH]ccc23)nc1] | 406 | $^1$H-NMR (400 MHz, $CD_3OD$) δ ppm 8.41 (d, 1H, J = 4.0 Hz), 8.05 (d, 2H, J = 7.2 Hz), 7.93 (d, 2H, J = 7.6 Hz), 7.68 (s, 1H), 7.56 (d, 1H, J = 4.4 Hz), 7.17-7.10 (m, 1H), 6.90 (s, 1H), 6.68 (d, 1H, J = 8.0 Hz), 5.49 (s, 1H), 4.36-4.33 (m, 1H), 4.22 (br. s, 1H), 2.19 (br. s, 2H). |
| 132 | 1, 4, 10 | 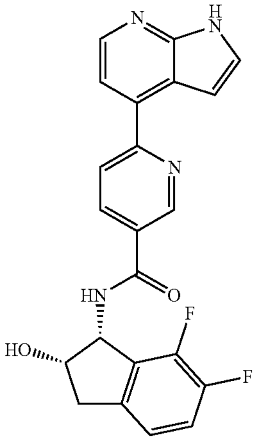 [SMILES: O=C(N[C@@H]1c2c(ccc(F)c2F)C[C@@H]1O)c1ccc(-c2ccnc3[nH]ccc23)nc1] | 407 | $^1$H-NMR (400 MHz, $CD_3OD$) δ ppm 9.28 (s, 1H), 8.49-8.44 (m, 2H), 8.24 (d, 1H, J = 8.4 Hz), 7.90 (d, 1H, J = 5.6 Hz), 7.71 (d, 1H, J = 3.2 Hz), 7.24 (d, 1H, J = 3.6 Hz), 7.17-7.15 (m 1H), 7.08-7.06 (m, 1H), 5.85 (d, 1H, J = 5.6 Hz), 4.74-4.70 (m, 1H), 3.21 (dd, 1H, J = 16.4, 5.2 Hz), 3.02 (d, 1H, J = 14.8 Hz). |
| 133 | 1, 13 | 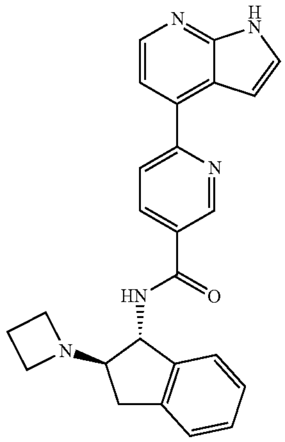 [SMILES: O=C(N[C@@H]1c2ccccc2C[C@H]1N1CCC1)c1ccc(-c2ccnc3[nH]ccc23)nc1] | 410 | $^1$H-NMR (400 MHz, $CD_3OD$) δ ppm 9.28 (s, 1H), 8.47 (dd, 1H, J = 8.4, 2.0 Hz), 8.44 (d, 1H, J = 5.6 Hz), 8.25 (d, 1H, J = 8.4 Hz), 7.84 (d, 1H, J = 5.6 Hz), 7.67 (d, 1H, J = 3.6 Hz), 7.44-7.40 (m, 4H), 7.18 (d, 1H, J = 3.2 Hz), 5.67 (d, 1H, J = 4.4 Hz), 4.54 (br. s, 1H), 4.34 (br. s, 3H), 4.26-4.22 (m, 1H), 3.62-3.56 (m, 1H), 3.03 (dd, 1H, J = 16.8, 5.2 Hz), 2.66 (br. s, 1H), 2.48 (br. s, 1H). |

TABLE 1-continued
| # | Synthetic protocol | Structure | LCMS (M + 1) | NMR |
| --- | --- | --- | --- | --- |
| 134 | 1, 16 | 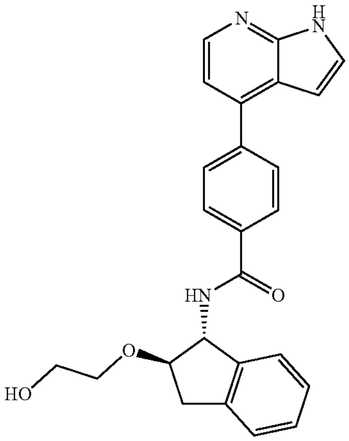 [SMILES: O=C(N[C@@H]1c2ccccc2C[C@H]1OCCO)c1ccc(-c2ccnc3[nH]ccc23)cc1] | 414 | $^1$H-NMR (400 MHz, $CD_3OD$) δ ppm 8.46 (d, 1H, J = 5.6 Hz), 8.13 (d, 2H, J = 8.0 Hz), 7.99 (d, 2H, J = 8.0 Hz), 7.76 (d, 1H, J = 3.2 Hz), 7.68 (d, 1H, J = 6.0 Hz), 7.25 (br. s, 4H), 7.00 (d, 1H, J = 3.2 Hz), 5.62 (d, 1H, J = 5.6 Hz), 4.39 (q, 1H, J = 6.4 Hz), 3.81-3.79 (m, 1H), 3.73-3.72 (m, 3H), 3.42 (dd, 1H, J = 16.0, 7.6 Hz), 2.96 (dd, 1H, J = 16.0, 6.4 Hz). |
| 135 | 2, 3 | 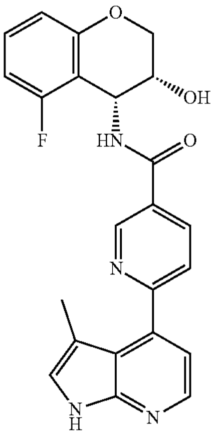 [SMILES: Cc1c[nH]c2nccc(-c3ccc(C(=O)N[C@@H]4c5c(F)cccc5OC[C@@H]4O)cn3)c12] | 419 | $^1$H-NMR (400 MHz, $CD_3OD$) δ ppm 9.17-9.16 (m, 1H), 8.44 (dd, 1H, J = 8.0, 2.0 Hz), 8.37 (d, 1H, J = 5.6 Hz), 7.83 (d, 1H, J = 8.0 Hz), 7.40 (d, 2H, J = 5.6 Hz), 7.25-7.19 (m 1H), 6.69 (d, 2H, J = 8.4 Hz), 5.74 (d, 1H, J = 4.8 Hz), 4.27-4.11 (m, 3H), 1.97 (s, 3H). |
| 136 | 1, 3, 9 | 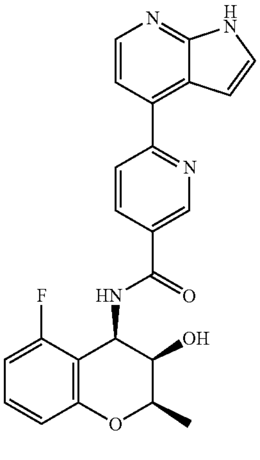 [SMILES: C[C@H]1Oc2cccc(F)c2[C@@H](NC(=O)c2ccc(-c3ccnc4[nH]ccc34)nc2)[C@H]1O] | 419 | $^1$H-NMR (400 MHz, $CD_3OD$) δ ppm 9.20-9.19 (m, 1H), 8.39 (dd, 1H, J = 8.4, 2.0 Hz), 8.31 (d, 1H, J = 5.2 Hz), 8.10 (d, 1H, J = 8.4 Hz), 7.58 (d, 1H, J = 5.2 Hz), 7.52 (d, 1H, J = 3.2 Hz), 7.17-7.15 (m, 1H), 6.95 (d, 1H, J = 3.6 Hz), 6.68-6.63 (m, 2H), 5.66 (d, 1H, J = 4.8 Hz), 4.28 (q, 1H, J = 6.4 Hz), 4.02 (d, 1H, J = 4.8 Hz), 1.47 (d, 3H, J = 6.4 Hz). |

TABLE 1-continued

| # | Synthetic protocol | Structure | LCMS (M + 1) | NMR |
|---|---|---|---|---|
| 137 | 1, 3, 9 | 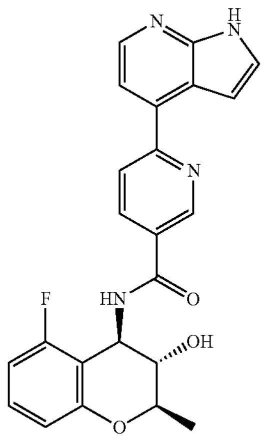 [SMILES: C[C@H]1Oc2cccc(F)c2[C@@H](NC(=O)c2ccc(-c3ccnc4[nH]ccc34)nc2)[C@@H]1O] | 419 | $^1$H-NMR (400 MHz, $CD_3OD$) δ ppm 9.14 (s, 1H), 8.36-8.31 (m, 2H), 8.11 (d, 1H, J = 8.0 Hz), 7.58 (d, 1H, J = 5.2 Hz), 7.51 (d, 1H, J = 3.6 Hz), 7.20-7.14 (m, 1H), 6.95 (d, 1H, J = 3.2 Hz), 6.69-6.64 (m, 2H), 5.40 (d, 1H, J = 8.0 Hz), 4.10-4.05 (m, 1H), 3.79-3.74 (m, 1H), 1.49 (d, 3H, J = 6.0 Hz). |
| 138 | 2, 20 | 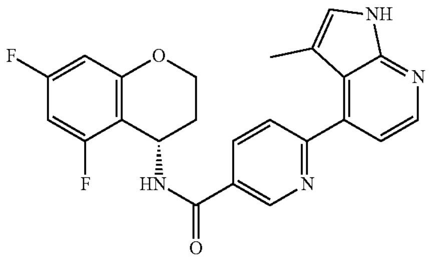 [SMILES: Cc1c[nH]c2nccc(-c3ccc(C(=O)N[C@H]4CCOc5cc(F)cc(F)c54)cn3)c12] | 421 | $^1$H NMR (400 MHz, DMSO-d6) δ 11.51 (s, 1H), 9.18 (d, J = 7.3 Hz, 1H), 9.13 (dd, J = 2.3, 0.8 Hz, 1H), 8.33 (dd, J = 8.2, 2.3 Hz, 1H), 8.24 (d, J = 4.9 Hz, 1H), 7.72 (dd, J = 8.2, 0.8 Hz, 1H), 7.30 (dd, J = 2.5, 1.2 Hz, 1H), 7.06 (d, J = 4.8 Hz, 1H), 6.78 (td, J = 9.7, 2.6 Hz, 1H), 6.64 (dt, J = 10.4, 2.1 Hz, 1H), 5.36-5.28 (m, 1H), 4.36 (d, J = 11.2 Hz, 1H), 4.26 (td, J = 10.9, 4.0 Hz, 1H), 2.09-2.01 (m, 2H), 1.91 (d, J = 1.0 Hz, 3H). |
| 139 | 1, 3 | 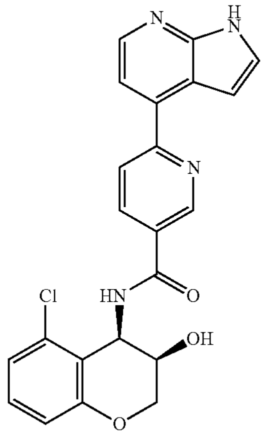 [SMILES: O=C(N[C@@H]1c2c(Cl)cccc2OC[C@@H]1O)c1ccc(-c2ccnc3[nH]ccc23)nc1] | 421 | $^1$H-NMR (400 MHz, $CD_3OD$) δ ppm 9.15 (d, 1H, J = 1.6 Hz), 8.38-8.32 (m, 2H), 8.11 (d, 1H, J = 8.0 Hz), 7.63 (d, 1H, J = 5.2 Hz), 7.54 (d, 1H, J = 3.6 Hz), 7.21 (t, 1H, J = 8.4 Hz), 7.03 (d, 1H, J = 6.8 Hz), 6.99 (d, 1H, J = 3.6 Hz), 6.84 (d, 1H, J = 8.4 Hz), 5.66 (d, 1H, J = 4.8 Hz), 4.25-4.13 (m, 2H), 4.03-3.97 (m, 1H). |
| 140 | 1, 3, 6 | 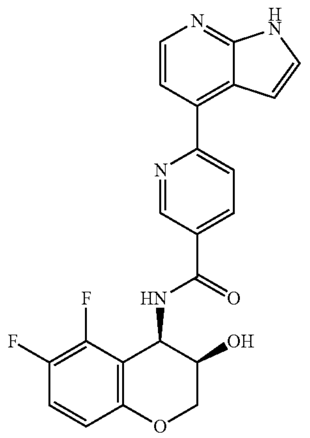 [SMILES: O=C(N[C@@H]1c2c(ccc(F)c2F)OC[C@@H]1O)c1ccc(-c2ccnc3[nH]ccc23)nc1] | 423 | $^1$H-NMR (400 MHz, $CD_3OD$) δ ppm 9.24 (s, 1H), 8.45-8.41 (m, 2H), 8.21 (d, 1H, J = 8.0 Hz), 7.83 (d, 1H, J = 5.6 Hz), 7.66 (d, 1H, J = 3.6 Hz), 7.17 (d, 1H, J = 2.4 Hz), 7.15-7.11 (m, 1H), 6.68 (d, 1H, J = 9.2 Hz), 5.77 (d, 1H, J = 4.0 Hz), 4.26-4.23 (m, 1H), 4.19-4.12 (m, 2H). |

TABLE 1-continued

| # | Synthetic protocol | Structure | LCMS (M + 1) | NMR |
|---|---|---|---|---|
| 141 | 2, 3 | 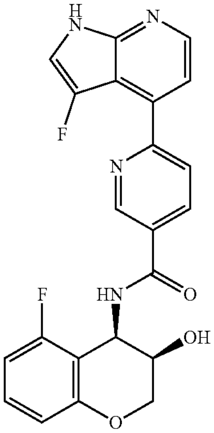 [SMILES: O=C(N[C@@H]1c2c(F)cccc2OC[C@@H]1O)c1ccc(-c2ccnc3[nH]cc(F)c23)nc1] | 423 | $^1$H-NMR (400 MHz, $CD_3OD$) δ ppm 9.14 (s, 1H), 8.41-8.38 (m, 2H), 7.96 (dd, 1H, J = 8.4, 2.8 Hz), 7.51 (d, 1H, J = 5.2 Hz), 7.39 (d, 1H, J = 2.0 Hz), 7.23-7.17 (m, 1H), 6.70-6.66 (m, 2H), 5.72 (d, 1H, J = 4.4 Hz), 4.24-4.21 (m, 1H), 4.18-4.10 (m, 2H). |
| 142 | 1, 13 | 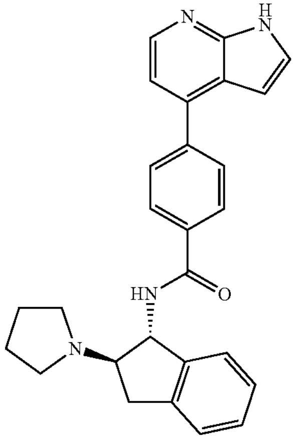 [SMILES: O=C(N[C@@H]1c2ccccc2C[C@H]1N1CCCC1)c1ccc(-c2ccnc3[nH]ccc23)cc1] | 423 | $^1$H-NMR (400 MHz, $CD_3OD$) δ ppm 8.42-8.36 (m, 1H), 8.17-8.11 (m, 2H), 7.97 (d, 2H, J = 7.6 Hz), 7.67-7.61 (m, 1H), 7.53-7.45 (m, 1H), 7.37 (s, 3H), 7.33-7.27 (m, 1H), 6.87-6.81 (m, 1H), 6.04 (d, 1H, J = 6.8 Hz), 4.16-4.08 (m, 1H), 3.86 (br. s, 2H), 3.64 (dd, 1H, J = 8.4, 16.4 Hz), 3.36 (br. s, 2H), .26-3.20 (m, 1H), 2.28-2.00 (m, 4H) |
| 143 | 1, 20 | 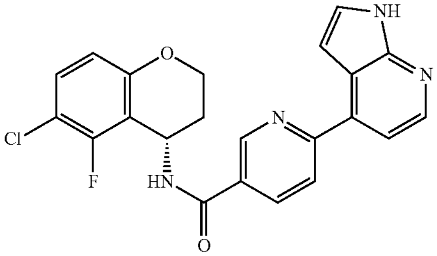 [SMILES: O=C(N[C@H]1CCOc2ccc(Cl)c(F)c21)c1ccc(-c2ccnc3[nH]ccc23)nc1] | 423 | $^1$H NMR (400 MHz, DMSO-d6) δ 11.83 (s, 1H), 9.27-9.15 (m, 2H), 8.42-8.29 (m, 2H), 8.25-8.11 (m, 1H), 7.62 (d, J = 5.0 Hz, 1H), 7.61-7.58 (m, 1H), 7.41 (t, J = 8.8 Hz, 1H), 6.98 (dd, J = 3.5, 1.9 Hz, 1H), 6.78 (dd, J = 9.0, 1.5 Hz, 1H), 5.46-5.34 (m, 1H), 4.35 (d, J = 11.2 Hz, 1H), 4.23 (td, J = 10.7, 4.2 Hz, 1H), 2.07 (dt, J = 7.3, 3.9 Hz, 2H). |
| 144 | 1, 4, 13 | 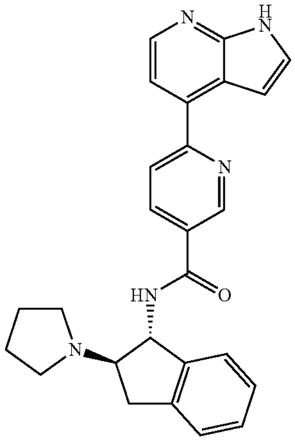 [SMILES: O=C(N[C@@H]1c2ccccc2C[C@H]1N1CCCC1)c1ccc(-c2ccnc3[nH]ccc23)nc1] | 424 | $^1$H NMR (400 MHz, DMSO-d6) δ 11.84 (s, 1H), 9.26 (dd, J = 2.3, 0.8 Hz, 1H), 9.17 (d, J = 9.0 Hz, 1H), 8.42 (dd, J = 8.3, 2.3 Hz, 1H), 8.34 (d, J = 5.0 Hz, 1H), 8.19 (dd, J = 8.3, 0.8 Hz, 1H), 7.64 (d, J = 5.0 Hz, 1H), 7.60 (dd, J = 3.5, 2.5 Hz, 1H), 7.21 (dddd, J = 14.0, 8.8, 6.7, 2.6 Hz, 3H), 7.13 (dt, J = 7.5, 1.3 Hz, 1H), 7.00 (dd, J = 3.5, 1.9 Hz, 1H), 5.55 (t, J = 8.2 Hz, 1H), 3.28-3.10 (m, 2H), 2.93-2.78 (m, 1H), 2.59 (s, 4H), 1.68 (s, 4H). |

TABLE 1-continued

| # | Synthetic protocol | Structure | LCMS (M + 1) | NMR |
|---|---|---|---|---|
| 145 | 1, 13 | 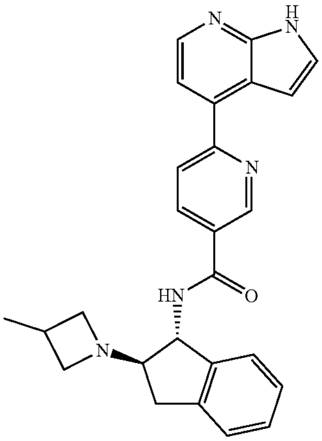 [SMILES: CC1CN([C@@H]2Cc3ccccc3[C@H]2NC(=O)c2ccc(-c3ccnc4[nH]ccc34)nc2)C1] | 424 | $^1$H-NMR (400 MHz, $CD_3OD$) δ ppm 9.21 (s, 1H), 8.41 (d, 1H, J = 8 Hz), 8.34 (d, 1H, J = 4.8 Hz), 8.15 (d, 1H, J = 8 Hz), 7.61 (d, 1H, J = 4.8 Hz), 7.54 (d, 1H, J = 3.6 Hz), 7.26 (s, 4H), 6.99 (d, 1H, J = 3.2 Hz), 5.52 (d, 1H, J = 5.6 Hz), 3.67 (td, 2H, J = 15.2 Hz, 8 Hz), 3.35 (br. s, 1H), 3.26-3.20 (m, 1H), 3.07 (t, 1H, J = 7.2 Hz), 2.99 (t, 1H, J = 7.2 Hz), 2.75-2.63 (m, 2H), 1.18 (d, 3H, J = 6.8 Hz). |
| 146 | 2, 4, 10 | 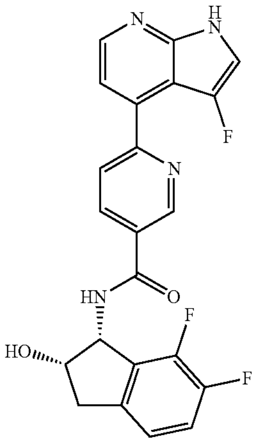 [SMILES: O=C(N[C@@H]1c2c(ccc(F)c2F)C[C@@H]1O)c1ccc(-c2ccnc3[nH]cc(F)c23)nc1] | 425 | $^1$H-NMR (400 MHz, $CD_3OD$) δ ppm 9.21 (d, 1H, J = 2.4 Hz), 8.46 (dd, 1H, J = 8.4, 2.0 Hz), 8.41 (d, 1H, J = 5.2 Hz), 8.01 (dd, 1H, J = 8.4, 3.2 Hz), 7.54 (d, 1H, J = 5.2 Hz), 7.41 (d, 1H, J = 2.4 Hz), 7.17-7.15 (m, 1H), 7.08-7.07 (m, 1H), 5.85 (d, 1H, J = 5.6 Hz), 4.73-4.70 (m, 1H), 3.18 (dd, 1H, J = 16.0, 5.6 Hz), 3.01 (dd, 1H, J = 16.4, 2.8 Hz). |
| 147 | 1, 17 | 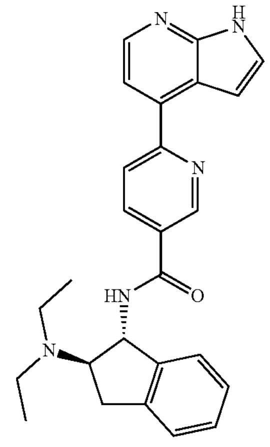 [SMILES: CCN(CC)[C@@H]1Cc2ccccc2[C@H]1NC(=O)c1ccc(-c2ccnc3[nH]ccc23)nc1] | 426 | $^1$H-NMR (400 MHz, $CD_3OD$) δ ppm 9.34 (d, 1H, J = 1.6 Hz), 8.52 (dd, 1H, J = 8.4, 2.0 Hz), 8.48 (d, 1H, J = 6.0 Hz), 8.30 (d, J = 8.3 Hz, 1H), 7.97 (d, 1H, J = 5.6 Hz), 7.74 (d, 1H, J = 3.6 Hz), 7.36 (d, 4H, J = 2.0 Hz), 7.29 (d, 1H, J = 3.6 Hz), 6.12 (d, 1H, J = 6.8 Hz), 4.43-4.37 (m, 1H), 3.64 (dd, 1H, J = 16.4, 8.8 Hz), 3.60-3.35 (m, 4H), 3.34-3.32 (m, 1H), 1.42 (br. s, 6H). |
| 148 | 1, 8, 20 | 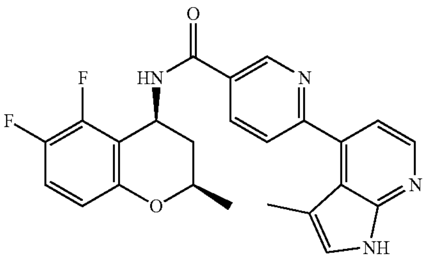 [SMILES: Cc1c[nH]c2nccc(-c3ccc(C(=O)N[C@H]4C[C@@H](C)Oc5ccc(F)c(F)c54)cn3)c12] | 435 | $^1$H NMR (400 MHz, DMSO-d6) δ 11.51 (s, 1H), 9.18-9.05 (m, 2H), 8.34-8.18 (m, 2H), 7.74 (dd, J = 8.1, 0.8 Hz, 1H), 7.40-7.18 (m, 2H), 7.08 (d, J = 4.8 Hz, 1H), 6.68 (ddd, J = 9.2, 4.1, 1.9 Hz, 1H), 5.62 (q, J = 8.6 Hz, 1H), 4.30 (ddt, J = 13.7, 7.3, 3.6 Hz, 1H), 2.40-2.26 (m, 1H), 1.92 (d, J = 1.1 Hz, 3H), 1.79 (dt, J = 13.5, 10.7 Hz, 1H), 1.35 (d, J = 6.3 Hz, 3H). |

TABLE 1-continued

| # | Synthetic protocol | Structure | LCMS (M + 1) | NMR |
|---|---|---|---|---|
| 149 | 1, 3, 8 | 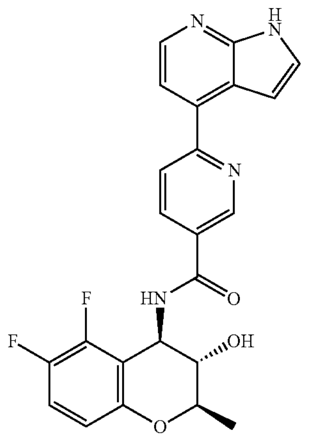 [SMILES: C[C@H]1Oc2ccc(F)c(F)c2[C@@H](NC(=O)c2ccc(-c3ccnc4[nH]ccc34)nc2)[C@@H]1O] | 437 | $^1$H NMR (400 MHz, DMSO-d6) δ 11.84 (s, 1H), 9.19 (dd, J = 2.4, 0.8 Hz, 1H), 9.04 (d, J = 8.4 Hz, 1H), 8.39-8.31 (m, 2H), 8.18 (dd, J = 8.3, 0.8 Hz, 1H), 7.63 (d, J = 5.0 Hz, 1H), 7.60 (dd, J = 3.5, 2.6 Hz, 1H), 7.25 (q, J = 9.4 Hz, 1H), 7.00 (dd, J = 3.5, 1.9 Hz, 1H), 6.74-6.63 (m, 1H), 5.68 (d, J = 6.0 Hz, 1H), 5.28 (t, J = 8.0 Hz, 1H), 4.17-4.04 (m, 1H), 3.71 (td, J = 8.1, 5.9 Hz, 1H), 1.39 (d, J = 6.3 Hz, 3H). |
| 150 | 1, 3, 8 | 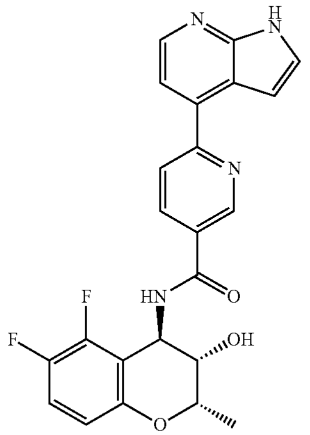 [SMILES: C[C@@H]1Oc2ccc(F)c(F)c2[C@@H](NC(=O)c2ccc(-c3ccnc4[nH]ccc34)nc2)[C@@H]1O] | 437 | $^1$H NMR (400 MHz, DMSO-d6) δ 11.83 (s, 1H), 9.26 (dd, J = 2.3, 0.8 Hz, 1H), 9.01 (d, J = 8.5 Hz, 1H), 8.44 (dd, J = 8.3, 2.3 Hz, 1H), 8.34 (d, J = 5.0 Hz, 1H), 8.16 (dd, J = 8.2, 0.8 Hz, 1H), 7.64 (d, J = 5.0 Hz, 1H), 7.60 (dd, J = 3.5, 2.6 Hz, 1H), 7.21 (q, J = 9.3 Hz, 1H), 7.00 (dd, J = 3.5, 1.9 Hz, 1H), 6.62 (ddd, J = 9.3, 4.2, 1.8 Hz, 1H), 5.65 (dd, J = 8.6, 4.5 Hz, 1H), 5.59 (d, J = 5.4 Hz, 1H), 4.31 (q, J = 6.4 Hz, 1H), 3.86 (t, J = 5.1 Hz, 1H), 1.35 (d, J = 6.4 Hz, 3H). |
| 151 | 1, 3, 8 | 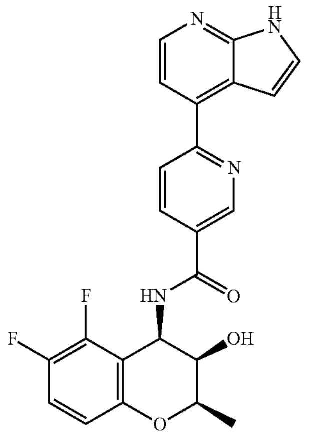 [SMILES: C[C@H]1Oc2ccc(F)c(F)c2[C@@H](NC(=O)c2ccc(-c3ccnc4[nH]ccc34)nc2)[C@H]1O] | 437 | $^1$H NMR (400 MHz, DMSO-d6) δ 11.83 (s, 1H), 9.26 (dd, J = 2.3, 0.8 Hz, 1H), 9.01 (d, J = 8.6 Hz, 1H), 8.44 (dd, J = 8.3, 2.3 Hz, 1H), 8.34 (d, J = 5.0 Hz, 1H), 8.16 (dd, J = 8.3, 0.8 Hz, 1H), 7.64 (d, J = 5.0 Hz, 1H), 7.60 (dd, J = 3.4, 2.5 Hz, 1H), 7.21 (q, J = 9.4 Hz, 1H), 7.00 (dd, J = 3.5, 1.9 Hz, 1H), 6.62 (ddd, J = 9.2, 4.2, 1.8 Hz, 1H), 5.65 (dd, J = 8.6, 4.5 Hz, 1H), 5.59 (d, J = 5.4 Hz, 1H), 4.31 (q, J = 6.4 Hz, 1H), 3.86 (t, J = 5.0 Hz, 1H), 1.35 (d, J = 6.4 Hz, 3H). |

TABLE 1-continued
| # | Synthetic protocol | Structure | LCMS (M + 1) | NMR |
|---|---|---|---|---|
| 152 | 2, 13 | 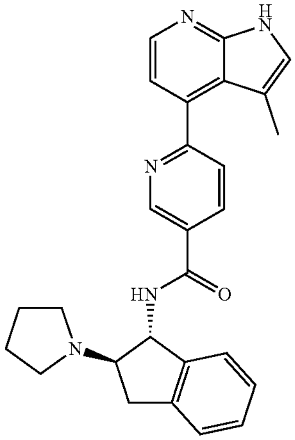 [SMILES: Cc1c[nH]c2nccc(-c3ccc(C(=O)N[C@@H]4c5ccccc5C[C@H]4N4CCCC4)cn3)c12] | 438 | $^1$H-NMR (400 MHz, $CD_3OD$) δ ppm 9.25 (d, 1H, J = 1.6 Hz), 8.50 (dd, 1H, J = 8.0, 2.0 Hz), 8.40 (d, 1H, J = 6.0 Hz), 7.89 (d, 1H, J = 8.4 Hz), 7.44-7.35 (m, 6H), 6.03 (d, 1H, J = 6.8 Hz), 4.14 (q, 1H, J = 8.0 Hz), 3.86 (br. s, 2H), 3.64 (dd, 1H, J = 16.4, 8.4 Hz), 3.36 (br. s, 2H), 3.25 (dd, 1H, J = 16.0, 8.0 Hz), 2.20 (br. s, 2H), 2.05 (br. s, 2H), 1.99 (s, 3H). |
| 153 | 1, 4, 13 | 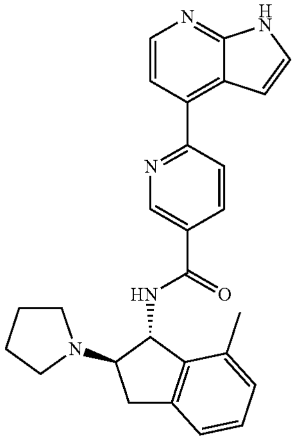 [SMILES: Cc1cccc2c1[C@@H](NC(=O)c1ccc(-c3ccnc4[nH]ccc34)nc1)[C@H](N1CCCC1)C2] | 438 | Not available |
| 154 | 1, 4, 5 | 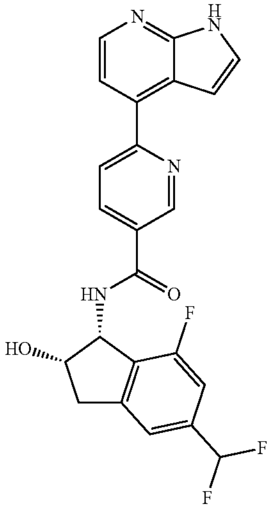 [SMILES: O=C(N[C@@H]1c2c(F)cc(C(F)F)cc2C[C@@H]1O)c1ccc(-c2ccnc3[nH]ccc23)nc1] | 439 | $^1$H-NMR (400 MHz, $CD_3OD$) δ ppm 9.28 (d, 1H, J = 2.4 Hz), 8.49-8.44 (m, 2H), 8.24 (d, 1H, J = 8.4 Hz), 7.88 (d, 1H, J = 5.6 Hz), 7.70 (d, 1H, J = 4.0 Hz), 7.32 (s, 1H), 7.23 (d, 1H, J = 3.6 Hz), 7.15 (d, 1H, J = 9.6 Hz), 6.77 (t, 1H, J = 56.0 Hz), 5.86 (d, 1H, J = 4.8 Hz), 4.77-4.73 (m, 1H), 3.28-3.26 (m, 1H), 3.10 (dd, 1H, J = 16.8, 2.8 Hz). |

TABLE 1-continued
| # | Synthetic protocol | Structure | LCMS (M + 1) | NMR |
|---|---|---|---|---|
| 155 | 1, 5, 24 | 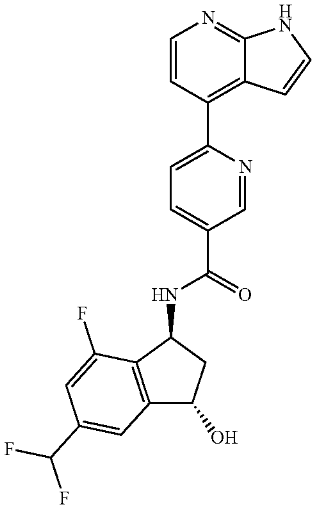 [SMILES: O=C(N[C@H]1C[C@H](O)c2cc(C(F)F)cc(F)c21)c1ccc(-c2ccnc3[nH]ccc23)nc1] | 439 | $^1$H-NMR (400 MHz, $CD_3OD$) δ ppm 9.13 (s, 1H), 8.35-8.30 (m, 2H), 8.12 (d, 1H, J = 8.4 Hz), 7.58 (d, 1H, J = 5.2 Hz), 7.51 (d, 1H, J = 3.6 Hz), 7.47 (s, 1H), 7.25 (d, 1H, J = 10.0 Hz), 6.95 (d, 1H, J = 3.6 Hz), 6.81 (d, 1H, J = 56.4 Hz), 6.01-5.98 (m, 1H), 5.46-5.43 (m, 1H), 2.52-2.49 (m, 2H). |
| 156 | 1, 5, 24 | 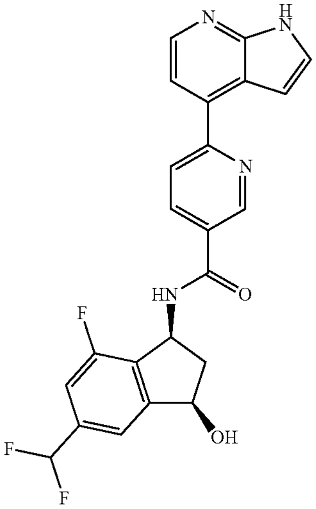 [SMILES: O=C(N[C@H]1C[C@@H](O)c2cc(C(F)F)cc(F)c21)c1ccc(-c2ccnc3[nH]ccc23)nc1] | 439 | $^1$H-NMR (400 MHz, $CD_3OD$) δ ppm 9.17 (d, 1H, J = 1.2 Hz), 8.37 (dd, 1H, J = 8.4 Hz), 8.32 (d, 1H, J = 4.4 Hz), 8.12 (dd, 1H, J = 8.4, 1.2 Hz), 7.58 (d, 1H, J = 4.8 Hz), 7.51 (d, 1H, J = 3.6 Hz), 7.47 (s, 1H), 7.23 (d, 1H, J = 9.6 Hz), 6.96 (d, 1H, J = 3.6 Hz), 6.81 (t, 1H, J = 56.0 Hz), 5.75-5.71 (m, 1H), 5.18-5.15 (m, 1H), 3.12-3.05 (m, 1H), 2.06-1.99 (m, 1H). |
| 157 | 1, 4, 14 | 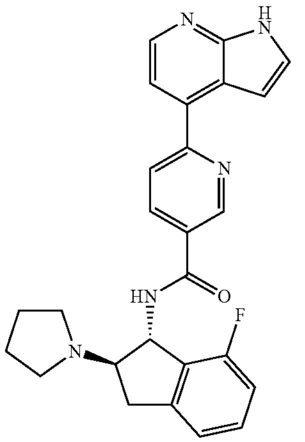 [SMILES: O=C(N[C@@H]1c2c(F)cccc2C[C@H]1N1CCCC1)c1ccc(-c2ccnc3[nH]ccc23)nc1] | 442 | $^1$H-NMR (400 MHz, $CD_3OD$) δ ppm 9.17 (d, 1H, J = 2.4 Hz), 8.39 (dd, 1H, J = 8.4, 2.0 Hz), 8.33 (d, 1H, J = 5.2 Hz), 8.14 (d, 1H, J = 8.4 Hz), 7.60 (d, 1H, J = 5.2 Hz), 7.53 (d, 1H, J = 3.6 Hz), 7.30-7.26 (m, 1H), 7.08 (d, 1H, J = 8.0 Hz), 6.97 (d, 1H, J = 3.2 Hz), 6.93 (t, 1H, J = 8.0 Hz), 5.92 (d, 1H, J = 5.6 Hz), 3.41-3.35 (m, 2H), 3.03-2.99 (m, 1H), 2.80 (br. s, 2H), 2.76 (br. s, 2H), 1.86 (br. s, 4H). |

TABLE 1-continued
| # | Synthetic protocol | Structure | LCMS (M + 1) | NMR |
|---|---|---|---|---|
| 158 | 1, 13 | 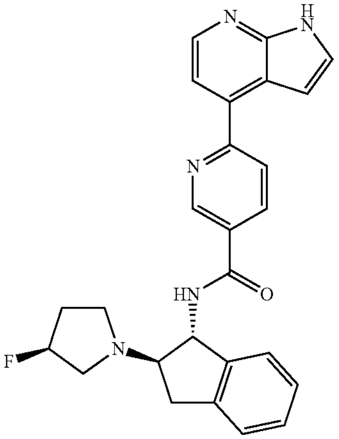 [SMILES: O=C(N[C@@H]1c2ccccc2C[C@H]1N1CC[C@H](F)C1)c1ccc(-c2ccnc3[nH]ccc23)nc1] | 442 | $^1$H-NMR (400 MHz, $CD_3OD$) δ ppm 9.32 (d, 1H, J = 2.0 Hz), 8.52-8.50 (m, 1H), 8.44 (d, 1H, J = 5.6 Hz), 8.26 (d, 1H, J = 8.4 Hz), 7.86 (d, 1H, J = 5.6 Hz), 7.38-7.36 (m, 4H), 7.20 (d, 1H, J = 3.6 Hz), 6.07 (d, 1H, J = 6.8 Hz), 5.57-5.44 (m, 1H), 4.29-4.23 (m, 1H), 4.06-4.05 (m, 1H), 3.75-3.70 (m, 3H), 3.67-3.63 (m, 1H), 3.31-3.30 (m, 1H), 2.49-2.43 (m, 2H). |
| 159 | 2, 13 | 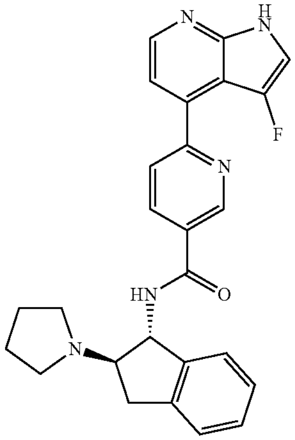 [SMILES: O=C(N[C@@H]1c2ccccc2C[C@H]1N1CCCC1)c1ccc(-c2ccnc3[nH]cc(F)c23)nc1] | 442 | $^1$H-NMR (400 MHz, DMSO-$d_6$) δ ppm 9.23-9.20 (m, 2H), 8.43-8.39 (m, 2H), 7.95-7.94 (m, 1H), 7.62-7.61 (m, 1H), 7.47 (d, 1H, J = 4.8 Hz), 7.24-7.15 (m, 4H), 5.56 (t, 1H, J = 8.0 Hz), 3.19-3.14 (m, 2H), 2.90-2.85 (m, 1H), 2.61 (br. s, 4H), 1.69 (br. s, 4H). |
| 160 | 1, 3, 8 | 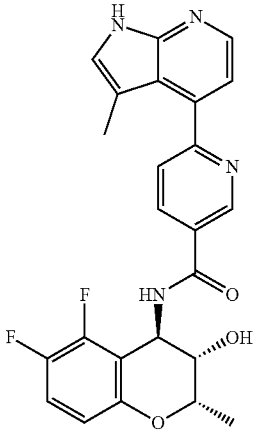 [SMILES: Cc1c[nH]c2nccc(-c3ccc(C(=O)N[C@@H]4c5c(ccc(F)c5F)O[C@@H](C)[C@H]4O)cn3)c12] | 451 | $^1$H NMR (400 MHz, DMSO-d6) δ 11.51 (s, 1H), 9.20 (dd, J = 2.3, 0.8 Hz, 1H), 9.02 (d, J = 8.5 Hz, 1H), 8.40 (dd, J = 8.2, 2.3 Hz, 1H), 8.25 (d, J = 4.8 Hz, 1H), 7.73 (dd, J = 8.1, 0.8 Hz, 1H), 7.30 (dd, J = 2.5, 1.2 Hz, 1H), 7.21 (q, J = 9.4 Hz, 1H), 7.08 (d, J = 4.8 Hz, 1H), 6.62 (ddd, J = 9.0, 4.2, 1.8 Hz, 1H), 5.67-5.62 (m, 1H), 5.59 (d, J = 5.4 Hz, 1H), 4.31 (q, J = 6.4 Hz, 1H), 3.85 (t, J = 5.1 Hz, 1H), 1.94 (d, J = 1.0 Hz, 3H), 1.35 (d, J = 6.4 Hz, 3H). |

TABLE 1-continued

| # | Synthetic protocol | Structure | LCMS (M + 1) | NMR |
|---|---|---|---|---|
| 161 | 1, 3, 8 | 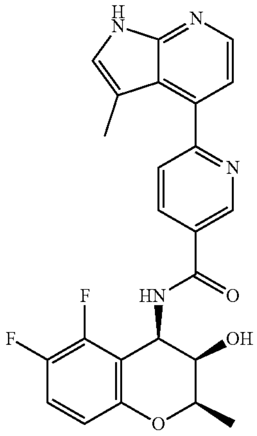 [SMILES: Cc1c[nH]c2nccc(-c3ccc(C(=O)N[C@@H]4c5c(ccc(F)c5F)O[C@H](C)[C@@H]4O)cn3)c12] | 451 | $^{1}$H NMR (400 MHz, DMSO-d6) δ 11.54-11.47 (m, 1H), 9.20 (dd, J = 2.3, 0.8 Hz, 1H), 9.02 (d, J = 8.4 Hz, 1H), 8.40 (dd, J = 8.1, 2.3 Hz, 1H), 8.25 (d, J = 4.8 Hz, 1H), 7.73 (dd, J = 8.1, 0.8 Hz, 1H), 7.30 (d, J = 1.2 Hz, 1H), 7.27-7.16 (m, 1H), 7.08 (d, J = 4.8 Hz, 1H), 6.62 (ddd, J = 9.3, 4.3, 1.8 Hz, 1H), 5.69-5.58 (m, 2H), 4.31 (q, J = 6.4 Hz, 1H), 3.85 (d, J = 4.6 Hz, 1H), 1.94 (d, J = 1.1 Hz, 3H), 1.35 (d, J = 6.4 Hz, 3H). |
| 162 | 1, 4, 5 | 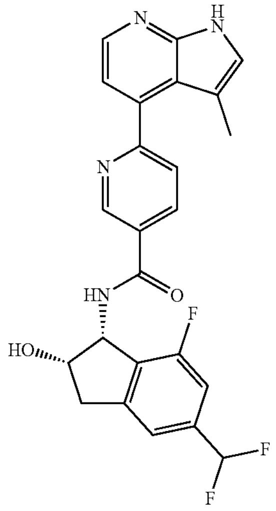 [SMILES: Cc1c[nH]c2nccc(-c3ccc(C(=O)N[C@@H]4c5c(F)cc(C(F)F)cc5C[C@@H]4O)cn3)c12] | 453 | $^{1}$H-NMR (400 MHz, DMSO-$d_6$) δ ppm 11.54 (s, 1H), 9.20 (d, 1H, J = 1.6 Hz), 8.95 (d, 1H, J = 8.8 Hz), 8.39 (dd, 1H, J = 8.0, 2.4 Hz), 8.26 (d, 1H, J = 4.8 Hz), 7.74 (d, 1H, J = 8.0 Hz), 7.32 (d, 2H, J = 10.4 Hz), 7.22 (d, 1H, J = 9.6 Hz), 7.09 (d, 1H, J = 4.8 Hz), 7.02 (t, 1H, J = 56.0 Hz), 5.77-5.73 (m 1H), 5.40-5.36 (m, 1H), 4.58-4.54 (m, 1H), 3.18 (dd, 1H, J = 16.4, 4.8 Hz), 2.99 (dd, 1H, J = 16.0, 3.2 Hz), 1.93 (s, 3H). |
| 163 | 1, 13 | 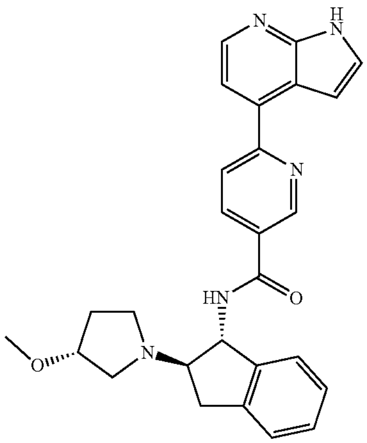 [SMILES: CO[C@@H]1CCN([C@@H]2Cc3ccccc3[C@H]2NC(=O)c2ccc(-c3ccnc4[nH]ccc34)nc2)C1] | 454 | $^{1}$H-NMR (400 MHz, $CD_3OD$) δ ppm 9.33 (s, 1H), 8.52 (dd, 1H, J = 8.4, 2.0 Hz), 8.44 (d, 1H, J = 5.2 Hz), 8.26 (d, 1H, J = 8.4 Hz), 7.85 (d, 1H, J = 6.0 Hz), 7.68 (d, 1H, J = 3.6 Hz), 7.37 (br. s, 4H), 7.18 (d, 1H, J = 3.6 Hz), 6.07 (d, 1H, J = 6.8 Hz), 4.22-4.18 (m, 2H), 3.91 (br. s, 2H), 3.69-3.56 (m, 3H), 3.39 (s, 3H), 3.29-3.25 (m, 1H), 2.34-2.26 (m, 2H). |

TABLE 1-continued
| # | Synthetic protocol | Structure | LCMS (M + 1) | NMR |
|---|---|---|---|---|
| 164 | 1, 3, 5, 7 | 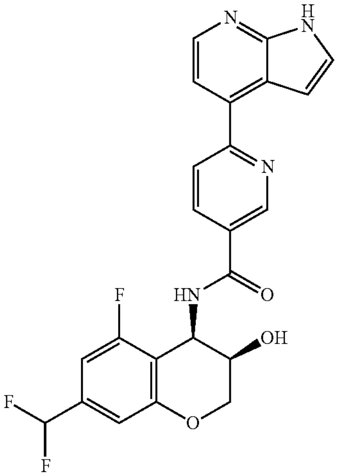 [SMILES: O=C(N[C@@H]1c2c(F)cc(C(F)F)cc2OC[C@@H]1O)c1ccc(-c2ccnc3[nH]ccc23)nc1] | 455 | $^1$H-NMR (400 MHz, $CD_3OD$) δ ppm 9.21 (d, 1H, J = 2.0 Hz), 8.42 (dd, 1H, J = 8.4, 2.0 Hz), 8.22 (d, 1H, J = 8.4 Hz), 7.88 (d, 1H, J = 6.4 Hz), 7.70 (d, 1H, J = 3.6 Hz), 7.22 (d, 1H, J = 3.6 Hz), 6.93 (d, 1H, J = 6.4 Hz), 6.90-6.73 (m, 3H), 5.32 (s, 1H), 4.34-4.29 (m, 2H), 4.16 (s, 1H). |
| 165 | 2, 4, 13 | 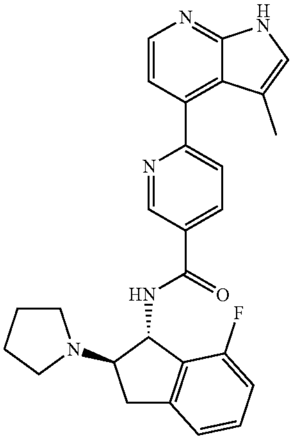 [SMILES: Cc1c[nH]c2nccc(-c3ccc(C(=O)N[C@@H]4c5c(F)cccc5C[C@H]4N4CCCC4)cn3)c12] | 456 | $^1$H-NMR (400 MHz, $CD_3OD$) δ ppm 9.19 (d, 1H, J = 1.6 Hz), 8.45 (dd, 1H, J = 8.0, 2.0 Hz), 8.39 (d, 1H, J = 5.6 Hz), 7.88 (d, 1H, J = 7.2 Hz), 7.45-7.41 (m, 3H), 7.20 (d, 1H, J = 7.6 Hz), 7.08-7.04 (m, 1H), 6.14 (d, 1H, J = 6.0 Hz), 4.23-4.21 (m, 1H), 3.85 (br. s, 2H), 3.75-3.69 (m, 1H), 3.4 (br. s, 2H), 3.26 (s, 1H), 2.21-2.08 (m, 4H), 1.98 (s, 3H). |
| 166 | 1, 4, 13 | 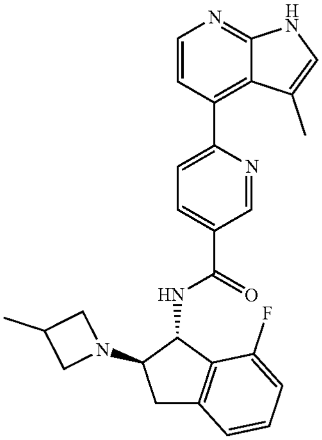 [SMILES: Cc1c[nH]c2nccc(-c3ccc(C(=O)N[C@@H]4c5c(F)cccc5C[C@H]4N4CC(C)C4)cn3)c12] | 456 | $^1$H-NMR (400 MHz, $CD_3OD$) δ ppm 9.09 (d, 1H, J = 1.2 Hz), 8.37 (dd, 1H, J = 8.0, 2.4 Hz), 8.25 (d, 1H, J = 4.8 Hz), 7.76 (dd, 1H, J = 8.0, 0.8 Hz), 7.33-7.31 (m, 1H), 7.24 (d, 1H, J = 0.8 Hz), 7.14 (d, 1H, J = 5.2 Hz), 7.10 (d, 1H, J = 7.8 Hz), 6.95 (t, 1H, J = 9.2 Hz), 5.58 (d, 1H, J = 2.4 Hz), 3.73-3.65 (m, 2H), 3.33-3.32 (m, 2H), 3.08 (t, 1H, J = 7.2 Hz), 2.99-2.95 (m, 1H), 2.75-2.60 (m, 2H), 1.94 (s, 3H), 1.18 (d, 3H, J = 6.8 Hz). |

TABLE 1-continued
| # | Synthetic protocol | Structure | LCMS (M + 1) | NMR |
|---|---|---|---|---|
| 167 | 1, 4, 14 | 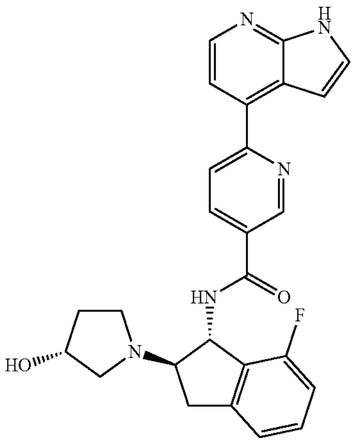 [SMILES: O=C(N[C@@H]1c2c(F)cccc2C[C@H]1N1CC[C@@H](O)C1)c1ccc(-c2ccnc3[nH]ccc23)nc1] | 458 | $^1$H-NMR (400 MHz, $CD_3OD$) δ ppm 9.32 (s, 1H), 8.52-8.50 (m, 2H), 8.33 (d, 1H, J = 8.0 Hz), 8.01 (d, 1H, J = 6.0 Hz), 7.78 (d, 1H, J = 3.2 Hz), 7.47-7.40 (m, 1H), 7.33 (d, 1H, J = 3.2 Hz), 7.22 (d, 1H, J = 7.6 Hz), 7.08 (t, 1H, J = 8.0 Hz), 6.21 (d, 1H, J = 6.4 Hz), 4.63 (br. s, 1H), 4.33 (br. s, 1H), 3.96-3.27 (m, 2H), 3.81-3.74 (m, 1H), 3.64-3.50 (m, 2H), 3.38-3.36 (m, 1H), 2.39 (br. s, 1H), 2.11 (br. s, 1H). |
| 168 | 1, 4, 13 | 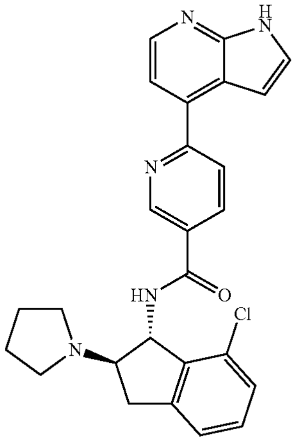 [SMILES: O=C(N[C@@H]1c2c(Cl)cccc2C[C@H]1N1CCCC1)c1ccc(-c2ccnc3[nH]ccc23)nc1] | 458 | $^1$H NMR (400 MHz, DMSO-d6) δ 11.84 (s, 1H), 9.20 (d, J = 2.3 Hz, 1H), 9.12 (d, J = 9.0 Hz, 1H), 8.40-8.31 (m, 2H), 8.17 (d, J = 8.3 Hz, 1H), 7.67-7.56 (m, 2H), 7.33-7.19 (m, 3H), 6.99 (dd, J = 3.5, 1.9 Hz, 1H), 5.62 (dd, J = 9.1, 5.7 Hz, 1H), 3.25 (s, 1H), 3.19 (s, 1H), 2.90 (dd, J = 15.8, 6.7 Hz, 1H), 2.67-2.53 (m, 5H), 1.67 (s, 3H). |
| 169 | 2, 4, 13 | 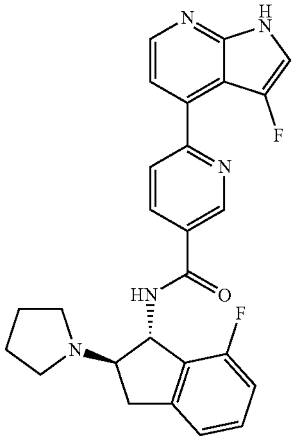 [SMILES: O=C(N[C@@H]1c2c(F)cccc2C[C@H]1N1CCCC1)c1ccc(-c2ccnc3[nH]cc(F)c23)nc1] | 460 | $^1$H-NMR (400 MHz, $CD_3OD$) δ ppm 9.18 (s, 1H), 8.43-8.39 (m, 2H), 8.01 (dd, 1H, J = 8.4, 2.0 Hz), 7.52 (d, 1H, J = 4.8 Hz), 7.42-7.39 (m, 2H), 7.20 (d, 1H, J = 7.6 Hz), 7.10-7.00 (m, 1H), 6.16 (d, 1H, J = 6.0 Hz), 4.26-4.20 (m, 1H), 3.86 (br. s, 2H), 3.76-3.70 (m, 1H), 3.34 (br. s, 2H), 3.28-3.27 (m, 1H), 2.22 (br. s, 2H), 2.10 (br. s, 2H). |

TABLE 1-continued
| # | Synthetic protocol | Structure | LCMS (M + 1) | NMR |
|---|---|---|---|---|
| 170 | 1, 4, 14 | 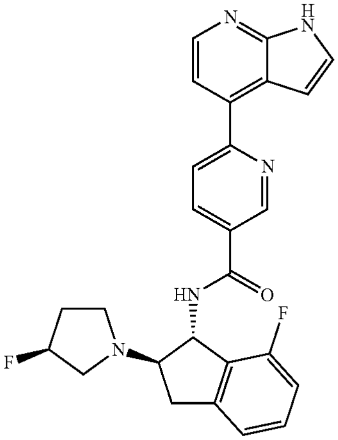 [SMILES: O=C(N[C@@H]1c2c(F)cccc2C[C@H]1N1CC[C@H](F)C1)c1ccc(-c2ccnc3[nH]ccc23)nc1] | 460 | $^1$H-NMR (400 MHz, $CD_3OD$) δ ppm 9.30 (s, 1H), 8.51-8.48 (m, 2H), 8.30 (d, 1H, J = 8.4 Hz), 8.00 (d, 1H, J = 3.2 Hz), 7.77 (d, 1H, J = 2.8 Hz), 7.48-7.40 (m, 1H), 7.32 (d, 1H, J = 3.6 Hz), 7.21 (d, 1H, J = 7.2 Hz), 7.07 (m, 1H), 6.18 (d, 1H, J = 3.2 Hz), 5.56 (d, 1H, J = 52.8 Hz), 4.34 (d, 1H, J = 7.2 Hz), 4.13-4.05 (m, 1H), 3.92 (br. s, 2H), 3.75 (dd, 2H, J = 16.8, 8.4 Hz), 3.37-3.32 (m, 1H), 2.50-2.44 (m, 2H). |
| 171 | 1, 3, 5, 7 | 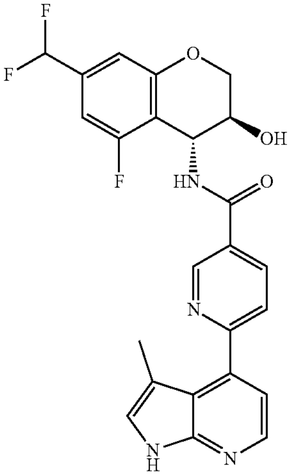 [SMILES: Cc1c[nH]c2nccc(-c3ccc(C(=O)N[C@@H]4c5c(F)cc(C(F)F)cc5OC[C@H]4O)cn3)c12] | 469 | $^1$H-NMR (400 MHz, $CD_3OD$) δ ppm 9.12 (s, 1H), 8.38 (d, 1H, J = 8.4 Hz), 8.24 (d, 1H, J = 4.0 Hz), 7.72 (d, 1H, J = 8.0 Hz), 7.22 (s, 1H), 7.11 (d, 1H, J = 4.8 Hz), 6.90-6.88 (m, 2H), 6.70 (t, 1H, J = 56.0 Hz), 5.76 (d, 1H, J = 3.6 Hz), 4.27-4.17 (m, 3H), 1.92 (s, 3H). |
| 172 | 1, 3, 5, 7 | 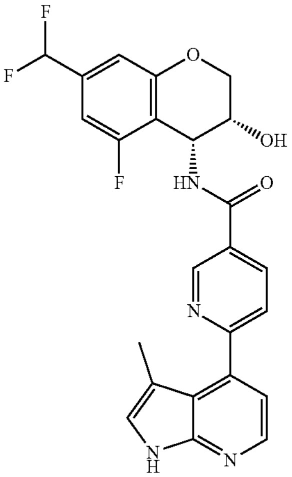 [SMILES: Cc1c[nH]c2nccc(-c3ccc(C(=O)N[C@@H]4c5c(F)cc(C(F)F)cc5OC[C@@H]4O)cn3)c12] | 469 | $^1$H-NMR (400 MHz, $CD_3OD$) δ ppm 9.11 (br. s, 1H), 8.37 (d, 1H, J = 7.6 Hz), 7.77 (d, 1H, J = 8.0 Hz), 7.28 (br. s, 1H), 7.27 (s, 1H), 6.93-6.90 (m, 3H), 6.72 (t, 1H, J = 56.0 Hz), 5.31 (s, 1H), 4.36-4.26 (m, 2H), 4.16 (s, 1H), 1.93 (s, 3H). |

TABLE 1-continued
| # | Synthetic protocol | Structure | LCMS (M + 1) | NMR |
|---|---|---|---|---|
| 173 | 1, 4, 14 | 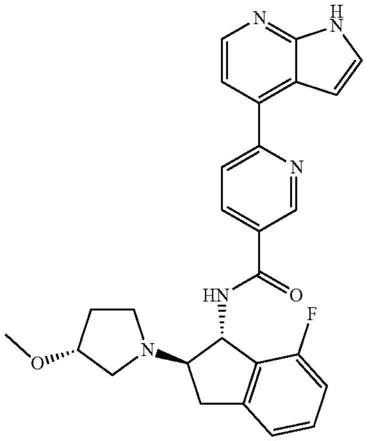 [SMILES: CO[C@@H]1CCN([C@@H]2Cc3cccc(F)c3[C@H]2NC(=O)c2ccc(-c3ccnc4[nH]ccc34)nc2)C1] | 472 | $^1$H-NMR (400 MHz, $CD_3OD$) δ ppm 9.28 (d, 1H, J = 1.6 Hz), 8.49-8.46 (m, 2H), 8.26 (d, 1H, J = 8.4 Hz), 7.88 (d, 1H, J = 5.6 Hz), 7.70 (d, 1H, J = 3.2 Hz), 7.44-7.40 (m, 1H), 7.21-7.19 (m, 2H), 7.07 (t, 1H, J = 9.2 Hz), 6.18 (d, 1H, J = 5.6 Hz), 4.31-4.26 (m, 1H), 4.22 (br. s, 1H), 3.89-3.71 (m, 4H), 3.57 (br. s, 1H), 3.39 (s, 3H), 3.29-3.27 (m, 1H), 2.28 (br. s, 2H). |
| 174 | 1, 4, 13 | 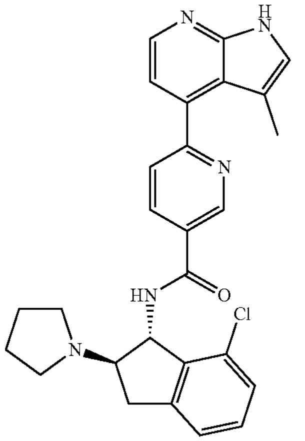 [SMILES: Cc1c[nH]c2nccc(-c3ccc(C(=O)N[C@@H]4c5c(Cl)cccc5C[C@H]4N4CCCC4)cn3)c12] | 472 | $^1$H NMR (400 MHz, DMSO-d6) δ 11.51 (s, 1H), 9.17-9.07 (m, 2H), 8.32 (dd, J = 8.2, 2.3 Hz, 1H), 8.25 (d, J = 4.9 Hz, 1H), 7.74 (dd, J = 8.1, 0.8 Hz, 1H), 7.33-7.20 (m, 4H), 7.08 (d, J = 4.9 Hz, 1H), 5.62 (t, J = 7.4 Hz, 1H), 3.26 (s, 1H), 3.19 (s, 1H), 2.91 (dd, J = 15.9, 6.4 Hz, 1H), 2.69-2.52 (m, 3H), 1.93 (d, J = 1.0 Hz, 3H), 1.93-1.89 (m, 1H), 1.68 (s, 4H). |
| 175 | 2, 4, 10, 13 | 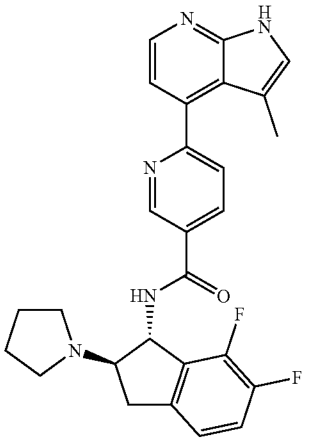 [SMILES: Cc1c[nH]c2nccc(-c3ccc(C(=O)N[C@@H]4c5c(ccc(F)c5F)C[C@H]4N4CCCC4)cn3)c12] | 474 | $^1$H-NMR (400 MHz, $CD_3OD$) δ ppm 9.22 (d, 1H, J = 2.0 Hz), 8.45 (dd, 1H, J = 8.4, 2.0 Hz), 8.39 (d, 1H, J = 6.0 Hz), 7.89 (d, 1H, J = 8.4 Hz), 7.33-7.31 (m, 2H), 7.29-7.28 (m, 1H), 7.19-7.18 (m, 1H), 6.19 (d, 1H, J = 5.2 Hz), 4.32-4.26 (m, 1H), 4.00 (br. s, 2H), 3.69 (dd, 1H, J = 16.4, 8.0 Hz), 3.42 (br. s, 1H), 3.27 (dd, 1H, J = 16.0, 6.8 Hz), 2.16 (br. s, 4H), 1.98 (s, 3H). |

TABLE 1-continued
| # | Synthetic protocol | Structure | LCMS (M + 1) | NMR |
|---|---|---|---|---|
| 176 | 1, 4, 14 | 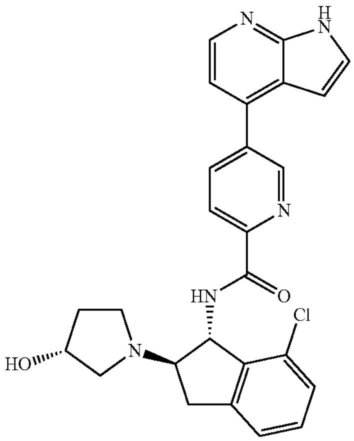 [SMILES: O=C(N[C@@H]1c2c(Cl)cccc2C[C@H]1N1CC[C@@H](O)C1)c1ccc(-c2ccnc3[nH]ccc23)cn1] | 474 | $^1$H-NMR (400 MHz, $CD_3OD$) δ ppm 9.11 (d, 1H, J = 2.0 Hz), 8.48-8.44 (m, 2H), 8.40-8.38 (m, 1H), 7.68 (d, 1H, J = 3.6 Hz), 7.52 (d, 1H, J = 5.6 Hz), 7.41-7.39 (m, 1H), 7.35-7.33 (m, 2H), 6.85 (d, 1H, J = 3.6 Hz), 6.08 (d, 1H, J = 5.2 Hz), 4.62 (br. s, 1H), 4.36 (br. s, 1H), 3.85-3.79 (m, 4H), 3.50-3.36 (m, 1H), 3.32-3.30 (m, 1H), 2.41 (br. s, 1H), 2.14 (br. s, 1H). |
| 177 | 1, 4, 13 | 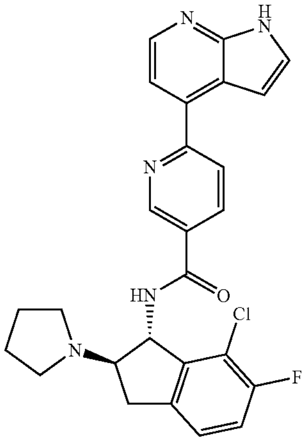 [SMILES: O=C(N[C@@H]1c2c(ccc(F)c2Cl)C[C@H]1N1CCCC1)c1ccc(-c2ccnc3[nH]ccc23)nc1] | 476 | $^1$H NMR (400 MHz, DMSO-d6) δ 11.86 (s, 1H), 9.22 (d, J = 2.3 Hz, 1H), 8.40-8.32 (m, 2H), 8.21 (d, J = 8.4 Hz, 1H), 7.66-7.56 (m, 2H), 7.43-7.30 (m, 2H), 6.99 (dd, J = 3.5, 1.9 Hz, 1H), 3.60 (td, J = 6.6, 3.9 Hz, 1H), 3.19-3.05 (m, 1H), 2.97 (s, 2H), 1.98-1.71 (m, 3H), 1.24 (td, J = 7.0, 5.3 Hz, 6H). |
| 178 | 1, 4, 13 | 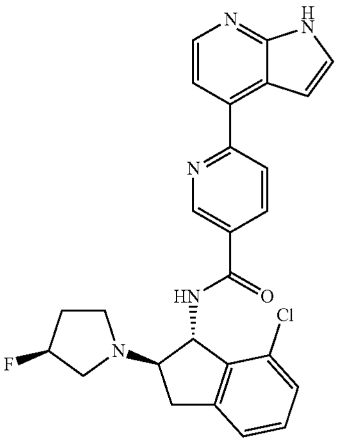 [SMILES: O=C(N[C@@H]1c2c(Cl)cccc2C[C@H]1N1CC[C@H](F)C1)c1ccc(-c2ccnc3[nH]ccc23)nc1] | 476 | $^1$H NMR (400 MHz, DMSO-d6) δ 11.84 (s, 1H), 9.20 (dd, J = 2.3, 0.8 Hz, 1H), 9.15 (d, J = 9.0 Hz, 1H), 8.39-8.31 (m, 2H), 8.17 (dd, J = 8.3, 0.8 Hz, 1H), 7.63 (d, J = 5.0 Hz, 1H), 7.60 (dd, J = 3.4, 2.6 Hz, 1H), 7.30-7.22 (m, 3H), 6.99 (dd, J = 3.5, 1.9 Hz, 1H), 5.62 (dd, J = 9.0, 5.2 Hz, 1H), 5.30-5.08 (m, 1H), 3.35-3.21 (m, 3H), 2.94 (t, J = 7.8 Hz, 2H), 2.91-2.84 (m, 1H), 2.11 (ddd, J = 28.4, 14.1, 7.4 Hz, 1H), 1.97-1.78 (m, 1H), 1.23 (d, J = 7.6 Hz, 1H). |

TABLE 1-continued
| # | Synthetic protocol | Structure | LCMS (M + 1) | NMR |
|---|---|---|---|---|
| 179 | 1, 4, 10, 13 | 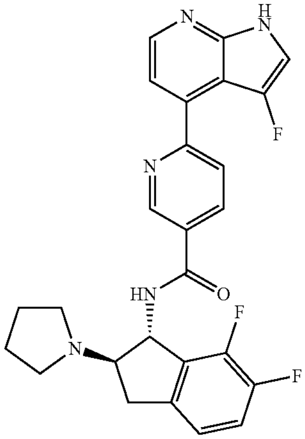 | 478 | $^1$H-NMR (400 MHz, $CD_3OD$) δ ppm 9.17 (d, 1H, J = 0.8 Hz), 8.43-8.38 (m, 2H), 8.02-7.99 (m, 1H), 7.51 (d, 1H, J = 5.2 Hz), 7.38 (d, 1H, J = 2.4 Hz), 7.39-7.32 (m, 1H), 7.18-7.16 (m, 1H), 6.16 (d, 1H, J = 6.0 Hz), 4.27-4.22 (m, 1H), 3.84 (br. s, 2H), 3.67 (q, 1H, J = 8.4 Hz), 3.36-3.33 (m, 2H), 3.27-3.23 (m, 1H), 2.21 (br. s, 2H), 2.08 (br. s, 2H). |
| 180 | 1, 4, 14 | 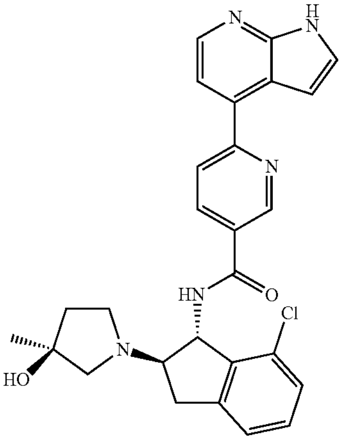 [SMILES: C[C@]1(O)CCN([C@@H]2Cc3cccc(Cl)c3[C@H]2NC(=O)c2ccc(-c3ccnc4[nH]ccc34)nc2)C1] | 488 | $^1$H-NMR (400 MHz, $CD_3OD$) δ ppm 9.19 (s, 1H), 8.39 (d, 1H, J = 8.4 Hz), 8.33 (d, 1H, J = 5.2 Hz), 8.13 (d, 1H, J = 8.4 Hz), 7.60 (d, 1H, J = 4.8 Hz), 7.53 (d, 1H, J = 3.6 Hz), 7.33-7.24 (m, 3H), 6.97 (d, 1H, J = 3.6 Hz), 5.88 (d, 1H, J = 4.8 Hz), 3.63 (d, 1H, J = 6.0 Hz), 3.50 (dd, 1H, J = 16.4, 8.0 Hz), 3.35-3.33 (m, 1H), 3.11-2.99 (m, 4H), 2.01-1.98 (m, 2H), 1.42 (s, 3H). |
| 181 | 1, 4, 13 | 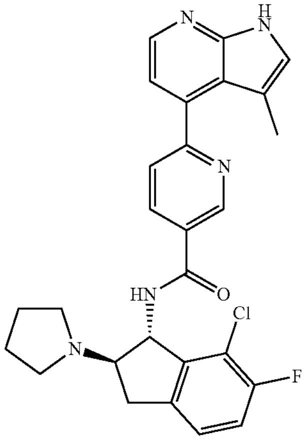 [SMILES: Cc1c[nH]c2nccc(-c3ccc(C(=O)N[C@@H]4c5c(ccc(F)c5Cl)C[C@H]4N4CCCC4)cn3)c12] | 490 | $^1$H NMR (400 MHz, DMSO-d6) δ 11.52 (s, 1H), 9.31 (s, 1H), 9.15 (d, J = 2.2 Hz, 1H), 8.33 (dd, J = 8.2, 2.3 Hz, 1H), 8.25 (d, J = 4.8 Hz, 1H), 7.77 (d, J = 8.1 Hz, 1H), 7.41-7.26 (m, 3H), 7.08 (d, J = 4.8 Hz, 1H), 5.79-5.72 (m, 1H), 4.01 (q, J = 7.1 Hz, 1H), 3.45-3.34 (m, 1H), 3.07-2.93 (m, 4H), 1.93 (d, J = 1.0 Hz, 3H), 1.85-1.73 (m, 4H), 1.16 (t, J = 7.1 Hz, 1H). |

TABLE 1-continued
| # | Synthetic protocol | Structure | LCMS (M + 1) | NMR |
|---|---|---|---|---|
| 182 | 1, 4, 13 | 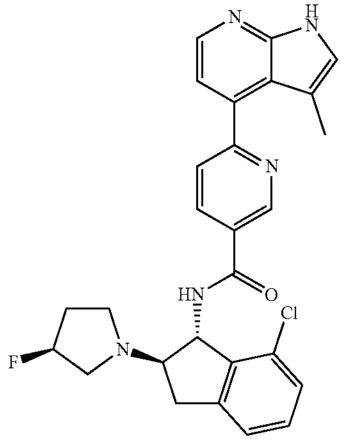 [SMILES: Cc1c[nH]c2nccc(-c3ccc(C(=O)N[C@@H]4c5c(Cl)cccc5C[C@H]4N4CC[C@H](F)C4)cn3)c12] | 490 | $^1$H NMR (400 MHz, DMSO-d6) δ 11.51 (s, 1H), 9.17-9.10 (m, 2H), 8.32 (dd, J = 8.2, 2.3 Hz, 1H), 7.78-7.72 (m, 1H), 7.32-7.21 (m, 4H), 7.08 (d, J = 4.9 Hz, 1H), 5.62 (dd, J = 8.9, 5.1 Hz, 1H), 5.19 (d, J = 56.1 Hz, 1H), 3.35-3.20 (m, 6H), 2.99-2.83 (m, 3H), 2.11 (ddd, J = 28.2, 13.9, 7.2 Hz, 1H), 1.93 (d, J = 1.0 Hz, 3H), 1.84 (d, J = 6.9 Hz, 0H). |
| 183 | 1, 4, 5, 14 | 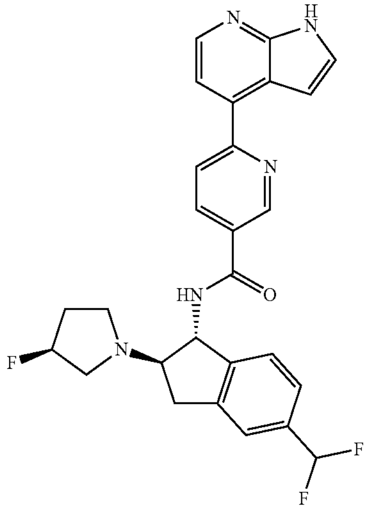 [SMILES: O=C(N[C@@H]1c2ccc(C(F)F)cc2C[C@H]1N1CC[C@H](F)C1)c1ccc(-c2ccnc3[nH]ccc23)nc1] | 492 | $^1$H-NMR (400 MHz, $CD_3OD$) δ ppm 9.26 (d, 1H, J = 2.4 Hz), 8.46 (dd, 1H, J = 8.4, 2.4 Hz), 8.36 (d, 1H, J = 5.2 Hz), 8.18 (d, 1H, J = 8.0 Hz), 7.64 (d, 1H, J = 4.8 Hz), 7.55 (d, 1H, J = 3.2 Hz), 7.47-7.44 (m, 2H), 7.37-7.34 (m, 1H), 7.01 (d, 1H, J = 3.6 Hz), 6.76 (t, 1H, J = 56.4 Hz), 5.83 (d, 1H, J = 6.8 Hz), 5.23 (dt, 1H, J = 56.0, 5.6 Hz), 3.40-3.36 (m, 2H), 3.18-3.11 (m, 2H), 3.09-3.00 (m, 1H), 3.00-2.85 (m, 1H), 2.70-2.68 (m, 1H), 2.29-2.22 (m, 1H), 2.15-2.00 (m, 1H). |
| 184 | 1, 4, 14 | 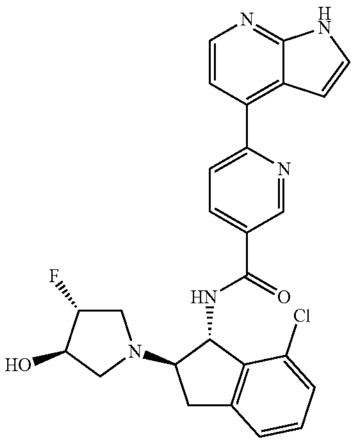 [SMILES: O=C(N[C@@H]1c2c(Cl)cccc2C[C@H]1N1C[C@@H](O)[C@H](F)C1)c1ccc(-c2ccnc3[nH]ccc23)nc1] | 492 | $^1$H-NMR (400 MHz, $CD_3OD$) δ ppm 9.28 (s, 1H), 8.49-8.47 (m, 2H), 8.26 (d, 1H, J = 8.0 Hz), 7.85 (d, 1H, J = 6.0 Hz), 7.69 (d, 1H, J = 3.2 Hz), 7.47-7.38 (m, 3H), 7.19 (d, 1H, J = 3.2 Hz), 6.06 (s, 1H), 5.20 (d, 1H, J = 50.0 Hz), 4.60 (br. s, 1H), 4.36 (br. s, 1H), 4.25-4.21 (m, 1H), 4.11-4.00 (m, 1H), 3.93-3.82 (m, 3H), 3.39 (s, 1H). |

TABLE 1-continued

| # | Synthetic protocol | Structure | LCMS (M + 1) | NMR |
|---|---|---|---|---|
| 185 | 1, 4, 14 | 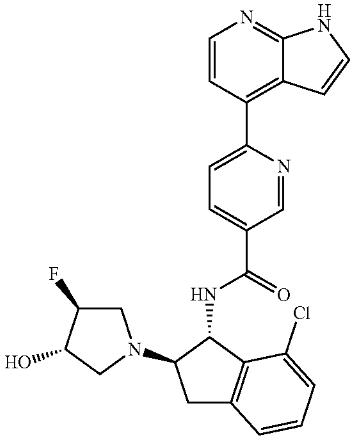 [SMILES: O=C(N[C@@H]1c2c(Cl)cccc2C[C@H]1N1C[C@H](O)[C@@H](F)C1)c1ccc(-c2ccnc3[nH]ccc23)nc1] | 492 | $^1$H-NMR (400 MHz, $CD_3OD$) δ ppm 9.29 (s, 1H), 8.49-8.45 (m, 2H), 8.26 (d, 1H, J = 8.0 Hz), 7.85 (d, 1H, J = 4.4 Hz), 7.69 (s, 1H), 7.46-7.37 (m, 3H), 7.19 (d, 1H, J = 3.6 Hz), 6.06 (d, 1H, J = 4.0 Hz), 5.25 (d, 1H, J = 50.4 Hz), 4.60 (d, 1H, J = 7.6 Hz), 4.35 (d, 1H, J = 3.6 Hz), 4.11-4.05 (m, 2H), 3.90-3.84 (m, 3H), 3.37 (d, 1H, J = 4.8 Hz). |
| 186 | 1, 4, 14 | 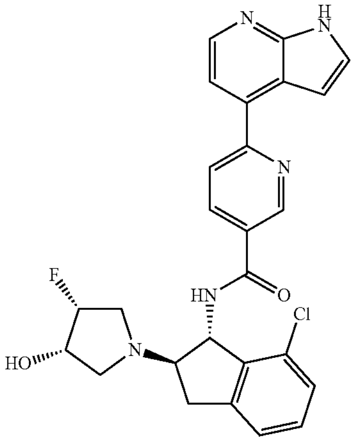 [SMILES: O=C(N[C@@H]1c2c(Cl)cccc2C[C@H]1N1C[C@@H](F)[C@@H](O)C1)c1ccc(-c2ccnc3[nH]ccc23)nc1] | 492 | $^1$H-NMR (400 MHz, $CD_3OD$) δ ppm 9.18 (s, 1H), 8.38 (d, 1H, J = 8.4 Hz), 8.33 (d, 1H, J = 4.8 Hz), 8.13 (d, 1H, J = 8.0 Hz), 7.60 (d, 1H, J = 5.2 Hz), 7.52 (d, 1H, J = 3.6 Hz), 7.28-7.22 (m, 3H), 6.97 (d, 1H, J = 3.6 Hz), 5.77 (d, 1H, J = 5.2 Hz), 5.01 (s, 1H), 4.25-4.20 (m, 1H), 3.47-3.43 (m, 2H), 3.39-3.37 (m, 1H), 3.23-3.19 (m, 1H), 3.15-3.05 (m, 1H), 2.99-2.95 (m, 1H), 2.75-2.74 (m, 1H). |
| 187 | 1, 4, 14 | 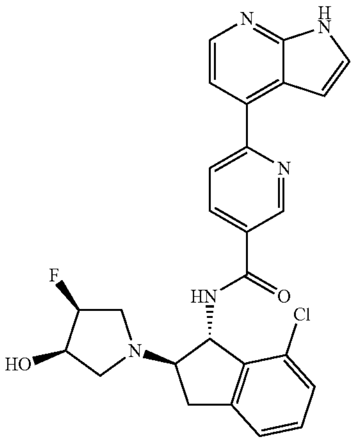 [SMILES: O=C(N[C@@H]1c2c(Cl)cccc2C[C@H]1N1C[C@@H](O)[C@@H](F)C1)c1ccc(-c2ccnc3[nH]ccc23)nc1] | 492 | $^1$H-NMR (400 MHz, $CD_3OD$) δ ppm 9.22 (d, 1H, J = 2.0 Hz), 8.42 (dd, 1H, J = 8.4, 2.4 Hz), 8.33 (d, 1H, J = 4.8 Hz), 8.15 (d, 1H, J = 8.0 Hz), 7.62 (d, 1H, J = 4.8 Hz), 7.54 (d, 1H, J = 3.6 Hz), 7.39-7.31 (m, 3H), 6.98 (d, 1H, J = 3.6 Hz), 5.98 (d, 1H, J = 4.4 Hz), 5.23 (d, 1H, J = 53.2 Hz), 4.60-4.56 (m, 1H), 4.29-4.27 (m, 1H), 4.01-3.82 (m, 3H), 3.75-3.70 (m, 1H), 3.65-3.63 (m, 1H), 3.33-3.32 (m, 1H). |

TABLE 1-continued

| # | Synthetic protocol | Structure | LCMS (M + 1) | NMR |
|---|---|---|---|---|
| 188 | 1, 4, 14 | 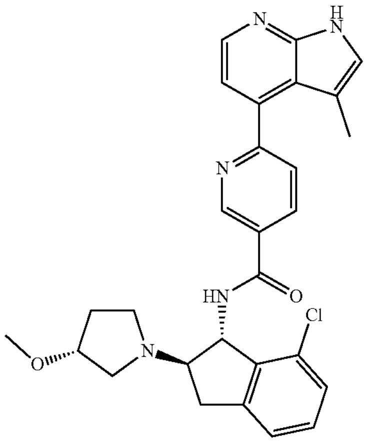 [SMILES: CO[C@@H]1CCN([C@@H]2Cc3cccc(Cl)c3[C@H]2NC(=O)c2ccc(-c3ccnc4[nH]cc(C)c34)nc2)C1] | 503 | $^1$H NMR (400 MHz, DMSO-d6) δ 11.51 (s, 1H), 9.16-9.09 (m, 2H), 8.32 (dd, J = 8.2, 2.3 Hz, 1H), 8.25 (d, J = 4.9 Hz, 1H), 7.74 (dd, J = 8.2, 0.8 Hz, 1H), 7.33-7.19 (m, 4H), 7.08 (d, J = 4.8 Hz, 1H), 5.59 (dd, J = 8.9, 5.5 Hz, 1H), 3.86 (s, 1H), 3.28-3.16 (m, 2H), 3.15 (s, 3H), 2.89 (dd, J = 15.8, 6.3 Hz, 1H), 2.77 (t, J = 8.2 Hz, 1H), 2.71-2.63 (m, 1H), 2.57 (d, J = 7.2 Hz, 1H), 1.93 (d, J = 1.0 Hz, 4H), 1.64 (s, 1H). |
| 189 | 1, 4, 14 | 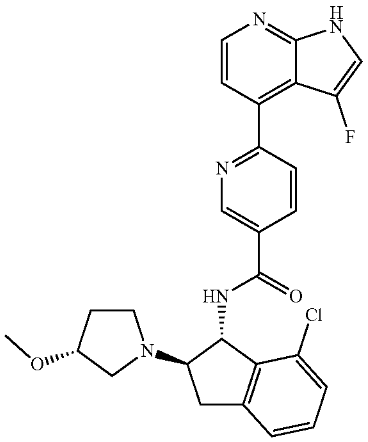 [SMILES: CO[C@@H]1CCN([C@@H]2Cc3cccc(Cl)c3[C@H]2NC(=O)c2ccc(-c3ccnc4[nH]cc(F)c34)nc2)C1] | 506 | $^1$H NMR (400 MHz, DMSO-d6) δ 11.75 (s, 1H), 9.21-9.08 (m, 2H), 8.39-8.30 (m, 2H), 7.92 (dd, J = 8.2, 3.3 Hz, 1H), 7.59 (t, J = 2.5 Hz, 1H), 7.46 (d, J = 4.9 Hz, 1H), 7.33-7.20 (m, 3H), 5.59 (dd, J = 9.0, 5.6 Hz, 1H), 3.89-3.79 (m, 1H), 3.27-3.16 (m, 2H), 3.15 (s, 3H), 2.89 (dd, J = 15.8, 6.5 Hz, 1H), 2.80-2.73 (m, 1H), 2.71-2.63 (m, 2H), 2.56 (d, J = 7.2 Hz, 1H), 1.94 (dd, J = 13.4, 6.7 Hz, 1H), 1.70-1.58 (m, 1H). |
| 190 | 1, 4, 5, 14 | 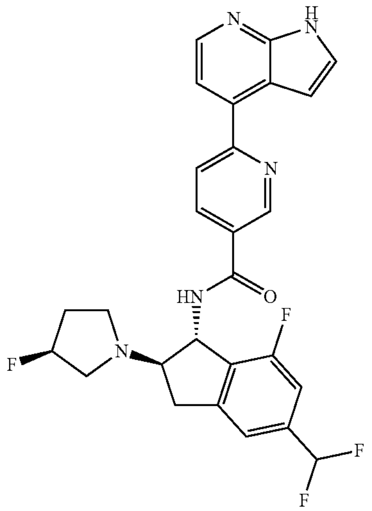 [SMILES: O=C(N[C@@H]1c2c(F)cc(C(F)F)cc2C[C@H]1N1CC[C@H](F)C1)c1ccc(-c2ccnc3[nH]ccc23)nc1] | 510 | $^1$H-NMR (400 MHz, $CD_3OD$) δ ppm 9.30 (d, 1H, J = 1.5 Hz), 8.49 (dd, 2H, J = 8.0, 2.0 Hz), 8.29 (d, 1H, J = 8.4 Hz), 7.97 (d, 1H, J = 6.0 Hz), 7.75 (d, 1H, J = 3.6 Hz), 7.42 (s, 1H), 7.30-7.27 (m, 2H), 6.82 (t, 1H, J = 55.6 Hz), 6.20 (d, 1H, J = 5.2 Hz), 5.52 (d, 1H, J = 53.2 Hz), 4.42-4.39 (m, 1H), 4.10-4.06 (m, 1H), 3.92-3.77 (m, 4H), 3.39 (dd, 1H, J = 17.2, 6.8 Hz), 2.56-2.45 (m, 2H). |

TABLE 1-continued

| # | Synthetic protocol | Structure | LCMS (M + 1) | NMR |
|---|---|---|---|---|
| 191 | 1, 4, 14 | 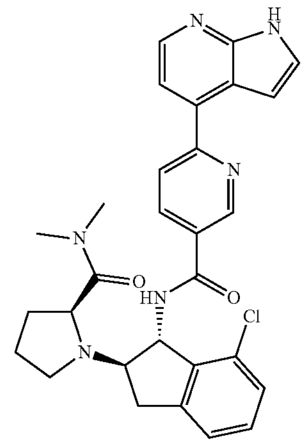 [SMILES: CN(C)C(=O)[C@@H]1CCCN1[C@@H]1Cc2cccc(Cl)c2[C@H]1NC(=O)c1ccc(-c2ccnc3[nH]ccc23)nc1] | 529 | $^1$H-NMR (400 MHz, $CD_3OD$) δ ppm 9.18 (s, 1H), 8.39-8.37 (m, 2H), 8.19 (d, 1H, J = 8.4 Hz), 7.88 (d, 1H, J = 6.0 Hz), 7.65 (d, 1H, J = 3.2 Hz), 7.37-7.33 (m, 1H), 7.29-7.27 (m, 2H), 7.20 (d, 1H, J = 3.6 Hz), 5.71 (s, 1H), 4.98-4.94 (m, 1H), 4.26-4.24 (m, 1H), 3.90-3.89 (m, 1H), 3.69-3.63 (m, 1H), 3.42-3.38 (m, 2H), 3.00 (s, 3H), 2.97 (s, 3H), 2.80-2.60 (m, 1H), 2.17-2.15 (m, 1H), 2.02-2.01 (m, 1H), 2.00-1.99 (m, 1H). |
| 192 | 1, 4, 14, 23 | 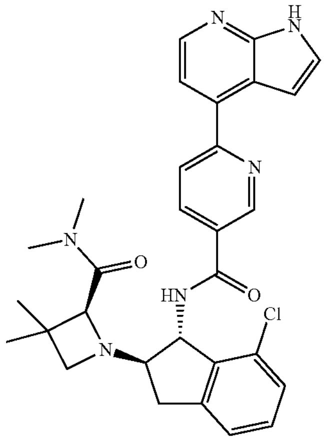 [SMILES: CN(C)C(=O)[C@H]1N([C@@H]2Cc3cccc(Cl)c3[C@H]2NC(=O)c2ccc(-c3ccnc4[nH]ccc34)nc2)CC1(C)C] | 543 | $^1$H-NMR (400 MHz, $CD_3OD$) δ ppm 9.28 (s, 1H), 8.49-8.47 (m, 2H), 8.26 (d, 1H, J = 8.4 Hz), 7.82 (br. s, 1H), 7.69 (br. s, 1H), 7.54-7.41 (m, 3H), 7.17 (br. s, 1H), 5.77 (s, 1H), 5.67 (s, 1H), 4.42 (d, 1H, J = 8.0 Hz), 4.04-4.02 (m, 1H), 3.94-3.91 (m, 1H), 3.81-3.74 (m, 1H), 3.25 (s, 3H), 3.19 (s, 3H), 3.14 (s, 1H), 1.67 (s, 3H), 1.32 (s, 3H). |
| 193 | 1, 4, 14, 23 | 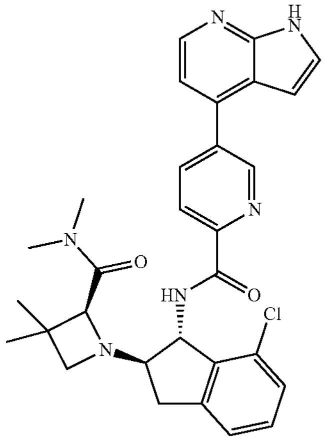 [SMILES: CN(C)C(=O)[C@H]1N([C@@H]2Cc3cccc(Cl)c3[C@H]2NC(=O)c2ccc(-c3ccnc4[nH]ccc34)cn2)CC1(C)C] | 543 | $^1$H-NMR (400 MHz, $CD_3OD$) δ ppm 9.10 (d, 1H, J = 1.6 Hz), 8.51-8.48 (m, 2H), 8.40 (d, 1H, J = 8.8 Hz), 7.76 (d, 1H, J = 3.6 Hz), 7.64 (d, 1H, J = 6.0 Hz), 7.45-7.43 (m, 1H), 7.38-7.35 (m, 2H), 6.94 (d, 1H, J = 4.0 Hz), 5.70-5.68 (m, 2H), 4.41-4.39 (m, 1H), 4.02-4.00 (m, 1H), 3.91-3.89 (m, 1H), 3.76 (dd, 1H, J = 17.6, 8.0 Hz), 3.15 (s, 3H), 3.13 (s, 3H), 3.10-3.09 (m, 1H), 1.60 (s, 3H), 1.28 (s, 3H). |

Pharmaceutically acceptable salts and solvates of the compounds described herein are also contemplated for the uses described herein.

"Pharmaceutically acceptable salt," as used herein, refers to any salt of a compound of the disclosure which retains its biological properties and which is not toxic or otherwise undesirable for pharmaceutical use. Pharmaceutically acceptable salts may be derived from a variety of organic and inorganic counter-ions. Such salts include one or more of: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion, or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Pharmaceutically acceptable salts further include, but are not limited to, sodium, potassium, calcium, magnesium, ammonium, tetraalkylammonium, and the like, and when the compound contains a basic functionality, salts of non-toxic organic or inorganic acids, such as hydrochloride, hydrobromide, tartrate, mesylate, besylate, acetate, maleate, oxalate, and the like. A pharmaceutically acceptable salt according to the disclosure includes at least one salt, and also includes mixtures of more than one salt.

Pharmaceutical compositions of the disclosure comprise one or more compounds of the disclosure and one or more pharmaceutically acceptable excipient(s). The term "pharmaceutically acceptable excipient," as used herein, refers to a pharmaceutically-acceptable material, composition, or vehicle, such as a liquid or solid filler, diluent, excipient, solvent, or encapsulating material, involved in carrying or transporting any subject composition or component thereof. Each excipient must be "acceptable" in the sense of being compatible with the subject composition and its components and not injurious to the patient. Some non-limiting examples of materials which may serve as pharmaceutically acceptable excipients include: (1) sugars, such as lactose, glucose, and sucrose; (2) starches, such as corn starch and potato starch; (3) cellulose and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compositions of the disclosure may be administered orally, parenterally, by inhalation spray, topically, rectally, nasally, buccally, vaginally, or via an implanted reservoir. The term "parenteral," as used herein includes subcutaneous, intravenous, intramuscular, intra-articular, intra-synovial, intrasternal, intrathecal, intrahepatic, intralesional, and intracranial injection or infusion techniques. In some embodiments, the compositions of the disclosure are administered orally, intraperitoneally, or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives, are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween, Spans, and other emulsifying agents or bioavailability enhancers which are commonly used in the manufacture of pharmaceutically acceptable solid, liquid, or other dosage forms may also be used for the purposes of formulation.

The pharmaceutically acceptable compositions of this disclosure may be orally administered in any orally acceptable dosage form including, but not limited to, capsules, tablets, aqueous suspensions, or solutions. In the case of tablets for oral use, excipients commonly used include lactose and corn starch. Lubricating agents, such as magnesium stearate, are typically also added. For oral administration in a capsule form, useful diluents include lactose and dried cornstarch. When aqueous suspensions are required for oral use, the active ingredient is typically combined with emulsifying and suspending agents. If desired, certain sweetening, flavoring, or coloring agents may also be added.

Alternatively, the pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax, and polyethylene glycols.

The pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more excipients. Excipients for topical administration of the compounds of this disclosure include, but are not limited to, mineral oil, liquid petrolatum, white petrolatum, propylene glycol, polyoxyethylene, polyoxypropylene compound, emulsifying wax, and water. Alternatively, the pharmaceutically acceptable compositions can be formulated in a suitable lotion or cream containing the active components suspended or dissolved in one or more pharmaceutically acceptable excipients. Suitable excipients include, but are not limited to, mineral oil, sorbitan monostearate, polysorbate 60, cetyl esters wax, cetearyl alcohol, 2-octyldodecanol, benzyl alcohol, and water.

The pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, the present disclosure features a method of treating a subject afflicted with a disease, comprising administering to the subject a therapeutically effective amount of a compound described herein (e.g., a compound of Formula (I)) or a pharmaceutically acceptable salt or solvate thereof, or a pharmaceutical composition thereof. In some embodiments, the disease may be characterized by constitutive activation of protein kinase A signaling. In some embodiments, the disease may be firbomellar carcinoma. In some embodiments, the disease may be a multiple neoplasia syndrome (e.g., Carney complex). In some embodiments, the disease may be polycystic kidney disease (PKD).

In some embodiments, the disease may be chosen from pituitary cancer, kidney cancer, ovarian cancer, testicular cancer (e.g., testicular human stromal Leydig cell tumor), thyroid ademona, Villous colon cancer, intraductal papillary mucinous neoplasms (IPMN), intrahepatic cholangiocarcinomas, inflammatory liver cancer (characterized by STAT3 activation), adrenocortical adenoma, and McCune-Albright syndrome. In some embodiments, the McCune-Albright syndrome may be associated with fibrous dysplasia of bone (FD), café-au-lait macules, precocious puberty, hyperthyroidism, Cushing syndrome, and/or pituitary gigantism/acromegaly.

Recent genomic data strongly suggest that DNAJB1-PRKACA kinase fusions are the drivers of most fibrolamellar carcinoma (FLC) cases (Honeyman, J. N. et al., *Science* 343(6174):1010-14 (2014); Cornella, H. et al., *Gastroenterology* 148(4):806-18 (2015)); Malouf, G. G. et al., *Hepatology* 59(6):2228-37 (2014)). In fact, DNAJB1-PRKACA fusions are found in 90 to 100% patients suffering from fibrolamellar variant of hepatocellular carcinoma (FL-HCC).

The driver function of DNAJB1-PRKACA fusions has been further demonstrated in mouse models. Expression of the DNAJB1-PRKACA fusion in mice leads to the formation of indolent liver tumors that closely resemble human FLC, providing further evidence for DNAJB1-PRKACA fusions being oncogenic drivers of FLC (Engelholm, L. H. et al., *Gastroenterology* 153(6):1662-73 (2017), Kastenhuber, E. R. et al., *PNAS* 114(50):13076-13084 (2017)).

Aberrant PKA signaling activation through catalytic PKA subunits, e.g., PRKACA and/or PRKACB, in the ACTH-cAMP-PKA pathway (Soon, P. et al, *Oncologist* 13:548-561 (2008)), has also been associated with various other diseases, including diseases described herein. Thus, compounds that inhibit catalytic PKA activity, such as compounds of Formula (I) and pharmaceutically acceptable salts and solvates thereof, should inhibit aberrant signaling activation and reverse disease phentotypes.

Carney complex is one non-limiting example of a disease associated with aberrant PKA signaling. 70% of patients with Carney complex (CNC), a multiple neoplasia syndrome, possess heterozygous germline inactivating mutations of the PKA regulatory subunit RIα and R2β genes (PRKAR1A and PRKAR2B) that lead to constitutive cAMP signaling (Salpea, P. et al., *J Clin Endocrinol Metab.* 99(1): e183-88 (2014)). Carney complex is characterized by spotty skin pigmentation, cardiac and other myxomas, and different types of endocrine tumors (Salpea, P. et al., *J Clin Endocrinol Metab.* 99(1):e183-88 (2014)). Additionally, 10% of the CNC patients present with adenomas and symptomatic acromegaly (Correa, R et al. *Eur J Endocrinol.* 173(4):M85-97 (2015)).

In addition, activating hotspot L205R mutations in PRKACA have been found in most cortisol-producing adrenocortical adenomas (ACAs) of Cushing's disease. Adrenal Cushing's syndrome is caused by excess production of glucocorticoid from adrenocortical tumors and hyperplasias, which can lead to metabolic disorders. (Sato, Y. et al., *Science* 344:917-20 (2014), Cao, Y. et al., *Science* 344:913-17 (2014), Beuschlein, F. et al., *N. Engl. J. Med.* 370:1019-28 (2014), Goh, G. et al., *Nat. Genet.* 46(6):613-17 (2014)).

Mutations in the GNAS gene may also result in aberrant PKA signaling that leads to disease phenotypes. For example, the GNAS complex locus encodes the alpha-subunit of the stimulatory G protein (Gsα), a ubiquitous signaling protein mediating the actions of many hormones, neurotransmitters, and paracrine/autocrine factors via generation of the second messenger cAMP. Somatic heterozygous gain-of-function mutations of the GNAS gene, originally found in pituitary tumors, can lead to aberrant PKA signaling activation (Landis, C. A. et al., *Nature* 340(6236): 692-96 (1989)). Somatic heterozygous gain-of-function mutations of the GNAS gene were subsequently found in several other tumor types, such as kidney cancer (Kalfa, N et al., *J. Urol.* 176(3):891-95 (2006)), ovarian and testicular human stromal Leydig cell tumors (Fragoso, M. C. et al., *J. Clin. Endocrinol.* 83(6):2074-78 (1998)), thyroid adenomas (Palos-Paz F, et al., *Eur. J. Endocrinol.* 159(5):623-31 (2008)), and villous colon cancers (Fecteau, R. E. et al., *PLOS One* 9(1):e87966 (2014)).

GNAS activating mutations were also found to be present in 66% of intraductal papillary mucinous neoplasms (IPMN), one of the most common cystic neoplasms of the pancreas and a precursor to invasive adenocarcinoma. (Wu, J. et al., *Sci. Transl. Med.* 3(92):92ra66 (2011)). These neoplastic lesions can develop into invasive cancer (Mino-Kenudson, M et al., Gut 60(12):1712-20 (2011)).

GNAS mutations were also found in patients with intrahepatic cholangiocarcinomas; the mutations were associated with poor overall survival in all patients (Jang, S. et al., *Modern Pathology* 27:731-39 (2014)), as well as STAT3 activation in a rare subgroup of inflammatory liver tumors (Nault, J. C. et al., *J. Hepatol.* 56(1):184-91 (2012)).

In addition, mosaic GNAS activating mutations have been shown to cause McCune-Albright syndrome (Weinstein, L. S. et al., *N. Engl. J. Med.* 325(24):1688-1695 (1991)). The main features of McCune-Albright syndrome are fibrous dysplasia of bone (FD), café-au-lait macules, and precocious puberty (Salpea, P. et al., *Mol. Cell. Endocrinol.* 386:85-91 (2014)). Additionally, hyperthyroidism, Cushing syndrome, and pituitary gigantism/acromegaly can be part of the clinical presentation of McCune-Albright syndrome if mutated cells are present in thyroid, adrenal, and/or pituitary tissues.

Furthermore, PKA is a key protein in both cAMP driven growth and fluid secretion. cAMP-driven PKA has been implicated in proliferation and fluid accumulation in cystic disease in both the kidney and liver, with evidence indicating that inhibition of PKA abrogates polycystic kidney disease (PKD) phenotype pre-clinically (Wang, X. et al., *Kidney Int.* 77(2):129-40 (2010), Banales, J. M. et al., *Hepatology* 49(1):160-74 (2009), Torres, V. E. & P. C. Harris, *J. Am. Soc. Nephrol.* 25(1):18-32 (2014)). Polycystic kidney disease (PKD) is a genetic disorder that causes numerous cysts to grow in the kidneys. A kidney cyst is an abnormal sac filled with fluid (Fedeles, S. V. et al., *Trends Mol. Med.* 20(5): 251-60 (2014)). PKD cysts can greatly enlarge the kidneys while replacing much of their normal structure, resulting in chronic kidney disease (CKD). CKD causes reduced kidney function over time. Estimates of PKD's prevalence range from one in 400 to one in 1,000 people. According to the United States Renal Data System, PKD accounts for 2.2 percent of new cases of kidney failure each year in the United States. ACE inhibitors (which control blood pressure), diet, and pain management are currently used to treat PKD and its symptoms (Torres, V. E. & P. C. Harris, *Kidney Int.* 76(2):149-68 (2009)).

Mutations in PKD1 (polycystin-1 protein, PC-1) and PKD2 (polycystin-2, PC-2 protein) are the most common cause of autosomal dominant polycystic kidney disease (ADPKD) (Fedeles, S. V. et al., *Trends Mol. Med.* 20(5): 251-60 (2014), Harris, P. C. & V. E. Torres, *Annu. Rev. Med.* 60:321-37 (2009)). PC-1 and PC-2 form a complex in the primary cilia that is believed to form an active $Ca^{2+}$ channel, altering hemostasis and increasing cAMP, which drives growth through ERK and fluid secretion through CFTR (Mekahli, D. et al., *Cell. Mol. Life Sci.* 70(15):2697-712 (2013)).

A person of ordinary skill in the art can determine whether a subject possesses a fusion e.g., using a method chosen from hybridization-based methods, amplification-based methods, microarray analysis, flow cytometry analysis, DNA sequencing, next-generation sequencing (NGS), primer extension, PCR, in situ hybridization, fluorescent in situ hybridization, dot blot, and Southern blot.

To detect a fusion, primary tumor samples may be collected from a subject. The samples are processed, the nucleic acids are isolated using techniques known in the art, then the nucleic acids are sequenced using methods known in the art. Sequences are then mapped to individual exons, and measures of transcriptional expression (such as RPKM, or reads per kilobase per million reads mapped), are quantified. Raw sequences and exon array data are available from sources such as TCGA, ICGC, and the NCBI Gene Expression Omnibus (GEO). For a given sample, individual exon coordinates are annotated with gene identifier information, and exons belonging to kinase domains are flagged. The exon levels are then z-score normalized across all tumors samples.

Next, genes in which 5' exons are expressed at significantly different levels than 3' exons are identified. A sliding frame is used to identify the breakpoint within an individual sample. Specifically, at each iteration, an incremental breakpoint divides the gene into 5' and 3' regions, and a t-statistic is used to measure the difference in expression (if any) between the two regions. The breakpoint with the maximal t-statistic is chosen as the likely fusion breakpoint. As used herein, "breakpoint" is the boundary at which two different genes are fused. It is sometimes referred to as a "fusion point." The location where the difference in exon expression is maximal between 5' and 3' is the inferred breakpoint of the fusion. Thousands of tumor samples can be rapidly profiled in this manner, generating a list of fusion candidates (ranked by t-statistic). High-ranking candidates can then be validated, and fusion partners identified by examining the raw RNA-seq data sets, and identifying chimeric pairs and/or split reads which support the fusion. Candidate fusions can then be experimentally confirmed as described below.

Alternatively, fusions may be identified by circulating tumor DNA (ctDNA) analysis of plasma (i.e., a liquid biopsy).

In addition, the methods described in Wang L et al., *Genes Chromosomes Cancer* 51(2):127-39 (2012). doi: 10.1002/gcc.20937, Epub 2011 Oct. 27; and Suehara Y et al., *Clin Cancer Res.* 18(24):6599-608 (2012). doi: 10.1158/1078-0432.CCR-12-0838, Epub 2012 Oct. 10 can also be used to detect a fusion.

Actual dosage levels of the active ingredients in the pharmaceutical compositions of this disclosure may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health, and prior medical history of the patient being treated, and like factors well-known in the medical arts.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In general, a suitable daily dose of a compound of the disclosure will be that amount of the compound that is the lowest dose effective to produce a therapeutic effect. Such an effective dose will generally depend upon the factors described above.

Toxicity and therapeutic efficacy of compounds of the disclosure, including pharmaceutically acceptable salts, solvates, and deuterated variants, can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans, as would be known by one of ordinary skill in the art. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms)

as determined in cell culture. Such information can be used to more accurately determine useful doses in humans. Levels in plasma may be measured, for example, by high performance liquid chromatography.

In some embodiments, the disclosure provides a kit (e.g., a pharmaceutical pack) comprising at least one compound chosen from compounds of Formula (I), pharmaceutically acceptable salts thereof, and solvates of any of the foregoing. The kits may be used for treating a disease described herein. In some embodiments, the kits optionally further include additional containers comprising at least one pharmaceutical excipient for dilution or suspension of one or more of the at least one compound chosen from compounds of Formula (I), pharmaceutically acceptable salts thereof, and solvates of any of the foregoing. In some embodiments, the at least one compound chosen from compounds of Formula (I), pharmaceutically acceptable salts thereof, and solvates of any of the foregoing and at least one pharmaceutical excipient for dilution or suspension in separate containers are combined to form a unit dosage form prior to administration.

The kit may further include written instructions for administration of the inhibitors (e.g., how to combine the at least one compound and at least one pharmaceutical excipient for dilution or suspension into a single dosage form, the types of cancer for which the kit is useful, the frequency of administration, and other information relevant to administration and/or co-administration, if applicable).

EXEMPLIFICATION

General Synthetic Methods and Intermediates

Compounds of the disclosure, including salts and N-oxides thereof, can be prepared using organic synthesis techniques known to one of ordinary skill in the art and/or by reference to the schemes shown below and the synthetic examples. The below Schemes are meant to provide general guidance in connection with preparing the compounds of the invention. One skilled in the art would understand that the preparations shown in the Schemes can be modified or optimized using general knowledge of organic chemistry to prepare various compounds of the invention.

Scheme 1: Synthetic Protocol 1

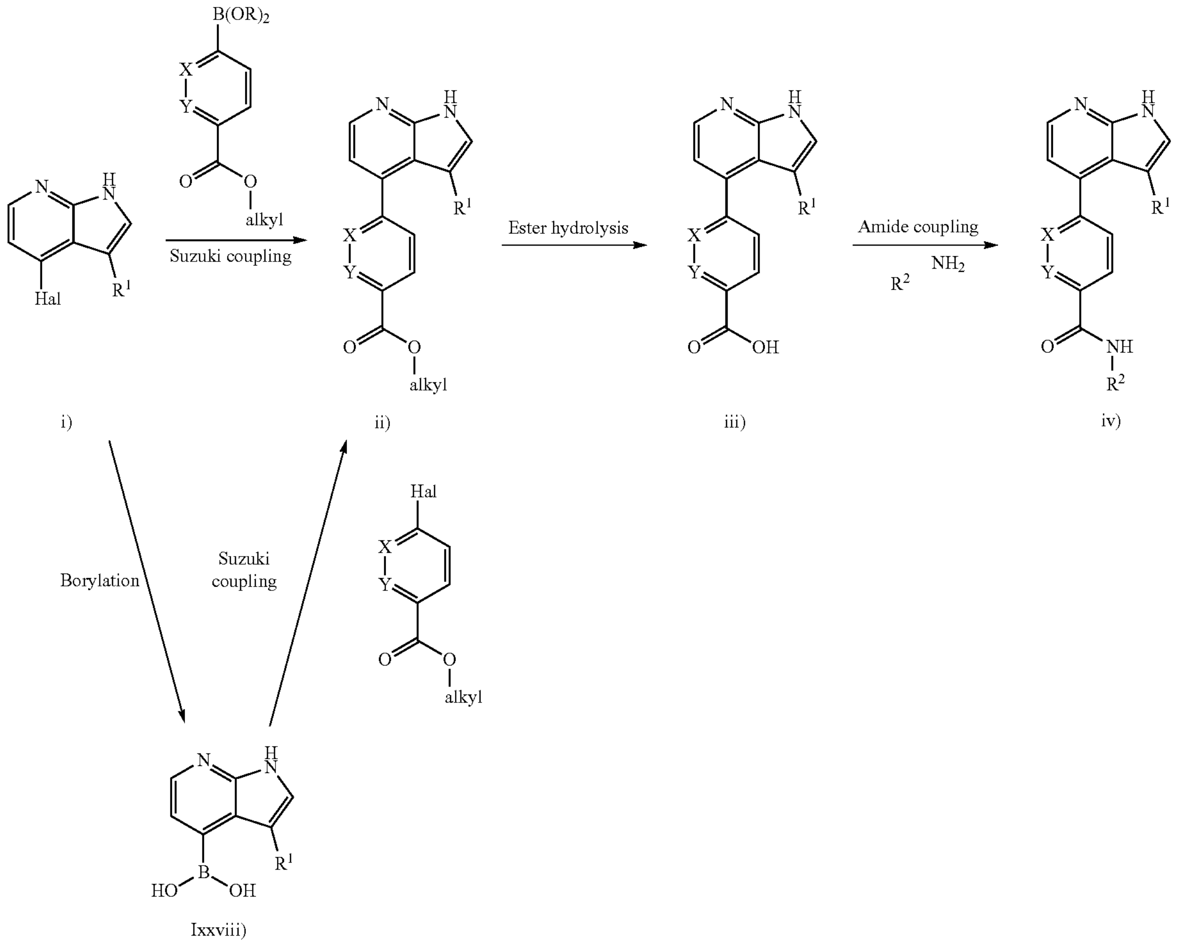

Scheme 1 shows a general route for the preparation of compounds of formula iv) starting from halides of formula i). Suzuki coupling with a 4-carboxy aryl boronate provides ester ii). Alternatively, ester ii) can be formed via borylation of i) to give boronate lxxviii) followed by Suzuki coupling with a 4-carboxy aryl halide. Subsequent hydrolysis gives acid precursor iii), with an amide coupling yielding final compounds iv). Mixtures of stereoisomers of iv) can be resolved by chiral chromatography.

Scheme 2: Synthetic Protocol 2

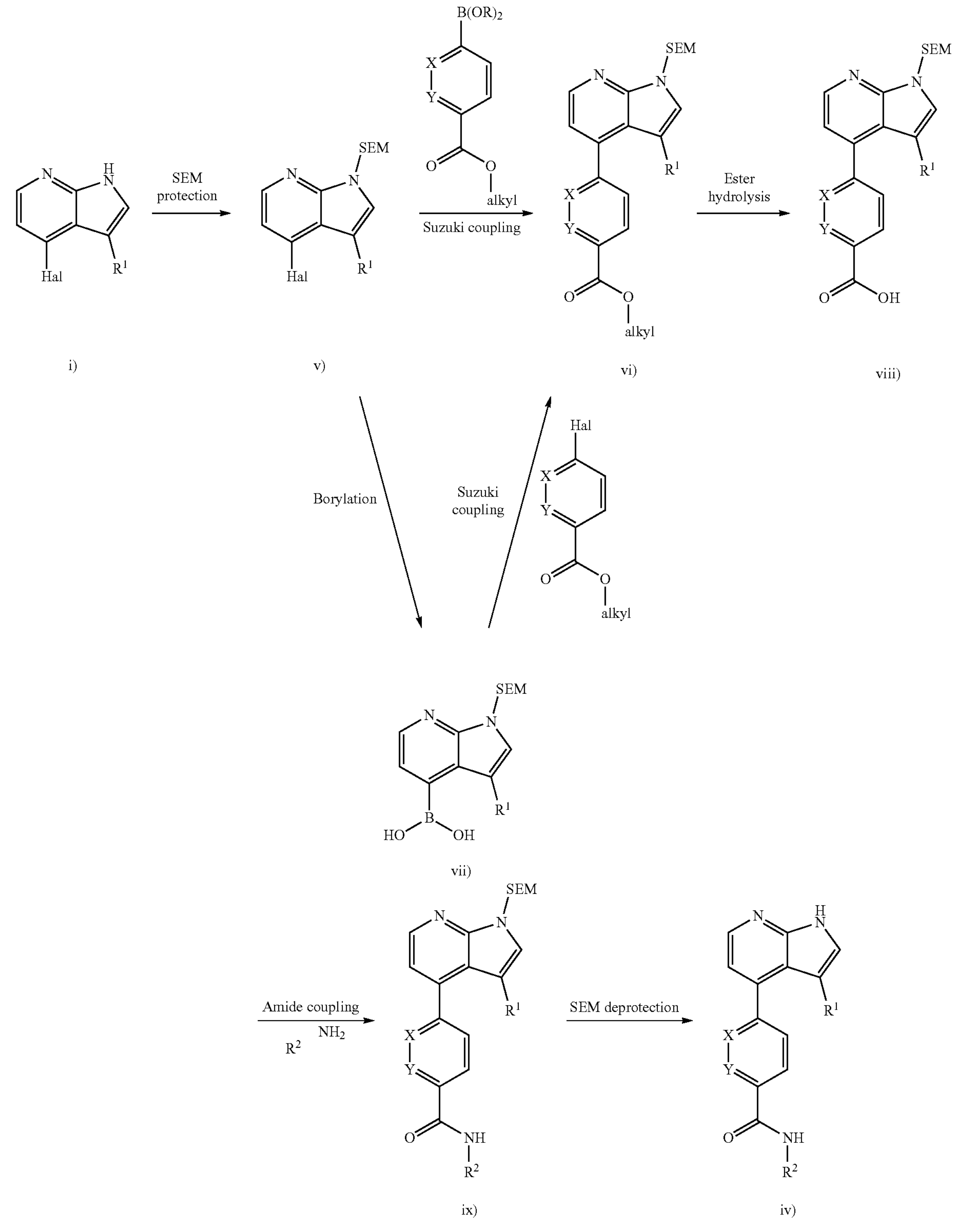

i) v) vi) viii) vii) ix) iv)

Scheme 2 shows a general route for the preparation of compounds of formula iv) starting from halides of formula i). SEM protection to give v) followed by Suzuki coupling with a 4-carboxy aryl boronate provides ester vi). Alternatively, ester vi) can be formed via borylation of v) to give boronate vii) followed by Suzuki coupling with a 4-carboxy aryl halide. Subsequent hydrolysis gives acid precursor viii), with an amide coupling yielding intermediate ix). Removal of the SEM group generates final compounds iv). Mixtures of stereoisomers of iv) can be resolved by chiral chromatography.

Scheme 3: Synthetic Protocol 3

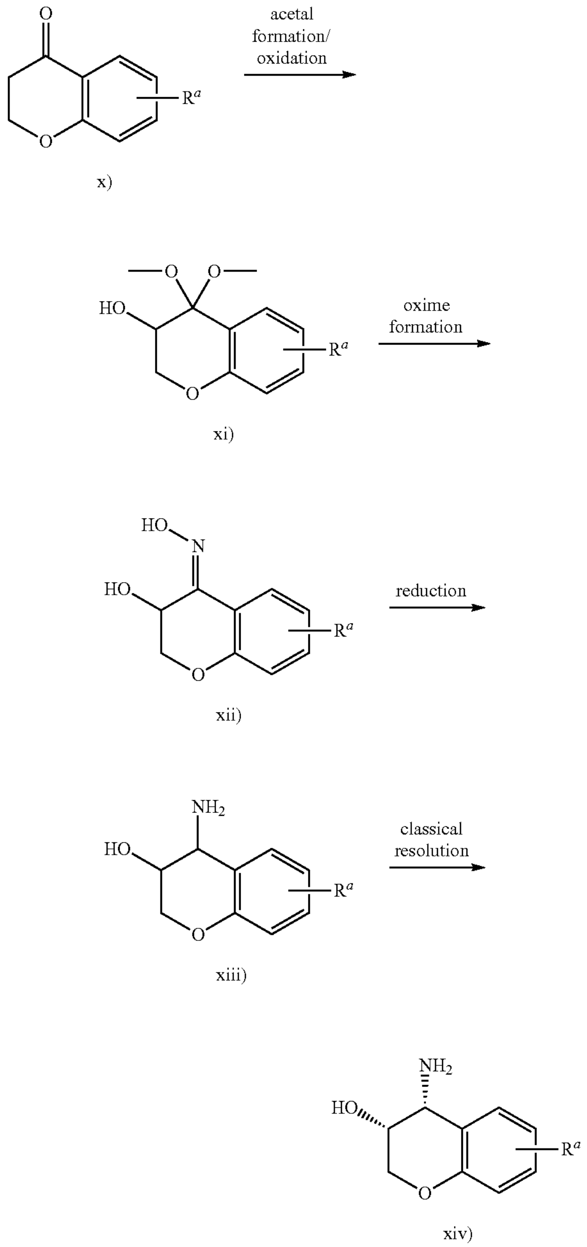

Scheme 3 shows a general route for the preparation of non-commercial amines of formula xiii) and xiv) starting from chroman-4-ones of formula x). Concomitant acetal formation and α-hydroxylation of the chroman-4-one gives intermediate xi). The acetal can be converted to oxime xii) with acid and hydroxylamine hydrochloride. Hydrogenation of the oxime provides amino alcohol xiii), which can be carried forward to the amide coupling in scheme 1 or 2. Alternatively, a classical resolution with a chiral salt can provide the desired isomer xiv), which can be carried forward to the amide coupling in scheme 1 or 2.

Scheme 4: Synthetic Protocol 4

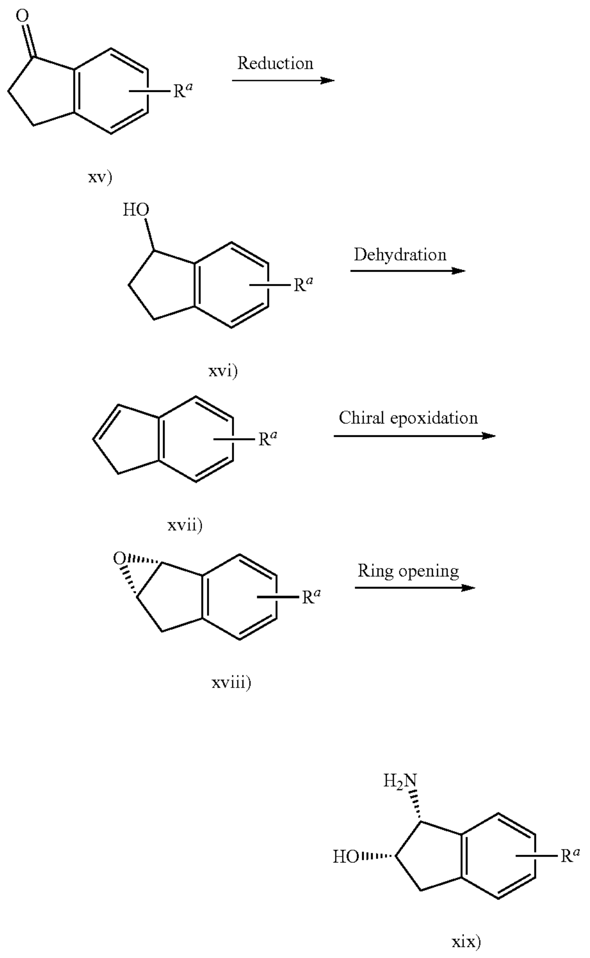

Scheme 4 shows a general route for the preparation of non-commercial amines of formula xix) starting from indan-1-ones of formula xv). The indan-1-one is reduced to form alcohol xvi). Dehydration under acidic conditions provides indene xvii). Chiral epoxidation with (R,R)-Jacobsen's catalyst provides the desired epoxide xviii) with moderate to high enantioselectivity. Ring opening using triflic acid in acetonitrile provides desired cis amino alcohol xix), which can be carried forward to the amide coupling in scheme 1, 2, 21 or 22. Alternatively, amino alcohol xix) can be carried forward according to the transformations in scheme 13 or 14.

Scheme 5: Synthetic Protocol 5

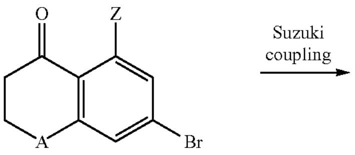

A = O or bond
Z = H or F
xx)

-continued

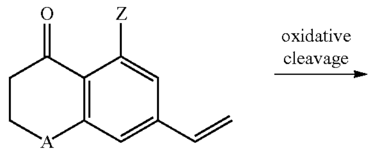

A = O or bond
Z = H or F
xxi)

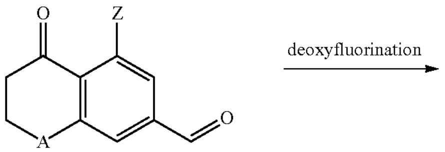

A = O or bond
Z = H or F
xxii)

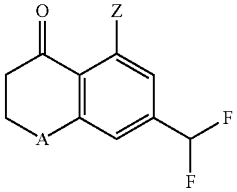

A = O or bond
Z = H or F
xxiii)

Scheme 5 shows a general route for the preparation of the non-commercial chroman-4-one and indan-1-one of formula xxiii) starting from the chroman-4-one and indan-1-one of formula xx). Suzuki coupling with a vinyl boronate gives intermediate xxi). Oxidative cleavage generates aldehyde xxii). Deoxyfluorination provides difluoromethyl product xxiii), which can be carried forward according to the transformations in scheme 3, 4 or 24.

Scheme 6: Synthetic Protocol 6

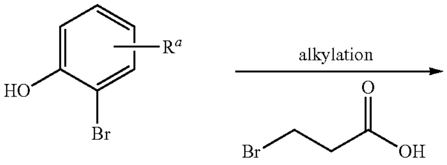

xxiv)

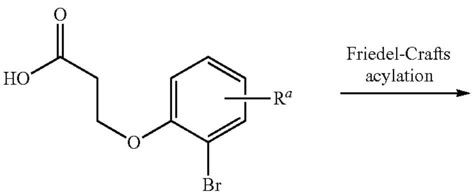

xxv)

-continued

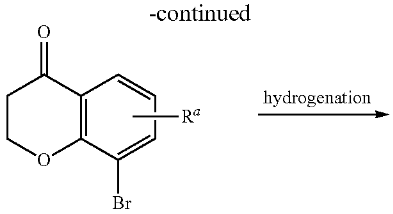

xxvi)

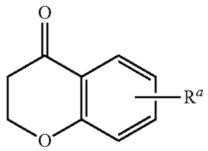

x)

Scheme 6 shows a general route for the preparation of non-commercial chroman-4-ones of formula x) starting from phenols of formula xxiv). Alkylation of the phenol with 3-bromopropanoic acid gives ether xxv). Friedel-Crafts acylation provides cyclized chroman-4-one xxvi). Removal of the bromide under hydrogenation conditions gives desired chroman-4-one x), which can be carried forward according to the transformations in scheme 3 or 20.

Scheme 7: Synthetic Protocol 7

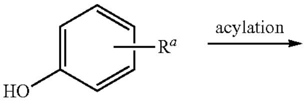

xxvii)

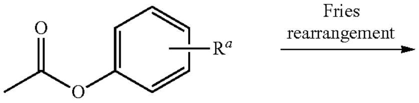

xxviii)

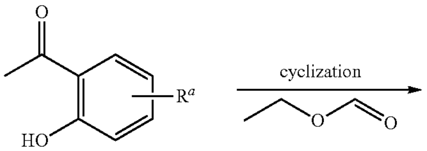

xxix)

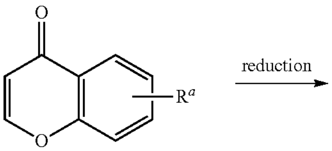

xxx)

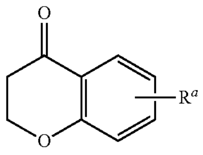

x)

Scheme 7 shows a general route for the preparation of non-commercial chroman-4-ones of formula x) starting from phenols of formula xxvii). Acylation of the phenol with acetyl chloride gives phenyl ester xxviii). Fries rearrangement of the ester gives acetophenone xxix). Cyclization with ethyl formate in the presence of a base gives chromen-4-one xxx). Reduction of the chromen-4-one gives desired chroman-4-one x), which can be carried forward according to the transformations in schemes 3 or 20.

Scheme 8: Synthetic Protocol 8

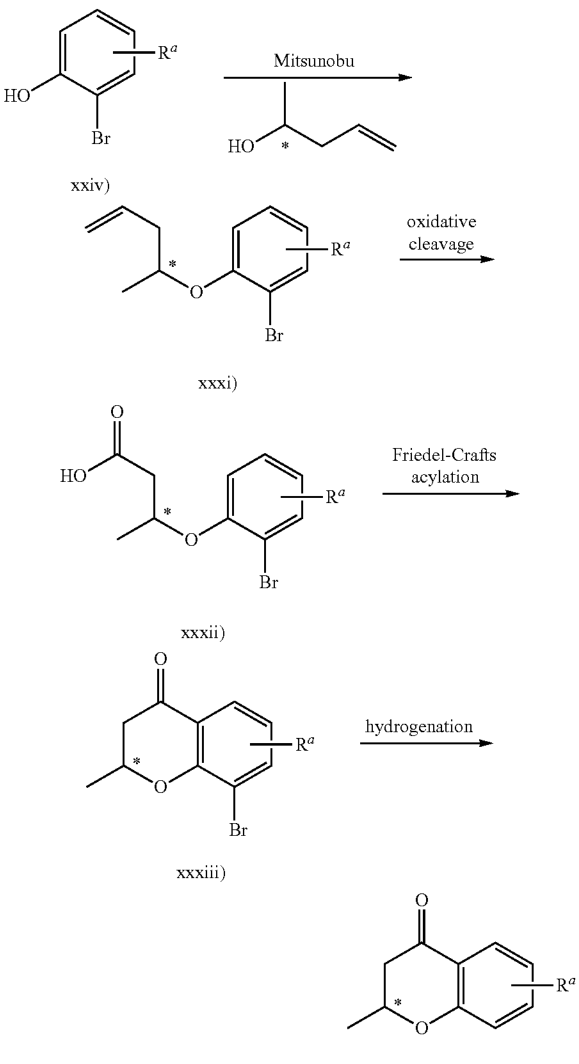

xxiv)

xxxi)

xxxii)

xxxiii)

xxxiv)

Scheme 8 shows a general route for the preparation of non-commercial chiral chroman-4-ones of formula xxxiv) starting from phenols of formula xxiv). Etherification of the phenol with (R)- or (S)-pent-4-en-2-ol under Mitsunobu conditions gives ether xxxi) with chiral inversion. Oxidation of the vinyl group gives carboxylic acid xxxii). Friedel-Crafts acylation provides cyclized chroman-4-one xxxiii). Removal of the bromide under hydrogenation conditions gives desired chroman-4-one xxxiv), which can be carried forward by analogy to the transformations in schemes 3 or 20.

Scheme 9: Synthetic Protocol 9

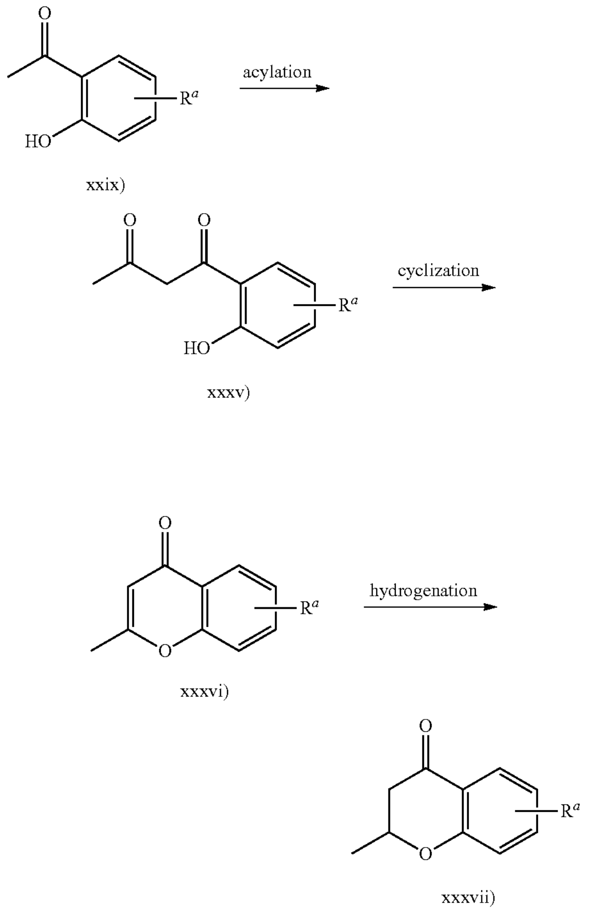

xxix)

xxxv)

xxxvi)

xxxvii)

Scheme 9 shows a general route for the preparation of non-commercial racemic chroman-4-ones of formula xxxvii) starting from phenols of formula xxix). Acylation of the acetophenone with ethyl acetate under basic conditions give diketone xxxv). Cyclization under acidic conditions gives chromen-4-one xxxvi). Reduction of the chromen-4-one gives desired chroman-4-one xxxvii), which can be carried forward by analogy to the transformations in schemes 3 or 20.

Scheme 10: Synthetic Protocol 10

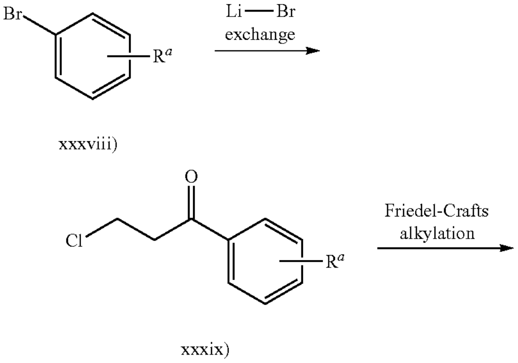

xxxviii)

xxxix)

-continued

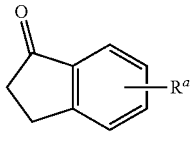

xv)

Scheme 10 shows a general route for the preparation of non-commercial indan-1-ones of formula xv) starting from aryl bromides of formula xxxviii). Lithium-halogen exchange followed by quenching with 3-chloropropanoyl chloride provides chloro ketone xxxix). Friedel-Crafts alkylation provides cyclized indan-1-one xv), which can be carried forward according to the transformations in schemes 4 or 24.

Scheme 11: Synthetic Protocol 11

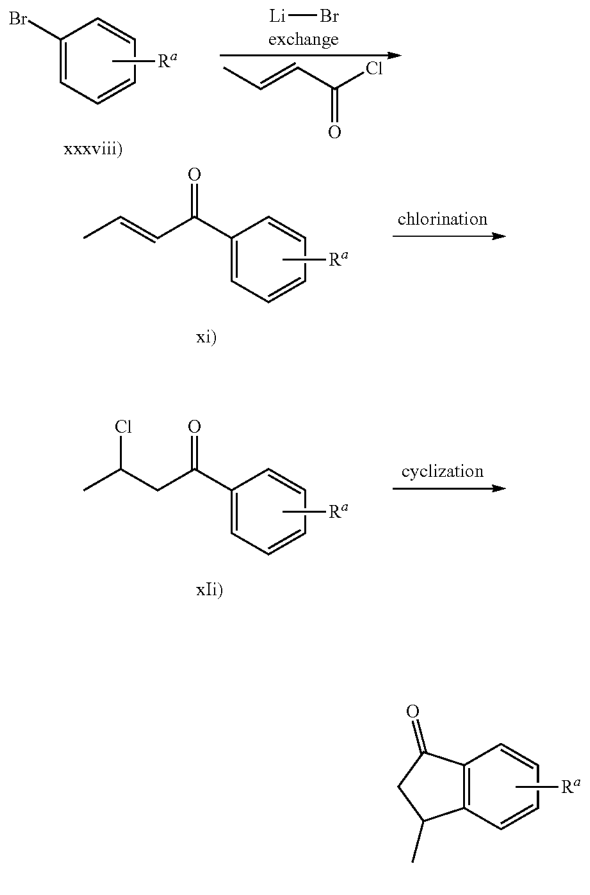

xxxviii)

xi)

xli)

xlii)

Scheme 11 shows a general route for the preparation of non-commercial indan-1-ones of formula xlii) starting from aryl bromides of formula xxxviii). Lithium-halogen exchange followed by quenching with (E)-but-2-enoyl chloride provides enone xl). Chlorination of the enone gives chloro ketone xli). Friedel-Crafts alkylation provides cyclized indan-1-one xlii), which can be carried forward by analogy to the transformations in scheme 4.

Scheme 12: Synthetic Protocol 12

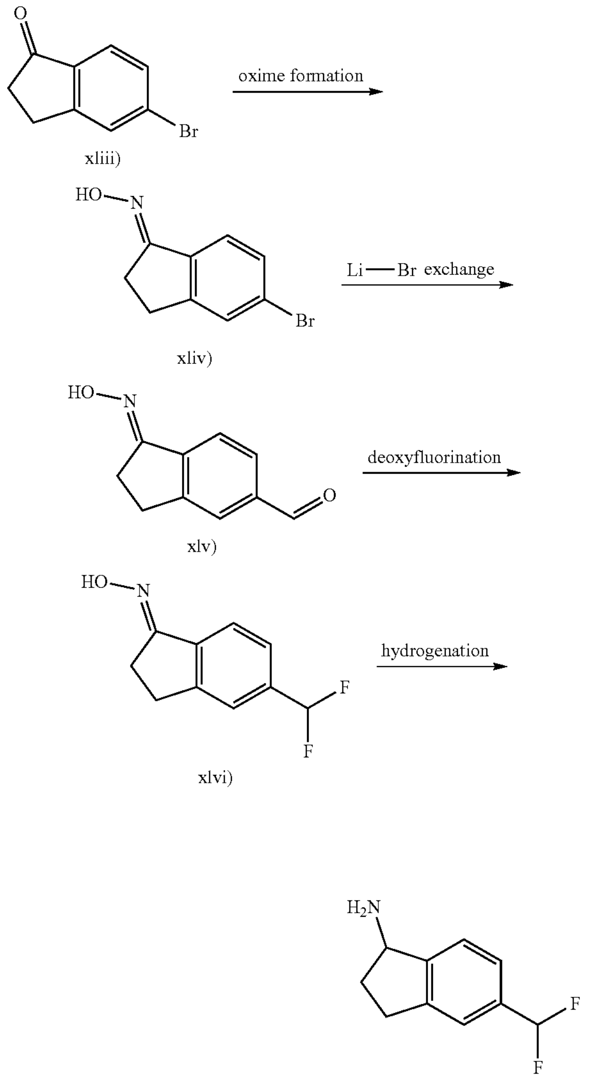

xliii)

xliv)

xlv)

xlvi)

xlvii)

Scheme 12 shows a synthetic route for the preparation of non-commercial amine of formula xlvii) starting from indan-1-one of formula xliii). The ketone can be converted to the oxime xliv) using hyxroxylamine hydrochloride. Lithium-halogen exchange and quenching with DMF provides aldehyde xlv). Deoxyfluorination of the aldehyde gives difluoromethyl product xlvi). Hydrogenation of the oxime gives desired amine xlvii), which can be carried forward to the amide coupling in scheme 1, 2, 21 or 22.

Scheme 13: Synthetic Protocol 13

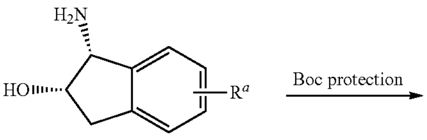

xix)

-continued

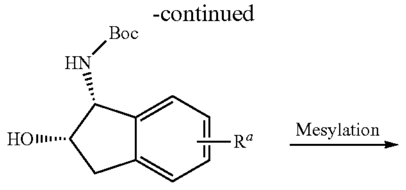

xlviii)

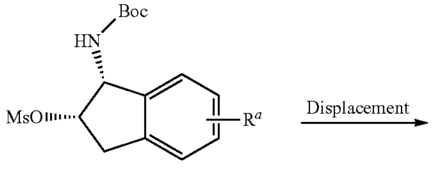

il)

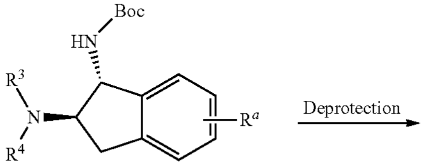

l)

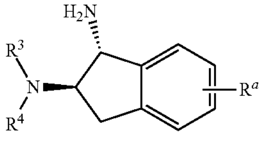

li)

Scheme 13 shows a general route for the preparation of chiral amines of formula li) starting from chiral amino alcohols of formula xix). The amine is first protected using a Boc group to give xlviii). Activation of the alcohol using mesyl chloride gives mesylate il). Displacement of the mesylate with an amine gives Boc-protected diamine l). Removal of the Boc group gives desired amine li), which can be carried forward to the amide coupling in scheme 1, 2, 21 or 22.

Scheme 14: Synthetic Protocol 14

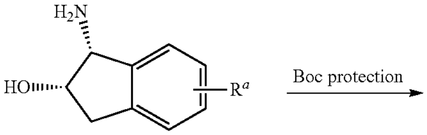

xix)

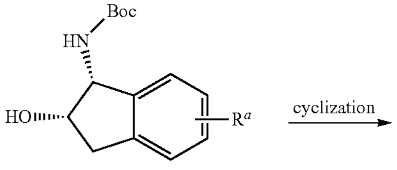

xlviii)

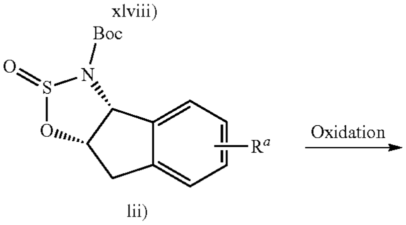

lii)

-continued

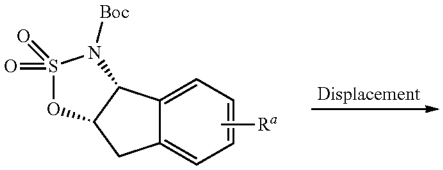

liii)

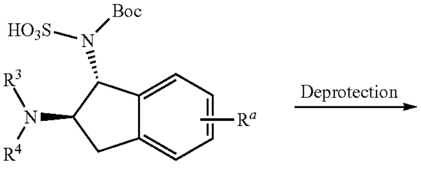

liv)

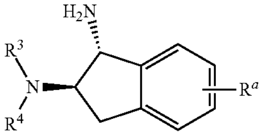

li)

Scheme 14 shows a general route for the preparation of chiral amines of formula li) starting from chiral amino alcohols of formula xix). The amine is first protected using a Boc group to give xlviii). Cyclization of the Boc-protected amino alcohol with thionyl chloride gives dihydro oxathiazole-1-oxide lii). Subsequent oxidation then gives dihydro oxathiazole-1,1-dioxide liii). Ring opening with an amine provides protected diamine liv). Simultaneous acid-mediated hydrolysis of the Boc group and sulfamic acid gives desired amine li), which can be carried forward to the amide coupling in scheme 1, 2, 21 or 22.

Scheme 15: Synthetic Protocol 15

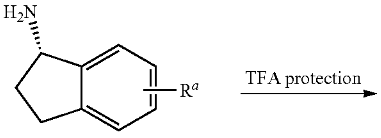

lv)

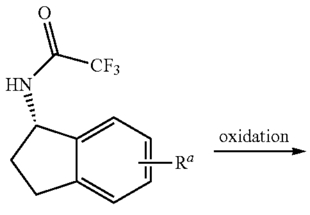

lvi)

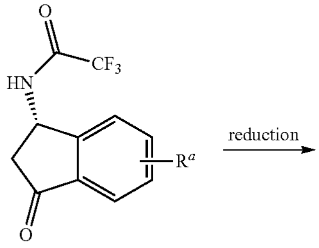

lvii)

-continued

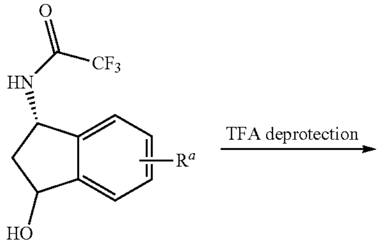

lviii)

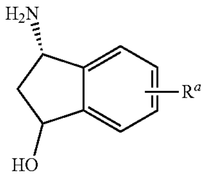

lix)

Scheme 15 shows a general route for the preparation of amino alcohols of formula lix) starting from amino indanes of formula lv). The amine is first protected as the trifluoroacetamide lvi) by treatment with trifluoroacetic anhydride. Oxidation gives amino ketone lvii), followed by reduction to give alcohol lviii). Hydrolysis of the trifluoroacetamide under basic conditions gives desired amine lix), which can be carried forward to the amide coupling in scheme 1, 2, 21 or 22.

Scheme 16: Synthetic Protocol 16

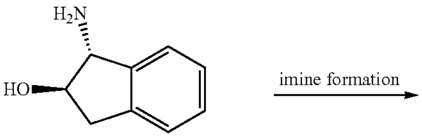

lx)

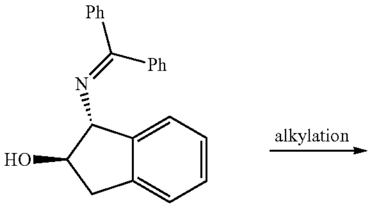

lxi)

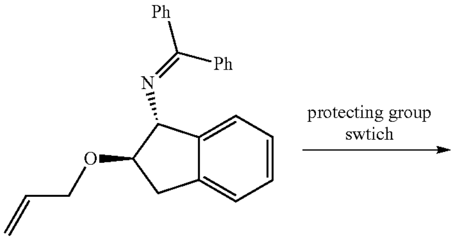

lxii)

-continued

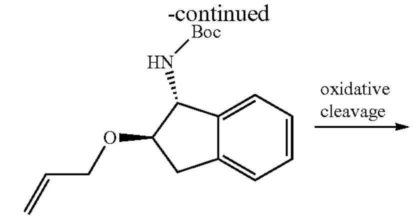

lxiii)

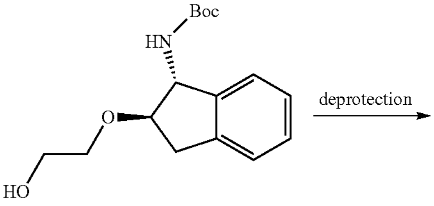

lxvi)

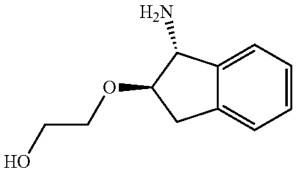

lxv)

Scheme 16 shows a synthetic route for the preparation of the amine of formula lxv) starting from the amino alcohol of formula lx). First, the amine is treated with diphenylmethanimine to give imine lxi). Alkylation of the alcohol with 3-bromoprop-1-ene in the presence of a base gives ether lxii). The protecting group is then switched by sequential treatment with acid followed by di-tert-butyl dicarbonate to give Boc-protected amine lxiii). Oxidative cleavage then provides hydroxy ether lxiv). Removal of the Boc group gives desired amine lxv), which can be carried forward to the amide coupling in scheme 1, 2, 21 or 22.

Scheme 17: Synthetic Protocol 17

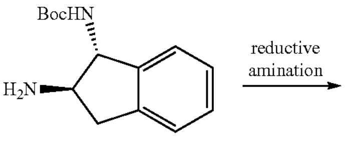

lxvi)

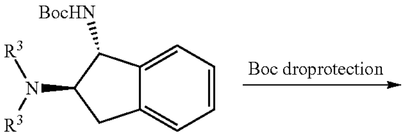

lxvii)

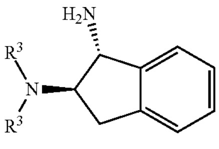

lxviii)

Scheme 17 shows a synthetic route for the preparation of the amine of formula lxviii) starting from the Boc-protected diamine of formula lxvi). First, the amine is treated with paraformaldehyde or acetaldehyde in the presence of a hydride source to give dialkylamine lxvii). Removal of the Boc group gives desired amine lxviii), which can be carried forward to the amide coupling in scheme 1, 2, 21 or 22.

Scheme 18: Synthetic Protocol 18

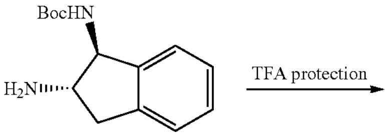

lxvi)

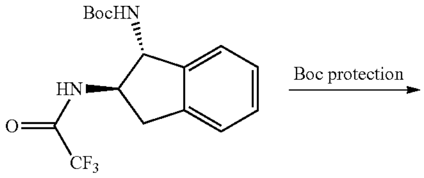

lxix)

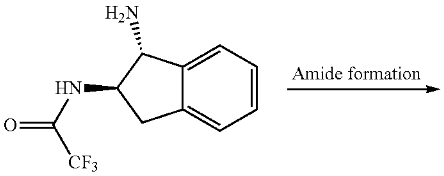

lxx)

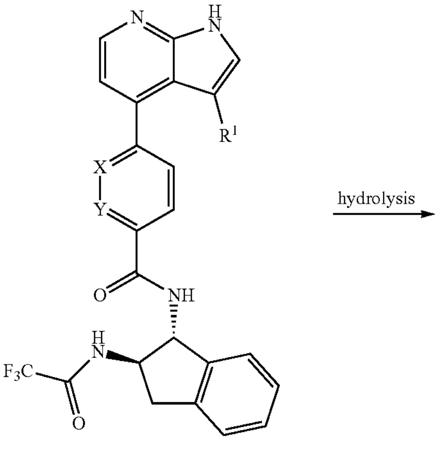

lxxi)

-continued

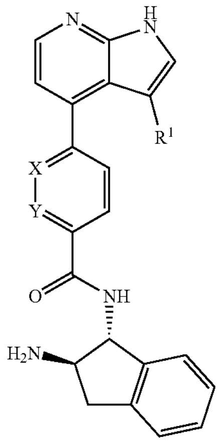

lxxii)

Scheme 18 shows a general route for the preparation of compounds of formula lxxii) starting from the Boc-protected diamine of formula lxvi). The free amine is first protected as the trifluoroacetamide lxix) by treatment with trifluoroacetic anhydride. Removal of the Boc group gives amine lxx). Coupling of the amine with acid iii) gives amide lxxi). Hydrolysis of the trifluoroacetamide under basic conditions gives final product lxxii).

Scheme 19: Synthetic Protocol 19

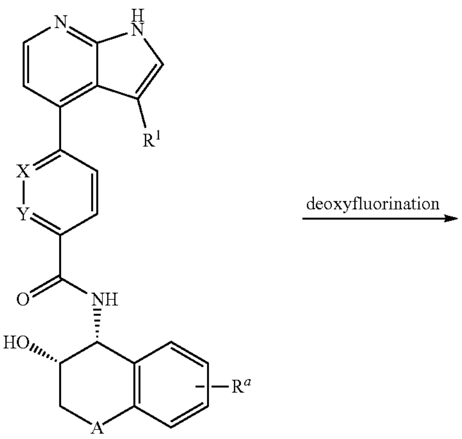

A = O or bond lxxiii)

-continued

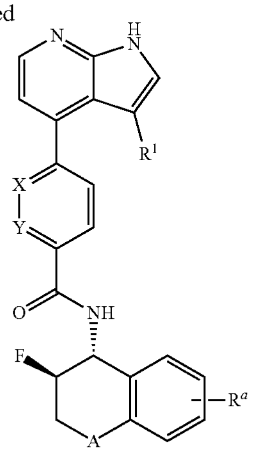

A = O or bond
lxxiv)

Scheme 19 shows a general route for the preparation of compounds of formula lxxiv) starting from alcohols of formula lxxiii). Deoxyfluorination of the alcohol gives final fluoro product lxxiv) with inverted stereochemistry.

Scheme 20: Synthetic Protocol 20

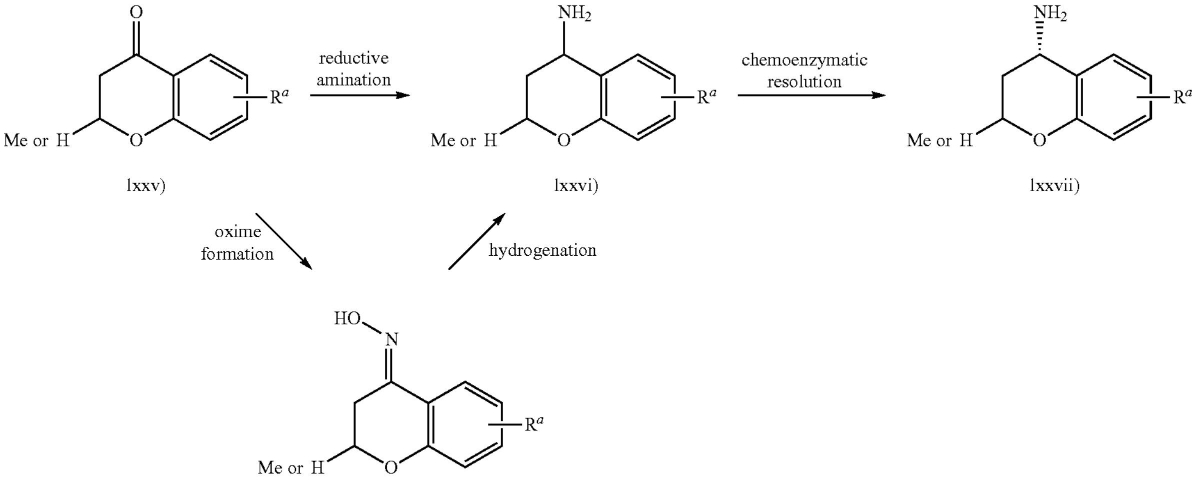

lxxv) lxxvi) lxxvii) xciii)

Scheme 20 shows a general route for the preparation of non-commercial amines of formula lxxvi) and lxxvii) starting from chroman-4-ones of formula lxxv). Reductive amination provides racemic amine lxxvi) directly. Racemate lxxvi) can also be accessed firstly by converting ketone lxxv) to oxime xciii), followed by hydrogenation. Racemate lxxvi) can then be carried forward to the amide coupling in scheme 1 or 2 or resolved by chiral chromatography to isolate the desired stereoisomer lxxvii). Alternatively, a chemoenzymatic resolution with a lipase and methyl-2-methoxyacetate according to the procedure described in US20040157739 can provide the desired amine stereoisomer lxxvii), which can be carried forward to the amide coupling in scheme 1, 2, 21 or 22.

Scheme 21: Synthetic Protocol 21

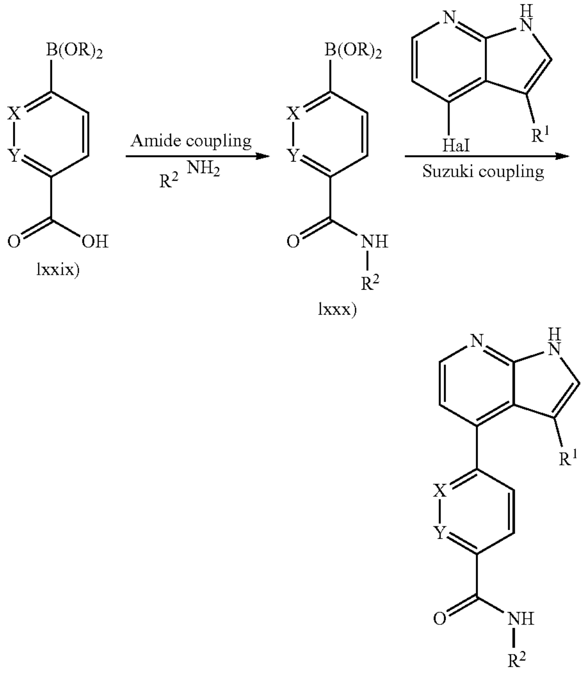

lxxix) lxxx) iv)

Scheme 21 shows a general route for the preparation of compounds of formula iv) starting from aryl carboxylates of formula lxxix). An amide coupling provides boronate lxxx). Suzuki coupling with an appropriately substituted halide yields final compounds iv). Mixtures of stereoisomers of iv) can be resolved by chiral chromatography.

Scheme 22: Synthetic Protocol 22

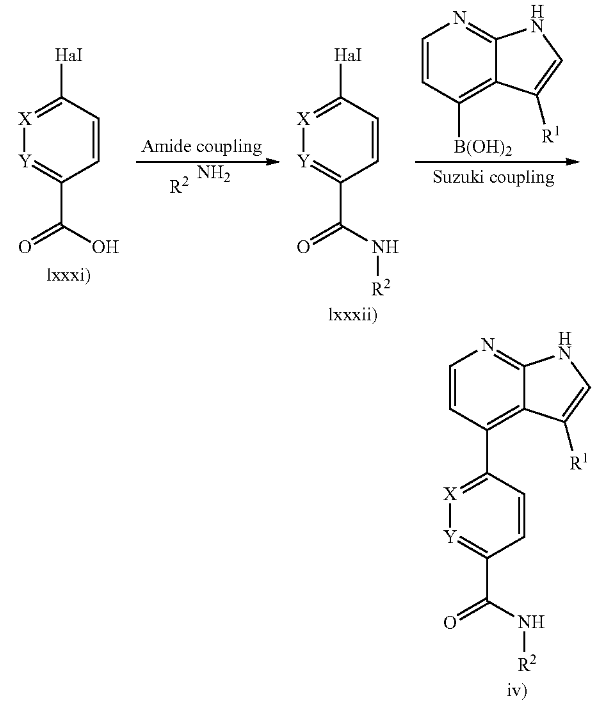

Scheme 22 shows a general route for the preparation of compounds of formula iv) starting from aryl carboxylates of formula lxxxi). An amide coupling provides halide lxxxii). Suzuki coupling with an appropriately substituted boronate yields final compounds iv). Mixtures of stereoisomers of iv) can be resolved by chiral chromatography.

Scheme 23: Synthetic Protocol 23

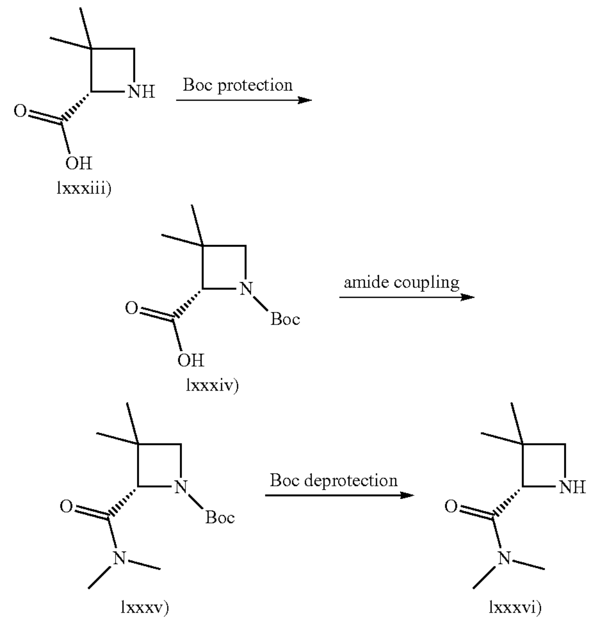

Scheme 23 shows a general route for the preparation of a compound of formula lxxxvi) starting from an amino acid of formula lxxxiii). Protection of the amine with a Boc group gives protected amino acid lxxxiv). Subsequent amide coupling gives protected amino amide lxxxv). Removal of the Boc group yields free amine lxxxvi), which can be carried forward to the displacement reaction in scheme 14.

Scheme 24: Synthetic Protocol 24

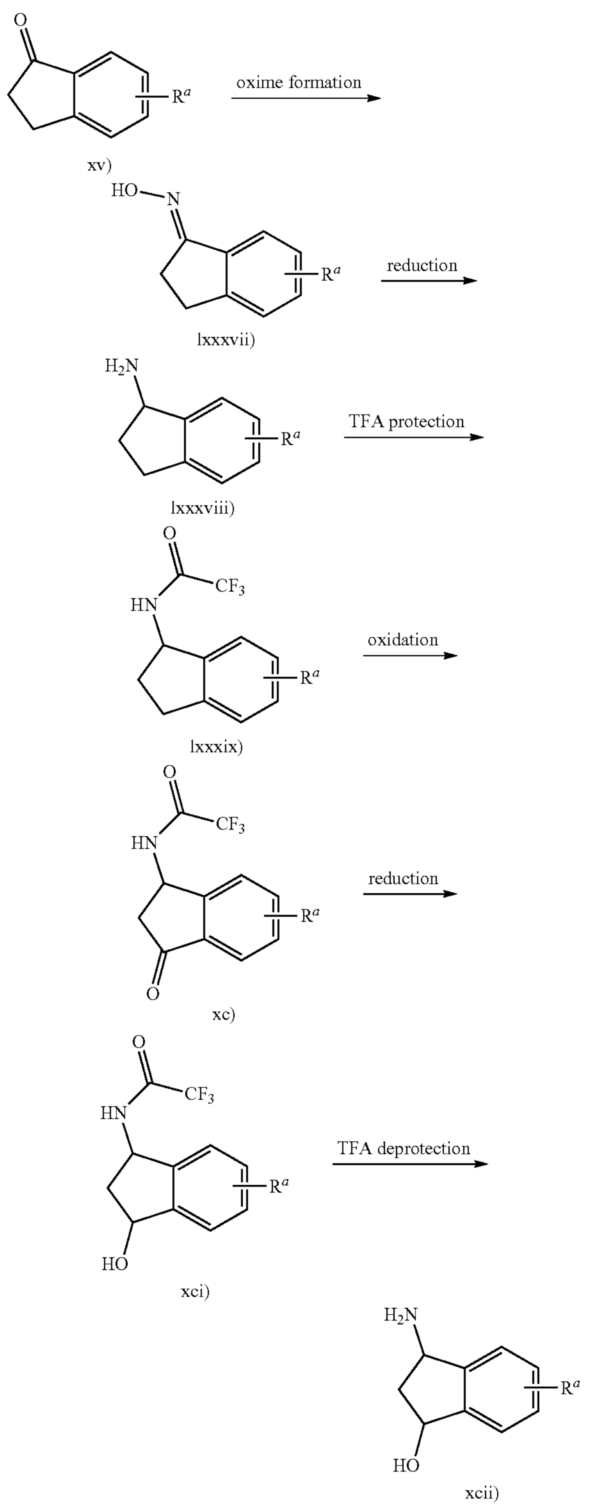

Scheme 24 shows a general route for the preparation of amino alcohols of formula xcii) starting from indan-1-ones of formula xv). The ketone can be converted to the oxime lxxxvii) using hyxroxylamine hydrochloride. Reduction of the oxime gives racemic amine lxxxviii). The amine is then protected as the trifluoroacetamide lxxxix) by treatment with trifluoroacetic anhydride. Oxidation gives protected amino ketone xc), followed by reduction to give alcohol xci). Hydrolysis of the trifluoroacetamide under basic conditions gives desired amine xcii), which can be carried forward to the amide coupling in scheme 1, 2, 21 or 22.

The reactions for preparing compounds of the disclosure can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 5th ed., John Wiley & Sons: New Jersey, (2014), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^{1}H$ or $^{13}C$), infrared (IR) spectroscopy, spectrophotometry (e.g., UV-visible), mass spectrometry (MS), or by chromatographic methods such as high performance liquid chromatography (HPLC) or thin layer chromatography (TLC). Analytical instruments and methods for compound characterization:

LC-MS: Unless otherwise indicated, all liquid chromatography-mass spectrometry (LC-MS) data (sample analyzed for purity and identity) were obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 4 minutes was utilized. The flow rate was constant at 1 mL/min.

Prep LC-MS: Preparative HPLC was performed on a Shimadzu Discovery VP® Preparative system fitted with a Luna 5u C18(2) 100A, AXIA packed, 250×21.2 mm reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 25 minutes was utilized. The flow rate was constant at 20 mL/min. Reactions carried out in a microwave were done so in a Biotage Initiator microwave unit.

Silica gel chromatography: Silica gel chromatography was performed on either a Teledyne Isco CombiFlash® Rf unit or a Biotage® Isolera Four unit.

Proton NMR: Unless otherwise indicated, all 1H NMR spectra were obtained with a Varian 400 MHz Unity Inova 400 MHz NMR instrument (acquisition time=3.5 seconds with a 1 second delay; 16 to 64 scans). Where characterized, all protons were reported in DMSO-d6 solvent as parts-per million (ppm) with respect to residual DMSO (2.50 ppm).

Example embodiments of the disclosure include:

1. A compound of Formula (I):

(I)

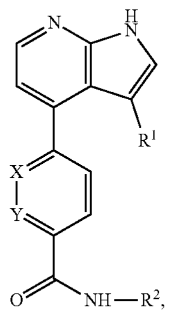

a pharmaceutically acceptable salt thereof, and/or a solvate of any of the foregoing, wherein:

X is chosen from CH and N;

Y is chosen from CH and N, provided that X and Y are not both N;

$R^1$ is chosen from H, halogens, and $C_1$-$C_4$ alkyls; and $R^2$ is chosen from optionally substituted indane and optionally substituted chromane, wherein each optional substituent is independently chosen from halogens, hydroxyl, $C_1$-$C_4$ alkyls, $C_1$-$C_4$ haloalkyls, 4-8-membered monocyclic heterocycles, 4-8-membered bicyclic heterocycles, $NR^3R^4$, and $OC_1$-$C_4$ alkyls, wherein:

each 4-8-membered monocyclic heterocycle, 4-8-membered bicyclic heterocycle, $C_1$-$C_4$ alkyl, and $OC_1$-$C_4$ alkyl is optionally substituted with one to three groups independently chosen from $C_1$-$C_4$ alkyls, $C_1$-$C_4$ hydroxyalkyls, $C_1$-$C_4$ haloalkyls, $OC_1$-$C_4$ alkyls, $OC_1$-$C_4$ hydroxyalkyls, halogens, hydroxyl, and $C(O)NR^5R^6$;

each $R^3$ and $R^4$ is independently chosen from hydrogen and $C_1$-$C_4$ alkyls; and each $R^5$ and $R^6$ is independently chosen from hydrogen and $C_1$-$C_4$ alkyls.

2. The compound of embodiment 1 chosen from compounds of Formula (Ia):

(Ia)

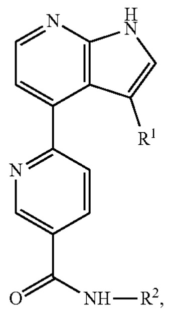

pharmaceutically acceptable salts thereof, and solvates of any of the foregoing, wherein:

$R^1$ is chosen from H, halogens, and $C_1$-$C_4$ alkyls; and $R^2$ is chosen from optionally substituted indane and optionally substituted chromane, wherein each optional substituent is independently chosen from halogens, hydroxyl, $C_1$-$C_4$ alkyls, $C_1$-$C_4$ haloalkyls, 4-8-membered monocyclic heterocycles, 4-8-membered bicyclic heterocycles, $NR^3R^4$, and $OC_1$-$C_4$ alkyls, wherein:

each 4-8-membered monocyclic heterocycle, 4-8-membered bicyclic heterocycle, $C_1$-$C_4$ alkyl, and $OC_1$-$C_4$ alkyl is optionally substituted with one to three groups independently chosen from $C_1$-$C_4$ alkyls, $C_1$-$C_4$ hydroxyalkyls, $C_1$-$C_4$ haloalkyls, $OC_1$-$C_4$ alkyls, $OC_1$-$C_4$ hydroxyalkyls, halogens, hydroxyl, and $C(O)NR^5R^6$;

each $R^3$ and $R^4$ is independently chosen from hydrogen and $C_1$-$C_4$ alkyls; and each $R^5$ and $R^6$ is independently chosen from hydrogen and $C_1$-$C_4$ alkyls.

3. The compound of embodiment 1 chosen from compounds of Formula (Ib):

(Ib)

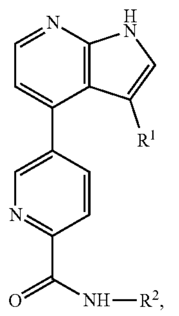

pharmaceutically acceptable salts thereof, and solvates of any of the foregoing, wherein:

$R^1$ is chosen from H, halogens, and $C_1$-$C_4$ alkyls; and $R^2$ is chosen from optionally substituted indane and optionally substituted chromane, wherein each optional substituent is independently chosen from halogens, hydroxyl, $C_1$-$C_4$ alkyls, $C_1$-$C_4$ haloalkyls, 4-8-membered monocyclic heterocycles, 4-8-membered bicyclic heterocycles, $NR^3R^4$, and $OC_1$-$C_4$ alkyls, wherein:

each 4-8-membered monocyclic heterocycle, 4-8-membered bicyclic heterocycle, $C_1$-$C_4$ alkyl, and $OC_1$-$C_4$ alkyl is optionally substituted with one to three groups independently chosen from $C_1$-$C_4$ alkyls, $C_1$-$C_4$ hydroxyalkyls, $C_1$-$C_4$ haloalkyls, $OC_1$-$C_4$ alkyls, $OC_1$-$C_4$ hydroxyalkyls, halogens, hydroxyl, and $C(O)NR^5R^6$;

each $R^3$ and $R^4$ is independently chosen from hydrogen and $C_1$-$C_4$ alkyls; and each $R^5$ and $R^6$ is independently chosen from hydrogen and $C_1$-$C_4$ alkyls.

4. The compound of embodiment 1 chosen from compounds of Formula (Ic):

(Ic)

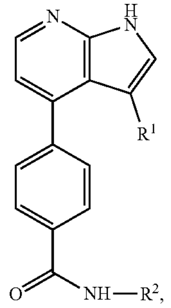

pharmaceutically acceptable salts thereof, and solvates of any of the foregoing, wherein:

$R^1$ is chosen from H, halogens, and $C_1$-$C_4$ alkyls; and $R^2$ is chosen from optionally substituted indane and optionally substituted chromane, wherein each optional substituent is independently chosen from halogens, hydroxyl, $C_1$-$C_4$ alkyls, $C_1$-$C_4$ haloalkyls, 4-8-membered monocyclic heterocycles, 4-8-membered bicyclic heterocycles, $NR^3R^4$, and $OC_1$-$C_4$ alkyls, wherein:

each 4-8-membered monocyclic heterocycle, 4-8-membered bicyclic heterocycle, $C_1$-$C_4$ alkyl, and $OC_1$-$C_4$ alkyl is optionally substituted with one to three groups independently chosen from $C_1$-$C_4$ alkyls, $C_1$-$C_4$ hydroxyalkyls, $C_1$-$C_4$ haloalkyls, $OC_1$-$C_4$ alkyls, $OC_1$-$C_4$ hydroxyalkyls, halogens, hydroxyl, and $C(O)NR^5R^6$;

each $R^3$ and $R^4$ is independently chosen from hydrogen and $C_1$-$C_4$ alkyls; and each $R^5$ and $R^6$ is independently chosen from hydrogen and $C_1$-$C_4$ alkyls.

5. The compound, pharmaceutically acceptable salt, or solvate of any one of embodiments 1 to 4, wherein $R^2$ is optionally substituted indane.

6. The compound, pharmaceutically acceptable salt, or solvate of any one of embodiments 1 to 4, wherein $R^2$ is optionally substituted chromane.

7. The compound, pharmaceutically acceptable salt thereof, or solvate of any one of embodiments 1 to 4, wherein:

$R^2$ is chosen from indane substituted with one to four Ra and chromane substituted with one to four Ra, wherein each Ra is independently chosen from halogens, hydroxyl, $C_1$-$C_4$ alkyls, $C_1$-$C_4$ haloalkyls, 4-8-membered monocyclic heterocycles, 4-8-membered bicyclic heterocycles, $NR^3R^4$, and $OC_1$-$C_4$ alkyls, wherein:

each 4-8-membered monocyclic heterocycle, 4-8-membered bicyclic heterocycle, $C_1$-$C_4$ alkyl, and $OC_1$-$C_4$ alkyl is optionally substituted with one to three groups independently chosen from $C_1$-$C_4$ alkyls, $C_1$-$C_4$ hydroxyalkyls, $C_1$-$C_4$ haloalkyls, $OC_1$-$C_4$ alkyls, $OC_1$-$C_4$ hydroxyalkyls, halogens, hydroxyl, and $C(O)NR^5R^6$;

each $R^3$ and $R^4$ is independently chosen from hydrogen and $C_1$-$C_4$ alkyls; and each $R^5$ and $R^6$ is independently chosen from hydrogen and $C_1$-$C_4$ alkyls.

8. The compound, pharmaceutically acceptable salt, or solvate of any one of embodiments 1 to 4, wherein $R^1$ is chosen from hydrogen, fluorine, and methyl.

9. The compound, pharmaceutically acceptable salt, or solvate of embodiment 8, wherein $R^1$ is hydrogen.

10. The compound, pharmaceutically acceptable salt, or solvate of embodiment 8, wherein $R^1$ is fluorine.

11. The compound, pharmaceutically acceptable salt, or solvate of embodiment 8, wherein $R^1$ is methyl.

12. The compound, pharmaceutically acceptable salt, or solvate of any one of embodiments 1 to 11, wherein $R^2$ is chosen from indane substituted with one group chosen from halogens, hydroxyl, or $C_1$-$C_4$ alkyls and chromane substituted with one group chosen from halogens, hydroxyl, or $C_1$-$C_4$ alkyls.

13. The compound, pharmaceutically acceptable salt, or solvate of any one of embodiments 1 to 11, wherein $R^2$ is chosen from indane substituted with one or two independently chosen halogens and chromane substituted with one or two independently chosen halogens.

14. The compound, pharmaceutically acceptable salt, or solvate of any one of embodiments 1 to 11, wherein $R^2$ is chosen from indane substituted with one group chosen from halogens and hydroxyl and chromane substituted with one group chosen from halogens and hydroxyl.

15. The compound, pharmaceutically acceptable salt, or solvate of any one of embodiments 1 to 11, wherein $R^2$ is chosen from indane substituted with one or two independently chosen halogens and one hydroxyl and chromane substituted with one or two independently chosen halogens and one hydroxyl.

16. The compound, pharmaceutically acceptable salt, or solvate of any one of embodiments 1 to 11, wherein $R^2$ is chosen from indane substituted with one or two independently chosen halogens, one hydroxyl, and one group chosen from $C_1$-$C_4$ alkyls and $C_1$-$C_4$ haloalkyls and chromane substituted with one or two independently chosen halogens, one hydroxyl, and one group chosen from $C_1$-$C_4$ alkyls and $C_1$-$C_4$ haloalkyls.

17. The compound, pharmaceutically acceptable salt, or solvate of any one of embodiments 1 to 11, wherein $R^2$ is chosen from indane substituted with one or two independently chosen halogens and one group chosen from 4-8-membered monocyclic heterocycles and 4-8-membered bicyclic heterocycles, wherein each 4-8 membered monocylic heterocycle and 4-8 membered bicyclic heterocycle is optionally substituted with one to three groups independently chosen from $C_1$-$C_4$ alkyls, $C_1$-$C_4$ haloalkyls, $C_1$-$C_4$ hydroxyalkyls, $OC_1$-$C_4$ alkyls, $OC_1$-$C_4$ hydroxyalkyls, halogens, hydroxyl, and $C(O)NR^5R^6$ and chromane substituted with one or two independently chosen halogens and one group chosen from 4-8-membered monocyclic heterocycles and 4-8-membered bicyclic heterocycles, wherein each 4-8 membered monocylic heterocycle and 4-8 membered bicyclic heterocycle is optionally substituted with one to three groups independently chosen from $C_1$-$C_4$ alkyls, $C_1$-$C_4$ haloalkyls, $C_1$-$C_4$ hydroxyalkyls, $OC_1$-$C_4$ alkyls, $OC_1$-$C_4$ hydroxyalkyls, halogens, hydroxyl, and $C(O)NR^5R^6$, wherein:

each $R^3$ and $R^4$ is independently chosen from hydrogen and $C_1$-$C_4$ alkyls; and each $R^5$ and $R^6$ is independently chosen from hydrogen and $C_1$-$C_4$ alkyls.

18. The compound, pharmaceutically acceptable salt, or solvate of embodiment 17, wherein the 4-8-membered monocyclic heterocycle is an azetidine optionally substituted with one or two groups independently chosen from $C_1$-$C_4$ alkyls, $OC_1$-$C_4$ alkyls, halogens, hydroxyl, $C(O)NH_2$, and $C(O)N(CH_3)_2$ or a pyrrolidine optionally substituted with one or two groups independently chosen from $C_1$-$C_4$ alkyls, $OC_1$-$C_4$ alkyls, halogens, hydroxyl, $C(O)NH_2$, and $C(O)N(CH_3)_2$.

19. The compound, pharmaceutically acceptable salt, or solvate of any one of embodiments 1 to 18, wherein each halogen is fluorine or chlorine.

20. The compound, pharmaceutically acceptable salt, or solvate of any one of embodiments 1 to 4, wherein $R^2$ is chosen from:

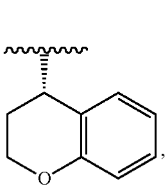,
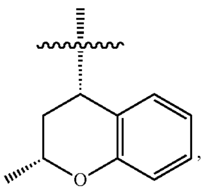,
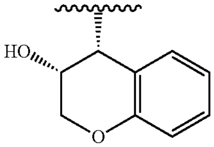,
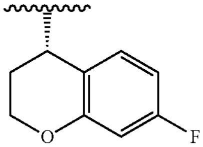,
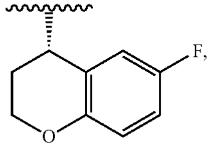,
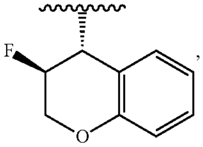,
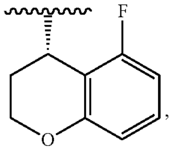,
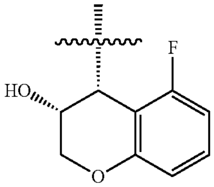,
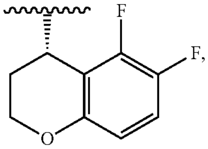,
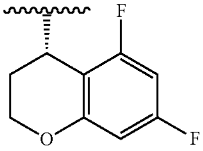,
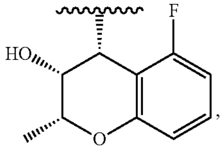,
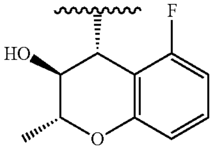,
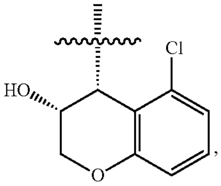,
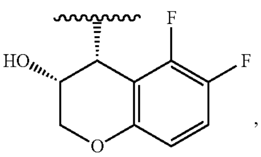, -continued
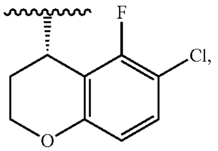
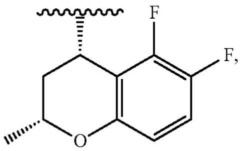
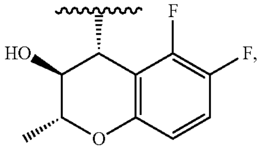
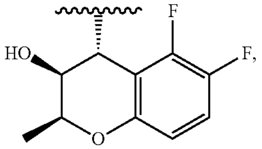
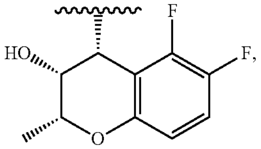
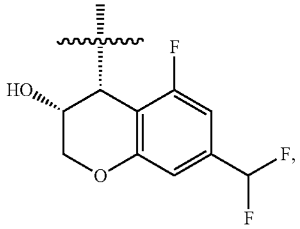
and
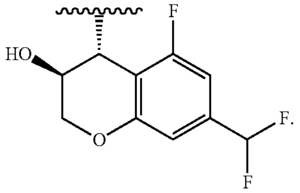 [SMILES: *[C@@H]1c2c(F)cc(C(F)F)cc2OC[C@H]1O]
21. The compound, pharmaceutically acceptable salt, or solvate of any one of embodiments 1 to 4, wherein $R^2$ is chosen from:
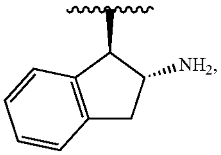
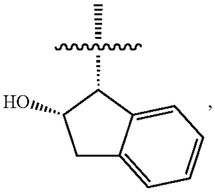
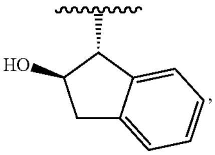
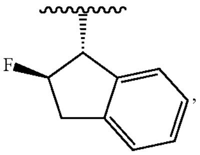
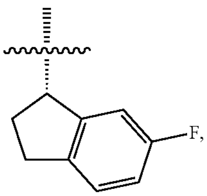
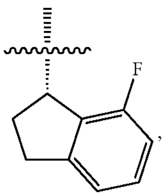
-continued
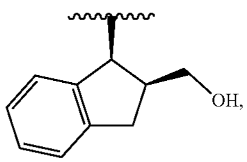
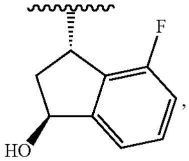
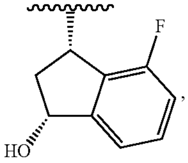
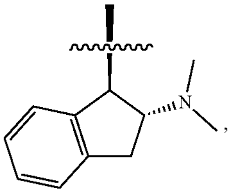
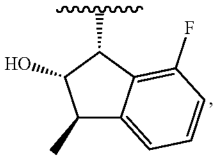
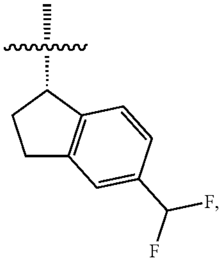
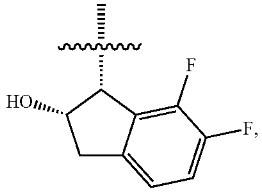
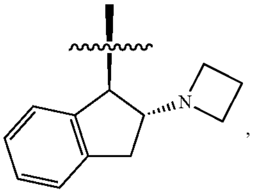
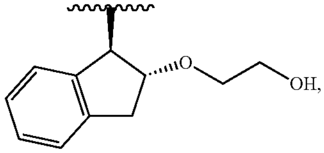
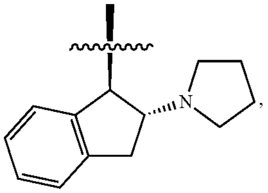
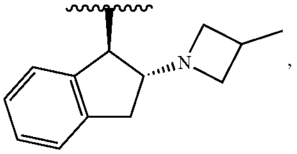
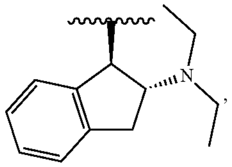
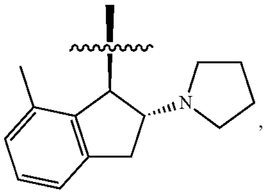
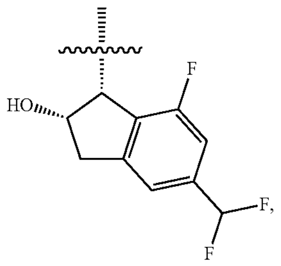
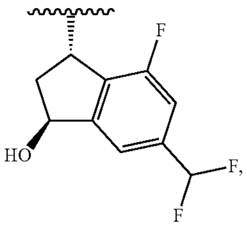

-continued
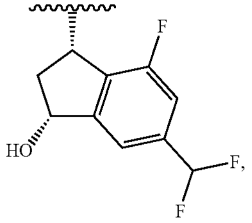
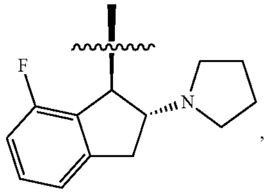
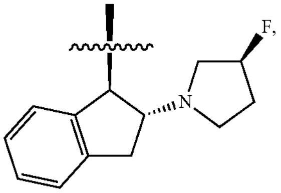
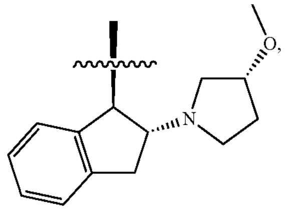
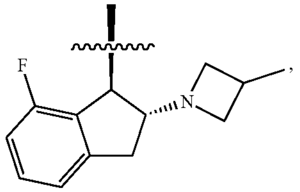
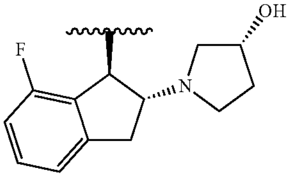
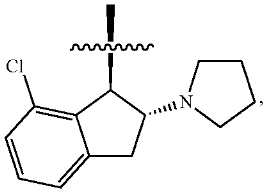
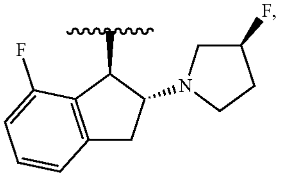
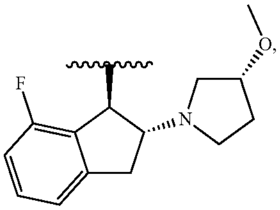
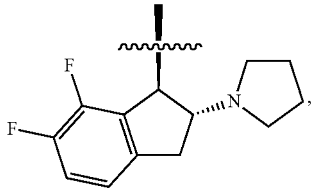
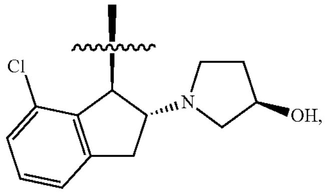
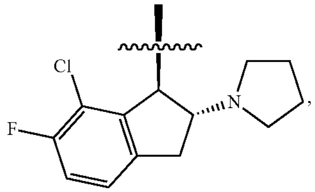
-continued
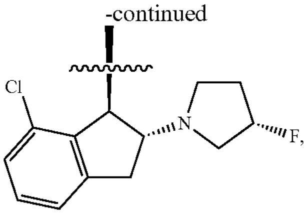
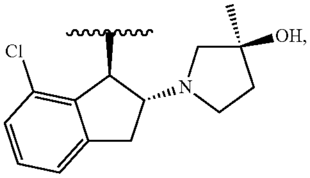
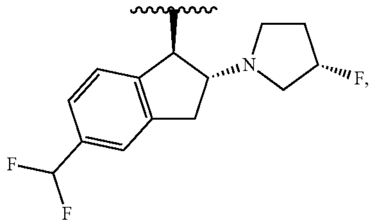
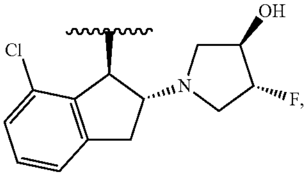
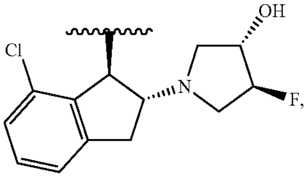
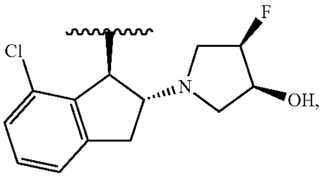
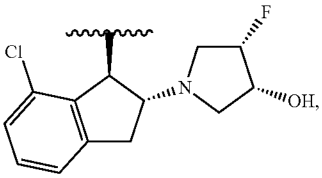
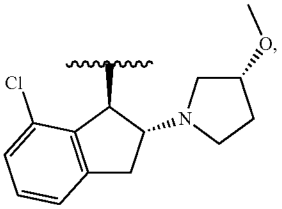
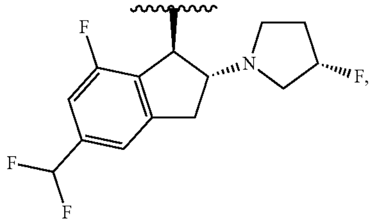

-continued

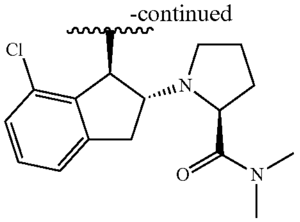

and

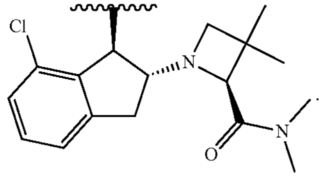

22. A pharmaceutical composition comprising:
- at least one compound chosen from compounds of any one of embodiments 1 to 21, pharmaceutically acceptable salts thereof, and solvates of any of the foregoing; and
- at least one pharmaceutically acceptable excipient.

23. A method of treating a subject afflicted with a disease mediated by protein kinase A (PKA) comprising administering to the subject a therapeutically effective amount of a compound chosen from compounds of any one of embodiments 1 to 21, pharmaceutically acceptable salts thereof, and solvates of any of the foregoing and/or a pharmaceutical composition of embodiment 22.

24. The method of embodiment 23, wherein the disease mediated by PKA is characterized by constitutive activation of PKA signaling.

25. The method of embodiment 23 or 24, wherein the disease mediated by PKA is characterized by a PRKACA fusion.

26. The method of any one of embodiments 23 to 25, wherein the disease mediated by PKA is characterized by a DNAJB1-PRKAC fusion.

27. The method of any one of embodiments 23 to 26, wherein the disease mediated by PKA is fibrolamellar carcinoma.

28. The method of any one of embodiments 23 to 26, wherein the disease mediated by PKA is a multiple neoplasia syndrome.

29. The method of any one of embodiments 23 to 26, wherein the disease mediated by PKA is Carney complex (CNC).

30. The method of embodiment 23 or 24, wherein the disease mediated by PKA is characterized by an activating mutation in PRKACA.

31. The method of any one of embodiments 23 to 24 and 30, wherein the disease mediated by PKA is characterized by an L205R mutation in PRKACA.

32. The method of embodiment 23 or 24, wherein the disease mediated by PKA is characterized by a GNAS gene mutation.

33. The method of any one of embodiments 23, 24, and 30-32, wherein the disease mediated by PKA is chosen from pituitary cancer, kidney cancer, ovarian cancer, testicular cancer, thyroid ademona, Villous colon cancer, intraductal papillary mucinous neoplasms (IPMN), intrahepatic cholangiocarcinomas, inflammatory liver cancer, and McCune-Albright syndrome.

34. The method of embodiment 33, wherein the disease mediated by PKA is a testicular human stromal Leydig cell tumor.

35. The method of embodiment 33, wherein the disease mediated by PKA is inflammatory liver cancer characterized by STAT3 activation.

36. The method of embodiment 33, wherein the disease mediated by PKA is McCune-Albright syndrome.

37. The method of embodiment 36, wherein the McCune-Albright syndrome is associated with fibrous dysplasia of bone (FD), café-au-lait macules, precocious puberty, hyperthyroidism, Cushing syndrome, and pituitary gigantism/acromegaly.

38. The method of any one of embodiments 23 to 25, wherein the disease is polycystic kidney disease (PKD).

39. The method of embodiment 38, wherein the PKD is characterized by one or more mutations in PKD1 (polycystin-1 protein, PC-1) and PKD2 (polycystin-2 protein, PC-2).

EXAMPLES

The following examples are intended to be illustrative and are not meant in any way to limit the scope of the disclosure.

The synthetic schemes listed below are meant to provide general guidance in connection with preparing compounds of the present disclosure. One of ordinary skill in the art would understand that the preparations shown can be modified and/or optimized using general knowledge of organic chemistry.

Preparation of Example Compounds of the Disclosure

Abbreviations

AcOH acetic acid
BAST bis(2-methoxyethyl)aminosulfur trifluoride
$Boc_2O$ di-tert-butyl dicarbonate
C Celsius
DAST (diethylamino)sulfur trifluoride
dba dibenzylideneacetone
DCM dichloromethane
DCE dichloroethane
DIAD diisopropyldicarboxylate
DIPEA diisopropylethylamine (also DIEA)
DMAP 4-(dimethylamino)pyridine
DMF dimethyl formamide
DMS dimethylsulfide
DMSO dimethylsulfoxide
dppf (diphenylphosphino)ferrocene
EDCI 1-ethyl-3-(3-dimethylaminopropyl)carbodiimide
EtOH ethanol
EtOAc ethyl acetate
h hours
HATU 1-[bis(dimethylamino)methylene]-1H-1,2,3-triazolo[4,5-b]pyridinium 3-oxid hexafluorophosphate
HPLC high performance liquid chromatography
HTRF Homogenous Time Resolved Fluorescence
HTS high throughput screening
$IC_{50}$ inhibitory concentration 50%
IMDM Iscove's Modified Dulbecco's Medium
IPA isopropyl alcohol
KOAc potassium acetate
LCMS liquid chromatography-mass spectrometry
mCPBA meta-chloroperbenzoic acid
MeCN acetonitrile
min minutes
MeOH methanol
MPLC medium performance liquid chromatography
MsCl mesyl chloride PE petroleum ether
Pin pinacolato
PyBOP® (benzotriazol-1-yloxy)tripyrrolidinophosphonium hexafluorophosphate
rpm revolutions per minute
rt room temperature (also r.t.)
SEM-Cl 2-(trimethylsilyl)ethoxymethyl chloride
SFC supercritical fluid chromatography
T3P® propylphosphonic anhydride
TEA triethylamine
TFA trifluoroacetic acid
TFAA trifluoroacetic anhydride
TfOH triflic acid
THF tetrahydrofuran
TLC thin layer chromatography
TsOH p-toluenesulfonic acid Methods for preparing compounds of the disclosure can be carried out in suitable solvents which can be readily selected by one of ordinary skill in the art of organic synthesis. Suitable solvents can be substantially non-reactive with the starting materials (reactants), intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one of ordinary skill in the art. The chemistry of protecting groups can be found, for example, in Wuts and Greene, Protective Groups in Organic Synthesis, 5th ed., John Wiley & Sons: New Jersey, (2014), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^{1}H$ or $^{13}C$), infrared (IR) spectroscopy, spectrophotometry (e.g., UV-visible), mass spectrometry (MS), or by chromatographic methods such as high performance liquid chromatography (HPLC) or thin layer chromatography (TLC). Analytical instruments and methods for compound characterization:

LC-MS: Unless otherwise indicated, all liquid chromatography-mass spectrometry (LC-MS) data (sample analyzed for purity and identity) were obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.1% formic acid in $H_2O$ and 0.1% formic acid in acetonitrile. A constant gradient from 95% aqueous/5% organic to 5% aqueous/95% organic mobile phase over the course of 4 minutes was utilized. The flow rate was constant at 1 mL/min.

Prep LC-MS: Preparative HPLC was performed on a Shimadzu Discovery VP® Preparative system fitted with a Luna 5u C18(2) 100A, AXIA packed, 250×21.2 mm reverse-phase column at 22.4 degrees Celsius. The mobile phase consisted of a mixture of solvent 0.1% formic acid in $H_2O$ and 0.1% formic acid in acetonitrile. A constant gradient from 95% aqueous/5% organic to 5% aqueous/95% organic mobile phase over the course of 25 minutes was utilized. The flow rate was constant at 20 mL/min. Reactions carried out in a microwave were done so in a Biotage Initiator microwave unit.

Silica gel chromatography: Silica gel chromatography was performed on either a Teledyne Isco CombiFlash® Rf unit or a Biotage® Isolera Four unit.

Proton NMR: Unless otherwise indicated, all $^{1}H$ NMR spectra were obtained with a Varian 400 MHz Unity Inova 400 MHz NMR instrument (acquisition time=3.5 seconds with a 1 second delay; 16 to 64 scans). Where characterized, all protons were reported in DMSO-d6 solvent as parts-per million (ppm) with respect to residual DMSO (2.50 ppm).

One of ordinary skill in the art will recognize that modifications of the gradient, column length, and flow rate are possible and that some conditions may be more suitable for compound characterization than others, depending on the chemical species being analyzed.

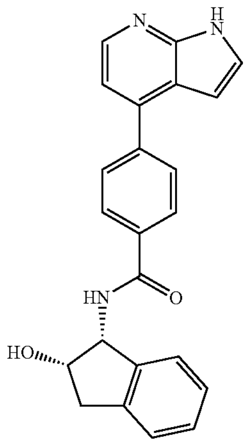 [SMILES: O=C(N[C@@H]1c2ccccc2C[C@@H]1O)c1ccc(-c2ccnc3[nH]ccc23)cc1]

Example 1: N-[(1R,2S)-2-Hydroxy-2,3-dihydro-1H-inden-1-yl]-4-{1H-pyrrolo[2,3-b]pyridin-4-yl}benzamide Step 1: Methyl 4-(1H-pyrrolo[2,3-b]pyridin-4-yl)benzoate To a mixture of 4-chloro-1H-pyrrolo[2,3-b]pyridine (4.00 g, 26.2 mmol) and (4-methoxycarbonylphenyl)boronic acid (5.43 g, 30.2 mmol) in $H_2O$ (30 mL) and 1,4-dioxane (120 mL) was added potassium carbonate (2.17 g, 15.7 mmol), $Pd(dppf)Cl_2$:DCM (1.07 g, 1.31 mmol) in one portion at 20° C. under $N_2$. The mixture was then heated to 100° C. and stirred for 16 h. The reaction mixture was diluted with $H_2O$ (20 mL) and extracted with EtOAc (25 mL×3). The combined organic layers were washed with brine (20 mL×3), dried over $Na_2SO_4$ and concentrated under vacuum. The residue was purified by silica gel column chromatography (PE:EtOAc=2:1-MeOH) to afford methyl 4-(1H-pyrrolo[2,3-b]pyridin-4-yl)benzoate (5.0 g, crude) as a yellow solid.

Step 2: 4-(1H-Pyrrolo[2,3-b]pyridin-4-yl)benzoic acid

A mixture of methyl 4-(1H-pyrrolo[2,3-b]pyridin-4-yl) benzoate (2.50 g, 9.91 mmol) and NaOH (0.8 g, 20 mmol) in MeOH (50 mL) and $H_2O$ (50 ml) was stirred at 20° C. for 16 h. This reaction was monitored by TLC (petroleum ether: ethyl acetate=1:1). The mixture was filtered and the aqueous phase was extracted with DCM (100 mL×3). The pH of the aqueous phase was adjusted to 2-3 with 2N HCl, the solid was filtered, washed with $H_2O$ and concentrated in vacuo to afford 4-(1H-pyrrolo[2,3-b]pyridin-4-yl)benzoic acid (500 mg, 22% yield) as a brown solid.

Step 3: N-[(1R,2S)-2-Hydroxy-2,3-dihydro-1H-inden-1-yl]-4-{1H-pyrrolo[2,3-b]pyridin-4-yl}benzamide To a mixture of 4-(1H-pyrrolo[2,3-b]pyridin-4-yl)benzoic acid (250 mg, 1.05 mmol, 1.00 eq) and (1R,2S)-1-aminoindan-2-ol (157 mg, 1.05 mmol, 1.00 eq) in pyridine (10.0 mL) was added EDCI (241.4 mg, 1.26 mmol, 1.20 eq) and DMAP (192.3 mg, 1.57 mmol, 1.50 eq). Then the mixture was stirred at 50° C. for 5 h. LCMS showed the reaction was complete. The mixture was concentrated to give crude product. The crude product was purified by neutral prep-HPLC to give N-[(1R,2S)-2-hydroxy-2,3-dihydro-1H-inden-1-yl]-4-{1H-pyrrolo[2,3-b]pyridin-4-yl}benzamide (216.7 mg, 586.60 umol, yield: 56%) as a white solid.

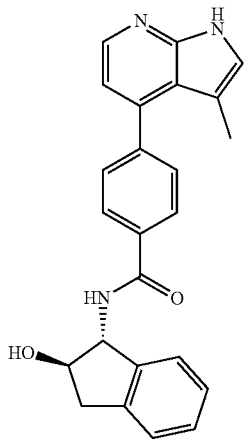

Example 2: N-[(1R,2R)-2-Hydroxy-2,3-dihydro-1H-inden-1-yl]-4-{3-methyl-1H-pyrrolo[2,3-b]pyridin-4-yl}benzamide Step 1: 4-Chloro-3-methyl-1-((2-(trimethylsilyl)ethoxy)methyl)-1H-pyrrolo[2,3-b]pyridine To a mixture of 4-chloro-3-methyl-1H-pyrrolo[2,3-b]pyridine (700 mg, 4.20 mmol, 1.00 eq) in DMF (25.0 mL) was added NaH (302.50 mg, 7.56 mmol, 60% purity, 1.80 eq) in one portion at 0° C. The mixture was stirred at 0° C. for 0.2 h. Then, SEM-Cl (841 mg, 5.04 mmol, 894 uL, 1.20 eq) was added and the mixture was stirred at 0° C. for 2 h. LCMS showed the reaction was complete. The mixture was quenched by saturated aq. $Na_2CO_3$ (30 mL) and the mixture was extracted with EtOAc (50 mL*3). The combined organic extracts were dried over $Na_2SO_4$, filtered and concentrated under vacuum to give 4-chloro-3-methyl-1-((2-(trimethylsilyl)ethoxy)methyl)-1H-pyrrolo[2,3-b]pyridine (1.20 g, 4.04 mmol, yield: 96.2%) as a yellow oil.

Step 2: Methyl 4-(3-methyl-1-((2-(trimethylsilyl)ethoxy)methyl)-1H-pyrrolo[2,3-b]pyridin-4-yl)benzoate To a mixture of 4-chloro-3-methyl-1-((2-(trimethylsilyl)ethoxy)methyl)-1H-pyrrolo[2,3-b]pyridine (600 mg, 2.02 mmol, 1.00 eq) and (4-methoxycarbonylphenyl)boronic acid (437 mg, 2.43 mmol, 1.20 eq) in EtOH (7.00 mL)/$H_2O$ (1.00 mL) was added Pd(Amphos)$_2$Cl$_2$ (143 mg, 0.20 mmol, 0.10 eq) and KOAc (594.73 mg, 6.06 mmol, 3.00 eq) in one portion under $N_2$. The mixture was stirred at 100° C. for 12 h under $N_2$. LCMS showed the reaction was complete. The mixture was filtered and the filtrate was concentrated. The residue was dissolved in $H_2O$ (40 mL) and the mixture was extracted with EtOAc (80 mL*3). The combined organic extracts were dried over $Na_2SO_4$, filtered and concentrated under vacuum to give methyl 4-(3-methyl-1-((2-(trimethylsilyl)ethoxy)methyl)-1H-pyrrolo[2,3-b]pyridin-4-yl)benzoate (850 mg, crude) as a brown oil.

Step 3: 4-(3-Methyl-1-((2-(trimethylsilyl)ethoxy)methyl)-1H-pyrrolo[2,3-b]pyridin-4-yl)benzoic acid To a mixture of methyl 4-(3-methyl-1-((2-(trimethylsilyl)ethoxy)methyl)-1H-pyrrolo[2,3-b]pyridin-4-yl)benzoate (850 mg, 2.14 mmol, 1.00 eq) in MeOH (20 mL)/$H_2O$ (10 mL) was added NaOH (256.8 mg, 6.42 mmol, 3.00 eq) in one portion. The mixture was stirred at 25° C. for 12 h. LCMS showed the reaction was complete. The mixture was concentrated under vacuum and the residue was dissolved in $H_2O$ (25 mL). The aqueous layer was acidified with 2N aq. HCl until pH=4, and the precipitate was filtered and dried to afford 4-(3-methyl-1-((2-(trimethylsilyl)ethoxy)methyl)-1H-pyrrolo[2,3-b]pyridin-4-yl)benzoic acid (780 mg, 2.04 mmol, yield: 95%) as a white solid.

Step 4: N-((1R,2R)-2-Hydroxy-2,3-dihydro-1H-inden-1-yl)-4-(3-methyl-1-((2-(trimethylsilyl)ethoxy)methyl)-1H-pyrrolo[2,3-b]pyridin-4-yl)benzamide To a mixture of 4-(3-methyl-1-((2-(trimethylsilyl)ethoxy)methyl)-1H-pyrrolo[2,3-b]pyridin-4-yl)benzoic acid (300 mg, 784.25 umol, 1.00 eq) and (1R,2R)-1-aminoindan-2-ol (119.3 mg, 799.94 umol, 1.02 eq) in DMF (20 mL) was added TEA (238.1 mg, 2.35 mmol, 326.1 uL, 3.00 eq) and HATU (357.84 mg, 941.10 umol, 1.20 eq). The mixture was stirred at 25° C. for 12 h. LCMS showed the reaction was complete. $H_2O$ (25 mL) was added and the mixture was extracted with EtOAc (60 mL*4). The combined organic extracts were dried over $Na_2SO_4$, filtered and concentrated under vacuum to afford N-((1R,2R)-2-hydroxy-2,3-dihydro-1H-inden-1-yl)-4-(3-methyl-1-((2-(trimethylsilyl)ethoxy)methyl)-1H-pyrrolo[2,3-b]pyridin-4-yl)benzamide (380 mg, crude) as a brown oil.

Step 5: N-((1R,2R)-2-Hydroxy-2,3-dihydro-1H-inden-1-yl)-4-(3-methyl-1H-pyrrolo[2,3-b]pyridin-4-yl)benzamide A mixture of N-((1R,2R)-2-hydroxy-2,3-dihydro-1H-inden-1-yl)-4-(3-methyl-1-((2-(trimethylsilyl)ethoxy)methyl)-1H-pyrrolo[2,3-b]pyridin-4-yl)benzamide (500 mg, 973.33 umol, 1.00 eq) in DCM (8.0 mL) and TFA (5.00 mL) was stirred at 25° C. for 3 h. The mixture was concentrated. KOAc (286.57 mg, 2.92 mmol, 3.00 eq) and MeOH (30 mL) were added and the mixture was stirred at 80° C. for 2 h. LCMS showed the reaction was complete. The mixture was concentrated. The residue was purified by acidic prep-HPLC (TFA) to afford N-((1R,2R)-2-hydroxy-2,3-dihydro-1H-inden-1-yl)-4-(3-methyl-1H-pyrrolo[2,3-b]pyridin-4-yl)benzamide (122 mg, 318.17 umol, yield: 33%) as a yellow solid.

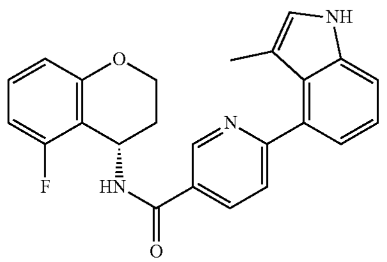 [SMILES: Cc1c[nH]c2cccc(-c3ccc(C(=O)N[C@H]4CCOc5cccc(F)c54)cn3)c12]

Example 3: (S)—N-(5-Fluorochroman-4-yl)-6-(3-methyl-1H-pyrrolo[2,3-b]pyridin-4-yl)nicotinamide Step 1: (3-Methyl-1-((2-(trimethylsilyl)ethoxy)methyl)-1H-pyrrolo[2,3-b]pyridin-4-yl)boronic acid To a mixture of 4-chloro-3-methyl-1-((2-(trimethylsilyl)ethoxy)methyl)-1H-pyrrolo[2,3-b]pyridine (Example 2 Step 1, 400 mg, 1.35 mmol, 1.00 eq) and 4,4,5,5-tetramethyl-2-(4,4,5,5-tetramethyl-1,3,2-dioxaborolan-2-yl)-1,3,2-dioxaborolane (684 mg, 2.69 mmol, 2.00 eq) in dioxane (2.0 mL) was added KOAc (396.7 mg, 4.04 mmol, 3.00 eq), Pd(dppf)$Cl_2$ (49.3 mg, 67.4 umol, 0.05 eq) and $PCy_3$ (37.8 mg, 134.74 umol, 43.4 uL, 0.10 eq). The mixture was stirred at 100° C. for 16 h. The reaction mixture was filtered and concentrated under reduced pressure. The residue was purified by column chromatography ($SiO_2$, PE/EtOAc=1:0-50:1) to give (3-methyl-1-((2-(trimethylsilyl)ethoxy)methyl)-1H-pyrrolo[2,3-b]pyridin-4-yl)boronic acid (300 mg, 980 umol, yield: 72.6%) as a colorless oil.

Step 2: Methyl 6-(3-methyl-1-((2-(trimethylsilyl)ethoxy)methyl)-1H-pyrrolo[2,3-b]pyridin-4-yl)nicotinate To a mixture of (3-methyl-1-((2-(trimethylsilyl)ethoxy)methyl)-1H-pyrrolo[2,3-b]pyridin-4-yl)boronic acid (280 mg, 914.3 umol, 1.00 eq) and methyl 6-bromopyridine-3-carboxylate (197.5 mg, 914.3 umol, 1.00 eq) in EtOH (4.0 mL) and $H_2O$ (1.0 mL) was added KOAc (179.5 mg, 1.83 mmol, 2.00 eq) and 4-di-tert-butylphosphanyl-N,N-dimethyl-aniline; dichloropalladium (64.7 mg, 91.43 umol, 64.7 uL, 0.10 eq). The mixture was stirred at 90° C. for 20 h. LCMS showed the reaction was complete. The reaction mixture was filtered and concentrated under reduced pressure. The residue was purified by column chromatography ($SiO_2$, PE/EtOAc=30/1 to 10/1) to give methyl 6-(3-methyl-1-((2-(trimethylsilyl)ethoxy)methyl)-1H-pyrrolo[2,3-b]pyridin-4-yl)nicotinate (120 mg, 301.9 umol, yield: 33.0%) as a yellow solid.

Step 3: 6-(3-Methyl-1-((2-(trimethylsilyl)ethoxy)methyl)-1H-pyrrolo[2,3-b]pyridin-4-yl)nicotinic acid Prepared from methyl 6-(3-methyl-1-((2-(trimethylsilyl)ethoxy)methyl)-1H-pyrrolo[2,3-b]pyridin-4-yl)nicotinate according to the procedure described in Example 2 Step 3.

Step 4: (S)—N-(5-Fluorochroman-4-yl)-6-(3-methyl-1-((2-(trimethylsilyl)ethoxy)methyl)-1H-pyrrolo[2,3-b]pyridin-4-yl)nicotinamide Prepared from 6-(3-methyl-1-((2-(trimethylsilyl)ethoxy)methyl)-1H-pyrrolo[2,3-b]pyridin-4-yl)nicotinic acid and (S)-5-fluorochroman-4-amine according to the procedure described in Example 2 Step 4.

Step 5: (S)—N-(5-Fluorochroman-4-yl)-6-(3-methyl-1H-pyrrolo[2,3-b]pyridin-4-yl)nicotinamide Prepared from (S)—N-(5-fluorochroman-4-yl)-6-(3-methyl-1-((2-(trimethylsilyl)ethoxy)methyl)-1H-pyrrolo[2,3-b]pyridin-4-yl)nicotinamide according to the procedure described in Example 2 Step 5.

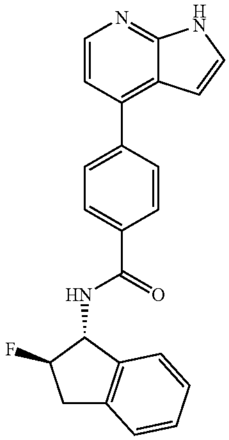 [SMILES: O=C(N[C@@H]1c2ccccc2C[C@H]1F)c1ccc(-c2ccnc3[nH]ccc23)cc1]

Example 4: N-((1R,2R)-2-Fluoro-2,3-dihydro-1H-inden-1-yl)-4-(1H-pyrrolo[2,3-b]pyridin-4-yl)benzamide Step 1: N-((1R,2R)-2-Fluoro-2,3-dihydro-1H-inden-1-yl)-4-(1H-pyrrolo[2,3-b]pyridin-4-yl)benzamide To a mixture of N-[(1R,2S)-2-hydroxy-2,3-dihydro-1H-inden-1-yl]-4-{1H-pyrrolo[2,3-b]pyridin-4-yl}benzamide (Example 1, 80.0 mg, 216.56 umol, 1.00 eq) in DCM (5.0 mL) was added dropwise BAST (57.5 mg, 259.87 umol, 56.9 uL, 1.20 eq) at −78° C. After addition, the mixture was stirred at 20° C. for 0.5 h. LCMS showed the reaction was complete. $NaHCO_3$ (aq. 20 mL) was added to the mixture, extracted with DCM (10 mL*2), the organic layer was dried over $Na_2SO_4$, and concentrated to give the crude product. The crude product was purified by prep-HPLC (TFA) to give the TFA salt of N-((1R,2R)-2-fluoro-2,3-dihydro-1H-inden-1-yl)-4-(1H-pyrrolo[2,3-b]pyridin-4-yl)benzamide (13.6 mg, 28.02 umol, yield: 12.9%) as a white solid.

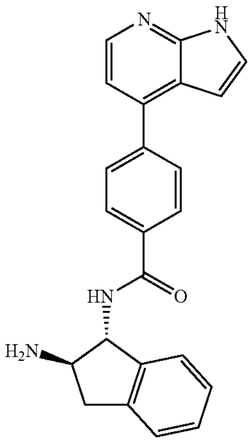 [SMILES: N[C@@H]1Cc2ccccc2[C@H]1NC(=O)c1ccc(-c2ccnc3[nH]ccc23)cc1]

Example 5: N-[(1R,2R)-2-Amino-2,3-dihydro-1H-inden-1-yl]-4-{1H-pyrrolo[2,3-b]pyridin-4-yl}benzamide Step 1: tert-Butyl ((1R,2R)-2-(2,2,2-trifluoroacetamido)-2,3-dihydro-1H-inden-1-yl)carbamate To a solution of tert-butyl ((1R,2R)-2-amino-2,3-dihydro-1H-inden-1-yl)carbamate (300 mg, 1.21 mmol, 1.00 eq) and DIPEA (469 mg, 3.63 mmol, 634 uL, 3.00 eq) in DCM (10.0 mL) was dropwise added TFAA (305 mg, 1.45 mmol, 202 uL, 1.20 eq) at 0° C. The reaction was stirred at 15° C. for 16 h. TLC (PE:EtOAc=1:1, Rf=0.7) showed the reaction was complete. The solution was washed with brine (10 mL). The organic layer was dried over $Na_2SO_4$ and concentrated. The residue was purified by column chromatography on silica gel (PE:EtOAc=4:1) to give tert-butyl ((1R,2R)-2-(2,2,2-trifluoroacetamido)-2,3-dihydro-1H-inden-1-yl)carbamate (340 mg, 987 umol, yield: 81.7%) as a white solid Step 2: N-((1R,2R)-1-Amino-2,3-dihydro-1H-inden-2-yl)-2,2,2-trifluoroacetamide A solution of tert-butyl ((1R,2R)-2-(2,2,2-trifluoroacetamido)-2,3-dihydro-1H-inden-1-yl)carbamate (340 mg, 987 umol, 1.00 eq) in TFA (2.0 mL) and DCM (4.0 mL) was stirred at 15° C. for 2.5 h. LCMS showed the reaction was complete. The solution was blown to dryness by $N_2$ to give the TFA salt of N-((1R,2R)-1-amino-2,3-dihydro-1H-inden-2-yl)-2,2,2-trifluoroacetamide (350 mg, 977 umol, yield: 98.9%) as a yellow oil.

Step 3: 4-(1H-Pyrrolo[2,3-b]pyridin-4-yl)-N-((1R,2R)-2-(2,2,2-trifluoroacetamido)-2,3-dihydro-1H-inden-1-yl)benzamide To a solution of N-((1R,2R)-1-amino-2,3-dihydro-1H-inden-2-yl)-2,2,2-trifluoroacetamide (112.78 mg, 314.81 umol, 1.00 eq, TFA salt) and 4-(1H-pyrrolo[2,3-b]pyridin-4-yl)benzoic acid (Example 1 Step 2, 75.0 mg, 314.8 umol, 1.00 eq) in DMF (2.0 mL) was added DIPEA (122 mg, 944 umol, 165 uL, 3.00 eq) and HATU (144 mg, 378 umol, 1.20 eq) at 15° C. The reaction was stirred at 15° C. for 3 h. LCMS showed the reaction was complete. The solution was extracted with EtOAc (10 mL) and washed with brine (5 mL). The organic layer was dried over $Na_2SO_4$ and concentrated to give 4-(1H-pyrrolo[2,3-b]pyridin-4-yl)-N-((1R,2R)-2-(2,2,2-trifluoroacetamido)-2,3-dihydro-1H-inden-1-yl)benzamide (120 mg, crude) as a brown oil.

Step 4: N-[(1R,2R)-2-Amino-2,3-dihydro-1H-inden-1-yl]-4-{1H-pyrrolo[2,3-b]pyridin-4-yl}benzamide To a solution of 4-(1H-pyrrolo[2,3-b]pyridin-4-yl)-N-((1R,2R)-2-(2,2,2-trifluoroacetamido)-2,3-dihydro-1H-inden-1-yl)benzamide (120 mg, 258.4 umol, 1.00 eq) in MeOH (10.0 mL) was added NaOH (31.01 mg, 775.14 umol, 3.00 eq) at 15° C. The reaction was stirred for 16 h at 15° C. LCMS showed the reaction was not complete, so $K_2CO_3$ (107 mg, 775 umol, 3.00 eq) was added to the reaction. The reaction was heated at 50° C. for 16 h. LCMS showed the reaction was not complete, so 3 eq. of NaOH was added to the reaction. The reaction was heated at 50° C. for 16 h. LCMS showed the reaction was complete. The solution was concentrated. The residue was purified by prep-HPLC (TFA) to give the TFA salt of N-[(1R,2R)-2-amino-2,3-dihydro-1H-inden-1-yl]-4-{1H-pyrrolo[2,3-b]pyridin-4-yl}benzamide (55.8 mg, 116 umol, yield: 44.8%) as a white solid.

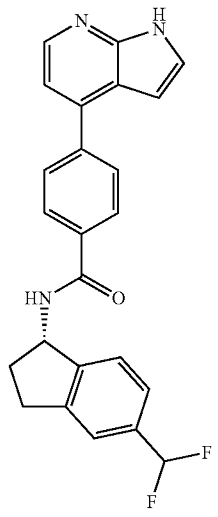 [SMILES: O=C(N[C@H]1CCc2cc(C(F)F)ccc21)c1ccc(-c2ccnc3[nH]ccc23)cc1]

Example 6: (S)—N-(5-(Difluoromethyl)-2,3-dihydro-1H-inden-1-yl)-4-(1H-pyrrolo[2,3-b]pyridin-4-yl)benzamide Step 1: 5-Bromo-2,3-dihydro-1H-inden-1-one O-methyl oxime To a solution of 5-bromo-2,3-dihydro-1H-inden-1-one (5.00 g, 23.69 mmol, 1.00 eq) in EtOH (150 mL) was added O-methylhydroxylamine hydrochloride (2.97 g, 35.54 mmol, 1.50 eq) and pyridine (3.75 g, 47.38 mmol, 3.82 mL, 2.00 eq). The resulting mixture was stirred at 20° C. for 3 h. When the reaction was complete by TLC (PE:EtOAc=3:1) and LCMS, the mixture was concentrated under vacuum to give a crude product. The crude product was dissolved in EtOAc (150 mL) and washed with $H_2O$ (30 mL*3). The organic layer was dried over anhydrous $Na_2SO_4$ and concentrated under vacuum to give 5-bromo-2,3-dihydro-1H-inden-1-one O-methyl oxime (5.50 g, 22.91 mmol, yield: 96.7%) as a yellow solid.

Step 2: 1-(Methoxyimino)-2,3-dihydro-1H-indene-5-carbaldehyde

5-Bromo-2,3-dihydro-1H-inden-1-one O-methyl oxime (2.50 g, 10.41 mmol, 1.00 eq) was dissolved in THF (30 mL) and cooled to −78° C. n-BuLi (2.5 M, 4.58 mL, 1.10 eq) was added dropwise, after addition, the resulting mixture was stirred at −78° C. for 5 mins. DMF (1.14 g, 15.62 mmol, 1.20 mL, 1.50 eq) was added and the resulting mixture was gradually warmed to 20° C. before stirring at 20° C. for 3 h. When the reaction was complete by TLC (PE:EtOAc=3:1) and LCMS, saturated aqueous $NaHCO_3$ solution (20 mL) was added and extracted with EtOAc (30 mL). The organic phase was washed with $H_2O$ (20 mL*3), dried over $Na_2SO_4$, and concentrated under vacuum to give a crude product. The crude product was purified by column chromatography on silica gel (PE:EtOAc=40:1) to obtain 1-(methoxyimino)-2,3-dihydro-1H-indene-5-carbaldehyde (2.40 g, 12.7 mmol, yield: 60.9%) as a yellow solid.

Step 3: 5-(Difluoromethyl)-2,3-dihydro-1H-inden-1-one O-methyl oxime

To a solution of 1-(methoxyimino)-2,3-dihydro-1H-indene-5-carbaldehyde (2.40 g, 12.7 mmol, 1.00 eq) in DCM (30.0 mL) was added DAST (10.22 g, 63.40 mmol, 8.4 mL, 5.00 eq) dropwise at −78° C. under $N_2$. After complete addition, the mixture was stirred at 20° C. for 16 h. TLC (PE:EtOAc=3:1) showed most of the starting material was consumed and there was a new spot produced. The reaction mixture was added dropwise to a saturated aqueous $NaHCO_3$ solution (100 mL) and the products were extracted into DCM (50 mL*3). The combined organic extracts were dried over $Na_2SO_4$ and concentrated under vacuum to give a crude product. The crude product was purified by column chromatography on silica gel (PE:EtOAc=1:0 to 100:1) to obtain 5-(difluoromethyl)-2,3-dihydro-1H-inden-1-one O-methyl oxime (2.30 g, 10.89 mmol, yield: 85.9%) as a red solid.

Step 4: 5-(Difluoromethyl)-2,3-dihydro-1H-inden-1-amine

To a solution of 5-(difluoromethyl)-2,3-dihydro-1H-inden-1-one O-methyl oxime (300 mg, 1.42 mmol, 1.00 eq) in MeOH (30 mL) was added Raney-Ni (1.00 g, 11.67 mmol, 8.22 eq) and ammonia solution (3.00 mL). The resulting mixture was stirred at 50° C. under $H_2$ at 50 psi for 12 h. The mixture was filtered and the filter cake was washed with MeOH (10 mL*3). The filtrate was concentrated under vacuum to give a crude product. The crude product was purified by prep-TLC (EtOAc) to give 60 mg of a 1:3 mixture of 5-(difluoromethyl)-2,3-dihydro-1H-inden-1-amine and 5-methyl-2,3-dihydro-1H-inden-1-amine as a white solid.

Step 5: (S)—N-(5-(Difluoromethyl)-2,3-dihydro-1H-inden-1-yl)-4-(1H-pyrrolo[2,3-b]pyridin-4-yl)benzamide To a solution of 4-(1H-pyrrolo[2,3-b]pyridin-4-yl)benzoic acid (Example 1 Step 2, 73 mg, 306 umol, 1.00 eq) in DMF (3.00 mL) was added HATU (139.5 mg, 367 umol, 1.20 eq) and DIPEA (79 mg, 611.3 umol, 107 uL, 2.00 eq), followed by addition of the mixture of 5-(difluoromethyl)-2,3-dihydro-1H-inden-1-amine and 5-methyl-2,3-dihydro-1H-inden-1-amine from the previous step (60 mg). The resulting mixture was stirred at 20° C. for 1 h. The reaction mixture was purified directly by neutral prep-HPLC to first obtain racemic N-(5-(difluoromethyl)-2,3-dihydro-1H-inden-1-yl)-4-(1H-pyrrolo[2,3-b]pyridin-4-yl)benzamide. The racemate was separated by prep-SFC (Instrument: Thar SFC80 preparative SFC, Column: Chiralcel OJ-H 250*30 mm i.d. 5u, Mobile phase: A for C02 and B for EtOH (0.1% NH3H2O); Gradient: B %=50%; Flow rate:70 g/min; Wavelength: 220 nm; Column temperature: 40° C.; System back pressure: 100 bar) to obtain (S)—N-(5-(difluoromethyl)-2,3-dihydro-1H-inden-1-yl)-4-(1H-pyrrolo[2,3-b]pyridin-4-yl)benzamide (14.7 mg, 36.44 umol, yield: 11.9%), the first eluting enantiomer, as a white solid.

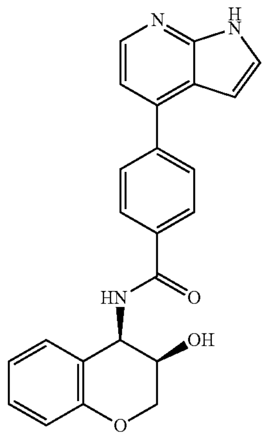 [SMILES: O=C(N[C@@H]1c2ccccc2OC[C@@H]1O)c1ccc(-c2ccnc3[nH]ccc23)cc1]

Example 7: TFA-salt of N-[(3R,4R)-3-Hydroxy-3,4-dihydro-2H-1-benzopyran-4-yl]-4-{1H-pyrrolo[2,3-b]pyridin-4-yl}benzamide Step 1: 4,4-Dimethoxychroman-3-ol To a solution of NaOH (92 g, 2.33 mol) in MeOH (640 mL) was added a solution of chroman-4-one (115 g, 0.77 mol) in MeOH (470 mL) at −10° C. The resulting yellow solution was stirred for 5 min at −10° C. and a slurry of $PhI(OAc)_2$ (255.3 g, 0.77 mol) in MeOH (700 mL) was added. The dark orange reaction mixture was stirred at −10° C. for 0.5 h and then allowed to warm to room temperature and stirred for 3 h to afford to afford 4,4-dimethoxychroman-3-ol that was used directly in the next step.

Step 2: 3-Hydroxychroman-4-one oxime

To aqueous HCl (4N, 2.72 mol) was added a solution of 4,4-dimethoxychroman-3-ol (0.77 mol) in MeOH (from the Step 1 directly above) at −10° C. over 15 min. The yellow slurry was stirred for 20 min at 0° C.-20° C. NaOAc (159 g, 1.94 mol) and hydroxylamine hydrochloride (108 g, 1.55 mol) were added in one portion. The reaction mixture was stirred at 50° C. for 1 hand then cooled to room temperature. The solution was concentrated to about one half of the volume and then diluted with $H_2O$ (1 L). The resulting mixture was washed with petroleum ether (1 L×2) and then the aqueous phase was extracted with EtOAc (1 L×2). The combined extracts were washed with $H_2O$ (1 L), dried over anhydrous $Na_2SO_4$ and concentrated. The residue was recrystallized from PE/EtOAc (4:1) to give 3-hydroxychroman-4-one oxime (106 g, 76% yield over two steps) as a white solid.

Step 3: 4-Aminochroman-3-ol

To a solution of 3-hydroxychroman-4-one oxime (50 g, 0.23 mol) in MeOH (900 mL) mol) was added HBr (40% aq, 48 mL) at 0° C. Pd/C (10 wt %, 10 g) was added and the mixture was hydrogenated in an autoclave at 0-5° C. (40 psi) for 18 h. The catalyst was removed by filtration and the filtrate was evaporated. The residue was diluted with EtOAc (200 mL) and stirred for 15 min. The resulting solid was collected by filtration, washed with EtOAc (100 mL) and then treated with saturated aqueous $Na_2CO_3$. The resulting mixture was extracted with EtOAc (250 mL×3) and the combined organic layers were dried over anhydrous $Na_2SO_4$ and concentrated to give 4-aminochroman-3-ol (17.5 g, 51% yield, cis/trans=89:6) as a yellow solid.

Step 4: (3R,4R)-4-Aminochroman-3-ol

To a solution of 4-aminochroman-3-ol (29 g, 0.177 mol) in EtOH (555 mL) was added a solution of (S)-mandelic acid (26.9 g, 0.177 mol) in EtOH (40 mL) and the mixture was stirred at 80° C. for 10 min. The mixture was cooled and the resulting salt was collected by filtration and recrystallized from EtOH (10V) a few times to give (R,R)-mandelate salt (>99% ee, 18 g).

To a slurry of this salt (18 g) in EtOAc (180 mL) was added ethanolamine (aq., 250 mL). The two layers were separated and the aqueous layer was extracted with EtOAc (200 mL×3). The combined organic layers were washed with $H_2O$ (200 mL) and concentrated to give (3R,4R)-4-aminochroman-3-ol (7.0 g, 24% yield) as a white solid.

Step 5: N-[(3R,4R)-3-Hydroxy-3,4-dihydro-2H-1-benzopyran-4-yl]-4-{1H-pyrrolo[2,3-b]pyridin-4-yl}benzamide To a solution of 4-(1H-pyrrolo[2,3-b]pyridin-4-yl)benzoic acid (Example 1 Step 2, 150 mg, 629.6 umol, 1.00 eq) in DMF (3.0 mL) was added DIPEA (162.74 mg, 1.26 mmol, 219.9 uL, 2.00 eq), HATU (287 mg, 756 umol, 1.20 eq) and (3R,4R)-4-aminochroman-3-ol (104 mg, 630 umol, 1.00 eq). The resulting mixture was stirred at 20° C. for 2 h. The mixture was purified by prep-HPLC (TFA) to give the TFA salt of N-[(3R,4R)-3-hydroxy-3,4-dihydro-2H-1-benzopyran-4-yl]-4-{1H-pyrrolo[2,3-b]pyridin-4-yl}benzamide (150 mg, 300.3 umol, 47.7% yield) as a yellow solid.

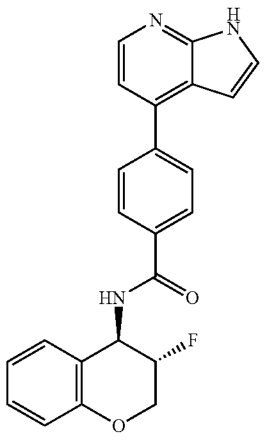 [SMILES: O=C(N[C@@H]1c2ccccc2OC[C@H]1F)c1ccc(-c2ccnc3[nH]ccc23)cc1]

Example 8: TFA-salt of N-[(3S,4R)-3-Fluoro-3,4-dihydro-2H-1-benzopyran-4-yl]-4-{1H-pyrrolo[2,3-b]pyridin-4-yl}benzamide Step 1: N-[(3S,4R)-3-Fluoro-3,4-dihydro-2H-1-benzopyran-4-yl]-4-{1H-pyrrolo[2,3-b]pyridin-4-yl}benzamide To a solution of N-[(3R,4R)-3-hydroxy-3,4-dihydro-2H-1-benzopyran-4-yl]-4-{1H-pyrrolo[2,3-b]pyridin-4-yl}benzamide (Example 7, 50.0 mg, 100.1 umol, 1.00 eq, TFA) in DCM (5.0 mL) was added DAST (32.3 mg, 200.2 umol, 26.5 uL, 2.00 eq) dropwise at −78° C. After complete addition the mixture was slowly raised to 20° C. and stirred at 20° C. for 1 h. Saturated aqueous $NH_4Cl$ solution (5 mL) was added and the mixture was extracted with DCM (10 mL*3). The combined organic layers were dried over $Na_2SO_4$ and concentrated under vacuum to give crude product. The crude product was purified by prep-HPLC (TFA) to obtain the TFA salt of N-[(3S,4R)-3-fluoro-3,4-dihydro-2H-1-benzopyran-4-yl]-4-{1H-pyrrolo[2,3-b]pyridin-4-yl}benzamide (19.6 mg, 39.1 umol, yield: 39.1%, TFA) as a yellow solid.

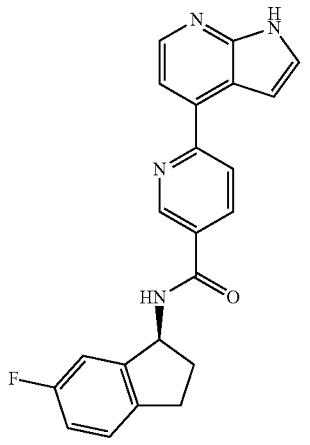 [SMILES: O=C(N[C@H]1CCc2ccc(F)cc21)c1ccc(-c2ccnc3[nH]ccc23)nc1]

Example 9: N-[(1S)-6-Fluoro-2,3-dihydro-1H-inden-1-yl]-6-{1H-pyrrolo[2,3-b]pyridin-4-yl}pyridine-3-carboxamide Step 1: 4-Chloro-1-((2-(trimethylsilyl)ethoxy)methyl)-1H-pyrrolo[2,3-b]pyridine Prepared from 4-chloro-1H-pyrrolo[2,3-b]pyridine according to the procedure described in Example 2 Step 1.

Step 2: (1-((2-(Trimethylsilyl)ethoxy)methyl)-1H-pyrrolo[2,3-b]pyridin-4-yl)boronic acid To a mixture of 4-chloro-1-((2-(trimethylsilyl)ethoxy)methyl)-1H-pyrrolo[2,3-b]pyridine (20.0 g, 70.7 mmol, 1.00 eq) and $B_2Pin_2$ (19.75 g, 77.8 mmol, 1.10 eq) in 1,4-dioxane (50.0 mL) was added KOAc (10.41 g, 106.07 mmol, 1.50 eq), $Pd_2(dba)_3$ (6.48 g, 7.07 mmol, 0.10 eq) and 2-(dicyclohexylphosphino)biphenyl (3.72 g, 10.61 mmol, 0.15 eq). The mixture was stirred at 100° C. for 16 h under $N_2$. The mixture was filtered via a Celite pad and concentrated to give crude product. The crude product was purified by column chromatography on silica gel (PE) to give (1-((2-

(trimethylsilyl)ethoxy)methyl)-1H-pyrrolo[2,3-b]pyridin-4-yl)boronic acid (20.0 g, 68.44 mmol, yield: 96.8%) as a yellow solid.

Step 3: Methyl 6-(1-((2-(trimethylsilyl)ethoxy) methyl)-1H-pyrrolo[2,3-b]pyridin-4-yl)nicotinate Prepared from (1-((2-(trimethylsilyl)ethoxy)methyl)-1H-pyrrolo[2,3-b]pyridin-4-yl)boronic acid and methyl 6-bromonicotinate according to the procedure described in Example 3 Step 2.

Step 4: 6-(1-((2-(Trimethylsilyl)ethoxy)methyl)-1H-pyrrolo[2,3-b]pyridin-4-yl)nicotinic acid Prepared from methyl 6-(1-((2-(trimethylsilyl)ethoxy) methyl)-1H-pyrrolo[2,3-b]pyridin-4-yl)nicotinate according to the procedure described in Example 2 Step 3.

Step 5: (S)—N-(6-Fluoro-2,3-dihydro-1H-inden-1-yl)-6-(1-((2-(trimethylsilyl)ethoxy)methyl)-1H-pyrrolo[2,3-b]pyridin-4-yl)nicotinamide Prepared from 6-(1-((2-(Trimethylsilyl)ethoxy)methyl)-1H-pyrrolo[2,3-b]pyridin-4-yl)nicotinic acid and (S)-6-fluoro-2,3-dihydro-1H-inden-1-amine according to the procedure described in Example 2 Step 4.

Step 6: N-[(1S)-6-Fluoro-2,3-dihydro-1H-inden-1-yl]-6-{1H-pyrrolo[2,3-b]pyridin-4-yl}pyridine-3-carboxamide Prepared from (S)—N-(6-Fluoro-2,3-dihydro-1H-inden-1-yl)-6-(1-((2-(trimethylsilyl)ethoxy)methyl)-1H-pyrrolo[2,3-b]pyridin-4-yl)nicotinamide according to the procedure described in Example 2 Step 5.

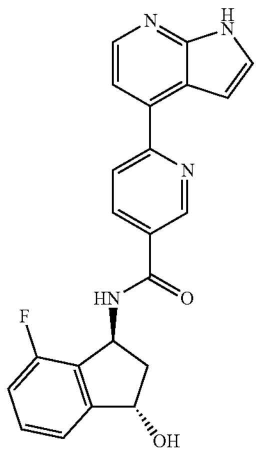

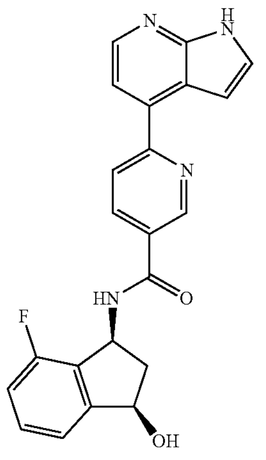

Examples 10 and 11: N-[(1S,3S)-7-Fluoro-3-hydroxy-2,3-dihydro-1H-inden-1-yl]-6-{1H-pyrrolo[2,3-b]pyridin-4-yl}pyridine-3-carboxamide and N-[(1S,3R)-7-fluoro-3-hydroxy-2,3-dihydro-1H-inden-1-yl]-6-{1H-pyrrolo[2,3-b]pyridin-4-yl}pyridine-3-carboxamide Step 1: (S)-2,2,2-Trifluoro-N-(7-fluoro-2,3-dihydro-1H-inden-1-yl)acetamide To a solution of (S)-7-fluoro-2,3-dihydro-1H-inden-1-amine (500 mg, 2.66 mmol, 1.00 eq, HCl salt) in DCM (10.0 mL) was added TFAA (615.6 mg, 2.93 mmol, 407.7 uL, 1.10 eq) and TEA (539.3 mg, 5.33 mmol, 739 uL, 2.00 eq). The resulting mixture was stirred at 20° C. for 1 h. $H_2O$ (10 ml) was added and the organic phase was separated, washed with $H_2O$ (10 ml*3), dried over $Na_2SO_4$, and concentrated under vacuum to give crude product. The crude product was purified by column chromatography on silica gel (PE:EtOAc=10:1) to obtain (S)-2,2,2-trifluoro-N-(7-fluoro-2,3-dihydro-1H-inden-1-yl)acetamide (600 mg, 2.43 mmol, yield: 91%) as a yellow solid.

Step 2: (S)-2,2,2-Trifluoro-N-(7-fluoro-3-oxo-2,3-dihydro-1H-inden-1-yl)acetamide To a solution of (S)-2,2,2-trifluoro-N-(7-fluoro-2,3-dihydro-1H-inden-1-yl)acetamide (550 mg, 2.23 mmol, 1.00 eq) in acetone (55.0 mL) was added $MgSO_4 \cdot 7H_2O$ (997 mg, 6.69 mmol, 3.00 eq) with $H_2O$ (33.0 mL) followed by $KMnO_4$ (1.06 g, 6.69 mmol, 3.00 eq) at 0° C. portionwise for 0.5 h. After complete addition, the mixture was stirred at 20° C. for 16 h. TLC (PE:EtOAc=3:1) showed part of the starting material was consumed, and one new spot was formed. The mixture was filtered, the filter cake was washed with acetone (3 mL*3). $H_2O$ (20 mL) was added to the filtrate and the products extracted into DCM (100 mL*3). The combined organic layers were dried over $Na_2SO_4$ and concentrated under vacuum to give a crude product. The crude product was purified by column chromatography on silica gel (PE:EtOAc=30:1 to 10:1) to obtain (S)-2,2,2-trifluoro-N-(7-fluoro-3-oxo-2,3-dihydro-1H-inden-1-yl)acetamide (160 mg, 612.6 umol, yield: 27.5%) as a white solid.

Step 3: 2,2,2-Trifluoro-N-((1S)-7-fluoro-3-hydroxy-2,3-dihydro-1H-inden-1-yl)acetamide To a solution of (S)-2,2,2-trifluoro-N-(7-fluoro-3-oxo-2,3-dihydro-1H-inden-1-yl)acetamide (190 mg, 728 umol, 1.00 eq) in MeOH (10.0 mL) was added $NaBH_4$ (33.0 mg, 873 umol, 1.20 eq). The resulting mixture was stirred at 20° C. for 1 h. Saturated aqueous $NH_4Cl$ solution (5 mL) was added and the mixture was dried by $N_2$. $H_2O$ (6 mL) was added and the products extracted into EtOAc (10 mL*3). The combined organic layers were dried over $Na_2SO_4$ and concentrated under vacuum to give crude 2,2,2-trifluoro-N-((1S)-7-fluoro-3-hydroxy-2,3-dihydro-1H-inden-1-yl)acetamide (180 mg) as an off-white solid which was used directly in the next step without further purification.

Step 4: (3S)-3-Amino-4-fluoro-2,3-dihydro-1H-inden-1-ol

To a solution of crude 2,2,2-trifluoro-N-((1S)-7-fluoro-3-hydroxy-2,3-dihydro-1H-inden-1-yl)acetamide (180 mg) in MeOH (10.0 mL) was added $K_2CO_3$ (284 mg, 2.05 mmol, 3.00 eq). The resulting mixture was stirred at 60° C. for 16 h. LCMS showed there was very little desired product, so additional $K_2CO_3$ (283.6 mg, 2.05 mmol, 3.00 eq) and NaOH (54.7 mg, 1.37 mmol, 2.00 eq) were added. The resulting mixture was stirred at 60° C. for another 20 h. The reaction was complete as detected by LCMS. The mixture was concentrated under vacuum to give a crude product. $H_2O$ (7 mL) was added and the products were extracted into EtOAc (10 mL*4). The combined organic layers were dried over $Na_2SO_4$ and concentrated under vacuum to give crude (3S)-3-amino-4-fluoro-2,3-dihydro-1H-inden-1-ol (100 mg) as a red solid which was used directly in the next step without further purification.

Step 5: N-((1S)-7-Fluoro-3-hydroxy-2,3-dihydro-1H-inden-1-yl)-6-(1-((2-(trimethylsilyl)ethoxy)methyl)-1H-pyrrolo[2,3-b]pyridin-4-yl)nicotinamide To a solution of 6-(1-((2-(trimethylsilyl)ethoxy)methyl)-1H-pyrrolo[2,3-b]pyridin-4-yl)nicotinic acid (Example 9 Step 4, 200 mg, 541.3 umol, 1.00 eq) in DMF (5.0 mL) was added HATU (247 mg, 649.6 umol, 1.20 eq), DIPEA (175 mg, 1.35 mmol, 236 uL, 2.50 eq) and (3S)-3-amino-4-fluoro-2,3-dihydro-1H-inden-1-ol (99.5 mg, 595.4 umol, 1.10 eq). The resulting mixture was stirred at 20° C. for 0.5 h $H_2O$ (7 mL) was added and the products were extracted into EtOAc (10 mL*3). The combined organic extracts were dried over $Na_2SO_4$ and concentrated under vacuum to give crude N-((1S)-7-fluoro-3-hydroxy-2,3-dihydro-1H-inden-1-yl)-6-(1-((2-(trimethylsilyl)ethoxy)methyl)-1H-pyrrolo[2,3-b]pyridin-4-yl)nicotinamide (480 mg) as a red oil which was used directly in the next step without further purification.

Step 6: N-[(1S,3S)-7-Fluoro-3-hydroxy-2,3-dihydro-1H-inden-1-yl]-6-{1H-pyrrolo[2,3-b]pyridin-4-yl}pyridine-3-carboxamide and N-((1S,3R)-7-fluoro-3-hydroxy-2,3-dihydro-1H-inden-1-yl)-6-(1H-pyrrolo[2,3-b]pyridin-4-yl)nicotinamide To a mixture of N-((1S)-7-fluoro-3-hydroxy-2,3-dihydro-1H-inden-1-yl)-6-(1-((2-(trimethylsilyl)ethoxy)methyl)-1H-pyrrolo[2,3-b]pyridin-4-yl)nicotinamide (200 mg, 385.6 umol, 1.00 eq) in DCM (5.0 mL) was added TFA (6.0 mL). The resulting mixture was stirred at 20° C. for 1 h. The mixture was concentrated by $N_2$, MeOH (10.0 mL) was added, and the mixture was basified by $Na_2CO_3$ to pH=7-8. KOAc (37.8 mg, 385.6 umol, 1.00 eq) was then added and the resulting mixture was stirred at 50° C. for 6 h. The mixture was concentrated under vacuum to give crude product. $H_2O$ (10 mL) was added and the products were extracted into EtOAc (10 mL*3). The combined organic layers were dried over $Na_2SO_4$ and concentrated under vacuum to give a crude product. The crude product was purified by prep-HPLC (TFA) to obtain the TFA salt of N-[(1S,3S)-7-fluoro-3-hydroxy-2,3-dihydro-1H-inden-1-yl]-6-{1H-pyrrolo[2,3-b]pyridin-4-yl}pyridine-3-carboxamide (9.2 mg, 18.3 umol, yield: 4.8%, peak 1) as a yellow solid and N-((1S,3R)-7-fluoro-3-hydroxy-2,3-dihydro-1H-inden-1-yl)-6-(1H-pyrrolo[2,3-b]pyridin-4-yl)nicotinamide (32.3 mg, 64.3 umol, yield: 16.7%, peak 2) as a yellow solid.

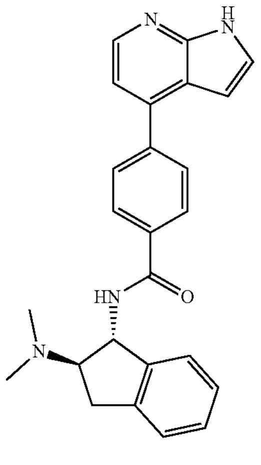 [SMILES: CN(C)[C@@H]1Cc2ccccc2[C@H]1NC(=O)c1ccc(-c2ccnc3[nH]ccc23)cc1]

Example 12: N-[(1R,2R)-2-(Dimethylamino)-2,3-dihydro-1H-inden-1-yl]-4-{1H-pyrrolo[2,3-b]pyridin-4-yl}benzamide Step 1: tert-Butyl ((1R,2R)-2-(dimethylamino)-2,3-dihydro-1H-inden-1-yl)carbamate To a mixture of tert-butyl ((1R,2R)-2-amino-2,3-dihydro-1H-inden-1-yl)carbamate (50.0 mg, 201.4 umol, 1.00 eq) and paraformaldehyde (45.3 mg, 503.4 umol, 2.50 eq) in DCE (4.00 mL) and AcOH (100.00 uL) was added $NaBH_3CN$ (25.31 mg, 402.70 umol, 2.00 eq). The mixture was stirred at 20° C. for 16 h. The pH of the reaction mixture was adjusted to around 6 with 1M HCl and concentrated under reduced pressure. The crude product was used directly in the next step without further purification. tert-butyl ((1R,2R)-2-(dimethylamino)-2,3-dihydro-1H-inden-1-yl)carbamate (40 mg, 144.7 umol, yield: 71.9%) was obtained as a white solid.

Step 2: (1R,2R)—$N^2$,$N^2$-Dimethyl-2,3-dihydro-1H-indene-1,2-diamine tert-Butyl ((1R,2R)-2-(dimethylamino)-2,3-dihydro-1H-inden-1-yl)carbamate (50 mg, 180.9 umol, 1.00 eq) was taken up in 4 M HCl/EtOAc (6.0 mL) and stirred at 20° C. for 1 h. The reaction mixture was concentrated under reduced pressure to give (1R,2R)—$N^2$,$N^2$-dimethyl-2,3-dihydro-1H-indene-1,2-diamine (30 mg, 170.2 umol, yield: 94.1%) as a white solid that was used directly without further purification.

Step 3: N-[(1R,2R)-2-(Dimethylamino)-2,3-dihydro-1H-inden-1-yl]-4-{1H-pyrrolo[2,3-b]pyridin-4-yl}benzamide Prepared from (1R,2R)—$N^2$,$N^2$-dimethyl-2,3-dihydro-1H-indene-1,2-diamine and 4-(1H-pyrrolo[2,3-b]pyridin-4-yl)benzoic acid (Example 1 Step 2) according to the procedure described in Example 2 Step 4.

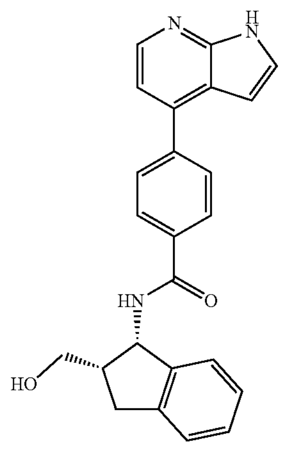 [SMILES: O=C(N[C@@H]1c2ccccc2C[C@@H]1CO)c1ccc(-c2ccnc3[nH]ccc23)cc1]

Example 13: N-[(1R,2R)-2-(Hydroxymethyl)-2,3-dihydro-1H-inden-1-yl]-4-{1H-pyrrolo[2,3-b]pyridin-4-yl}benzamide Step 1: cis rac N-(2-(Hydroxymethyl)-2,3-dihydro-1H-inden-1-yl)-4-(1H-pyrrolo[2,3-b]pyridin-4-yl)benzamide Prepared from cis rac (1-amino-2,3-dihydro-1H-inden-2-yl)methanol and 4-(1H-pyrrolo[2,3-b]pyridin-4-yl)benzoic acid (Example 1 Step 2) according to the procedure described in Example 2 Step 4.

Step 2: N-[(1R,2R)-2-(Hydroxymethyl)-2,3-dihydro-1H-inden-1-yl]-4-{1H-pyrrolo[2,3-b]pyridin-4-yl}benzamide The enantiomers of cis rac N-(2-(hydroxymethyl)-2,3-dihydro-1H-inden-1-yl)-4-(1H-pyrrolo[2,3-b]pyridin-4-yl) benzamide (100 mg) were separated by chiral SFC using the method as below:

Instrument: Thar SFC80 preparative SFC

Column: Chiralcel OD-H 250*30 mm i.d. 5u

Mobile phase: A for CO2 and B for MeOH (0.1% $NH3H_2O$)

Gradient: B %=40%

Flow rate: 65 g/min

Wavelength: 220 nm

Column temperature: 40° C.

System back pressure: 100 bar

After separation by SFC, the TFA salt of N-[(1R,2R)-2-(hydroxymethyl)-2,3-dihydro-1H-inden-1-yl]-4-{1H-pyrrolo[2,3-b]pyridin-4-yl}benzamide was obtained as peak 2 (Rt=3.88) (19.4 mg, yield: 9.3%) as a yellow solid.

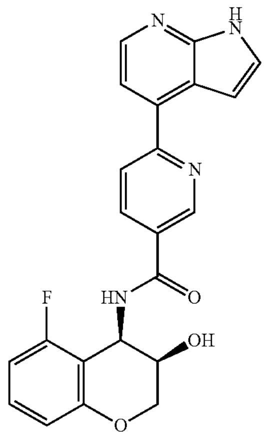 [SMILES: O=C(N[C@@H]1c2c(F)cccc2OC[C@@H]1O)c1ccc(-c2ccnc3[nH]ccc23)nc1]

Example 14: N-[(3R,4R)-5-Fluoro-3-hydroxy-3,4-dihydro-2H-1-benzopyran-4-yl]-6-{1H-pyrrolo[2,3-b]pyridin-4-yl}pyridine-3-carboxamide Step 1: 4-(4,4,5,5-Tetramethyl-1,3,2-dioxaborolan-2-yl)-1H-pyrrolo[2,3-b]pyridine To a mixture of 4-bromo-1H-pyrrolo[2,3-b]pyridine (11.50 g, 58.37 mmol, 1.00 eq) and 4,4,5,5-tetramethyl-2-(4,4,5,5-tetramethyl-1,3,2-dioxaborolan-2-yl)-1,3,2-dioxaborolane (29.64 g, 116.74 mmol, 2.00 eq) in dioxane (300 mL) were added KOAc (17.18 g, 175.11 mmol, 3.00 eq) and $Pd(dppf)Cl_2$.DCM (2.38 g, 2.92 mmol, 0.05 eq) at 12° C. The resulting mixture was stirred at 90° C. for 18 h. The solvent was concentrated and to the residue was added 500 mL of EtOAc, then filtered through Celite®. The filtrate was concentrated and the residue was purified by column chromatography on silica gel (PE/EtOAc=10/1, then EtOAc) to give 4-(4,4,5,5-tetramethyl-1,3,2-dioxaborolan-2-yl)-1H-pyrrolo[2,3-b]pyridine (15.50 g, crude) as a yellow gum.

Step 2: Methyl 6-(1H-pyrrolo[2,3-b]pyridin-4-yl) nicotinate

To a mixture of 4-(4,4,5,5-tetramethyl-1,3,2-dioxaborolan-2-yl)-1H-pyrrolo[2,3-b]pyridine (14.40 g, 58.99 mmol, 1.00 eq) and methyl 6-bromopyridine-3-carboxylate (12.74 g, 58.99 mmol, 1.00 eq) in EtOH (390.0 mL) and $H_2O$ (65.0 mL) were added KOAc (11.58 g, 117.98 mmol, 2.00 eq) and 4-ditert-butylphosphanyl-N,N-dimethyl-aniline; dichloropalladium (2.09 g, 2.95 mmol, 2.09 mL, 0.05 eq) at 15° C. The resulting mixture was stirred at 90° C. for 16 h. The solvent was concentrated and the crude product was purified by column chromatography on silica gel (PE/EtOAc=8/1, 3/1, 1/1, then DCM, DCM/MeOH=50/1) to give methyl 6-(1H-pyrrolo[2,3-b]pyridin-4-yl)nicotinate (5.65 g, 22.31 mmol, yield: 37.8%) as a red solid.

Step 3: 6-(1H-Pyrrolo[2,3-b]pyridin-4-yl)nicotinic acid

Prepared from methyl 6-(1H-pyrrolo[2,3-b]pyridin-4-yl) nicotinate according to the procedure described in Example 1 Step 2.

Step 4: 5-Fluoro-3-hydroxychroman-4-one oxime

Prepared from 5-fluorochroman-4-one according to the procedures described in Example 7 Steps 1-2.

Step 5: 4-Amino-5-fluorochroman-3-ol

Prepared from 5-fluoro-3-hydroxychroman-4-one oxime according to the procedure described in Example 7 Step 3.

Step 6: (3R,4R)-4-Amino-5-fluorochroman-3-ol

To a stirred cloudy mixture of 4-amino-5-fluorochroman-3-ol in ethanol (~9.6 mL) at 70° C. was added a solution of (R)-(−)-mandelic acid in ethanol (~6.8 mL). The mixture became a yellow solution upon addition of the acid. The solution was stirred for 10 minutes at 70° C. before turning off the oil bath and allowing the solution to cool gradually overnight to rt. Large amounts of off-white precipitate had formed overnight. The mixture was poured onto a filter, and 1.266 g of white cake was isolated by filtration (including 3×5 mL ethanol washes). The white cake was treated with EtOAc (~20 mL) and a mix of $H_2O$ (9 mL) and ethanolamine (1 mL). The mixture was thoroughly shaken until the cake had completely dissolved. The layers were separated, and the cloudy aqueous layer was extracted with EtOAc (20 mL). The combined organic layers (clear solution) were dried over $Na_2SO_4$, filtered, concentrated and dried to give (3R,4R)-4-amino-5-fluorochroman-3-ol (571 mg, 3.12 mmol, yield: 69%).

Step 7: N-[(3R,4R)-5-Fluoro-3-hydroxy-3,4-dihydro-2H-1-benzopyran-4-yl]-6-{1H-pyrrolo[2,3-b]pyridin-4-yl}pyridine-3-carboxamide To a solution of 6-(1H-pyrrolo[2,3-b]pyridin-4-yl)nicotinic acid (Example 14 Step 3, 100.0 mg, 418.0 umol, 1.00 eq) and DIPEA (162.1 mg, 1.25 mmol, 219 uL, 3.00 eq) in DMF (2.00 mL) was added T3P (399 mg, 627.0 umol, 373 uL, 50% purity, 1.50 eq) and (3R,4R)-4-amino-5-fluorochroman-3-ol (76.6 mg, 418 umol, 1.00 eq) at 20° C. The reaction was stirred at 20° C. for 1 h. The mixture was purified directly by prep-HPLC (TFA) to give the TFA salt of N-[(3R,4R)-5-fluoro-3-hydroxy-3,4-dihydro-2H-1-benzopyran-4-yl]-6-{1H-pyrrolo[2,3-b]pyridin-4-yl}pyridine-3-carboxamide (105.3 mg, 203.1 umol, yield: 48.6%) as a yellow solid.

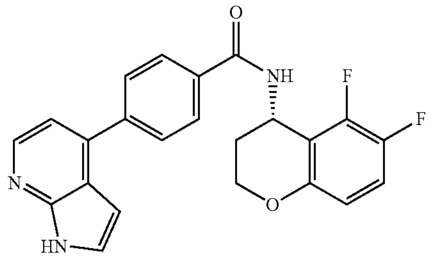 [SMILES: O=C(N[C@H]1CCOc2ccc(F)c(F)c21)c1ccc(-c2ccnc3[nH]ccc23)cc1]

Example 15: N-[(4S)-5,6-Difluoro-3,4-dihydro-2H-1-benzopyran-4-yl]-4-{1H-pyrrolo[2,3-b]pyridin-4-yl}benzamide Step 1: 3-(2-Bromo-4,5-difluorophenoxy)propanoic acid A solution of NaOH (9.09 g, 227.27 mmol, 2.50 eq) in $H_2O$ (22.5 mL) was added slowly to a suspension of 3-bromopropanoic acid (13.91 g, 90.91 mmol, 9.40 mL, 1.00 eq) and 2-bromo-4,5-difluorophenol (19.00 g, 90.91 mmol, 1.00 eq). The reaction mixture was stirred at 100° C. for 5 h. TLC (PE:EtOAc=5:1) showed the starting material was not consumed completely and a new spot was generated. The reaction was cooled to room temperature and then acidified with 12 M of HCl to pH=6. The products were extracted into EtOAc (100 mL*4). The combined organics were dried over $Na_2SO_4$ and concentrated. The crude product was purified by column chromatography on silica gel (PE:EtOAc=20/1, then 15:1, then EtOAc) to afford 3-(2-bromo-4,5-difluorophenoxy)propanoic acid (8.50 g, 30.24 mmol, yield: 33.26%) as a light brown solid.

Step 2: 8-Bromo-5,6-difluorochroman-4-one

Oxalyl chloride (453 mg, 3.56 mmol, 312 uL, 2.00 eq) was added to a solution of 3-(2-bromo-4,5-difluorophenoxy) propanoic acid (500 mg, 1.78 mmol, 1.00 eq) in DCM (10.0 mL) followed by DMF (1 drop). After 1.5 h at rt, the mixture was cooled in an ice-$H_2O$ bath. $AlCl_3$ (268 mg, 2.01 mmol, 110 uL, 1.13 eq) was added and the dark red solution was allowed to slowly reach 20° C., then stirred for 16 h at 20° C. The mixture was poured into ice-$H_2O$ (30 mL) and the organic layer was separated. The aqueous layer was extracted with DCM (10 mL*2). The combined organic extracts were washed with 0.5 M NaOH (20 mL) and brine (10 mL), dried over $Na_2SO_4$ and concentrated to give 8-bromo-5,6-difluorochrhoman-4-one (400 mg, 1.52 mmol, yield: 85.4%) as a white solid.

Step 3: 5,6-Difluorochroman-4-one

To a mixture of 8-bromo-5,6-difluorochroman-4-one (400 mg, 1.52 mmol, 1.00 eq) in MeOH (10.0 mL) was added 10 wt % Pd/C (100 mg, 1.52 mmol). After addition, the mixture was stirred at 30° C. for 16 h under $H_2$ (50 Psi). The mixture was filtered and the filtrate was concentrated to give 5,6-difluorochroman-4-one (300 mg, crude) as a red solid.

Step 4: 5,6-Difluorochroman-4-one oxime

To a mixture of 5,6-difluorochroman-4-one (200.0 mg, 1.09 mmol, 1.00 eq) and NaOAc (98.35 mg, 1.20 mmol, 1.10 eq) in EtOH (6.00 mL) was added $NH_2OH{\cdot}HCl$ (83.02 mg, 1.19 mmol, 1.10 eq) at 15° C. The resulting mixture was stirred at 80° C. for 20 h. TLC (PE:EtOAc=3:1) showed the starting material was not consumed completely, then 240 mg of $NH_2OH{\cdot}HCl$ and 400 mg of NaOAc were added, the resulting mixture was stirred for another 20 h at 80° C. TLC (PE:EtOAc=3:1) showed the reaction was nearly complete. The solvent was removed under vacuum. To the residue was added 50 mL of EtOAc and 10 mL of $H_2O$, the organic layer was separated, dried over $Na_2SO_4$ and concentrated to give 5,6-difluorochroman-4-one oxime (200 mg, 1.00 mmol, yield: 92.1%) as a white solid.

Step 5: (S)-5,6-Difluorochroman-4-amine

To a mixture of Raney Ni (200.0 mg, 1.00 mmol) in MeOH (20.0 mL) was added 5,6-difluorochroman-4-one oxime (200.0 mg, 1.00 mmol, 1.00 eq) at 15° C. The resulting mixture was stirred at 30° C. under 50 psi of $H_2$ for 20 h. The catalyst was removed by filtration and the filtrate was concentrated. The crude product was purified by acidic prep-HPLC (TFA) to afford 120 mg of the TFA salt of racemic 5,6-difluorochroman-4-amine as a white solid. The enantiomers were separated by chiral SFC following the method as below:

Instrument: Thar SFC80 preparative SFC

Column: Chiralpak AD-H 250*30 mm i.d. 5u

Mobile phase: A for C02 and B for EtOH (0.1% NH3$H_2$O)

Gradient: B %=30%

Flow rate: 65 g/min

Wavelength: 220 nm

Column temperature: 40° C.

System back pressure: 100 bar

Cycle time: 5 min

Injection amount: 25 mg per injection (S)-5,6-Difluorochroman-4-amine was obtained as the second eluting isomer (25 mg, yield: 13.50%) as a light brown solid.

Step 6: N-[(4S)-5,6-Difluoro-3,4-dihydro-2H-1-benzopyran-4-yl]-4-{1H-pyrrolo[2,3-b]pyridin-4-yl}benzamide Prepared from (S)-5,6-difluorochroman-4-amine and 4-(1H-pyrrolo[2,3-b]pyridin-4-yl)benzoic acid (Example 1 Step 2) according to the procedure described in Example 2 Step 4.

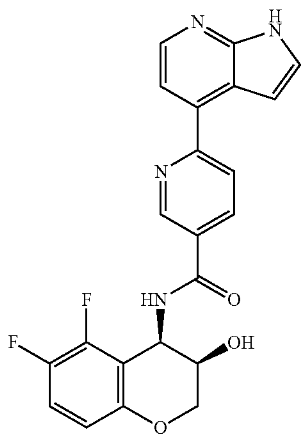 [SMILES: O=C(N[C@@H]1c2c(ccc(F)c2F)OC[C@@H]1O)c1ccc(-c2ccnc3[nH]ccc23)nc1]

Example 16: N-[(3S,4S)-5,6-Difluoro-3-hydroxy-3,4-dihydro-2H-1-benzopyran-4-yl]-6-{1H-pyrrolo[2,3-b]pyridin-4-yl}pyridine-3-carboxamide Step 1: 5,6-Difluoro-3-hydroxychroman-4-one oxime Prepared from 5,6-difluorochroman-4-one (Example 15 Step 3) according to the procedures described in Example 7 Steps 1-2.

Step 2: Cis 4-amino-5,6-difluorochroman-3-ol

To a solution of 5,6-difluoro-3-hydroxychroman-4-one oxime (2.10 g, 9.76 mmol, 1.00 eq) in MeOH (50.0 mL) at 0° C. was added 48% aqueous HBr (2.42 g, 29.87 mmol, 1.62 mL, 3.06 eq) and 10 wt % Pd/C (2.00 g, 929.58 umol). After addition, the mixture was stirred at 20° C. for 5 days under $H_2$ (50 psi). The mixture was filtered and the filtrate was concentrated to give the crude product. The crude product was washed with EtOAc (2 mL*2), filtered and the filter cake was the HBr salt of cis 4-amino-5,6-difluorochroman-3-ol. The product was dissolved in MeOH (20 mL) and Dowex® (3.0 g) was added to the solution. The mixture was stirred at 20° C. for 2 h and filtered. The filtrate was concentrated to give cis 4-amino-5,6-difluorochroman-3-ol (1.90 g, 9.44 mmol, yield: 96.7%) as a white solid.

Step 3: tert-Butyl ((3R,4R)-5,6-difluoro-3-hydroxychroman-4-yl)carbamate

To a mixture of cis 4-amino-5,6-difluorochroman-3-ol (200.0 mg, 994.2 umol, 1.00 eq) in DCM (10.0 mL) was added TEA (201.2 mg, 1.99 mmol, 275.6 uL, 2.00 eq) and $Boc_2O$ (238.7 mg, 1.09 mmol, 251.2 uL, 1.10 eq). After addition, the mixture was stirred at 20° C. for 16 h. The mixture was washed with $H_2O$ (3 mL*2). The organic layer was dried over $Na_2SO_4$ and concentrated to give crude product. The crude product was purified by Chiral SFC (Instrument: Thar SFC80 preparative SFC. Column: Chiralpak AY-H 250*30 mm i.d. 5u. Mobile phase: A for C02 and B for IPA (0.1% $NH_3H_2O$); Gradient: B %=30%; Flow rate: 65 g/min; Wavelength: 220 nm; Column temperature: 40° C.; System back pressure: 100 bar) to give tert-butyl ((3R,4R)-5,6-difluoro-3-hydroxychroman-4-yl)carbamate (80.0 mg, 266 umol, yield: 26.7%, Rt=2.69 min) as the first eluting enantiomer as a white solid.

Step 4: (3R,4R)-4-Amino-5,6-difluorochroman-3-ol

The mixture of tert-butyl ((3R,4R)-5,6-difluoro-3-hydroxychroman-4-yl)carbamate (80.0 mg, 265.5 umol, 1.00 eq) in HCl/EtOAc (6.0 mL, 4 M) was stirred at 20° C. for 1 h. The mixture was concentrated to give the HCl salt of (3R,4R)-4-amino-5,6-difluorochroman-3-ol (60 mg, crude) as a white solid.

Step 5: N-[(3S,4S)-5,6-Difluoro-3-hydroxy-3,4-dihydro-2H-1-benzopyran-4-yl]-6-{1H-pyrrolo[2,3-b]pyridin-4-yl}pyridine-3-carboxamide Prepared from (3R,4R)-4-amino-5,6-difluorochroman-3-ol and 6-(1H-pyrrolo[2,3-b]pyridin-4-yl)nicotinic acid (Example 14 Step 3) according to the procedure described in Example 2 Step 4.

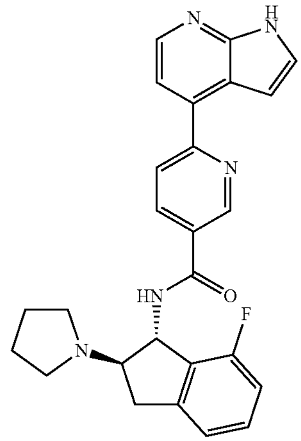 [SMILES: O=C(N[C@@H]1c2c(F)cccc2C[C@H]1N1CCCC1)c1ccc(-c2ccnc3[nH]ccc23)nc1]

Example 17: N-[(1R,2R)-7-Fluoro-2-(pyrrolidin-1-yl)-2,3-dihydro-1H-inden-1-yl]-6-{1H-pyrrolo[2,3-b]pyridin-4-yl}pyridine-3-carboxamide Step 1: 7-Fluoro-2,3-dihydro-1H-inden-1-ol To the suspension of 7-fluoro-2,3-dihydro-1H-inden-1-one (3.0 g, 20.0 mmol, 1.00 eq) in MeOH (45.0 mL) was added portionwise $NaBH_4$ (907.0 mg, 24.0 mmol, 1.20 eq) at 15° C. over 1 h. The resulting mixture was stirred at 15° C. for 1 h. The reaction mixture was diluted with 30 mL of $H_2O$, followed by 30 mL of 1 M of aq. HCl. The products were extracted into EtOAc (45 mL*3). The combined organics were washed with brine (30 mL*3), dried over $Na_2SO_4$ and concentrated to give 7-fluoro-2,3-dihydro-1H-inden-1-ol (2.75 g, 18.1 mmol, yield: 90.5%) as yellow oil.

Step 2: 4-Fluoro-1H-indene

To a mixture of 7-fluoro-2,3-dihydro-1H-inden-1-ol (2.75 g, 18.1 mmol, 1.00 eq) in toluene (45.0 mL) was added $TsOH \cdot H_2O$ (171.9 mg, 903.6 umol, 0.05 eq) at 15° C. The resulting mixture was stirred at 110° C. for 1 h. The reaction mixture was cooled to room temperature and washed with 10% of $K_2CO_3$ solution (15 mL*2) and brine (15 mL), dried over $Na_2SO_4$ and concentrated to give 4-fluoro-1H-indene (2.40 g, 17.9 mmol, yield: 98.9%) as a yellow oil.

Step 3: (1αR,6αS)-2-Fluoro-1α,6α-dihydro-6H-indeno[1,2-β]oxirene

A stirred mixture of 4-fluoro-1H-indene (2.40 g, 17.9 mmol, 1.00 eq), R,R-Jacobsen's catalyst (1.14 g, 1.79 mmol, 0.10 eq) and 1-oxido-4-phenyl-pyridin-1-ium (306.3 mg, 1.79 mmol, 0.10 eq) in DCM (30.0 mL) was cooled to 5° C. A cold aqueous solution of NaOCl (18.15 g, 243.8 mmol, 15.0 mL, 13.63 eq) was added slowly to the above mixture while keeping the temperature at 5-10° C. After addition, the mixture was stirred at 5° C. for 1 h, then stirred at 20° C. for 16 h. To the mixture was added petroleum ether (150 mL) before filtering through Celite®. The filtrate was washed with brine (50 mL*3), dried over $Na_2SO_4$ and concentrated under vacuum to give (1αR,6αS)-2-fluoro-1α,6α-dihydro-6H-indeno[1,2-b]oxirene (2.69 g, crude) as a black gum.

Step 4: (1R,2S)-1-Amino-7-fluoro-2,3-dihydro-1H-inden-2-ol

A three-necked flask under $N_2$ atmosphere was charged with (1αR,6αS)-2-fluoro-1α,6α-dihydro-6H-indeno[1,2-b]oxirene (2.69 g, 17.92 mmol, 1.00 eq), $CH_3CN$ (50.0 mL), then stirred and cooled to −40° C. To this slurry was added TfOH (5.38 g, 35.84 mmol, 3.16 mL, 2.00 eq) while maintaining the reaction temperature at −30° C. The reaction mixture was warmed to room temperature (12° C.) and stirred for 1 h. $H_2O$ (30 mL) was added and the mixture stirred for 0.25 h at 12° C. The $CH_3CN$ was removed by evaporation under vacuum. The aqueous phase was stirred at 100° C. for 3 h. After cooling to room temperature, the aqueous phase was washed with DCM (20 mL*3), then basified with NaOH pellets to pH=10. The products were extracted into EtOAc (25 mL*4). The combined organics were dried over $Na_2SO_4$ and concentrated to give (1R,2S)-1-amino-7-fluoro-2,3-dihydro-1H-inden-2-ol (2.10 g, crude) as a brown gum.

Step 5: tert-Butyl ((1R,2S)-7-fluoro-2-hydroxy-2,3-dihydro-1H-inden-1-yl)carbamate To a mixture of (1R,2S)-1-amino-7-fluoro-2,3-dihydro-1H-inden-2-ol (1.60 g, 7.18 mmol, 75% purity, 1.00 eq) and TEA (1.45 g, 14.4 mmol, 2.0 mL, 2.00 eq) in DCM (30.0 mL) was added $Boc_2O$ (1.88 g, 8.62 mmol, 1.98 mL, 1.20 eq) in one portion at 20° C. The reaction mixture was stirred at 20° C. for 16 h. The organic layer was washed with $H_2O$ (10 mL*4), dried over $Na_2SO_4$ and concentrated to afford tert-butyl ((1R,2S)-7-fluoro-2-hydroxy-2,3-dihydro-1H-inden-1-yl)carbamate (1.80 g, 6.73 mmol, yield: 93.8%) as a brown solid.

Step 6: tert-Butyl (3αR,8αS)-4-fluoro-8,8α-dihydroindeno[1,2-d][1,2,3]oxathiazole-3(3aH)-carboxylate 2-oxide To a solution of tert-butyl ((1R,2S)-7-fluoro-2-hydroxy-2,3-dihydro-1H-inden-1-yl)carbamate (500 mg, 1.87 mmol) in THF (15 mL) was added thionyl chloride (334 mg, 2.81 mmol, 204 uL) in THF (5 mL) dropwise over 10 min at −70° C. Triethylamine (568 mg, 5.61 mmol, 777.88 uL) in THF (5 mL) was then added over 10 min at −70° C. The reaction mixture was kept stirring for 0.5 h at this temperature. The reaction mixture was quenched with saturated $NaHCO_3$ (10 mL) at −70° C., diluted with $H_2O$ (40 mL), and then extracted with EtOAc (50 mL×3). The combined organic layers were dried over $Na_2SO_4$, filtered and concentrated to dryness. The residue was purified by silica gel chromatography (PE:EtOAc=3:1) to obtain tert-butyl (3aR,8aS)-4-fluoro-8,8a-dihydroindeno[1,2-d][1,2,3]oxathiazole-3(3aH)-carboxylate 2-oxide (438 mg, 1.40 mmol, 75% yield) as white gum.

Step 7: tert-Butyl (3αR,8αS)-4-fluoro-8,8cα-dihydroindeno[1,2-δ][1,2,3]oxathiazole-3(3αH)-carboxylate 2,2-dioxide A solution of ruthenium (III) chloride hydrate (30.6 mg, 136 umol) and sodium periodate (580 mg, 2.72 mmol) in $H_2O$ (5 mL) was cooled to 0° C., followed by addition of tert-butyl (3αR,8αS)-4-fluoro-8,8a-dihydroindeno[1,2-δ][1,2,3]oxathiazole-3(3αH)-carboxylate 2-oxide (430 mg, 1.36 mmol) in MeCN (5 mL). The mixture was stirred at 0° C. for 1 hour. The reaction mixture was quenched with saturated $Na_2SO_3$ (10 ml), then extracted with EtOAc (10 mL*3). The combined organic layers were dried over $Na_2SO_4$, filtered and concentrated to dryness. The residue was purified by silica gel chromatography (PE:EtOAc=5:1-1:1) to obtain tert-butyl (3αR,8αS)-4-fluoro-8,8a-dihydroindeno[1,2-δ][1,2,3]oxathiazole-3(3αH)-carboxylate 2,2-dioxide (366 mg, 1.11 mmol, 81% yield).

Step 8: (tert-Butoxycarbonyl)((1R,2R)-7-fluoro-2-(pyrrolidin-1-yl)-2,3-dihydro-1H-inden-1-yl)sulfamic acid A mixture of tert-butyl (3αR,8αS)-4-fluoro-8,8a-dihydroindeno[1,2-d][1,2,3]oxathiazole-3(3αH)-carboxylate 2,2-dioxide (366 mg, 1.11 mmol) and pyrrolidine (790 mg, 11.1 mmol) was stirred for 1 h at 25° C. The reaction mixture was concentrated to dryness directly to give (tert-butoxycarbonyl)((1R,2R)-7-fluoro-2-(pyrrolidin-1-yl)-2,3-dihydro-1H-inden-1-yl)sulfamic acid (560 mg, crude) was obtained as black gum which was used directly in the next step.

Step 9: (1R,2R)-7-Fluoro-2-(pyrrolidin-1-yl)-2,3-dihydro-1H-inden-1-amine

To the solution of (tert-butoxycarbonyl)((1R,2R)-7-fluoro-2-(pyrrolidin-1-yl)-2,3-dihydro-1H-inden-1-yl)sulfamic acid (560 mg, crude) in MeOH (10 mL) was added HCl/MeOH (4 M, 3 mL) at 0° C. The reaction mixture was stirred for 1 h at 25° C. The reaction mixture was concentrated to dryness to give crude HCl salt of (1R,2R)-7-fluoro-2-(pyrrolidin-1-yl)-2,3-dihydro-1H-inden-1-amine which was used directly in the next step.

Step 10: N-[(1R,2R)-7-Fluoro-2-(pyrrolidin-1-yl)-2,3-dihydro-1H-inden-1-yl]-6-{1H-pyrrolo[2,3-b]pyridin-4-yl}pyridine-3-carboxamide Prepared from (1R,2R)-7-fluoro-2-(pyrrolidin-1-yl)-2,3-dihydro-1H-inden-1-amine and 6-(1H-Pyrrolo[2,3-b]pyridin-4-yl)nicotinic acid (Example 14 Step 3) according to the procedure described in Example 14 Step 7.

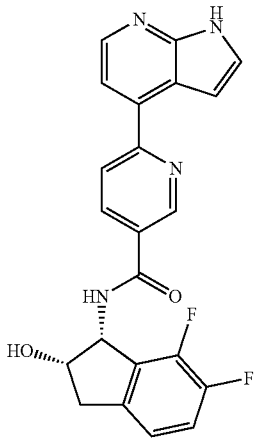 [SMILES: O=C(N[C@@H]1c2c(ccc(F)c2F)C[C@@H]1O)c1ccc(-c2ccnc3[nH]ccc23)nc1]

Example 18: N-[(1R,2S)-6,7-Difluoro-2-hydroxy-2,3-dihydro-1H-inden-1-yl]-6-{1H-pyrrolo[2,3-b]pyridin-4-yl}pyridine-3-carboxamide Step 1: 3-Chloro-1-(2,3-difluorophenyl)propan-1-one To a mixture of 1-bromo-2,3-difluorobenzene (19.3 g, 100.0 mmol, 11.2 mL, 1.00 eq) in THF (10.0 mL) was added n-BuLi (2.5 M, 42.0 mL, 1.05 eq) at −78° C. under $N_2$. After complete addition, the mixture was stirred at −78° C. for 0.5 h. CuCl (5.45 g, 55.0 mmol, 1.32 mL, 0.55 eq) was then added portionwise. After complete addition, the mixture was stirred at −75° C. to −60° C. for 0.5 h. The mixture was warmed to −20° C. and stirred at −20° C. for 1 h. 3-Chloropropanoyl chloride (13.33 g, 105.0 mmol, 10.1 mL, 1.05 eq) was added and the resulting mixture stirred at −20° C. for 2 h. The mixture was poured into $H_2O$ (15 mL) and acidified by HCl solution (4 M) until pH=1. The aqueous mixture was extracted with EtOAc (20 mL*3). The combined organic extracts were dried over $Na_2SO_4$ and concentrated. The crude product was purified by column chromatography on silica gel (PE:EtOAc=50:1-40:1) to give 3-chloro-1-(2,3-difluorophenyl)propan-1-one (4.50 g, 22.0 mmol, yield: 22.0%) as a yellow oil.

Step 2: 6,7-Difluoro-2,3-dihydro-1H-inden-1-one

A mixture of $AlCl_3$ (29.2 g, 218.8 mmol, 12.0 mL, 9.95 eq) and NaCl (7.69 g, 131.52 mmol, 5.98 eq) was heated to 140° C. before dropwise addition of 3-chloro-1-(2,3-difluorophenyl)propan-1-one (4.50 g, 21.99 mmol, 1.00 eq). After complete addition, the mixture was heated to 180° C. for 2 h. The mixture was cooled to 20° C. and $H_2O$ (50 mL) was added. The aqueous mixture was extracted with EtOAc (30 mL*3). The combined organic extracts were dried over $Na_2SO_4$ and concentrated. The crude product was purified by column chromatography on silica gel (PE:EtOAc=30:1-20:1) to give 6,7-difluoro-2,3-dihydro-1H-inden-1-one (1.10 g, 6.54 mmol, yield: 29.8%) as a yellow solid.

Step 3: 6,7-Difluoro-2,3-dihydro-1H-inden-1-ol

Prepared from 6,7-difluoro-2,3-dihydro-1H-inden-1-one according to the procedure described in Example 17 Step 1.

Step 4: 4,5-Difluoro-1H-indene

Prepared from 6,7-difluoro-2,3-dihydro-1H-inden-1-ol according to the procedure described in Example 17 Step 2.

Step 5: (1αR,6αS)-2,3-Difluoro-1α,6α-dihydro-6H-indeno[1,2-b]oxirene

Prepared from 4,5-difluoro-1H-indene according to the procedure described in Example 17 Step 3.

Step 6: (1R,2S)-1-Amino-6,7-difluoro-2,3-dihydro-1H-inden-2-ol

Prepared from (1αR,6αS)-2,3-difluoro-1α,6α-dihydro-6H-indeno[1,2-β]oxirene according to the procedure described in Example 17 Step 4.

Step 7: N-[(1R,2S)-6,7-Difluoro-2-hydroxy-2,3-dihydro-1H-inden-1-yl]-6-{1H-pyrrolo[2,3-b]pyridin-4-yl}pyridine-3-carboxamide Prepared from (1R,2S)-1-amino-6,7-difluoro-2,3-dihydro-1H-inden-2-ol and 6-(1H-pyrrolo[2,3-b]pyridin-4-yl) nicotinic acid (Example 14 Step 3) according to the procedure described in Example 2 Step 4.

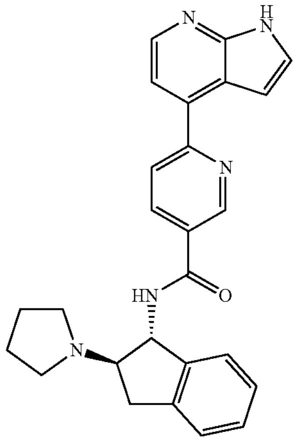 [SMILES: O=C(N[C@@H]1c2ccccc2C[C@H]1N1CCCC1)c1ccc(-c2ccnc3[nH]ccc23)nc1]

Example 19: N-[(1R,2R)-2-(Pyrrolidin-1-yl)-2,3-dihydro-1H-inden-1-yl]-6-{1H-pyrrolo[2,3-b]pyridin-4-yl}pyridine-3-carboxamide Step 1: tert-Butyl ((1R,2S)-2-hydroxy-2,3-dihydro-1H-inden-1-yl)carbamate Prepared from (1R,2S)-1-amino-2,3-dihydro-1H-inden-2-ol according to the procedure described in Example 17 Step 5.

Step 2: (1R,2S)-1-((tert-Butoxycarbonyl)amino)-2,3-dihydro-1H-inden-2-yl methanesulfonate To a mixture of tert-butyl ((1R,2S)-2-hydroxy-2,3-dihydro-1H-inden-1-yl)carbamate (35.00 g, 140.39 mmol, 1.00 eq) and TEA (28.41 g, 280.79 mmol, 38.92 mL, 2.00 eq) in DCM (50.0 mL) was added MsCl (16.08 g, 140.39 mmol, 10.87 mL, 1.00 eq) drop wise at 0° C. The reaction mixture was stirred at 25° C. for 1 hr. LCMS showed the starting material was consumed and the desired MS was detected. The reaction solution was washed with $H_2O$ (50 mL×3) and the organic phase was dried over $Na_2SO_4$, filtered and concentrated under reduced pressure to give (1R,2S)-1-((tert-butoxycarbonyl)amino)-2,3-dihydro-1H-inden-2-yl methanesulfonate (50.00 g, yield: 100%) as a brown solid that was used directly in the next step without further purification.

Step 3: tert-Butyl ((1R,2R)-2-(pyrrolidin-1-yl)-2,3-dihydro-1H-inden-1-yl)carbamate A solution of (1R,2S)-1-((tert-butoxycarbonyl)amino)-2,3-dihydro-1H-inden-2-yl methanesulfonate (3.00 g, 9.16 mmol, 1.00 eq) and pyrrolidine (1.96 g, 27.49 mmol, 2.30 mL, 3.00 eq) in EtOH (45.0 mL) and stirred at 100° C. for 16 hrs in a sealed tube. The reaction mixture was cooled then concentrated under reduced pressure. The crude product was purified by silica gel chromatography (PE/EtOAc=10:1-5:1-3:1) to give tert-butyl ((1R,2R)-2-(pyrrolidin-1-yl)-2,3-dihydro-1H-inden-1-yl)carbamate (1.1 g, yield: 46.3%) as a dark solid.

Step 4: (1R,2R)-2-(Pyrrolidin-1-yl)-2,3-dihydro-1H-inden-1-amine

A mixture of tert-butyl ((1R,2R)-2-(pyrrolidin-1-yl)-2,3-dihydro-1H-inden-1-yl)carbamate (1.10 g, 3.64 mmol, 1.00 eq) in HCl/EtOAc (20.0 mL) and EtOAc (20.0 mL) was stirred at 25° C. for 1.5 hrs. LCMS showed that the reaction was complete. The mixture was concentrated under reduced pressure to give the HCl salt of (1R,2R)-2-(pyrrolidin-1-yl)-2,3-dihydro-1H-inden-1-amine (0.8 g, yield: 92.0%)) as a dark solid and used into the next step without further purification.

Step 5: N-[(1R,2R)-2-(Pyrrolidin-1-yl)-2,3-dihydro-1H-inden-1-yl]-6-{1H-pyrrolo[2,3-b]pyridin-4-yl}pyridine-3-carboxamide A mixture of 6-(1H-pyrrolo[2,3-b]pyridin-4-yl)nicotinic acid (Example 14 Step 3, 150 mg, 627.0 umol, 1.0 eq), (1R,2R)-2-(pyrrolidin-1-yl)-2,3-dihydro-1H-inden-1-amine (179.7 mg, 752.4 umol, 1.20 eq, HCl), $T_3P$ (518.7 mg, 815.1 umol, 484.8 uL, 50% purity, 1.30 eq), DIPEA (162.1 mg, 1.25 mmol, 219.0 uL, 2.00 eq) in DMF (3.0 mL) was stirred at 25° C. for 0.5h. LCMS showed the reaction was complete and one main peak with desired MS was detected. The mixture reaction was filtered. The filtrate was purified by neutral prep-HPLC to give N-[(1R,2R)-2-(pyrrolidin-1-yl)-2,3-dihydro-1H-inden-1-yl]-6-{1H-pyrrolo[2,3-b]pyridin-4-yl}pyridine-3-carboxamide (70.7 mg, yield: 26.6%) as a light yellow solid.

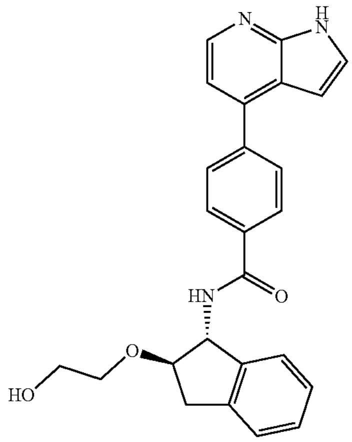 [SMILES: O=C(N[C@@H]1c2ccccc2C[C@H]1OCCO)c1ccc(-c2ccnc3[nH]ccc23)cc1]

Example 20: N-[(1R,2R)-2-(2-Hydroxyethoxy)-2,3-dihydro-1H-inden-1-yl]-4-{1H-pyrrolo[2,3-b]pyridin-4-yl}benzamide Step 1: (1R,2R)-1-((Diphenylmethylene)amino)-2,3-dihydro-1H-inden-2-ol To a solution of (1R,2R)-1-amino-2,3-dihydro-1H-inden-2-ol (482 mg, 3.23 mmol, 1.00 eq) in $CHCl_3$ (8.00 mL) was added DIPEA (417.5 mg, 3.23 mmol, 564 uL, 1.00 eq) and diphenylmethanimine (643.9 mg, 3.55 mmol, 596.2 uL, 1.10 eq). The mixture was stirred at 80° C. for 16 h. To the mixture was added $H_2O$ (10 mL) and the products were extracted into DCM (10 mL*3). The combined organic extracts were dried over $Na_2SO_4$ and concentrated under vacuum to give (1R,2R)-1-((diphenylmethylene)amino)-2,3-dihydro-1H-inden-2-ol (1.30 g, crude) as a yellow oil.

Step 2: N-((1R,2R)-2-(Allyloxy)-2,3-dihydro-1H-inden-1-yl)-1,1-diphenylmethanimine To a solution of (1R,2R)-1-((diphenylmethylene)amino)-2,3-dihydro-1H-inden-2-ol (600 mg, 1.91 mmol, 1.00 eq) in DMF (10.0 mL) was added NaH (114.60 mg, 2.87 mmol, 60% purity, 1.50 eq) at 0° C. The mixture was stirred at 0° C. for 0.5 h, then to the mixture was added 3-bromoprop-1-ene (277.29 mg, 2.29 mmol, 1.20 eq), and the mixture was stirred at 60° C. for 15.5 h. To the mixture was added $H_2O$ (10 mL) and the products were extracted into EtOAc (10 mL*3). The combined organic layers were dried over $Na_2SO_4$ and concentrated under vacuum to give N-((1R,2R)-2-(allyloxy)-2,3-dihydro-1H-inden-1-yl)-1,1-diphenylmethanimine (450 mg, 1.27 mmol, yield: 66.7%) as a yellow oil.

Step 3: (1R,2R)-2-(Allyloxy)-2,3-dihydro-1H-inden-1-amine

A mixture of N-((1R,2R)-2-(allyloxy)-2,3-dihydro-1H-inden-1-yl)-1,1-diphenylmethanimine (450 mg, 1.27 mmol, 1.00 eq) in 1M HCl (5.0 mL) and MeCN (5.0 mL) was stirred at 60° C. for 5 h. The mixture was cooled to 15° C. and extracted with EtOAc (10 mL*3). The aqueous phase was dried under vacuum to give the HCl salt of (1R,2R)-2-(allyloxy)-2,3-dihydro-1H-inden-1-amine (310 mg, crude) as a yellow oil.

Step 4: tert-Butyl ((1R,2R)-2-(allyloxy)-2,3-dihydro-1H-inden-1-yl)carbamate

Prepared from (1R,2R)-2-(allyloxy)-2,3-dihydro-1H-inden-1-amine according to the procedure described in Example 17 Step 5.

Step 5: tert-Butyl ((1R,2R)-2-(2-hydroxyethoxy)-2,3-dihydro-1H-inden-1-yl)carbamate To a solution of tert-butyl ((1R,2R)-2-(allyloxy)-2,3-dihydro-1H-inden-1-yl)carbamate (260 mg, 898.5 umol, 1.00 eq) in DCM (5.0 mL) was bubbled 03 for 0.1 h at −78° C. DMS (558.2 mg, 8.99 mmol, 656.8 uL, 10.0 eq) was then added to the mixture at −78° C. before warming to 15° C. and stirring for 2 h. The mixture was concentrated under vacuum to give a crude oil that was dissolved in MeOH (8.0 mL). To the solution was added $NaBH_4$ (67.5 mg, 1.78 mmol, 2.00 eq) at 15° C. before stirring at 15° C. for 2 h. The reaction was quenched with $H_2O$ (3 mL) before concentrating under vacuum. The residue was purified by prep-TLC (EtOAc) to give tert-butyl ((1R,2R)-2-(2-hydroxyethoxy)-2,3-dihydro-1H-inden-1-yl)carbamate (110 mg, 375.0 umol, yield: 42.0%) as a colorless oil.

Step 6: 2-(((1R,2R)-1-Amino-2,3-dihydro-1H-inden-2-yl)oxy)ethan-1-ol

Prepared from tert-butyl ((1R,2R)-2-(2-hydroxyethoxy)-2,3-dihydro-1H-inden-1-yl)carbamate according to the procedure described in Example 16 Step 4.

Step 7: N-[(1R,2R)-2-(2-Hydroxyethoxy)-2,3-dihydro-1H-inden-1-yl]-4-{1H-pyrrolo[2,3-b]pyridin-4-yl}benzamide Prepared from 2-(((1R,2R)-1-amino-2,3-dihydro-1H-inden-2-yl)oxy)ethan-1-ol and 4-(1H-pyrrolo[2,3-b]pyridin-4-yl)benzoic acid (Example 1 Step 2) according to the procedure described in Example 14 Step 7.

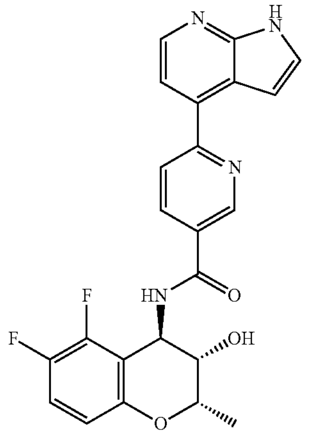 [SMILES: C[C@@H]1Oc2ccc(F)c(F)c2[C@@H](NC(=O)c2ccc(-c3ccnc4[nH]ccc34)nc2)[C@@H]1O]

Example 21: N-[(2S,3S,4R)-5,6-Difluoro-3-hydroxy-2-methyl-3,4-dihydro-2H-1-benzopyran-4-yl]-6-{1H-pyrrolo[2,3-b]pyridin-4-yl}pyridine-3-carboxamide Step 1: (S)-1-Bromo-4,5-difluoro-2-(pent-4-en-2-yloxy)benzene DIAD (16.93 ml, 87 mmol) was added dropwise to an ice bath cooled solution of (R)-pent-4-en-2-ol (5 g, 58.1 mmol), 2-bromo-4,5-difluorophenol (12.13 g, 58.1 mmol) and $Ph_3P$ (18.27 g, 69.7 mmol) in THF (300 ml). The reaction was stirred while warming to room temperature overnight. The reaction mixture was concentrated, the residue was treated with 1:1 hexanes:diethethyl ether (200 ml) and the white solid removed by filtration. The filtrate was dried onto silica and purified by column chromatography (0-50% EtOAc/hexanes) to give (S)-1-bromo-4,5-difluoro-2-(pent-4-en-2-yloxy)benzene (13.2 g, 47.6 mmol, 82% yield) as a clear oil.

Step 2: (S)-3-(2-Bromo-4,5-difluorophenoxy)butanoic acid $KMnO_4$ (22.24 g, 141 mmol) was taken up in $H_2O$ (250 ml) and toluene (71.4 ml) and cooled to 0° C. Tetrabutylammonium bromide (1.512 g, 4.69 mmol) added followed by (S)-1-bromo-4,5-difluoro-2-(pent-4-en-2-yloxy)benzene (13 g, 46.9 mmol). The mixture was stirred while warming to RT overnight. The reaction was then cooled to 0° C. before addition of sodium bisulfite (19.53 g, 188 mmol) followed by 6 N HCl (46.9 ml, 281 mmol). After stirring for 30 minutes the mixture turned white and biphasic. The aqueous mixture was extracted with EtOAc (×4). The combined organic extracts were dried over $Na_2SO_4$ and concentrated under vacuum. The residue was purified by column chromatography (0-40% Hex/EtOAc) to give (S)-3-(2-bromo-4,5-difluorophenoxy)butanoic acid (9.3 g, 31.5 mmol, 67.2% yield) as a clear oil.

Step 3: (S)-8-Bromo-5,6-difluoro-2-methylchroman-4-one (S)-3-(2-Bromo-4,5-difluorophenoxy)butanoic acid (9.3 g, 31.5 mmol) was taken up in DCM (100 ml) and oxalyl chloride (5.52 ml, 63.0 mmol) was added dropwise followed by 1 drop of DMF. T reaction was stirred at ambient temperature for 1 hour before cooling to 0° C. $AlCl_3$ (4.62 g, 34.7 mmol) was added at 0° C. before warming to RT and stirring overnight. Ice $H_2O$ was added and the aqueous mixture was extracted with (DCM×3). The combined organic extracts were washed with brine, dried over $Na_2SO_4$ and concentrated under vacuum to give (S)-8-bromo-5,6-difluoro-2-methylchroman-4-one (8.3 g, 30.0 mmol, 95% yield) which was carried on without further purification.

Step 4: (S)-5,6-Difluoro-2-methylchroman-4-one (S)-8-Bromo-5,6-difluoro-2-methylchroman-4-one (8.3 g, 30.0 mmol) was taken up in MeOH (100 mL) and Pd/C (0.638 g, 5.99 mmol) was added. The mixture was stirred under $H_2$ (50 psi) for 3 h. The catalyst was removed by filtering through Celite. The filtrate was concentrated under vacuum to give (S)-5,6-difluoro-2-methylchroman-4-one (8.3 g, 30.0 mmol) that was used without further purification.

Step 5: (2S,3S)-5,6-Difluoro-3-hydroxy-2-methylchroman-4-one oxime

A stirred 3N solution of NaOH in MeOH (10 mL) was cooled to −10° C. A suspension of (S)-5,6-difluoro-2-methylchroman-4-one (1.6 g, 8.07 mmol) in methanol (26 mL), also pre-cooled to −10° C., was added. After addition, the mixture was stirred for 20 minutes at −10° C. before adding a slurry of (diacetoxyiodo)benzene (2.65 g, 8.07 mmol) in MeOH (10 mL). The mixture was stirred at −10° C. for 30 minutes before warming gradually to 20° C. over 1 hour. The mixture became a brown solution, which was stirred for 3 h at R.T., then poured over several minutes into a stirred, cooled (0° C.) 4N HCl aqueous solution (8 mL). The mixture was stirred 10 minutes at 0° C. and then 30 minutes at R.T. Sodium acetate (1.987 g, 24.22 mmol) was added to the reaction followed by hydroxylamine hydrochloride (1.122 g, 16.15 mmol). The mixture was stirred 40 minutes at 50° C. The reaction mixture was concentrated under vacuum, diluted with $H_2O$ (~30-40 mL) and extracted with hexanes (2×40 mL). The aqueous layer was then extracted with EtOAc (2×50 mL). The combined EtOAc extracts were dried over $Na_2SO_4$, filtered and concentrated under vacuum to yield (2S,3S)-5,6-difluoro-3-hydroxy-2-methylchroman-4-one oxime (1.4 g, 6.11 mmol, 76% yield).

Step 6: (2S,3S)-4-Amino-5,6-difluoro-2-methylchroman-3-ol

To a stirred solution of (2S,3S)-5,6-difluoro-3-hydroxy-2-methylchroman-4-one oxime (1.4 g, 6.11 mmol) in methanol was added hydrobromic acid (0.940 ml) followed by 10% Pd/C (700 mg), which was wet with 3.2 mL of $H_2O$. The mixture was cooled in an ice bath and stirred under 40 psi of $H_2$ overnight while allowing reaction to warm gradually from −5° C. to 20° C. The catalyst was removed by filtering through Celite. The filtrate was treated with 4N NaOH until pH-12. The aqueous mixture was extracted with EtOAc (×3). The combined organic extracts were dried over $Na_2SO_4$ and concentrated under vacuum to give (2S,3S)-4-amino-5,6-difluoro-2-methylchroman-3-ol (0.986 g, 4.58 mmol, 75% yield) that was used without further purification.

Step 7: N-((2S,3S)-5,6-Difluoro-3-hydroxy-2-methylchroman-4-yl)-6-(1H-pyrrolo[2,3-b]pyridin-4-yl) nicotinamide A mixture of (2S,3S)-4-amino-5,6-difluoro-2-methylchroman-3-ol (0.112 g, 0.523 mmol), 6-(1H-pyrrolo[2,3-b]pyridin-4-yl)nicotinic acid (Example 14 Step 3, 0.125 g, 0.523 mmol), PyBOP (0.272 g, 0.523 mmol) and DIEA (0.274 mL, 1.568 mmol) in DMF (1 mL) was stirred at room temperature for 1 h. The mixture was diluted with EtOAc and washed with brine (×3), dried over $Na_2SO_4$ and concentrated under vacuum. The residue was purified via flash chromatography (0-10% DCM/MeOH) to give N-((2S,3S)-5,6-difluoro-3-hydroxy-2-methylchroman-4-yl)-6-(1H-pyrrolo[2,3-b]pyridin-4-yl)nicotinamide (0.21 g, 0.479 mmol, 92% yield).

Step 8: N-((2S,3S,4R)-5,6-Difluoro-3-hydroxy-2-methylchroman-4-yl)-6-(1H-pyrrolo[2,3-b]pyridin-4-yl)nicotinamide The diastereoisomers of N-((2S,3S)-5,6-difluoro-3-hydroxy-2-methylchroman-4-yl)-6-(1H-pyrrolo[2,3-b]pyridin-4-yl)nicotinamide (0.21 g, 0.479 mmol) were separated according to the chiral SFC conditions below.

Column: Regis Whelk 01 (S,S) 21×250 mm
Mobile Phase: 40% Ethanol containing 0.25% DEA in C02
Flow rate: 70 mL/min
Sample: 209.3 mg sample was dissolved in 30 mL methanol+30 mL DCM
Injection: 1.5 mL per run
Detection: 254 nm N-((2S,3S,4R)-5,6-Difluoro-3-hydroxy-2-methylchroman-4-yl)-6-(1H-pyrrolo[2,3-b]pyridin-4-yl)nicotinamide was obtained as peak 1 (28.1 mg, 0.064 mmol, 13.4% yield).

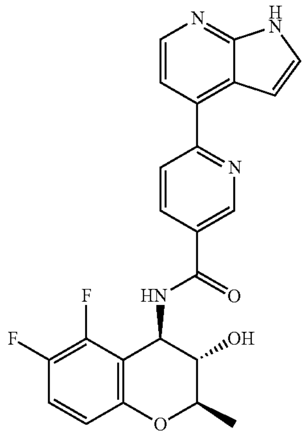 [SMILES: C[C@H]1Oc2ccc(F)c(F)c2[C@@H](NC(=O)c2ccc(-c3ccnc4[nH]ccc34)nc2)[C@@H]1O]

Example 22: N-[(2R,3S,4R)-5,6-Difluoro-3-hydroxy-2-methyl-3,4-dihydro-2H-1-benzopyran-4-yl]-6-{1H-pyrrolo[2,3-b]pyridin-4-yl}pyridine-3-carboxamide

Step 1: (R)-1-Bromo-4,5-difluoro-2-(pent-4-en-2-yloxy)benzene

Prepared from (S)-pent-4-en-2-ol and 2-bromo-4,5-difluorophenol according to the procedure described in Example 21 Step 1.

Step 2: (R)-3-(2-Bromo-4,5-difluorophenoxy)butanoic acid

Prepared from (R)-1-bromo-4,5-difluoro-2-(pent-4-en-2-yloxy)benzene according to the procedure described in Example 21 Step 2.

Step 3: (R)-8-Bromo-5,6-difluoro-2-methylchroman-4-one

Prepared from (R)-3-(2-bromo-4,5-difluorophenoxy)butanoic acid according to the procedure described in Example 21 Step 3.

Step 4: (R)-5,6-Difluoro-2-methylchroman-4-one

Prepared from (R)-8-bromo-5,6-difluoro-2-methylchroman-4-one according to the procedure described in Example 21 Step 4.

Step 5: (2R,3R)-5,6-Difluoro-3-hydroxy-2-methylchroman-4-one (R)-5,6-Difluoro-2-methylchroman-4-one (1.0 g, 5.05 mmol) was taken up in THF (20 ml) and cooled to −78° C. Sodium bis(trimethylsilyl)amide solution, 1M in THF (7.06 ml, 7.06 mmol) was added and stirred for 15 minutes, followed by addition of 3-phenyl-2-(phenylsulfonyl)oxaziridine (1.846 g, 7.06 mmol) in THF (5 mL). The resulting mixture was stirred at −78° C. for 3 h. Saturated $NH_4Cl$ was added and the mixture stirred for 2 h while warming to room temperature. The aqueous mixture was extracted with DCM (×3). The combined organic extracts were dried over $Na_2SO_4$ and concentrated under vacuum. The residue was purified via flash chromatography (0-100% Hex/EtOAc) to give (2R,3R)-5,6-difluoro-3-hydroxy-2-methylchroman-4-one (0.568 g, 0.700 mmol, 52.6% yield) as an off white solid.

Step 6: (2R,3S)-4-Amino-5,6-difluoro-2-methylchroman-3-ol (2R,3R)-5,6-Difluoro-3-hydroxy-2-methylchroman-4-one (0.568 g, 2.65 mmol), ammonium formate (1.672 g, 26.5 mmol) and sodium cyanoborohydride (0.167 g, 2.65 mmol) were taken up in MeOH (20 mL) and stirred at 50° C. overnight. The solvent was removed under vacuum, the residue was taken up in EtOAc and washed with 10% HCl (×3). The aqueous phase was made basic with 2N NaOH and extracted with EtOAc (×3). The combined organic extracts were dried over $Na_2SO_4$ and concentrated under vacuum to give (2R,3S)-4-amino-5,6-difluoro-2-methylchroman-3-ol (0.498 g, 2.314 mmol, 87% yield) as a yellow oil.

Step 7: N-[(2R,3S)-5,6-Difluoro-3-hydroxy-2-methyl-3,4-dihydro-2H-1-benzopyran-4-yl]-6-{1H-pyrrolo[2,3-b]pyridin-4-yl}pyridine-3-carboxamide Prepared N-[(2R,3S)-5,6-Difluoro-3-hydroxy-2-methyl-3,4-dihydro-2H-1-benzopyran-4-yl]-6-{1H-pyrrolo[2,3-b]pyridin-4-yl}pyridine-3-carboxamide according to the procedure described in Example 21 Step 7.

Step 8: N-[(2R,3S,4R)-5,6-Difluoro-3-hydroxy-2-methyl-3,4-dihydro-2H-1-benzopyran-4-yl]-6-{1H-pyrrolo[2,3-b]pyridin-4-yl}pyridine-3-carboxamide The diastereoisomers of N-[(2R,3S)-5,6-difluoro-3-hydroxy-2-methyl-3,4-dihydro-2H-1-benzopyran-4-yl]-6-{1H-pyrrolo[2,3-b]pyridin-4-yl}pyridine-3-carboxamide (80 mg, 0.183 mmol) were separated according to the chiral SFC conditions below.

Column: ChiralCel OJ 20×250 mm

Mobile Phase: 25% Ethanol containing 0.25% DEA in C02

Flow rate: 70 ml/min

Sample: 80 mg crude sample was dissolved in 5 mL Methanol+5 mL DCM

Injection: 1.0 mL per run

Detection: 254 nm

N-[(2R,3S,4R)-5,6-Difluoro-3-hydroxy-2-methyl-3,4-dihydro-2H-1-benzopyran-4-yl]-6-{1H-pyrrolo[2,3-b]pyridin-4-yl}pyridine-3-carboxamide was obtained as peak 1 (29.8 mg, 0.068 mmol, 37.3% yield).

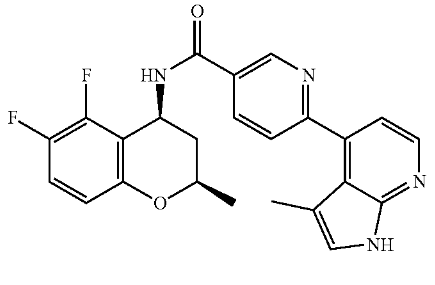 [SMILES: Cc1c[nH]c2nccc(-c3ccc(C(=O)N[C@H]4C[C@@H](C)Oc5ccc(F)c(F)c54)cn3)c12]

Example 23: N-[(2R,4S)-5,6-Difluoro-2-methyl-3,4-dihydro-2H-1-benzopyran-4-yl]-6-{3-methyl-1H-pyrrolo[2,3-b]pyridin-4-yl}pyridine-3-carboxamide Step 1: (2R)-5,6-Difluoro-2-methylchroman-4-amine Prepared from (R)-5,6-difluoro-2-methylchroman-4-one (Example 22 Step 4) according to the procedure described in Example 22 Step 6.

Step 2: (2R,4S)-5,6-Difluoro-2-methylchroman-4-amine hydrochloride

Prepared from (2R)-5,6-difluoro-2-methylchroman-4-amine according to the procedure described in US20040157739 for (4S)-aminochromane hydrochloride.

Step 3: N-[(2R,4S)-5,6-Difluoro-2-methyl-3,4-dihydro-2H-1-benzopyran-4-yl]-6-{3-methyl-1H-pyrrolo[2,3-b]pyridin-4-yl}pyridine-3-carboxamide Prepared from (2R,4S)-5,6-difluoro-2-methylchroman-4-amine hydrochloride and 6-(1H-pyrrolo[2,3-b]pyridin-4-yl) nicotinic acid (Example 14 Step 3) according to the procedure described in Example 21 Step 7.

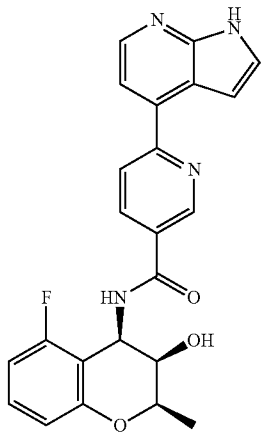 [SMILES: C[C@H]1Oc2cccc(F)c2[C@@H](NC(=O)c2ccc(-c3ccnc4[nH]ccc34)nc2)[C@H]1O]

Example 24: N-[(2R,3R,4R)-5-Fluoro-3-hydroxy-2-methyl-3,4-dihydro-2H-1-benzopyran-4-yl]-6-{1H-pyrrolo[2,3-b]pyridin-4-yl}pyridine-3-carboxamide Step 1: 1-(2-Fluoro-6-hydroxyphenyl)butane-1,3-dione To a mixture of 1-(2-fluoro-6-hydroxyphenyl)ethan-1-one (5.0 g, 32.44 mmol, 1.00 eq) in EtOAc (350 mL) was added sodium metal (4.47 g, 194.64 mmol, 4.61 mL, 6.00 eq) in portions. The mixture was stirred at 20° C. for 18 h. Cold aq. HCl (0.5 M) was added until the pH=7. The organic layer was separated, dried over $Na_2SO_4$ and concentrated under vacuum. The residue was purified by silica gel chromatography (PE/EtOAc=40/1, 30/1, 10/1, 5/1) to afford 1-(2-fluoro-6-hydroxyphenyl)butane-1,3-dione (5.50 g, 28.04 mmol, yield: 86.43%) as a dark oil.

Step 2: 5-Fluoro-2-methyl-4H-chromen-4-one

To a mixture of 1-(2-fluoro-6-hydroxyphenyl)butane-1,3-dione (7.0 g, 35.68 mmol, 1.00 eq) in MeOH (2.0 mL) was added conc. HCl (4.0 mL). The mixture was stirred at 20° C. for 12 h. The mixture was concentrated under reduced pressure and the residue was diluted with EtOAc (50 mL)/$H_2O$ (30 mL). The organic phase was separated and washed successively with saturated aq. $NaHCO_3$ (30 mL) and brine (30 mL). The organic phase was then dried over $Na_2SO_4$ and concentrated under vacuum. The residue was purified by silica gel chromatography (PE/EtOAc=30/1, 20/1, 5/1) to afford 5-fluoro-2-methyl-4H-chromen-4-one (5.20 g, 29.2 mmol, yield: 81.8%) as a yellow solid.

Step 3: 5-Fluoro-2-methylchroman-4-one

To a mixture of 5-fluoro-2-methyl-4H-chromen-4-one (4.0 g, 22.45 mmol, 1.00 eq) in toluene (20 mL) was added Pd/C (2.00 g, 19.65 mmol) in one portion. The mixture was stirred at 50° C. for 16 h under $H_2$ (50 psi). The catalyst was removed by filtration and the filtrate was concentrated under vacuum. The residue was purified by silica gel chromatography (PE/EtOAc=50/1, 40/1, 30/1) to afford 5-fluoro-2-methylchroman-4-one (3.30 g, 18.32 mmol, yield: 81.6%) as white solid.

Step 4: rac cis 5-Fluoro-3-hydroxy-2-methylchroman-4-one

To a mixture of NaOH (2.00 g, 49.95 mmol, 3.00 eq) in MeOH (20.0 mL) was added 5-fluoro-2-methylchroman-4-one (3.0 g, 16.65 mmol, 1.00 eq) in MeOH (20.00 mL) dropwise. The mixture was stirred at −10° C. for 0.1 h, then (diacetoxyiodo)benzene (6.44 g, 19.98 mmol, 1.20 eq) in MeOH (30.0 mL) was added dropwise at −10° C. The mixture was stirred at −10° C. for 0.5 h and at 20° C. for 3 h. Aq. HCl (4 M) was added to the mixture until the pH=3. The solvent was removed under vacuum and the residue was purified by silica gel chromatography (PE/EtOAc=40/1, 30/1, 20/1) to afford rac cis 5-fluoro-3-hydroxy-2-methylchroman-4-one (1.50 g, 7.65 mmol, yield: 45.9%) as white solid.

Step 5: rac cis 5-Fluoro-3-hydroxy-2-methylchroman-4-one oxime

To a mixture of rac cis 5-fluoro-3-hydroxy-2-methylchroman-4-one (300 mg, 1.53 mmol, 1.00 eq) in MeOH (20.0 mL) was added $NH_2OH \cdot HCl$ (212.64 mg, 3.06 mmol, 2.00 eq) and NaOAc (313.76 mg, 3.83 mmol, 2.50 eq) in one portion. The mixture was stirred at 50° C. for 1 h. The solvent was removed under vacuum and $H_2O$ (10 mL) was added. The products were extracted into EtOAc (20 mL*3). The combined organic layers were dried over $Na_2SO_4$, filtered and concentrated under vacuum to afford rac cis 5-fluoro-3-hydroxy-2-methylchroman-4-one oxime (300.0 mg, 1.42 mmol, yield: 92.84%) as white solid.

Step 6: rac cis 4-Amino-5-fluoro-2-methylchroman-3-ol

Prepared from rac cis 5-fluoro-3-hydroxy-2-methylchroman-4-one oxime according to the procedure described in Example 7 Step 3.

Step 7: rac cis N-(5-Fluoro-3-hydroxy-2-methylchroman-4-yl)-6-(1H-pyrrolo[2,3-b]pyridin-4-yl)nicotinamide Prepared from rac cis 4-amino-5-fluoro-2-methylchroman-3-ol and 6-(1H-pyrrolo[2,3-b]pyridin-4-yl)nicotinic acid (Example 14 Step 3) according to the procedure described in Example 2 Step 4.

Step 8: N-[(2R,3R,4R)-5-Fluoro-3-hydroxy-2-methyl-3,4-dihydro-2H-1-benzopyran-4-yl]-6-{1H-pyrrolo[2,3-b]pyridin-4-yl}pyridine-3-carboxamide The enantiomers of rac cis N-(5-fluoro-3-hydroxy-2-methylchroman-4-yl)-6-(1H-pyrrolo[2,3-b]pyridin-4-yl)nicotinamide were separated according to the following chiral SFC conditions.

Instrument: Thar SFC80 preparative SFC
Column: Chiralpak AD-H 250*30 mm i.d. 5u
Mobile phase: A for $CO_2$ and B for 2-propanol (0.1% $NH_3H_2O$)
Gradient: B %=50%
Flow rate: 80 g/min
Wavelength: 220 nm
Column temperature: 40° C.
System back pressure: 100 bar
Cycle time: 3 min
Injection amount: 10 mg per injection N-[(2R,3R,4R)-5-Fluoro-3-hydroxy-2-methyl-3,4-dihydro-2H-1-benzopyran-4-yl]-6-{1H-pyrrolo[2,3-b]pyridin-4-yl}pyridine-3-carboxamide (91.9 mg, 219.64 umol, yield: 33.3%) was obtained as peak 1 as a light yellow solid.

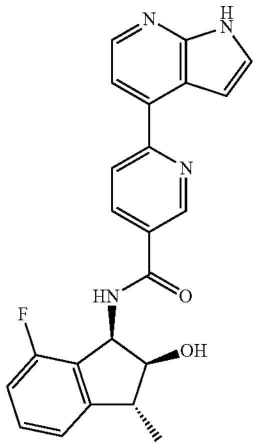 [SMILES: C[C@@H]1c2cccc(F)c2[C@@H](NC(=O)c2ccc(-c3ccnc4[nH]ccc34)nc2)[C@H]1O]

Example 25: N-[(1R,2S,3R)-7-Fluoro-2-hydroxy-3-methyl-2,3-dihydro-1H-inden-1-yl]-6-{1H-pyrrolo[2,3-b]pyridin-4-yl}pyridine-3-carboxamide Step 1: (E)-1-(2-Fluorophenyl)but-2-en-1-one To a mixture of 1-bromo-2-fluorobenzene (20.0 g, 114.29 mmol, 1.00 eq) in THF (150 mL) was added drop wise nBuLi (2.5 M, 48.0 mL, 1.05 eq) at −70° C. under $N_2$. The mixture was stirred at −70° C. for 0.5 h. CuCl (11.31 g, 114.29 mmol, 2.73 mL, 1.00 eq) was added by portions to the above mixture at −70° C. After addition, the mixture was stirred at −70° C. for 0.5 h then warmed to −20° C. and stirred at −20° C. for 1 h. (E)-But-2-enoyl chloride (12.55 g, 120.0 mmol, 11.51 mL, 1.05 eq) was added and stirred at −20° C. for 2 h. The mixture was poured into $H_2O$ (150 mL) and acidified with HCl (4 M) until pH=1. The aqueous mixture was extracted with EtOAc (200 mL*3). The combined organic extracts were dried over $Na_2SO_4$ and concentrated under vacuum. The residue was purified by column chromatography on silica gel (PE:EtOAc=100:1) to give (E)-1-(2-fluorophenyl)but-2-en-1-one (20.0 g, 121.82 mmol, yield: 53.3%) as a yellow oil.

Step 2: 3-Chloro-1-(2-fluorophenyl)butan-1-one

To a mixture of (E)-1-(2-fluorophenyl)but-2-en-1-one (19.0 g, 115.73 mmol, 1.00 eq) and ethylene glycol (17.24 g, 278 mmol, 2.40 eq) in DCM (200 mL) was added dropwise $BCl_3$ (1 M, 36.16 mL, 2.40 eq) at 0° C. After addition, the mixture was stirred at 0° C. for 0.5 h then warmed to 25° C. and stirred for 16 h. The reaction mixture was washed with $H_2O$ (100 mL*2). The organic layer was dried over $Na_2SO_4$ and concentrated under vacuum. The residue was purified by column chromatography on silica gel (PE:EtOAc=100:1) to give 3-chloro-1-(2-fluorophenyl) butan-1-one (20.0 g, 99.7 mmol, yield: 86.1%) as a yellow oil.

Step 3:
7-Fluoro-3-methyl-2,3-dihydro-1H-inden-1-one

A mixture of 3-chloro-1-(2-fluorophenyl)butan-1-one (5.00 g, 24.92 mmol, 1.00 eq) in $H_2SO_4$ (24.44 g, 249.20 mmol, 10.00 eq) was heated to 90° C. for 1 h. The reaction was cooled and added to $H_2O$ (10 mL), and the products were extracted into EtOAc (10 mL*3). The combined organic extracts were dried over $Na_2SO_4$ and concentrated under vacuum. The residue was purified by prep-TLC (PE: EtOAc=5:1) to give 7-fluoro-3-methyl-2,3-dihydro-1H-inden-1-one (1.25 g, 7.61 mmol, yield: 30.6%) as a black oil.

Step 4:
7-Fluoro-3-methyl-2,3-dihydro-1H-inden-1-ol

Prepared from 7-fluoro-3-methyl-2,3-dihydro-1H-inden-1-one according to the procedure described in Example 17 Step 1.

Step 5: 4-Fluoro-1-methyl-1H-indene

Prepared from 7-fluoro-3-methyl-2,3-dihydro-1H-inden-1-ol according to the procedure described in Example 17 Step 2.

Step 6: 2-Fluoro-6-methyl-1a,6a-dihydro-6H-indeno [1,2-b]oxirene

To a mixture of 4-fluoro-1-methyl-1H-indene (700 mg, 4.72 mmol, 1.00 eq) in DCM (20.0 mL) was added mCPBA (1.15 g, 5.66 mmol, 85% purity, 1.20 eq). After addition, the mixture was stirred at 20° C. for 1 h. The mixture was washed with aq. $Na_2SO_3$ (30 mL) and $NaHCO_3$ (aq, 30 mL*3). The organic layer was dried over $Na_2SO_4$ and concentrated under vacuum to give 2-fluoro-6-methyl-1α,6α-dihydro-6H-indeno[1,2-β]oxirene (600 mg, crude) as a yellow oil.

Step 7: 3-Amino-4-fluoro-1-methyl-2,3-dihydro-1H-inden-2-ol (mixture of racemic (1R,2S,3R)/(1S,2R,3S) and (1R,2S,3S)/(1S,2R,3R) diastereoisomers)

Prepared from 2-fluoro-6-methyl-1α,6α-dihydro-6H-indeno[1,2-β]oxirene according to the procedure described in Example 17 Step 4.

Step 8: N-(7-fluoro-2-hydroxy-3-methyl-2,3-dihydro-1H-inden-1-yl)-6-(1H-pyrrolo[2,3-b]pyridin-4-yl)nicotinamide (racemic (1R,2S,3R)/(1S,2R,3S) diastereoisomer)

To a mixture of 6-(1H-pyrrolo[2,3-b]pyridin-4-yl)nicotinic acid (Example 14 Step 3, 200 mg, 836.02 umol, 1.00 eq) in DMF (5.0 mL) was added T3P (638.4 mg, 1.00 mmol, 597 uL, 50% purity, 1.20 eq), DIPEA (324.1 mg, 2.51 mmol, 438 uL, 3.00 eq) and 3-amino-4-fluoro-1-methyl-2,3-dihydro-1H-inden-2-ol (mixture of racemic (1R,2S,3R)/(1S,2R,3S) and (1R,2S,3S)/(1S,2R,3R) diastereoisomers, 151.5 mg, 836.0 umol, 1.00 eq). After addition, the mixture was stirred at 20° C. for 0.5 h before concentrating under vacuum. The diastereoisomers were separated by prep-HPLC (TFA) to give N-(7-fluoro-2-hydroxy-3-methyl-2,3-dihydro-1H-inden-1-yl)-6-(1H-pyrrolo[2,3-b]pyridin-4-yl) nicotinamide (racemic (1R,2S,3R)/(1S,2R,3S) diastereoisomer) as peak 1 (confirmed by Nuclear Overhauser Effect Spectroscopy).

Step 9: N-[(1R,2S,3R)-7-Fluoro-2-hydroxy-3-methyl-2,3-dihydro-1H-inden-1-yl]-6-{1H-pyrrolo [2,3-b]pyridin-4-yl}pyridine-3-carboxamide The enantiomers of the racemic (1R,2S,3R)/(1S,2R,3S) diastereoisomer of N-(7-fluoro-2-hydroxy-3-methyl-2,3-dihydro-1H-inden-1-yl)-6-(1H-pyrrolo[2,3-b]pyridin-4-yl) nicotinamide were separated according to the following chiral SFC conditions.

Instrument: Thar SFC80 preparative SFC

Column: Chiralpak IC-H 250*30 mm i.d. 5u

Mobile phase: A for C02 and B for MeOH (0.1% $NH_3H_2O$)

Gradient: B %=40%

Flow rate: 65 g/min

Wavelength: 220 nm

Column temperature: 40° C.

System back pressure: 100 bar

N-[(1R,2S,3R)-7-Fluoro-2-hydroxy-3-methyl-2,3-dihydro-1H-inden-1-yl]-6-{1H-pyrrolo[2,3-b]pyridin-4-yl}pyridine-3-carboxamide (26.7 mg, 66.4 umol, yield: 7.9%) was obtained as peak 2 as a white solid.

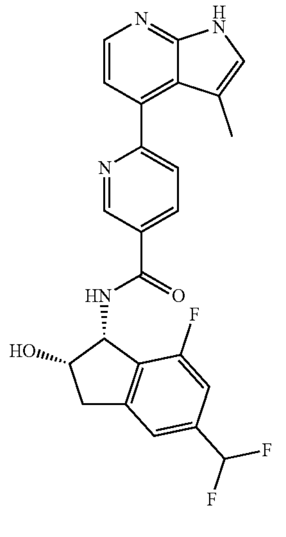

Example 26: N-[(1R,2S)-5-(Difluoromethyl)-7-fluoro-2-hydroxy-2,3-dihydro-1H-inden-1-yl]-6-{3-methyl-1H-pyrrolo[2,3-b]pyridin-4-yl}pyridine-3-carboxamide Step 1: 3-Methyl-4-(4,4,5,5-tetramethyl-1,3,2-dioxaborolan-2-yl)-1H-pyrrolo[2,3-b]pyridine Prepared from 4-bromo-3-methyl-1H-pyrrolo[2,3-b]pyridine according to the procedure described in Example 14 Step 1.

Step 2: Methyl 6-(3-methyl-1H-pyrrolo[2,3-b]pyridin-4-yl)nicotinate

Prepared from 3-methyl-4-(4,4,5,5-tetramethyl-1,3,2-dioxaborolan-2-yl)-1H-pyrrolo[2,3-b]pyridine and methyl 6-bromonicotinate according to the procedure described in Example 14 Step 2.

Step 3: 6-(3-Methyl-1H-pyrrolo[2,3-b]pyridin-4-yl) nicotinic acid

Prepared from methyl 6-(3-methyl-1H-pyrrolo[2,3-b]pyridin-4-yl)nicotinate according to the procedure described in Example 1 Step 2.

Step 4: 7-Fluoro-5-vinyl-2,3-dihydro-1H-inden-1-one

To a mixture of 5-bromo-7-fluoro-2,3-dihydro-1H-inden-1-one (15.0 g, 65.49 mmol, 1.00 eq) and 4,4,5,5-tetramethyl-2-vinyl-1,3,2-dioxaborolane (12.10 g, 78.59 mmol, 13.30 mL, 1.20 eq) in $H_2O$ (35.0 mL)/dioxane (200 mL) was added $Na_2CO_3$ (13.88 g, 131.0 mmol, 2.00 eq) and Pd(dppf)$Cl_2$ (1.44 g, 1.96 mmol, 0.03 eq) in one portion under $N_2$. The mixture was stirred at 90° C. for 12 h under $N_2$. The mixture was concentrated under vacuum and the residue was purified by silica gel chromatography (PE:EtOAc=1:0-50:1-40:1-30:1) to afford 7-fluoro-5-vinyl-2,3-dihydro-1H-inden-1-one (10.40 g, 59.03 mmol, yield: 90.1%) as a white solid.

Step 5: 7-Fluoro-1-oxo-2,3-dihydro-1H-indene-5-carbaldehyde

Ozone was bubbled into a solution of 7-fluoro-5-vinyl-2,3-dihydro-1H-inden-1-one (5.20 g, 29.51 mmol, 1.00 eq) in DCM (50.0 mL) at −78° C. for 25 min. After excess ozone was purged by oxygen, $Me_2S$ (20 mL) was added at −78° C. The reaction mixture was stirred at −78° C. for 20 mins, then stirred at 18° C. for 30 min. The mixture was concentrated and PE (40 mL), DCM (5 mL) and EtOAc (5 mL) were added. The mixture was filtered and the filter cake was dried to afford 7-fluoro-1-oxo-2,3-dihydro-1H-indene-5-carbaldehyde (4.25 g, 23.9 mmol, yield: 80.8%) as a yellow solid.

Step 6: 5-(Difluoromethyl)-7-fluoro-2,3-dihydro-1H-inden-1-one

To a mixture of 5-(difluoromethyl)-7-fluoro-2,3-dihydro-1H-inden-1-one (8.50 g, 47.71 mmol, 1.00 eq) in DCM (100 mL) was added DAST (30.76 g, 190.84 mmol, 25.21 mL, 4.00 eq) dropwise at −78° C. under $N_2$. The mixture was stirred at 25° C. for 12 h under $N_2$. The reaction mixture was diluted with DCM (100 mL) and quenched with sat. aq. $NaHCO_3$ (200 mL). The organic layer was separated, dried over anhydrous $Na_2SO_4$ and concentrated in vacuo. The residue was purified by (PE/EtOAc=50:1-40:1-30:1) to afford 5-(difluoromethyl)-7-fluoro-2,3-dihydro-1H-inden-1-one (6.80 g, 33.97 mmol, yield: 71.21%) as a brown solid.

Step 7: 5-(Difluoromethyl)-7-fluoro-2,3-dihydro-1H-inden-1-ol

To a solution of 5-(difluoromethyl)-7-fluoro-2,3-dihydro-1H-inden-1-one (3.40 g, 16.99 mmol, 1.00 eq) in MeOH (40.0 mL) was added $NaBH_4$ (771 mg, 20.38 mmol, 1.20 eq) in portions. The mixture was stirred at 15° C. for 2 h. The reaction mixture was concentrated (at 30° C.), diluted with $H_2O$ (20 mL) and acidified with 1 M hydrochloric acid until pH=5, then extracted with EtOAc (30 mL*2). The combined organic extracts were washed with brine (25 mL), dried over $Na_2SO_4$ and concentrated under vacuum to afford 5-(difluoromethyl)-7-fluoro-2,3-dihydro-1H-inden-1-ol (3.40 g, 16.8 mmol, yield: 99.0%) as a brown oil.

Step 8: 6-(Difluoromethyl)-4-fluoro-1H-indene

To a mixture of 5-(difluoromethyl)-7-fluoro-2,3-dihydro-1H-inden-1-ol (3.40 g, 12.92 mmol, 1.00 eq) in toluene (65.0 mL) was added TsOH·$H_2O$ (122.9 mg, 646.19 umol, 0.05 eq) in one portion under $N_2$. The mixture was stirred at 100° C. for 1 h under $N_2$. The mixture was washed with 10% aq. $K_2CO_3$ (30 mL*3) and brine (35 mL). The organic layer was dried over $Na_2SO_4$, filtered and concentrated under vacuum. The residue was purified by silica gel chromatography (PE/EtOAc=1:0-50:1-30:1-20:1) to afford 6-(difluoromethyl)-4-fluoro-1H-indene (2.10 g, 8.57 mmol, yield: 66.3%) as a colorless oil.

Step 9: (1αR,6αS)-4-(Difluoromethyl)-2-fluoro-1a,6a-dihydro-6H-indeno[1,2-β]oxirene To a mixture of 6-(difluoromethyl)-4-fluoro-1H-indene (1.00 g, 5.43 mmol, 1.00 eq), 1-oxido-4-phenyl-pyridin-1-ium (92.96 mg, 543.00 umol, 0.10 eq) and R,R-Jacobsen's catalyst (344.9 mg, 543.00 umol, 0.10 eq) in DCM (8.0 mL) at 0° C. was added cold NaClO (36.30 g, 58.52 mmol, 30.00 mL, 12% purity, 10.78 eq) slowly with vigorous stirring while maintaining the reaction temperature between 0-2° C. The reaction mixture was stirred at 0° C. for 1 h and 10° C. for 11 h. PE (20 mL) was added and the mixture was filtered through a pad of Celite® on a large Buchner funnel. The filtrate organic layer was washed with brine (10 mL*2), dried over $Na_2SO_4$, filtered and concentrated under vacuum to afford (1αR,6αS)-4-(difluoromethyl)-2-fluoro-1α,6α-dihydro-6H-indeno[1,2-β]oxirene as a dark brown liquid.

Step 10: (1R,2S)-1-Amino-5-(difluoromethyl)-7-fluoro-2,3-dihydro-1H-inden-2-ol

To a mixture of (1αR,6αS)-4-(difluoromethyl)-2-fluoro-1α,6α-dihydro-6H-indeno[1,2-b]oxirene (2.30 g, 11.49 mmol, 1.00 eq) in $CH_3CN$ (20.0 mL) was added TfOH (3.45 g, 22.98 mmol, 2.03 mL, 2.00 eq) dropwise at −30° C. under $N_2$. The mixture was stirred at 10° C. for 1 h, then $H_2O$ (30 mL) was added and the mixture was stirred at 10° C. for 0.2 h. The mixture was concentrated to remove $CH_3CN$ and stirred for 3 h at 100° C. After cooling to room temperature, DCM (20 mL) was added and stirred for 0.2 h. The two phases were separated and the aqueous layer was basified with 1 M NaOH (until pH=8) and extracted with EtOAc (50 mL*2). The combined organic layers were dried over $Na_2SO_4$, filtered and concentrated under vacuum to afford (1R,2S)-1-amino-5-(difluoromethyl)-7-fluoro-2,3-dihydro-1H-inden-2-ol (1.40 g, crude) as a brown oil.

Step 11: N-[(1R,2S)-5-(Difluoromethyl)-7-fluoro-2-hydroxy-2,3-dihydro-1H-inden-1-yl]-6-{3-methyl-1H-pyrrolo[2,3-b]pyridin-4-yl}pyridine-3-carboxamide To a mixture of 6-(3-methyl-1H-pyrrolo[2,3-b]pyridin-4-yl)nicotinic acid (400 mg, 1.58 mmol, 1.00 eq) and (1R, 2S)-1-amino-5-(difluoromethyl)-7-fluoro-2,3-dihydro-1H-inden-2-ol (343.0 mg, 1.58 mmol, 1.00 eq) in DMF (8.00 mL) was added DIPEA (612.4 mg, 4.74 mmol, 827.5 uL, 3.00 eq) and HATU (720.6 mg, 1.90 mmol, 1.20 eq) in one portion. The mixture was stirred at 10° C. for 3 h. $H_2O$ (15 mL) was added to the mixture and the mixture was extracted with EtOAc (20 mL*3). The combined organic extracts were dried over $Na_2SO_4$, filtered and concentrated under vacuum. The residue was purified by neutral prep-HPLC to afford N-[(1R,2S)-5-(difluoromethyl)-7-fluoro-2-hydroxy-2,3-dihydro-1H-inden-1-yl]-6-{3-methyl-1H-pyrrolo[2,3-β]pyridin-4-yl}pyridine-3-carboxamide (190.9 mg, 421.94 umol, yield: 26.7%) as a brown solid.

The chiral purity could be upgraded to 100% e.e. by chiral SFC according to the following conditions.

Instrument: Thar SFC80 preparative SFC

Column: Daicel Chiralpak AD (250 mm*30 mm, 10 um)

Mobile phase: A for $CO_2$ and B for MeOH (0.1% $NH_3H_2O$)

Gradient: B %=40%

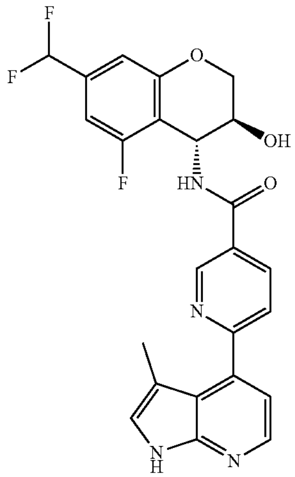

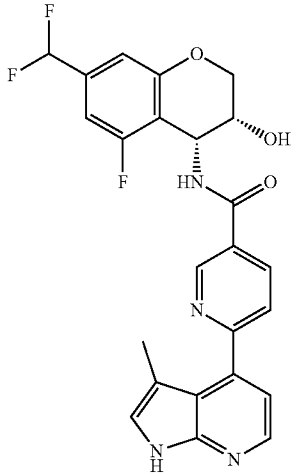

Examples 27 and 28: N-((3S,4R)-7-(Difluoromethyl)-5-fluoro-3-hydroxychroman-4-yl)-6-(3-methyl-1H-pyrrolo[2,3-b]pyridin-4-yl)nicotinamide and N-((3R,4R)-7-(difluoromethyl)-5-fluoro-3-hydroxychroman-4-yl)-6-(3-methyl-1H-pyrrolo[2,3-b]pyridin-4-yl)nicotinamide Step 1: 3-Bromo-5-fluorophenyl acetate To a solution of 3-bromo-5-fluorophenol (7.0 g, 36.65 mmol, 1.00 eq) in DCM (50 mL) was added DIPEA (9.47 g, 73.3 mmol, 12.8 mL, 2.00 eq). The mixture was cooled to 0° C. and acetyl chloride (4.32 g, 54.98 mmol, 3.92 mL, 1.50 eq) in DCM (10 mL) was added dropwise. The resulting mixture was allowed to stir at 0° C. for 1 h, and then at 12° C. for 3 h. $H_2O$ (40 mL) was added and the products were extracted into EtOAc (40 mL*3). The combined organic extracts were dried over $Na_2SO_4$ and concentrated under vacuum. The residue was purified by column chromatography on silica gel (PE:EtOAc=1:0-100:1) to obtain 3-bromo-5-fluorophenyl acetate (6.70 g, 28.75 mmol, yield: 78.5%) as a colorless oil.

Step 2: 1-(4-Bromo-2-fluoro-6-hydroxyphenyl)ethan-1-one

A mixture of 3-bromo-5-fluorophenyl acetate (6.70 g, 28.75 mmol, 1.00 eq) in DCM (70.0 mL) was cooled to 0°

C., and $AlCl_3$ (11.50 g, 86.25 mmol, 4.71 mL, 3.00 eq) was added portionwise at 0° C. After addition, the resulting mixture was stirred at 0° C. for 0.5 h, and then it was concentrated under vacuum. The semi-solid residue obtained was heated at 140° C. for 3 h. The mixture was cooled to 80° C. and $H_2O$ (8 mL) was added to quench it. The mixture was further cooled to 0° C. before adding EtOAc (85 mL) and $H_2O$ (55 mL). The mixture was stirred at 0° C. for 0.5 h until the solid disappeared. The products were extracted into EtOAc (60 mL*3). The combined organic extracts were dried over $Na_2SO_4$ and concentrated under vacuum. The crude product was purified by column chromatography on silica gel (PE:EtOAc=1:0, 100:1) to obtain 1-(4-bromo-2-fluoro-6-hydroxyphenyl)ethan-1-one (4.00 g, 17.2 mmol, yield: 59.7%) as a light yellow solid.

Step 3: 7-Bromo-5-fluoro-4H-chromen-4-one

NaH (4.12 g, 103.02 mmol, 60% purity, 6.00 eq) was washed three times with PE then added portionwise to a solution of 1-(4-bromo-2-fluoro-6-hydroxyphenyl)ethan-1-one (4.00 g, 17.17 mmol, 1.00 eq) in ethyl formate (128.8 g, 1.74 mol, 140 mL, 101 eq) and THF (140 mL) at 0° C. over 1 h. After addition, the resulting mixture was stirred at 15° C. for another 1.5 h. MeOH (8 mL) was added to quench, followed by addition of concentrated HCl (27 mL). The resulting mixture was stirred at 15° C. for 16 h. $H_2O$ (70 mL) was added and the products were extracted into EtOAc (60 mL*3). The combined organic layers were dried over $Na_2SO_4$ and concentrated under vacuum. The crude product was purified by column chromatography on silica gel (PE:EtOAc=100:1, 50:1, 30:1, 15:1, 10:1) to obtain 7-bromo-5-fluoro-4H-chromen-4-one (3.00 g, 12.34 mmol, yield: 71.9%) as light yellow solid.

Step 4: 7-Bromo-5-fluorochroman-4-one

DIBAL-H (1 M, 37.0 mL, 3.00 eq) was added dropwise to the solution of 7-bromo-5-fluoro-4H-chromen-4-one (3.00 g, 12.34 mmol, 1.00 eq) in THF (100 mL) at −78° C. The resulting mixture was stirred at −78° C. under $N_2$ for 0.5 h. The mixture was quenched with MeOH (5 mL) at 0° C., followed by addition of saturated aqueous potassium sodium tartrate solution (200 mL) at 0° C. The resulting solution was stirred at 15° C. for 0.5 h, then the products were extracted into EtOAc (50 mL*5). The combined organic extracts were dried over $Na_2SO_4$, filtered and concentrated under vacuum to give 7-bromo-5-fluorochroman-4-one (2.20 g, crude) as a light yellow solid which was used directly in the next step without further purification.

Step 5: 5-Fluoro-7-vinylchroman-4-one

To a solution of 7-bromo-5-fluorochroman-4-one (2.20 g, 8.98 mmol, 1.00 eq) in dioxane (30 mL) and $H_2O$ (6.0 mL) was added 4,4,5,5-tetramethyl-2-vinyl-1,3,2-dioxaborolane (2.07 g, 13.47 mmol, 2.3 mL, 1.50 eq), $Na_2CO_3$ (1.90 g, 17.96 mmol, 2.00 eq) and Pd(dppf)$Cl_2$ (328.5 mg, 449.0 umol, 0.05 eq). The resulting mixture was stirred at 90° C. under $N_2$ for 16 h. Additional Pd(dppf)$Cl_2$ (0.02 eq) and 4,4,5,5-tetramethyl-2-vinyl-1,3,2-dioxaborolane (0.5 eq) were added and the resulting mixture stirred at 90° C. under $N_2$ for 4 h. The mixture was concentrated under vacuum and the residue was purified by MPLC (PE:EtOAc=1:0-100:1-50:1-40:1) to obtain 5-fluoro-7-vinylchroman-4-one (2.25 g, 11.71 mmol) as a yellow solid.

Step 6: 5-Fluoro-4-oxochromane-7-carbaldehyde $O_3$ was bubbled into the mixture of 5-fluoro-7-vinylchroman-4-one (2.25 g, 11.71 mmol, 1.00 eq) in DCM (50 mL) at −78° C. for 1 h. DMS (1.82 g, 29.28 mmol, 2.14 mL, 2.50 eq) was added at −78° C., and then the resulting mixture was stirred at 15° C. for 0.5 h. The mixture was concentrated under vacuum and the crude product was purified by MPLC (PE:EtOAc=100:1, 50:1, 30:1, 15:1, 10:1, 5:1) to obtain 5-fluoro-4-oxochromane-7-carbaldehyde (2.00 g, 10.3 mmol) as a yellow solid.

Step 7: 7-(Difluoromethyl)-5-fluorochroman-4-one

To a solution of 5-fluoro-4-oxochromane-7-carbaldehyde (1.00 g, 5.15 mmol, 1.00 eq) in DCM (15.0 mL) was added DAST (3.32 g, 20.60 mmol, 2.7 mL, 4.00 eq) at −78° C. under $N_2$. After addition, the resulting mixture was stirred at 15° C. for 2 h. The mixture was added portionwise to saturated aqueous $NaHCO_3$ solution (150 mL) at 0° C. and the products were extracted into DCM (50 mL*3). The combined organic extracts were dried over $Na_2SO_4$ and concentrated under vacuum. The crude product was purified by MPLC (PE:EtOAc=50:1, 30:1, 20:1) to obtain 7-(difluoromethyl)-5-fluorochroman-4-one (1.00 g, 4.63 mmol) as a white solid.

Step 8: 7-(Difluoromethyl)-5-fluoro-3-hydroxychroman-4-one oxime

Prepared from 7-(difluoromethyl)-5-fluorochroman-4-one according to the procedures described in Example 7 Steps 1 and 2.

Step 9: 4-Amino-7-(difluoromethyl)-5-fluorochroman-3-ol

To a solution of Raney-Ni (1.50 g, 17.5 mmol, 14.5 eq) in MeOH (30.0 mL) was added 7-(difluoromethyl)-5-fluoro-3-hydroxychroman-4-one oxime (300 mg, 1.21 mmol, 1.00 eq). The resulting mixture was stirred at 15° C. under $H_2$ (15 psi) for 20 h. The mixture was filtered and the filter cake was washed with MeOH (5 mL*6). The filtrate was concentrated under vacuum to give 4-amino-7-(difluoromethyl)-5-fluorochroman-3-ol (230 mg, crude, mixture of racemic cis and trans isomers) as a yellow oil which was used directly in the next step without further purification.

Step 10: N-((3S,4R)-7-(Difluoromethyl)-5-fluoro-3-hydroxychroman-4-yl)-6-(3-methyl-1H-pyrrolo[2,3-b]pyridin-4-yl)nicotinamide and N-((3R,4R)-7-(difluoromethyl)-5-fluoro-3-hydroxychroman-4-yl)-6-(3-methyl-1H-pyrrolo[2,3-b]pyridin-4-yl)nicotinamide A mixture of 4-amino-7-(difluoromethyl)-5-fluorochroman-3-ol (230 mg, 986.3 umol, 1.00 eq), 6-(3-methyl-1H-pyrrolo[2,3-b]pyridin-4-yl)nicotinic acid (Example 26 Step 3, 212.3 mg, 838.4 umol, 0.85 eq), HATU (450.03 mg, 1.18 mmol, 1.20 eq) and DIPEA (382. mg, 2.96 mmol, 517 uL, 3.00 eq) in DMF (3.00 mL) was stirred at 15° C. for 0.5 h. $H_2O$ (5 mL) was added and the products were extracted into EtOAc (5 mL*6). The combined organic extracts were dried over $Na_2SO_4$ and concentrated under vacuum. The crude product was purified by prep-HPLC (TFA) to obtain two pairs of diastereoisomers. The product with shorter retention time was the cis isomer which was confirmed by $^1$H NMR and NOE. The product with longer retention time was the trans isomer which was confirmed by $^1$H NMR.

The trans isomer was separated by chiral SFC according to the following conditions.

Instrument: Thar SFC80 preparative SFC
Column: Chiralpak AD-H 250*30 mm i.d. 5u
Mobile phase: A for $CO_2$ and B for EtOH (0.1% $NH_3H_2O$)
Gradient: B %=45%
Flow rate: 70 g/min
Wavelength: 220 nm
Column temperature: 40° C.
System back pressure: 100 bar N-((3S,4R)-7-(Difluoromethyl)-5-fluoro-3-hydroxychroman-4-yl)-6-(3-methyl-1H-pyrrolo[2,3-b]pyridin-4-yl) nicotinamide (30.5 mg, 65.1 umol, yield: 6.6%) was obtained as peak 1 as a brown solid.

The cis isomer was separated by chiral SFC according to the following conditions.

Instrument: Thar SFC80 preparative SFC
Column: Chiralpak AD-H 250*30 mm i.d. 5u
Mobile phase: A for $CO_2$ and B for EtOH (0.1% $NH_3H_2O$)
Gradient: B %=35%
Flow rate: 65 g/min
Wavelength: 220 nm
Column temperature: 40° C.
System back pressure: 100 bar N-((3R,4R)-7-(Difluoromethyl)-5-fluoro-3-hydroxychroman-4-yl)-6-(3-methyl-1H-pyrrolo[2,3-b]pyridin-4-yl) nicotinamide (12.4 mg, 26.2 umol, yield: 2.7%) was obtained as peak 2 as a brown gum.

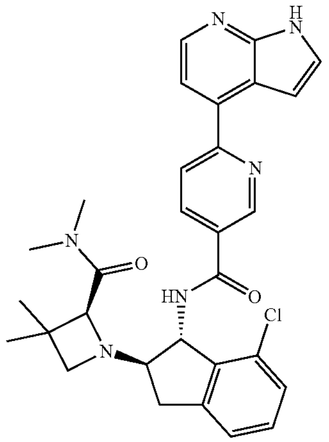 [SMILES: CN(C)C(=O)[C@H]1N([C@@H]2Cc3cccc(Cl)c3[C@H]2NC(=O)c2ccc(-c3ccnc4[nH]ccc34)nc2)CC1(C)C]

Example 29: N-[(1R,2R)-7-Chloro-2-[(2S)-2-(dimethylcarbamoyl)-3,3-dimethylazetidin-1-yl]-2,3-dihydro-1H-inden-1-yl]-6-{1H-pyrrolo[2,3-b]pyridin-4-yl}pyridine-3-carboxamide Step 1: (S)-1-(tert-Butoxycarbonyl)-3,3-dimethylazetidine-2-carboxylic acid To a mixture of (S)-3,3-dimethylazetidine-2-carboxylic acid (230 mg, 1.78 mmol, 1 eq) and $Boc_2O$ (427.5 mg, 1.96 mmol, 450 uL, 1.1 eq) in THF (3 mL)/$H_2O$ (3 mL) was added $Na_2CO_3$ (377.49 mg, 3.56 mmol, 2 eq) at 15° C. The reaction was stirred at 15° C. for 16 h. The mixture was washed with EtOAc:PE (1:1, 2 mL) and the organic layer was discarded. The aqueous layer was acidified with 1N aq. HCl to pH=5 and extracted with EtOAc (5 mL*3). The combined organic extracts were washed with brine (1 mL), dried over $Na_2SO_4$ and concentrated under vacuum to give (S)-1-(tert-butoxycarbonyl)-3,3-dimethylazetidine-2-carboxylic acid (330 mg, 1.44 mmol, yield: 80.8%) as a white solid.

Step 2: tert-Butyl (S)-2-(dimethylcarbamoyl)-3,3-dimethylazetidine-1-carboxylate To a mixture of (S)-1-(tert-butoxycarbonyl)-3,3-dimethylazetidine-2-carboxylic acid (1.5 g, 7.45 mmol, 1 eq), dimethylamine hydrochloride (1.22 g, 14.91 mmol, 2 eq) and DIPEA (2.89 g, 22.36 mmol, 3.90 mL, 3 eq) in DMF (20 mL) was added HATU (3.40 g, 8.95 mmol, 1.2 eq) at 15° C. The reaction mixture was stirred at 15° C. for 2 h. EtOAc (50 mL) was added and the solution washed with brine (10 mL*3). The organic layer was separated, dried over $Na_2SO_4$ and concentrated under vacuum. The crude product was purified by prep-HPLC (TFA) to give tert-butyl (S)-2-(dimethylcarbamoyl)-3,3-dimethylazetidine-1-carboxylate (1.1 g, 4.82 mmol, yield: 64.6%) as a colorless oil.

Step 3: (S)—N,N,3,3-Tetramethylazetidine-2-carboxamide

A mixture of tert-butyl (S)-2-(dimethylcarbamoyl)-3,3-dimethylazetidine-1-carboxylate (1.1 g, 4.82 mmol, 1 eq) in TFA (5 mL) and DCM (5 mL) was stirred at 15° C. for 1 h. The mixture was blown to dryness by $N_2$ to give the TFA salt of (S)—N,N,3,3-tetramethylazetidine-2-carboxamide (1.1 g, 4.54 mmol, yield: 94.3%, TFA) as a colorless oil.

Step 4: tert-Butyl (3aR,8aS)-4-chloro-8,8a-dihydroindeno[1,2-d][1,2,3]oxathiazole-3(3aH)-carboxylate 2,2-dioxide Prepared from 7-chloro-2,3-dihydro-1H-inden-1-one according to the procedures described in Example 17 Steps 1-7.

Step 5: (tert-Butoxycarbonyl)((1R,2R)-7-chloro-2-((S)-2-(dimethylcarbamoyl)-3,3-dimethylazetidin-1-yl)-2,3-dihydro-1H-inden-1-yl)sulfamic acid Prepared from (S)—N,N,3,3-tetramethylazetidine-2-carboxamide and tert-butyl (3aR,8aS)-4-chloro-8,8a-dihydroindeno[1,2-d][1,2,3]oxathiazole-3(3aH)-carboxylate 2,2-dioxide according to the procedure described in Example 17 Step 8.

Step 6: (S)-1-((1R,2R)-1-Amino-7-chloro-2,3-dihydro-1H-inden-2-yl)-N,N,3,3-tetramethylazetidine-2-carboxamide Prepared from (tert-butoxycarbonyl)((1R,2R)-7-chloro-2-((S)-2-(dimethylcarbamoyl)-3,3-dimethylazetidin-1-yl)-2,3-dihydro-1H-inden-1-yl)sulfamic acid according to the procedure described in Example 17 Step 9.

Step 7: N-[(1R,2R)-7-Chloro-2-[(2S)-2-(dimethylcarbamoyl)-3,3-dimethylazetidin-1-yl]-2,3-dihydro-1H-inden-1-yl]-6-{1H-pyrrolo[2,3-b]pyridin-4-yl}pyridine-3-carboxamide Prepared from (S)-1-((1R,2R)-1-amino-7-chloro-2,3-dihydro-1H-inden-2-yl)-N,N,3,3-tetramethylazetidine-2-carboxamide and 6-(1H-pyrrolo[2,3-b]pyridin-4-yl)nicotinic acid (Example 14 Step 3) according to the procedure described in Example 2 Step 4.

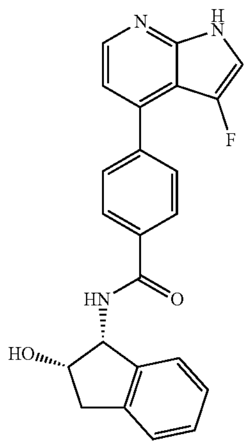 [SMILES: O=C(N[C@@H]1c2ccccc2C[C@@H]1O)c1ccc(-c2ccnc3[nH]cc(F)c23)cc1]

Example 30: 4-(3-Fluoro-1H-pyrrolo[2,3-b]pyridin-4-yl)-N-((1R,2S)-2-hydroxy-2,3-dihydro-1H-inden-1-yl)benzamide Step 1: N-((1R,2S)-2-Hydroxy-2,3-dihydro-1H-inden-1-yl)-4-(4,4,5,5-tetramethyl-1,3,2-dioxaborolan-2-yl)benzamide (1R,2S)-1-Amino-2,3-dihydro-1H-inden-2-ol (1.323 g, 8.87 mmol) and 4-(4,4,5,5-tetramethyl-1,3,2-dioxaborolan-2-yl)benzoic acid (2.2 g, 8.87 mmol) were taken up in DMF (15 ml). HATU (4.05 g, 10.64 mmol) and DIEA (4.65 ml, 26.6 mmol) added. The reaction was stirred at ambient temperature for 1 hour. It was then diluted with 100 ml EtOAc and washed with brine (×3), dried over sodium sulfate and the solvent removed in vacuo. The residue was purified via silica gel chromatography (0-100% Hex/EtOAc; 40 g column) to give N-((1R,2S)-2-hydroxy-2,3-dihydro-1H-inden-1-yl)-4-(4,4,5,5-tetramethyl-1,3,2-dioxaborolan-2-yl)benzamide (2.6 g, 6.86 mmol, 77% yield) as an off white solid.

Step 2: 4-(3-Fluoro-1H-pyrrolo[2,3-b]pyridin-4-yl)-N-((1R,2S)-2-hydroxy-2,3-dihydro-1H-inden-1-yl)benzamide To a 5 ml microwave vial, 4-chloro-3-fluoro-1H-pyrrolo[2,3-b]pyridine (0.300 g, 1.759 mmol), N-((1R,2S)-2-hydroxy-2,3-dihydro-1H-inden-1-yl)-4-(4,4,5,5-tetramethyl-1,3,2-dioxaborolan-2-yl)benzamide (0.667 g, 1.759 mmol), bis(tri-t-butylphosphine)palladium(0) (0.090 g, 0.176 mmol) and $Cs_2CO_3$ (1.719 g, 5.28 mmol) were added and taken up in dioxane (2 ml) and water (0.500 ml). The vial was sealed and heated to 100° C. for 90 minutes in microwave. Upon cooling to room temperature the reaction was diluted with EtOAc (20 ml) and washed with water, brine (×2), dried over sodium sulfate and the solvent removed in vacuo. The residue was purified via column chromatography (0-100% Hex/EtOAc; 12 g column) to give 4-(3-fluoro-1H-pyrrolo[2,3-b]pyridin-4-yl)-N-((1R,2S)-2-hydroxy-2,3-dihydro-1H-inden-1-yl)benzamide (0.097 g, 0.250 mmol, 14.24% yield) as an off white solid.

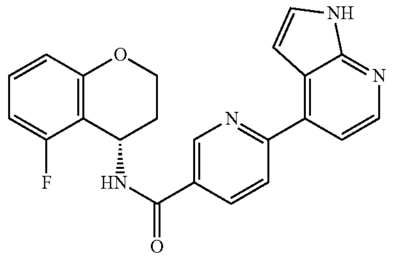 [SMILES: O=C(N[C@H]1CCOc2cccc(F)c21)c1ccc(-c2ccnc3[nH]ccc23)nc1]

Example 31: (S)—N-(5-Fluorochroman-4-yl)-6-(1H-pyrrolo[2,3-b]pyridin-4-yl)nicotinamide Step 1: (S)-6-bromo-N-(5-fluorochroman-4-yl)nicotinamide 6-bromonicotinic acid (0.100 g, 0.495 mmol), (S)-5-fluorochroman-4-amine (0.083 g, 0.495 mmol) and PyBOP (0.309 g, 0.594 mmol) were taken up in DMF (1 ml). DIEA (0.259 ml, 1.485 mmol) was added and the reaction stirred at ambient temperature overnight. The reaction was diluted with EtOAc (10 ml) and washed with brine (×3), dried over sodium sulfate and the solvent removed. Crude (S)-6-bromo-N-(5-fluorochroman-4-yl)nicotinamide (0.165 g, 0.470 mmol, 95% yield) was used in the next step without further purification.

Step 2: (S)—N-(5-Fluorochroman-4-yl)-6-(1H-pyrrolo[2,3-b]pyridin-4-yl)nicotinamide To a microwave vial, 4-(4,4,5,5-tetramethyl-1,3,2-dioxaborolan-2-yl)-1H-pyrrolo[2,3-b]pyridine (0.115 g, 0.471 mmol), (S)-6-bromo-N-(5-fluorochroman-4-yl)nicotinamide (0.165 g, 0.471 mmol), bis(tri-t-butylphosphine)palladium(0) (0.024 g, 0.047 mmol) and $K_2CO_3$ (0.195 g, 1.413 mmol) were added followed by dioxane (2 ml) and water (0.500 ml). The vial was sealed and heated to 120° C. for 90 minutes in microwave. After cooling to room temperature the reaction was diluted with EtOAc and washed with water and brine (×2), dried over sodium sulfate and the solvent removed in vacuo. The residue was purified via column chromatography (0-100% Hex/EtOAc; 12 g column) to afford (S)—N-(5-fluorochroman-4-yl)-6-(1H-pyrrolo[2,3-b]pyridin-4-yl)nicotinamide (0.080 g, 0.206 mmol, 43.7% yield) as an off white solid.

Example 32: Biological Evaluation of Compounds of Formula (I)

A. Biochemical Activity of Compounds of Formula (I)

A Perkin Elmer electrophoretic mobility shift platform (the EZ Reader 2) was used to assess the activity of test compounds against a kinase of interest. Fluorescently labeled substrate peptide was incubated in the presence of kinase, ATP, and the test compound, so that a portion of the peptide was phosphorylated by the enzyme. At the end of the reaction, the mix of phosphorylated (product) and non-phosphorylated (substrate) peptide containing solutions was passed through the microfluidic system of the Perkin Elmer EZ Reader 2 under an applied potential difference. The presence of the phosphate group on the product peptide provided a difference in mass and charge between those of the substrate peptide, resulting in a separation of the substrate and product pools in the sample. As the stopped solutions passed under the instrument's LED light the phosphorylated and un-phosphorylated fluorophore bound peptides were detected and resolved as separate peaks. The ratio between these peaks therefore reflected the test compound's impact on the kinase at that concentration in that well under those conditions.

PRKACA assay at Km: In each well of a 384-well plate, 0.007 ng/ul (0.18 nM) of PRKACA enzyme (Millipore: 539482) was incubated in a total of 12.5 μl of buffer (100 mM HEPES pH 7.5, 0.015% Brij 35, 10 mM $MgCl_2$, 1 mM DTT) with 1 μM Kemptide peptide substrate (5-FAM-LRRASLG) (Anaspec 29933) and 5 μM ATP at 25 C for 90 minutes in the presence or absence of a dosed concentration series of test compounds (1% DMSO final concentration). The reaction was stopped by the addition of 80 μl of Stop buffer (100 mM HEPES pH 7.5, 0.015% Brij 35, 35 mM EDTA and 0.2% of Coating Reagent 3 (Perkin Elmer)). The plate was then read on the EZ Reader 2 (protocol settings: −2.0 psi, upstream voltage −700, downstream voltage −2700, post sample sip 60 seconds). Data was normalized to 0% and 100% inhibition controls and the $IC_{50}$ calculated using a 4-parameter fit using GraphPad Prism.

B. Cellular Potency Assay

PKA directly phosphorylate VASP on Serine 157. Phosphorylation of VASP on Serine 157. P-VASP(157) was therefore used as a readout of PKA cellular activity. P-VASP (157) was detected with a HTRF assay, which is based on a TR-FRET sandwich immunoassay-based format comprising two specific anti-VASP antibodies following the manufactors protocol (Cisbio, Catalog No. 63ADK066PEH). PKA was activated in the assay by the addition of Forskolin (Sigma-Aldrich, Catalog No. F3917).

Dose response in Forskolin-stimulated human Huh7 cells was measured as follows. Briefly, Huh7 cells cells were plated at a density of $2\times10^4$ cells per well in a 384-well opti-well cell culture plate in 15 μl of serum- and phenol-free Dulbecco's Modified Eagle Medium (DMEM, Gibco Catalog No. 21063-029), and incubated for over night at 37° C., 5% $CO_2$. The next day, 3 μl of a dosed concentration series of test compound (0.24%) DMSO final concentration) was added to the wells, and the cells were incubated for an additional 4 hours at 37° C., 5% $CO_2$. 2 μl of Forskolin was added at a final concentration of 5 μM and the plates were incubated for 30 minutes at 37° C., 5% CO2. 5 μl of lysis buffer containing 1% HALT protease cocktail inhibitors (ThermoFisher, Catalog No. 78430), was added to the cells and the mixture was incubated under gentle shaking for 30 min at room temperature. 10 μl of this lysate was transferred to a 384-well proxi plate and 2.5 μL of the premixed antibody solution was added. An antibody solution was prepared by combining phopho-VASP cryptate antibody and phospho-VASP d2 antibody, at twenty-fold dilution into a buffer solution following the manufactors' protocol. The lysate and antibody mixture was incubated for either 3 h at room temperature or overnight at 4° C. The fluorescence emission at two different wavelengths (665 nm and 620 nm) was read on an EnVision instrument.

C. PRKACA Knockdown Studies in a Fibromellar Carcinoma Cell Line

Biological data obtained using fibromellar carcinoma (FLC) xenograft tumors suggests that the tumors are sensitive to reduction in DNAJB1-PRKACA levels. Thus, PRKACA may be a promising therapeutic target for treating FLC.

Generating Engineered FLC Cell Lines

To assess FLC tumor sensitivity to DNAJB1-PRKACA expression levels, engineered FLC cell lines were generated using conventional methods such that the cells exhibited doxycycline (dox)-inducible non-targeting (NT) and PRKACA shRNA expression systems. Specifically, FLC patient-derived xenograft (PDX) tumors were obtained from Crown Bioscience (Catalog No. LI5132) dissociated with 2.5 mg/ml Collagenase B (Roche Catalog No. 11088831001) in Roswell Park Memorial Institute (RPMI) 1640 medium. Mouse cells were depleted using a Mouse Cell Depletion Kit (Miltenyi Biotec Order No. 130-104-694) according to the manufacturer's protocol (Milenyi Biotech Inc., Mouse Cell Depletion Kit Datasheet 1-2 (2016)). The remaining FLC PDX cells were then cultured in Dulbecco's Modified Eagle Medium/Nutrient Mixture F-12 (DMEM/F12, Gibco Catalog No. 11320-033) containing 20 ng/ml EGF (StemCell Catalog No. 02633), 10 ng/ml FGF (R&D System Catalog No. 233-FB-025), 2% B27 (Life Technologies Catalog No. 12587010), and 1% N2 (Life Technologies 17502048) for up to 10 passages on low attachment plates (Corning Catalog No. 3814).

Subsequently, FLC PDX cells were isolated and plated on low attachment six-well plates (Corning, Catalog No. CLS3471) at 100,000 cells per well in 1 mL DMEM/F12 medium (supplemented DMEM/F12 as described above). The cells were transduced with $10^6$ shRNA-containing viral particles per well (PRKACA shRNA clone ID: V3ISHEG-6603667, Dharmacon catalog number: V3SH7670; or NT shRNA clone ID: Dharmacon catalog number: VSC6586) in cell culture medium (supplemented DMEM/F12 as described above) containing 8 μg/mL polybrene. The next day, the FLC PDX cells were centrifuged and resuspended in 2 mL fresh culture medium to remove the viral particles. Starting one day after viral transduction, stable clones expressing the PRKACA shRNA or NT shRNA were selected via puromycin selection using cell culture medium containing 2 μg/mL puromycin. Puromycin selection of transduced cells continued for 10 days, with centrifugation and resuspension in fresh media containing puromycin every 3-4 days.

In Vivo Model

Xenografts of the engineered cell lines were grown in immunodeficient female NOD-SCID mice. Specifically, female NOD-SCID mice were inoculated with 500,000 engineered FLC cells per mouse. The engineered FLCs cells were generated as described above and included either doxycycline-inducible non-targeting control shRNA or doxycycline-inducible PRKACA shRNA. Once the average tumor volume reached 150-250 $mm^3$ (study day 1), mice inoculated with each engineered cell line were randomly allocated to the treatment or control study group. In the treatment study group, shRNA expression was induced by adding 2 mg/ml doxycycline and 5% sucrose to the mouse's drinking water once its tumor grew to a volume of 150-250 $mm^3$. A control cohort of mice with PRKACA and NT shRNA FLC xenografts was only supplied with 5% sucrose containing drinking water. Tumors were measured with calipers, and the mice were weighed twice a week. At the end of the dosing study, or as indicated herein, appropriate tumor samples were taken. No significant differences in body weight were observed between study groups throughout the dosing study, and no significant doxycycline-related toxicity effects were observed in the treated mice.

Figure 2:
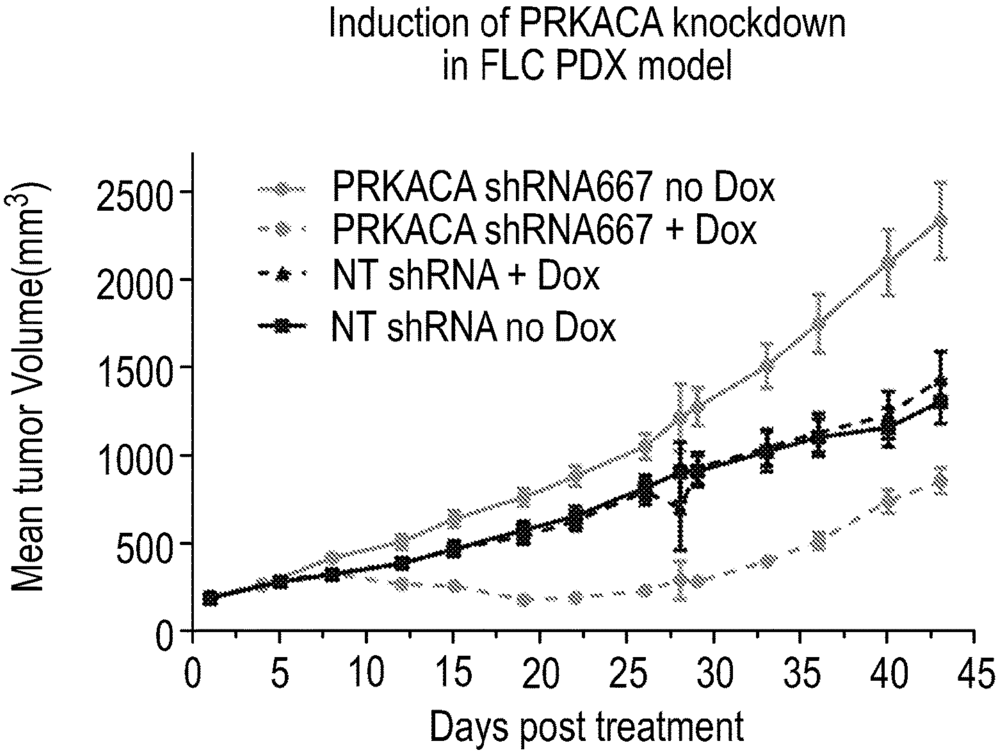
FIG. 2 is a graph which shows that dox-induced expression of PRKACA shRNA inhibited tumor growth in a FLC PDX mouse model; in contrast, dox-induction of NT shRNA expression did not affect tumor growth. Each data point in the graph is the mean±SEM tumor volume derived from eleven mice in the study group.

In the dosing study, doxycycline induction of PRKACA shRNA, but not NT shRNA expression, inhibited tumor growth in the immunodeficient NON-SCID mice (FIG. 2). Of note, a PRKACA shRNA tumor started to re-grow about twenty days after doxycycline induction. Regrowth of the tumor correlated with increased expression of DNAJB1-

PRKACA. Thus, the regrowth may have been caused by the outgrowth of clones with a weaker knockdown.

Western blot analysis of tumor samples showed doxycycline-induced reduction of DNAJB1-PRKACA expression following PRKACA shRNA expression, but not NT shRNA induction (FIG. 1). To perform western blot analysis, tumor pieces were lysed in PhosphoSafe Extraction Reagent (Millipore, Catalog No. 71296) with added Halt protease inhibitor cocktail (ThermoScientific, Catalog No. 78430). An SDS-PAGE (4-12% gel) was used to resolve the proteins in the cell lysate. Following electrophoresis, the resolved proteins were electrotransferred onto a polyvinylidene fluoride microporous membrane and immunodetected using standard procedures.

D. Efficacy Study in FL-HCC (LI5132) Patient-Derived Xenograph (PDX) Model

The efficacy of a PRKACA inhibitor of the present invention was tested in an FL-HCC (LI5132) PDX model (CrownBio, AACR17 poster, Abstract 4203).

Efficacy: To establish the PDX model, 72 mice were inoculated with patient tumor cells to yield at least 36 mice with tumors of the required size. 18 of these mice were selected for the study. Once daily dosing of compound 144 for 34 days began on day 1 of the study, when the average tumor volume reached to 150 $mm^3$, and the mice were harvested at 2, 6 and 24 hr post last dose.

Compound Formulation

| | |
|---|---|
| Name | Test agent (Cmpd 144) |
| Physical State | Solid |
| Pre formulation Storage Conditions | Room Temperature |
| Post formulation Storage Conditions | 4° C. |
| Vehicle | 10% DMSO in water |
| Estimated Needs (25 g animal + 50% overage) | 182.25 mg (estimated for 25 g mice, 50% overage) |
| Formulation Frequency | Every 5 days |

Efficacy Dosing Regimen

| Group | Treatment | N | Dose Route | Dosing Frequency & Duration | Dose Level (mg/kg) | Dose Volume (mL/kg) | Serum and tumor collection (after the last dose) |
|---|---|---|---|---|---|---|---|
| 1 | Vehicle (20% solutol in 0.5% MC) | 9 | PO | QDX34 | NA | 10 | 2, 6, 24 hr, n = 3 |
| 2 | Cmpd # 144 | 9 | PO | QDX34 | 30 | 10 | 2, 6, 24 hr, n = 3 |

Figure 3:
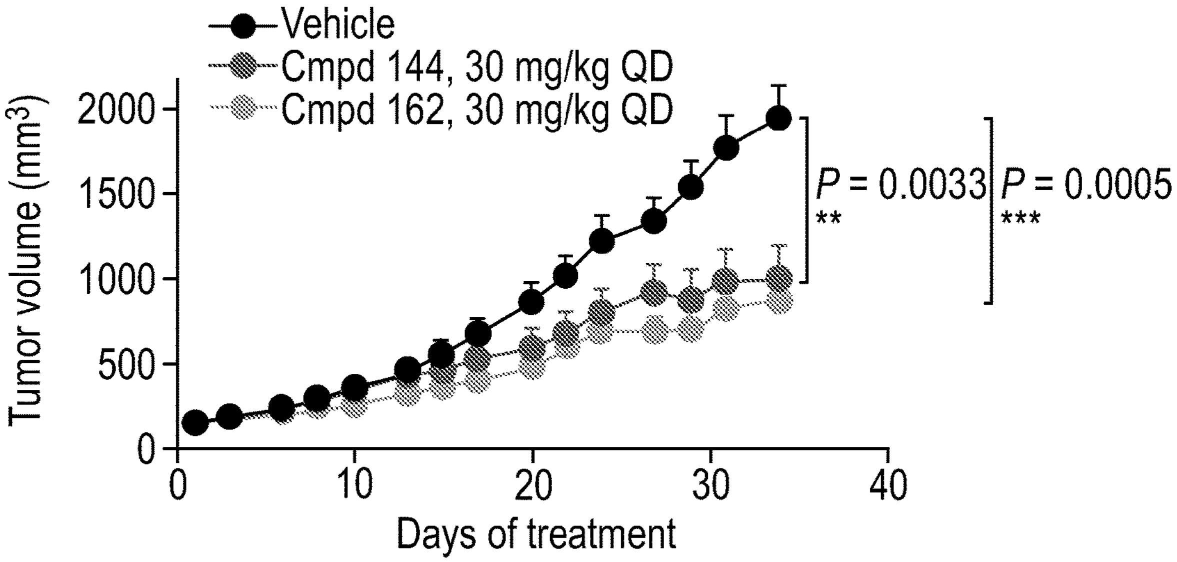
FIG. 3 is a graph which shows FLC tumor growth inhibition at a tolerated dose for two representative compounds of the present invention.

FIG. 3 demonstrates that oral delivery of compound 144 and compound 162 achieved significant FLC tumor growth inhibition at a tolerated dose.

Figure 4:
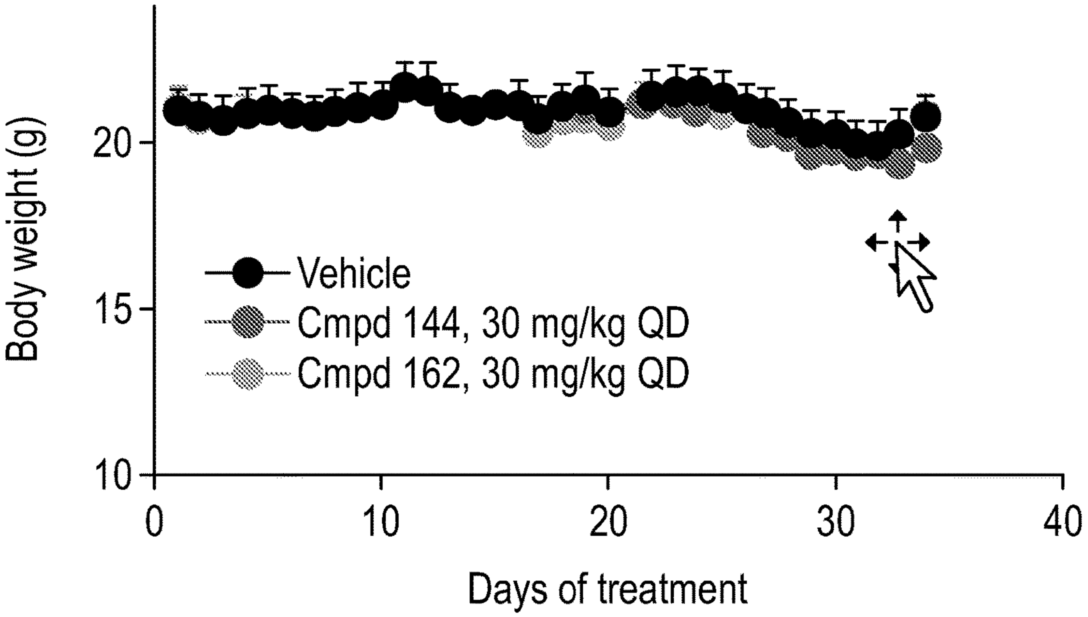
FIG. 4 is a graph which shows the body weight of each of the tested mice over time in days during the study.

FIG. 4 shows body weight of each tested mice over time in days during the study.

Biological Activity of Compounds of Formula (I)

Table 2 includes the inhibitory concentration (50%) value for various compounds of Formula (I) tested in the aforementioned examples.

In the Table below, the following designations are used:

PRKACA and PRKACA-DNAJB1 Enzyme: ≤1.00 nM=A; 1.01-5.00 nM B; >5.00 nM=C;

Phos VASP: 50 nM=A; ≤0.01-100 nM=B; and >100 nM=C.

TABLE 2

| # | Enz PRKACA IC50 (nM) | Enz PRKACA-DNAJB1 IC50 (nM) | Phos VASP(S157) IC50 (nM) |
|---|---|---|---|
| 100 | A | A | A |
| 101 | A | A | A |
| 102 | A | A | B |
| 103 | A | A | A |
| 104 | A | A | B |
| 105 | B | | B |
| 106 | A | | B |
| 107 | A | A | A |
| 108 | A | A | A |
| 109 | A | A | A |
| 110 | A | A | A |
| 111 | A | A | A |
| 112 | A | A | B |
| 113 | A | B | B |
| 114 | A | A | A |
| 115 | A | A | A |
| 116 | A | | B |
| 117 | A | A | A |
| 118 | A | | B |
| 119 | A | B | C |
| 120 | A | A | A |
| 121 | A | B | B |
| 122 | A | | A |
| 123 | A | A | A |
| 124 | A | | A |
| 125 | A | A | A |
| 126 | A | B | A |
| 127 | A | B | A |
| 128 | A | A | A |
| 129 | A | A | A |
| 130 | A | B | A |
| 131 | A | | A |
| 132 | A | | A |
| 133 | B | | B |
| 134 | A | A | A |
| 135 | A | A | B |
| 136 | A | A | B |
| 137 | A | | B |
| 138 | A | | B |
| 139 | A | B | B |

TABLE 2-continued

| # | Enz PRKACA IC50 (nM) | Enz PRKACA-DNAJB1 IC50 (nM) | Phos VASP(S157) IC50 (nM) |
|---|---|---|---|
| 140 | A | | B |
| 141 | A | A | B |
| 142 | A | A | A |
| 143 | A | | A |
| 144 | A | | A |
| 145 | A | | B |
| 146 | A | A | B |
| 147 | B | | A |
| 148 | A | A | B |
| 149 | A | | A |
| 150 | A | A | A |
| 151 | A | A | A |

TABLE 2-continued

| # | Enz PRKACA IC50 (nM) | Enz PRKACA-DNAJB1 IC50 (nM) | Phos VASP(S157) IC50 (nM) |
|---|---|---|---|
| 152 | B | B | B |
| 153 | A | | B |
| 154 | A | A | A |
| 155 | A | | A |
| 156 | A | | A |
| 157 | A | A | A |
| 158 | A | | B |
| 159 | A | B | B |
| 160 | A | A | A |
| 161 | A | A | B |
| 162 | A | A | A |
| 163 | A | | B |
| 164 | A | | A |
| 165 | A | A | A |
| 166 | A | | B |
| 167 | A | A | B |
| 168 | A | | A |
| 169 | A | A | A |
| 170 | A | A | A |
| 171 | A | A | A |
| 172 | A | A | A |
| 173 | A | A | B |
| 174 | A | | A |
| 175 | A | A | A |
| 176 | A | A | A |
| 177 | A | | A |
| 178 | A | | A |
| 179 | A | | A |
| 180 | A | A | A |
| 181 | A | | A |
| 182 | A | | B |
| 183 | B | | B |
| 184 | B | | |
| 185 | A | A | A |
| 186 | A | B | A |
| 187 | B | | C |
| 188 | A | B | B |
| 189 | A | A | B |
| 190 | A | A | A |
| 191 | A | A | A |
| 192 | A | | A |
| 193 | A | | A |

All publications and patents mentioned herein are hereby incorporated by reference in their entirety as if each individual publication or patent was specifically and individually indicated to be incorporated by reference.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the disclosure, or aspects of the disclosure, is/are referred to as comprising particular elements and/or features, embodiments of the disclosure or aspects of the disclosure consist, or consist essentially of, such elements and/or features. For purposes of simplicity, those embodiments have not been specifically set forth in haec verba herein. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

Those skilled in the art will recognize, or be able to ascertain using no more than routine experimentation, many equivalents to the specific embodiments of the disclosure described herein. Such equivalents are intended to be encompassed by the following claims.

We claim:

1. A compound of Formula (I):

(I)

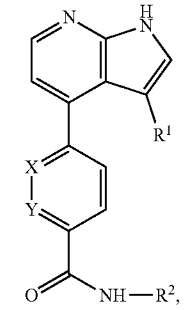

a pharmaceutically acceptable salt thereof, and/or a solvate of any of the foregoing, wherein:

X is chosen from CH and N;

Y is chosen from CH and N, provided that X and Y are not both N;

$R^1$ is chosen from H, halogens, and $C_1$-$C_4$ alkyls; and $R^2$ is chosen from optionally substituted indane and optionally substituted chromane, wherein each optional substituent is independently chosen from halogens, hydroxyl, $C_1$-$C_4$ alkyls, $C_1$-$C_4$ haloalkyls, 4-8-membered monocyclic heterocycles, 4-8-membered bicyclic heterocycles, $NR^3R^4$, and $OC_1$-$C_4$ alkyls, wherein:

each 4-8-membered monocyclic heterocycle, 4-8-membered bicyclic heterocycle, $C_1$-$C_4$ alkyl, and $OC_1$-$C_4$ alkyl is optionally substituted with one to three groups independently chosen from $C_1$-$C_4$ alkyls, $C_1$-$C_4$ hydroxyalkyls, $C_1$-$C_4$ haloalkyls, $OC_1$-$C_4$ alkyls, $OC_1$-$C_4$ hydroxyalkyls, halogens, hydroxyl, and C (O) $NR^5R^6$;

each $R^3$ and $R^4$ is independently chosen from hydrogen and $C_1$-$C_4$ alkyls; and each $R^5$ and $R^6$ is independently chosen from hydrogen and $C_1$-$C_4$ alkyls.

2. The compound of claim 1 chosen from compounds of Formula (Ia):

(Ia)

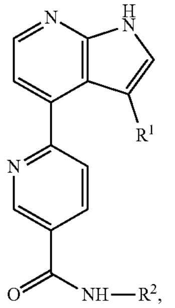

pharmaceutically acceptable salts thereof, and solvates of any of the foregoing, wherein:

$R^1$ is chosen from H, halogens, and $C_1$-$C_4$ alkyls; and $R^2$ is chosen from optionally substituted indane and optionally substituted chromane, wherein each optional substituent is independently chosen from halogens, hydroxyl, $C_1$-$C_4$ alkyls, $C_1$-$C_4$ haloalkyls, 4-8-membered monocyclic heterocycles, 4-8-membered bicyclic heterocycles, $NR^3R^4$, and $OC_1$-$C_4$ alkyls, wherein:

each 4-8-membered monocyclic heterocycle, 4-8-membered bicyclic heterocycle, $C_1$-$C_4$ alkyl, and $OC_1$-$C_4$ alkyl is optionally substituted with one to three groups independently chosen from $C_1$-$C_4$ alkyls, $C_1$-$C_4$ hydroxyalkyls, $C_1$-$C_4$ haloalkyls, $OC_1$-$C_4$ alkyls, $OC_1$-$C_4$ hydroxyalkyls, halogens, hydroxyl, and C (O) $NR^5R^6$;

each $R^3$ and $R^4$ is independently chosen from hydrogen and $C_1$-$C_4$ alkyls; and each $R^5$ and $R^6$ is independently chosen from hydrogen and $C_1$-$C_4$ alkyls.

3. The compound of claim 1 chosen from compounds of Formula (Ib):

(Ib)

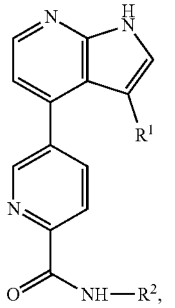

pharmaceutically acceptable salts thereof, and solvates of any of the foregoing, wherein:

$R^1$ is chosen from H, halogens, and $C_1$-$C_4$ alkyls; and $R^2$ is chosen from optionally substituted indane and optionally substituted chromane, wherein each optional substituent is independently chosen from halogens, hydroxyl, $C_1$-$C_4$ alkyls, $C_1$-$C_4$ haloalkyls, 4-8-membered monocyclic heterocycles, 4-8-membered bicyclic heterocycles, $NR^3R^4$, and $OC_1$-$C_4$ alkyls, wherein:

each 4-8-membered monocyclic heterocycle, 4-8-membered bicyclic heterocycle, $C_1$-$C_4$ alkyl, and $OC_1$-$C_4$ alkyl is optionally substituted with one to three groups independently chosen from $C_1$-$C_4$ alkyls, $C_1$-$C_4$ hydroxyalkyls, $C_1$-$C_4$ haloalkyls, $OC_1$-$C_4$ alkyls, $OC_1$-$C_4$ hydroxyalkyls, halogens, hydroxyl, and C (O) $NR^5R^6$, each $R^3$ and $R^4$ is independently chosen from hydrogen and $C_1$-$C_4$ alkyls; and each $R^5$ and $R^6$ is independently chosen from hydrogen and $C_1$-$C_4$ alkyls.

4. The compound of claim 1 chosen from compounds of Formula (Ic):

(Ic)

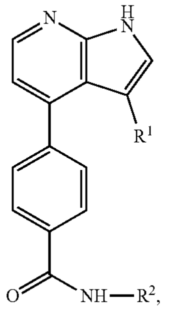

pharmaceutically acceptable salts thereof, and solvates of any of the foregoing, wherein:

$R^1$ is chosen from H, halogens, and $C_1$-$C_4$ alkyls; and $R^2$ is chosen from optionally substituted indane and optionally substituted chromane, wherein each optional substituent is independently chosen from halogens, hydroxyl, $C_1$-$C_4$ alkyls, $C_1$-$C_4$ haloalkyls, 4-8-membered monocyclic heterocycles, 4-8-membered bicyclic heterocycles, $NR^3R^4$, and $OC_1$-$C_4$ alkyls, wherein:

each 4-8-membered monocyclic heterocycle, 4-8-membered bicyclic heterocycle, $C_1$-$C_4$ alkyl, and $OC_1$-$C_4$ alkyl is optionally substituted with one to three groups independently chosen from $C_1$-$C_4$ alkyls, $C_1$-$C_4$ hydroxyalkyls, $C_1$-$C_4$ haloalkyls, $OC_1$-$C_4$ alkyls, $OC_1$-$C_4$ hydroxyalkyls, halogens, hydroxyl, and C (O) $NR^5R^6$;

each $R^3$ and $R^4$ is independently chosen from hydrogen and $C_1$-$C_4$ alkyls; and each $R^5$ and $R^6$ is independently chosen from hydrogen and $C_1$-$C_4$ alkyls.

5. The compound, pharmaceutically acceptable salt, or solvate of claim 1, wherein $R^2$ is optionally substituted indane.

6. The compound, pharmaceutically acceptable salt, or solvate of claim 1, wherein $R^2$ is optionally substituted chromane.

7. The compound, pharmaceutically acceptable salt thereof, or solvate of claim 1, wherein:

$R^2$ is chosen from indane substituted with one to four Ra and chromane substituted with one to four $R^a$, wherein each $R^a$ is independently chosen from halogens, hydroxyl, $C_1$-$C_4$ alkyls, $C_1$-$C_4$ haloalkyls, 4-8-membered monocyclic heterocycles, 4-8-membered bicyclic heterocycles, $NR^3R^4$, and $OC_1$-$C_4$ alkyls, wherein:

each 4-8-membered monocyclic heterocycle, 4-8-membered bicyclic heterocycle, $C_1$-$C_4$ alkyl, and $OC_1$-$C_4$ alkyl is optionally substituted with one to three groups independently chosen from $C_1$-$C_4$ alkyls, $C_1$-$C_4$ hydroxyalkyls, $C_1$-$C_4$ haloalkyls, $OC_1$-$C_4$ alkyls, $OC_1$-$C_4$ hydroxyalkyls, halogens, hydroxyl, and C (O) $NR^5R^6$;

each $R^3$ and $R^4$ is independently chosen from hydrogen and $C_1$-$C_4$ alkyls; and each $R^5$ and $R^6$ is independently chosen from hydrogen and $C_1$-$C_4$ alkyls.

8. The compound, pharmaceutically acceptable salt, or solvate of claim 1, wherein $R^1$ is chosen from hydrogen, fluorine, and methyl.

9. The compound, pharmaceutically acceptable salt, or solvate of claim 1, wherein $R^2$ is chosen from indane substituted with one group chosen from halogens, hydroxyl, or $C_1$-$C_4$ alkyls and chromane substituted with one group chosen from halogens, hydroxyl, or $C_1$-$C_4$ alkyls.

10. The compound, pharmaceutically acceptable salt, or solvate of claim 1, wherein $R^2$ is chosen from indane substituted with one group chosen from halogens and hydroxyl and chromane substituted with one group chosen from halogens and hydroxyl.

11. The compound, pharmaceutically acceptable salt, or solvate of claim 1, wherein $R^2$ is chosen from indane substituted with one or two independently chosen halogens and one hydroxyl and chromane substituted with one or two independently chosen halogens and one hydroxyl.

12. The compound, pharmaceutically acceptable salt, or solvate of claim 1, wherein $R^2$ is chosen from indane substituted with one or two independently chosen halogens, one hydroxyl, and one group chosen from $C_1$-$C_4$ alkyls and $C_1$-$C_4$ haloalkyls and chromane substituted with one or two independently chosen halogens, one hydroxyl, and one group chosen from $C_1$-$C_4$ alkyls and $C_1$-$C_4$ haloalkyls.

13. The compound, pharmaceutically acceptable salt, or solvate of claim 1, wherein $R^2$ is chosen from indane substituted with one or two independently chosen halogens and one group chosen from 4-8-membered monocyclic heterocycles and 4-8-membered bicyclic heterocycles, wherein each 4-8 membered monocylic heterocycle and 4-8 membered bicyclic heterocycle is optionally substituted with one to three groups independently chosen from $C_1$-$C_4$ alkyls, $C_1$-$C_4$ haloalkyls, $C_1$-$C_4$ hydroxyalkyls, $OC_1$-$C_4$ alkyls, $OC_1$-$C_4$ hydroxyalkyls, halogens, hydroxyl, and C (O) $NR^5R^6$ and chromane substituted with one or two independently chosen halogens and one group chosen from 4-8-membered monocyclic heterocycles and 4-8-membered bicyclic heterocycles, wherein each 4-8 membered monocylic heterocycle and 4-8 membered bicyclic heterocycle is optionally substituted with one to three groups independently chosen from $C_1$-$C_4$ alkyls, $C_1$-$C_4$ haloalkyls, $C_1$-$C_4$ hydroxyalkyls, $OC_1$-$C_4$ alkyls, $OC_1$-$C_4$ hydroxyalkyls, halogens, hydroxyl, and C (O) $NR^5R^6$, wherein:

each $R^3$ and $R^4$ is independently chosen from hydrogen and $C_1$-$C_4$ alkyls; and each $R^5$ and $R^6$ is independently chosen from hydrogen and $C_1$-$C_4$ alkyls.

14. The compound, pharmaceutically acceptable salt, or solvate of claim 13, wherein the 4-8-membered monocyclic heterocycle is an azetidine optionally substituted with one or two groups independently chosen from $C_1$-$C_4$ alkyls, $OC_1$-$C_4$ alkyls, halogens, hydroxyl, $C(O)NH_2$, and $C(O)N(CH_3)_2$ or a pyrrolidine optionally substituted with one or two groups independently chosen from $C_1$-$C_4$ alkyls, $OC_1$-$C_4$ alkyls, halogens, hydroxyl, $C(O)NH_2$, and $C(O)N(CH_3)_2$.

15. The compound, pharmaceutically acceptable salt, or solvate of claim 1, wherein $R^2$ is chosen from:

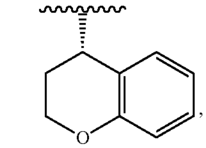

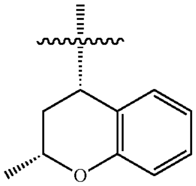,

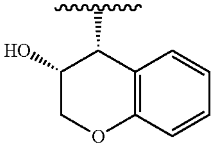,

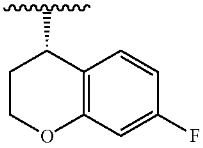,

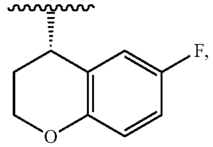,

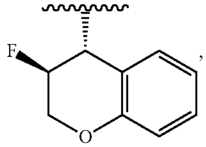,

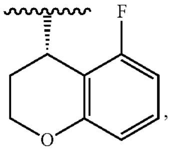,

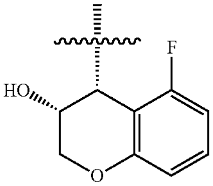,

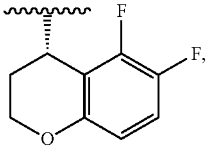,

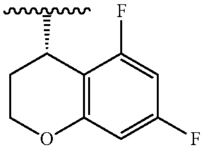,

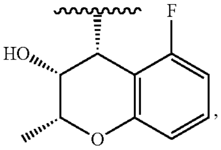,

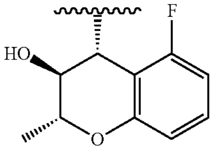,

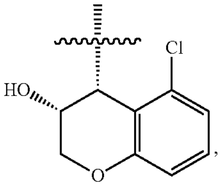,

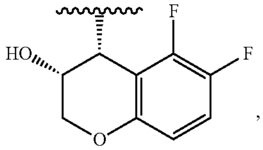,

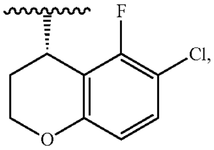,

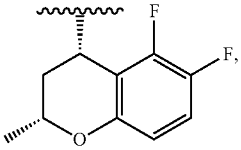,

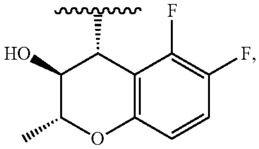,

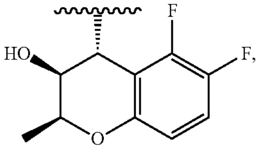,

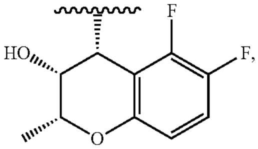,

-continued
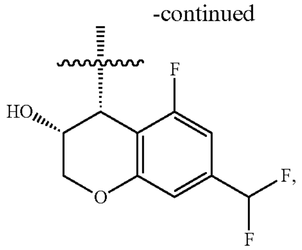
and
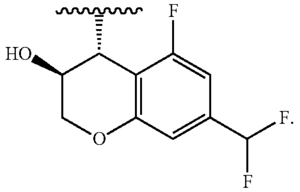 [SMILES: *[C@@H]1c2c(F)cc(C(F)F)cc2OC[C@H]1O]
16. The compound, pharmaceutically acceptable salt, or solvate of claim 1, wherein $R^2$ is chosen from:
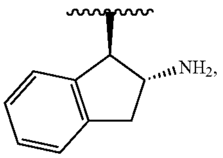
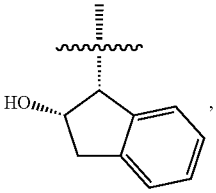,
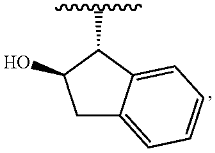,
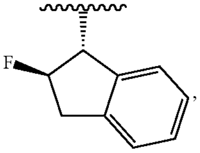,
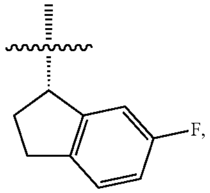
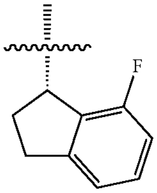,
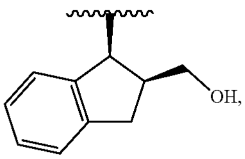
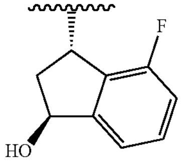,
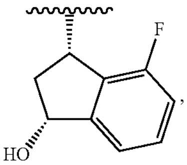,
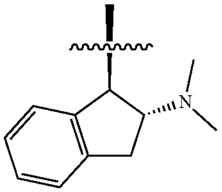,
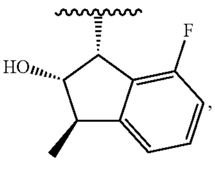,
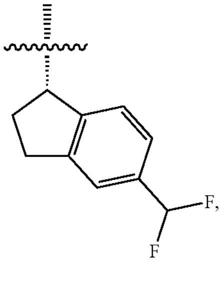
-continued
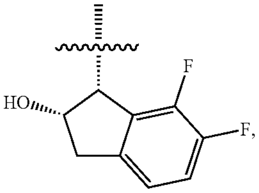
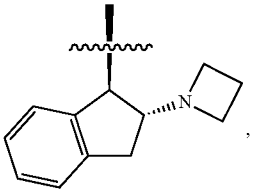,
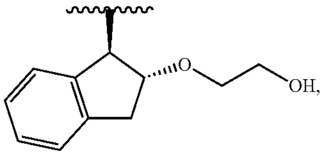
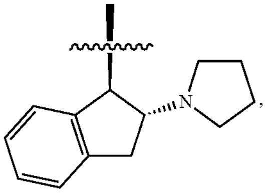
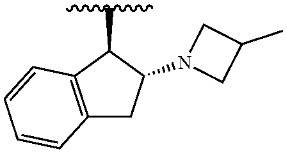,
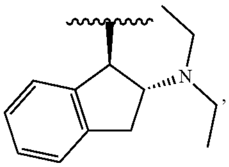,
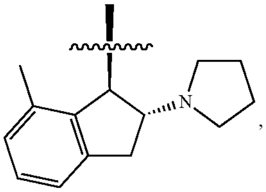,
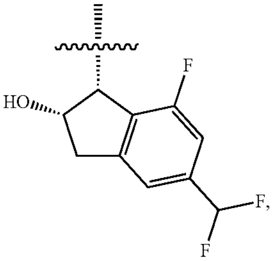
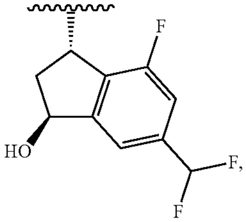
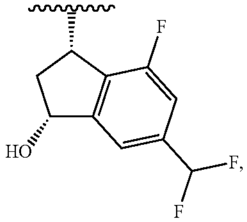
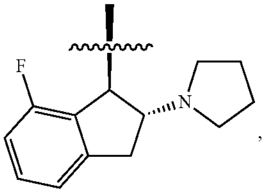,
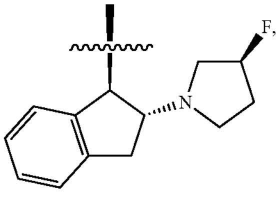
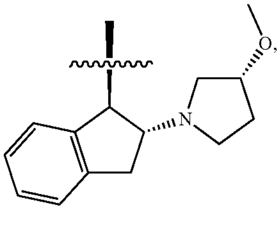
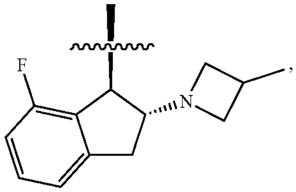, -continued

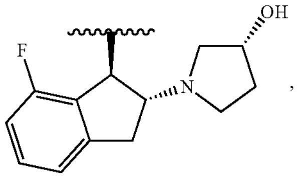

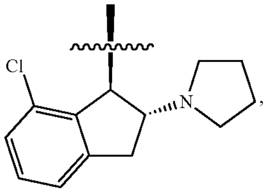

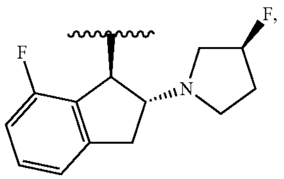

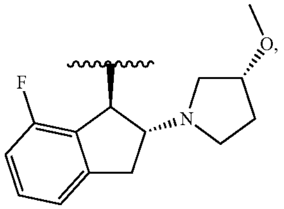

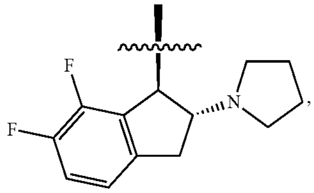

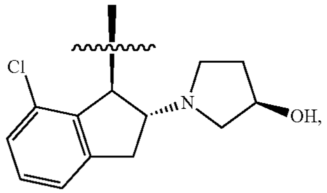

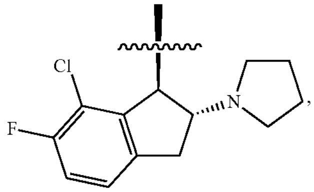

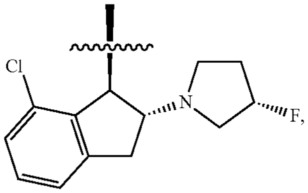

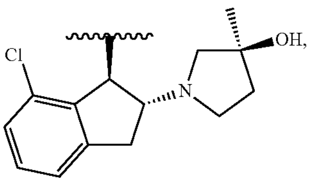

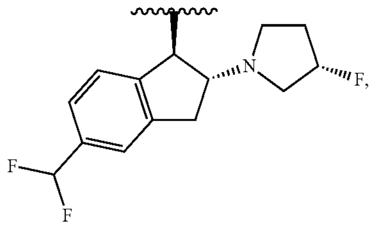

-continued

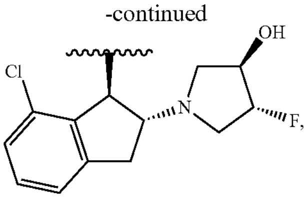

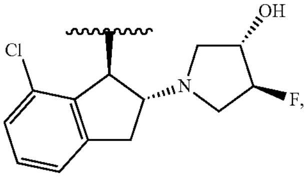

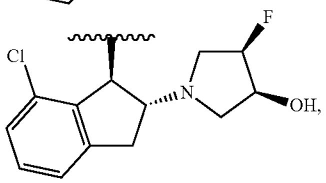

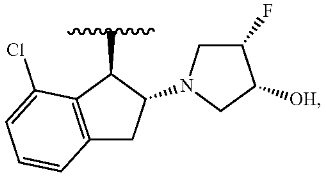

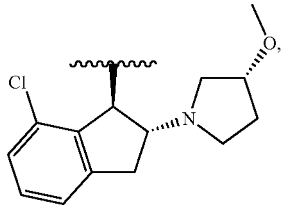

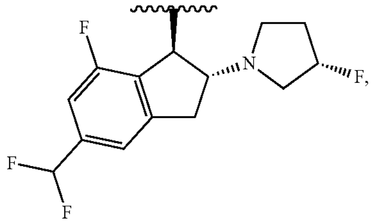

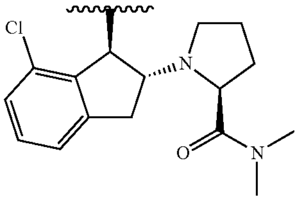

and

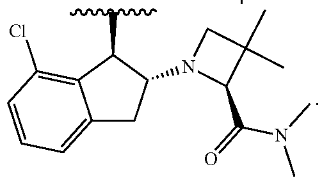

17. A pharmaceutical composition comprising:

at least one compound chosen from compounds of claim 1, pharmaceutically acceptable salts thereof, and solvates of any of the foregoing; and at least one pharmaceutically acceptable excipient.

18. A method of treating a subject afflicted with a disease mediated by protein kinase A (PKA) comprising administering to the subject a therapeutically effective amount of a compound chosen from compounds of claim 1.

19. The method of claim 1, wherein the disease mediated by PKA is characterized by a DNAJB1-PRKAC fusion.

20. The method of claim 18, wherein the disease mediated by PKA is chosen from pituitary cancer, kidney cancer, ovarian cancer, testicular cancer, thyroid ademona, Villous colon cancer, intraductal papillary mucinous neoplasms (IPMN), intrahepatic cholangiocarcinomas, inflammatory liver cancer, fibrolamellar carcinoma, multiple neoplasia syndrome, Carney complex (CNC), polycystic kidney disease (PKD), and McCune-Albright syndrome.

* * * * *